(12) United States Patent
Johnson, Jr. et al.

(10) Patent No.: US 6,872,745 B2
(45) Date of Patent: Mar. 29, 2005

(54) ANTIPICORNAVIRAL COMPOUNDS AND COMPOSITIONS, THEIR PHARMACEUTICAL USES, AND MATERIALS FOR THEIR SYNTHESIS

(75) Inventors: Theodore O. Johnson, Jr., San Diego, CA (US); Ye Hua, La Jolla, CA (US); Hiep T. Luu, San Diego, CA (US); Peter S. Dragovich, Encinitas, CA (US)

(73) Assignee: Agouron Pharmaceuticals, Inc., San Diego, CA (US)

( * ) Notice: Subject to any disclaimer, the term of this patent is extended or adjusted under 35 U.S.C. 154(b) by 6 days.

(21) Appl. No.: 10/435,082

(22) Filed: May 12, 2003

(65) Prior Publication Data

US 2003/0225042 A1 Dec. 4, 2003

Related U.S. Application Data

(62) Division of application No. 09/834,783, filed on Apr. 12, 2001, now Pat. No. 6,610,730.
(60) Provisional application No. 60/198,497, filed on Apr. 18, 2000, and provisional application No. 60/197,796, filed on Apr. 14, 2000.

(51) Int. Cl.$^7$ .................. A61K 31/4015; C07D 207/04
(52) U.S. Cl. ...................... 514/424; 514/428; 548/541; 548/543; 548/550; 548/551
(58) Field of Search ................................ 548/550, 551, 548/541, 543; 514/424, 428

(56) References Cited

U.S. PATENT DOCUMENTS

| | | | |
|---|---|---|---|
| 5,374,623 A | 12/1994 | Zimmerman et al. | 514/17 |
| 5,498,616 A | 3/1996 | Mallamo et al. | 514/300 |
| 5,856,530 A | 1/1999 | Webber et al. | 549/478 |
| 5,962,487 A | 10/1999 | Webber et al. | 514/378 |
| 6,020,371 A | 2/2000 | Dragovich et al. | 514/514 |
| 6,331,554 B1 | 12/2001 | Dragovich et al. | 514/357 |

FOREIGN PATENT DOCUMENTS

| | | |
|---|---|---|
| WO | WO 94/04172 | 3/1994 |
| WO | WO 95/15749 | 6/1995 |
| WO | WO 95/23222 | 8/1995 |
| WO | WO 95/31433 | 11/1995 |
| WO | WO 96/30395 | 10/1996 |
| WO | WO 97/43305 | 11/1997 |
| WO | WO 97/49668 | 12/1997 |
| WO | WO 98/43950 | 10/1998 |
| WO | WO 99/31122 | 6/1999 |
| WO | WO 99/57135 | 11/1999 |
| WO | WO 00/78708 | 12/2000 |
| WO | WO 01/10894 | 2/2001 |
| WO | WO 01/14329 | 3/2001 |
| WO | WO 01/14576 | 3/2001 |
| WO | WO 01/40189 | 6/2001 |

OTHER PUBLICATIONS

Dragovich, et al., "Structure–Based Design, Synthesis, and Biological Evaluation of Irreversible Human Rhinovirus 3C Protease Inhibitors. 4. Incorporation of $P_1$ Lactam Moieties as L–Glutamine Replacements", *J. Med. Chem.* (1999) vol. 42, No. 7, pp. 1213–1224.

Dragovich, et al., "Structure–Based Design, Synthesis and Biological Evaluation of Irreversible Human Rhinovirus 3C Protease Inhibitors. 3. Structure–Activity Studies of Ketomethylene–Containing Peptidomimetics", *J. Med. Chem.* (1999) vol. 42, No. 7 pp. 1203–1212.

Dragovich, et al., "Structure–Based Design, Synthesis, and Biological Evaluation of Irreversible Human Rhinovirus 3C Protease Inhibitors. 2. Peptide Structure–Activity Studies", *Med Chem.* (1998) vol. 41, No. 15, pp. 2819–2834.

Dragovich, et al., "Solid–phase Synthesis of Irreversible Human Rhinovirus 3C Protease Inhibitors. Part 1: Optimization of Tripeptides Incorporating N–terminal Amides", *Bioorg. & Med. Chem.* (1999) (7), pp. 589–598.

Birch, et al., "Purification of Recombinant Human Rhinovirus 14 3C Protease Expressed in *Escherichia coli*," Protein Expr. Pur. (1995) vol. 6(5) 609–618.

Baldwin, "Diarylmethylene–tetracyanoethylene Cycloadditions", J. Org. Chem. (1971) vol. 36, No. 10, pp. 1441–1443.

Hartke, et al., "αβ–ungesattigte Thion– und Dithioester durch Kondensationsreaktionen", *Leibigs Ann. Chem.* (1989), pp. 321–330.

Hartke, "A Simple Route to 2–Alkenethioic O–Esters and 2–Alkenedithioic Esters" [Thiono–and Dithioesters, 37], *Synthesis* (1985) pp. 960–961.

Kruse, et al., "New Methods for the Synthesis of 2–ArylPyrroles", *Heterocycles* (1987) vol. 26, No. 12, pp. 3141–3151.

Bailey, et al., "Ethyl Pyrrole–2–Carboxylate", *Org. Synth.* (1971) vol. 51, 100–102.

(List continued on next page.)

*Primary Examiner*—Golam M M Shameem
(74) *Attorney, Agent, or Firm*—Fitzpatrick, Cella, Harper & Scinto

(57) ABSTRACT

Compounds of the formula:

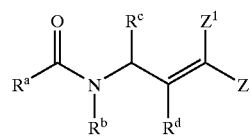

where the formula variables are as defined in the disclosure, advantageously inhibit or block the biological activity of the picornaviral 3C protease. These compounds, as well as pharmaceutical compositions containing these compounds, are useful for treating patients or hosts infected with one or more picornaviruses, such as RVP. Intermediates and synthetic methods for preparing such compounds are also described.

9 Claims, No Drawings

OTHER PUBLICATIONS

Gonzalez–Muniz et al., "Synthesis of 2–Substituted 8–Amino–3–oxoindolizoline–2–carboxylic Acid Derivatives as Peptide Conformation Mimetics". *Tetrahedron* (1992) vol. 48, No. 24, pp. 5191–5198.

Garcia–Lopez, et al., "A Simple and Versatile Route to Ketomethylene Dipeptide Analogs". *Tetrahedron* (1988) vol. 29, No. 13, pp. 1577–1580.

Garcia–Lopez, et al., "Synthesis of Ketomethylene Dipeptides Containing Basic Amino Acid Analogues at C–Terminus", Tetrahedron (1988), vol. 44, No. 16, 5131–5138.

Charlton, et al., "Asymmetric synthesis of lignans using oxazolidinones as chiral auxillaries", NRC–CNRC Canadian Journal of Chemistry (1997), vol. 75, No. 8, pp. 1076–1083.

Silverstein, et al., "2–Pyrrolealdehyde", Org. Synth. (1963) Coll. vol. IV, 831–833.

Hoffman, R.V., Tao, J. "A Simple, Stereoselective Synthesis of Ketomethylene Dipeptide Isosteres", *Tetrahedron* (1997) vol. 53, No. 21, pp. 7119–7126.

Sunberg, et al., "3–(3–Pyrrolyl) thiopyrrolidones as Precursors of Benzo [1,2-b:4,3-b']dipyrroles. Synthesis of Structures Related to the Phosphodiesterase Inihibitors PDE–I and PDE–II", *J. Org. Chem.* (1985) vol. 50, No. 4, pp. 425–432.

Weislow, et al., "New Soluble–Formazan Assay for HIV–1 Cytopathic Effects: Application to High–Flux Screening of Synthetic and Natural Products for AIDS–Antiviral Activity", *J. Natl. Cancer* (1989) vol. 81, No. 8, pp. 577–586.

Kaldor et al., "Glutamine–Derived Aldehydes for the Inhibition of Human Rhinovirus 3C Protease", *Bioorganic & Medicinal Chemistry Letters*, vol. 5, No. 17 (1995) pp. 2021–2026.

Murray et al., "The enantiospecific synthesis of novel lysine analogues incorporting a pyrrolidine containing side chain", *Tetrahedron Letters*, vol. 39 (1998) pp. 6721–6724.

Webber et al., "Design, Synthesis, and Evaluation of Nonpeptidic Inhibitors of Human Rhinovirus 3C Protease", J. Med. Chem. (1996) vol. 39, No. 26, pp. 5072–5082.

Kong et al., "Synthesis and Evaluation of Peptidyl Michael Acceptors That Inactivate Human Rhinovirus 3C Protease and Inhibit Virus Replication", *J. Med. Chem.* (1998) vol. 41, No. 14, pp. 2579–2587.

Webber et al., "Tripeptide Aldehyde Inhibitors of Human Rhinovirus 3C Protease: Design, Synthesis, Biological Evaluation, and Cocrystal Structure Solution of $P_1$ Glutamine Isosteric Replacements", J. Med. *Chem.* (1998) vol. 41, No. 15, pp. 2786–2805.

Bradbury et al., "An Efficient Synthesis of the γ–Lactone Corresponding to a Hydroxylethylene Dipeptide Isostere Using Stereoselective Bromolactonisation of a Chiral Acyloxazolidinone", Tetrahedron Letters (1989) vol. 30, No. 29, pp. 3845–3848.

Chida et al., "Total Synthesis and Absolute Configuration of Bengamide A", J. Chem. Soc., Chem. Commun. (1992) pp. 1064–1066.

Dondoni et al., "Thiazole–Based Stereoselective Routes to Leucine and Phenylalanine Hydroxyethylene Dipeptide Isostere Inhibitors of Renin and HIV–1 Aspartic Protease", *J. Org. Chem.* (1995) vol. 60, No. 24, pp. 7927–7933.

Herold et al., "A Versatile and Stereocontrolled Synthesis of Hydroxyethylene Dipeptide Isosteres", *J. Org. Chem.* (1989) vol. 54, No. 5, pp. 1178–1185.

Hanzlik et al., "Structure–Activity Relationships for Inhibition of Papain by Peptide Michael Acceptors", J. Med. Chem. (1992) vol. 35, No. 6, pp. 1067–1075.

Luly et al., "A Synthesis of Protected Aminoalkyl Epoxides from α–Amino Acids", J. Org. Chem. (1987) vol. 52, No. 8, pp. 1487–1492.

McWilliams et al., "Tandem Asymmetric Transformations: An Asymmetric 1,2–Mmigration from a Higher Order Zincate Coupled with a Stereoselective Homoaldol Reaction", J. Am. Chem. Soc. (1996) vol. 118, No. 47, pp. 11970–11971.

Jones et al., "A Short Stereocontrolled Synthesis of Hydroxyethylene Dipeptide Isosteres", J. Org. Chem. (1993) vol. 58, No. 8, pp. 2286–2290.

Pegorier et al., "A General Stereocontrolled Synthesis of Hydroxyethylene Dipeptide Isosteres", Tetrahedron *Letters* (1995) vol. 36, No. 16, pp. 2753–2756.

Wuts et al., "Synthesis of the Hydroxyethylene Isostere of Leu–Val", J. Org. Chem. (1992) vol. 57, No. 25, pp. 6696–6700.

Hanzlik et al., "Vinylogous Amino Acid Esters: A New Class of Inactivators for Thiol Proteases", J. Med. Chem. (1984), vol. 27, No. 6, pp. 711–712.

Venkatraman et al., "Synthesis of Potential Inhibitors for Human Rhinovirus 3C Protease", The Second Winter Conference on Medicinal and Bioorganic Chemistry, Steamboat Springs, CO, Jan. 26–31, 1997.

Bowden et al., "Organophosphorus Chemistry, Part XIV. Reaction of Phosphorodiamidous Chlorides with Sulphonamides: a New Route to Diazadiphophetidines", *J. Chem. Soc.* Perkin Transactions I Orgnic and Bio–organic Chemistry (1973) 516–520.

Dragovich, et al., "Structure–Based Design, Synthesis, and Biological Evaluation of Irreversible Human Rhinovirus 3C Protease Inhibitors. 1. Michael Acceptor Structure–Activity Studies", *J. Med. Chem.* (1998) vol. A1, No. 15, pp. 2806–2818.

DeJohn, et. al., "Functionalization of Substituted 2(1–H)–Pyridones. III. The Preparation of Substituted 6–Vinyl–1,2 –dihyrdo–2–oxo– and 1,4–Dihyrdo–4–oxo–3–pyridinecarboxylic Acids through the Chemistry of Pyridone Dianions", *J. Heterocyclic Chem.* (1983) vol. 20, No. 5, pp. 1295–1302.

Fasseur et al., Studies on Pyrrolidones Synthesis and N–Alkylation of β–Enaminoesters Derives from Pyroglutamic Acid:, *J. Heterocyclic Chem.* (1992) vol. 29, No. 5, pp. 1285–1291.

Straub, et al., "Synthesis of the Angiotensin Converting enzyme Inhibitor (–)–A58365A via an Isomunchnone cycloadditon Reaction", *Org, Lett*, (1999) vol. 1, No. 1, pp. 83–85.

Fang et al., "Total Synthesis of the Angiotensin–Converting Enzyme Inhibitor A58365A: On the Use of Pyroglutamate as a Chiral Educt", *Tetrahedron Lett.* (1989) vol. 30, No. 28, pp. 3621–3624.

Crossley et al., "Convenient Route to γ–nitro–α–amino acids: conjugate addition of nitroalkanes to dehydroalanine derivatives", *J. Chem. Soc. Perkin Trans.* 1 (1998 No. 6, pp 1113–1121.

Bellus, "Incorporation of Sulfur Dioxide into the Products of Reaction of Schiff Bases with Halo–or Alkylthio–Ketones in Liquid $SO_2$", *Helvetica Chimica Acta* (1975) vol. 58, No. 271 pp. 2509–2511.

Diana et al., "Picornavirus Inhibitors: Trifluoromethyl Substitutions Provides a Global Protective Effect against Hepatic Metabolism", *Med. Chem.* (1995), vol. 38, pp. 1355–1371.

Jackson et. al., "Preparation of Enantiomerically Pure Protected 4–Oxo–α–amnio Acids and 3–Aryl–α–amino Acids from Serine", *J. Org, Chem.* (1992), vol. 57, 12 pp. 3397–3404.

Dragovich et al. "Structure–Based Design of Irreversible, Tripeptidyl Human Rhinovirus 3C Protease Inhibitors Containing N–Methyl Amino Acids", *Bioorg. & Med. Chem. Let.* (1999), vol. 9, No. 15, pp. 2189–2194.

Van der Bent et al., "Synthesis and Biological Evaluation of Lorglumide–Like Hybrid Cholecystokinin–A Receptor Antagonists", *Drug Dev. Res.* (1994), vol. 31, No. 3, pp. 197–205.

Askin et al., "Highly Diastereoselective Alkylations of Chiral Amide Enolates: New Routes to Hydroxyethylene Dipeptide Isotere Inhibitors of HIV–1 Protease", *J. Org.*, 57, 2774–2773 (1992).

Liu et al., "Structure–Activity Relationships for Inhibition of Papain by Peptide Michael Acceptors" *J. Med. Chem.*, 35, 1067–1075 (1992).

ANTIPICORNAVIRAL COMPOUNDS AND COMPOSITIONS, THEIR PHARMACEUTICAL USES, AND MATERIALS FOR THEIR SYNTHESIS

This application is a divisional of U.S. patent application Ser. No. 09/834,783, filed Apr. 12, 2001, now U.S. Pat No. 6,610,780 which claims the benefit of U.S. Provisional Patent Application No. 60/197,796, filed Apr. 14, 2000 and U.S. Provisional Patent Application No. 60/198,497, filed Apr. 18, 2000, the disclosures of each of which are incorporated by reference herein.

BACKGROUND OF THE INVENTION

1. Field of the Invention

The invention relates to pyrrole-containing peptidomimetic compounds that inhibit the enzymatic activity of picornaviral 3C proteases, especially rhinovirus 3C proteases (RVPs), and that retard viral growth in cell culture. The invention also relates to the use of these compounds in pharmaceutical compositions, methods of treatment of rhinoviral infections using these compounds and compositions, and processes for the synthesis of these compounds and compounds useful in the syntheses thereof.

2. Related Background Art

The picornaviruses are a family of tiny non-enveloped positive-stranded RNA-containing viruses that infect humans and other animals. These viruses include the human rhinoviruses, human polioviruses, human coxsackieviruses, human echoviruses, human and bovine enteroviruses, encephalomyocarditis viruses, meningitis virus, foot and mouth viruses, hepatitis A virus, and others. The human rhinoviruses are a major cause of the common cold. To date, there are no effective therapies on the market that cure the common cold, only treatments that relieve the symptoms.

Picornaviral infections may be treated by inhibiting the proteolytic picornaviral 3C enzymes. These enzymes are required for the natural maturation of the picornaviruses. They are responsible for the autocatalytic cleavage of the genomic, large polyprotein into the essential viral proteins. Members of the 3C protease family are cysteine proteases, where the sulfhydryl group most often cleaves the glutamine-glycine amide bond. Inhibition of 3C proteases is believed to block proteolytic cleavage of the viral polyprotein, which in turn can retard the maturation and replication of the viruses by interfering with viral particle production. Therefore, inhibiting the processing of this cysteine protease with selective small molecules that are specifically recognized should represent an important and useful approach to treat and cure viral infections of this nature and, in particular, the common cold.

Some small-molecule inhibitors of the enzymatic activity of picornaviral 3C proteases (i.e., antipicornaviral compounds) have been recently discovered. See, for example: U.S. Pat. No. 5,856,530; U.S. Pat. No. 5,962,487; U.S. Pat. No. 6,020,371; and U.S. patent application Ser. No. 09/301,977, filed Apr. 29, 1999, by Dragovich et al. See also: Dragovich et al., "Structure-Based Design, Synthesis, and Biological Evaluation of Irreversible Human Rhinovirus 3C Protease Inhibitors . . . ," J. Med. Chem. (1999), Vol. 42, No. 7, 1203–1212, 1213–1224; and Dragovich et al., "Solid-phase Synthesis of Irreversible Human Rhinovirus 3C Protease Inhibitors . . . ," Bioorg. & Med. Chem. (1999), Vol. 7, 589–598. There remains a desire, to discover small-molecule compounds that are especially potent antipicornaviral agents.

Inhibitors of other related cysteine proteases such as cathepsins have been described in, e.g., U.S. Pat. No. 5,374,623; U.S. Pat. No. 5,498,616; and WIPO International Publication Nos. WO 94/04172, WO 95/15749, WO 97/19231, and WO 97/49668. There yet remains a need for inhibitors targeting the picornaviral 3C cysteine protease with desirable pharmaceutical properties, such as high specificity, good therapeutic index or low toxicity.

SUMMARY OF THE INVENTION

This invention relates to compounds useful for inhibiting the activity of picornaviral 3C proteases having the general Formula I:

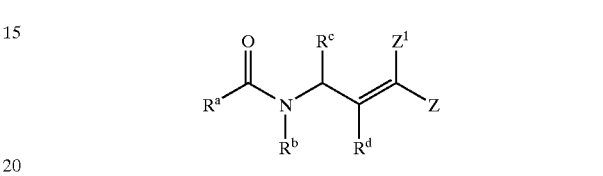

wherein:

$R^a$ is an alkylcarbonylalkyl, cycloalkylcarbonylalkyl, arylcarbonylalkyl, heteroarylcarbonylalkyl, alkylcarbonylaminoalkyl, cycloalkylcarbonylaminoalkyl, heterocycloalkylcarbonylaminoalkyl, arylcarbonylaminoalkyl, heteroarylcarbonylaminoalkyl, alkylaminocarbonylalkyl, cycloalkylaminocarbonylalkyl, heterocycloalkylaminocarbonylalkyl, arylaminocarbonylalkyl, heteroarylaminocarbonylalkyl group, where each alkyl, cycloalkyl, heterocycloalkyl, aryl and heteroaryl moiety thereof is unsubstituted or substituted with one or more suitable substituents;

$R^b$ is H or an alkyl group, unsubstituted or substituted with one or more suitable substituents;

$R^d$ is H, halo, hydroxyl, or an alkyl, alkoxy or alkylthio group, where the alkyl, alkoxy or alkylthio group is unsubstituted or substituted with one or more suitable substituents;

$R^c$ is a moiety having the formula:

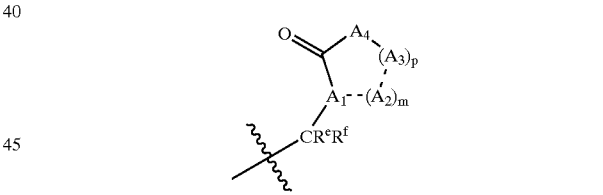

$R^e$ and $R^f$ are each independently H or a lower alkyl group;

m is 0 or 1, provided that when m is 1, $R^a$ is not an amino-substituted alkylcarbonylalkyl or amino-substituted alkylcarbonylaminoalkyl group, and when m is 0, $R^a$ is selected from an alkylaminocarbonylalkyl, cycloalkylaminocarbonylalkyl, heterocycloalkylaminocarbonylalkyl, arylaminocarbonylalkyl, heteroarylaminocarbonylalkyl and heteroarylcarbonylaminoalkyl group, provided that $R^a$ is not substituted indolecarbonylaminoalkyl;

p is an integer of from 0 to 5;

$A_1$ is CH or N;

when p is 1, 2, 3, 4, or 5, $A_2$ is $C(R^g)(R^h)$, $N(R^i)$, S, S(O), $S(O)_2$, or O, and when p is 0, $A_2$ is $C(R^g)(R^h)(R^i)$, $N(R^g)(R^i)$, $S(R^g)$, $S(O)(R^g)$, $S(O)_2(R^g)$, or $O(R^g)$, where each $R^g$, $R^h$ and $R^i$ is independently H or a lower alkyl group;

each $A_3$ present is each independently $C(R^g)(R^h)$, $N(R^i)$, S, S(O), $S(O)_2$, or O, where each $R^g$, $R^h$ and $R^i$ is independently H or a lower alkyl group;

when p is 1, 2, 3, 4, or 5, $A_4$ is $N(R^j)$, $C(R^g)(R^h)$, or O, and when p is 0 (i.e., $A_3$ is not present), $A_4$ is $N(R^j)(R^k)$, $C(R^g)(R^h)(R^i)$, and $O(R^k)$, where each $R^g$, $R^h$ and $R^i$ is independently H or a lower alkyl group, each $R^j$ is H, an alkyl, aryl, or acyl group, and each $R^k$ is H or an alkyl or aryl group;

provided that no more than two heteroatoms occur consecutively in the above-depicted ring formed by $A_1$, $(A_2)_m$, $(A_3)_p$, $A_4$, and C=O, where each dotted line in the ring depicts a single bond when $A_2$ is present (i.e., m=1) and a hydrogen atom when $A_2$ is absent (i.e., n=0); and Z and $Z^1$ are each independently H, F, an alkyl, cycloalkyl, heterocycloalkyl, aryl or heteroaryl group, where the alkyl, cycloalkyl, heterocycloalkyl, aryl or heteroaryl group is unsubstituted or substituted with one or more suitable substituents, —C(O)$R^l$, —CO$_2R^l$, —CN, —C(O)NR$^l$R$^m$, —C(O)NR$^l$OR$^m$, —C(S)R$^l$, —C(S)OR$^l$ —C(S)NR$^l$R$^m$, —C(=NR$^l$)R$^m$, —C(=NR$^l$)OR$^m$, —NO$_2$, —SOR$^m$, —SO$_2$R$^l$, —SO$_2$NR$^l$R$^m$, —SO$_2$(NR$^l$)(OR$^m$), —SONR$^l$, —SO$_3$R$^l$, —PO(OR$^l$)$_2$, —PO(OR$^l$)(OR$^m$), —PO(NR$^l$R$^m$)(OR$^n$), —PO(NR$^l$R$^m$)(NR$^n$R$^o$), —C(O)NR$^l$NR$^m$R$^n$, —C(S)NR$^l$NR$^m$R$^n$, where R$^l$, R$^m$, R$^n$ and R$^o$ are each independently H or an alkyl, cycloalkyl, aryl, heterocycloalkyl, acyl or thioacyl group, where the alkyl, cycloalkyl, aryl, heterocycloalkyl, acyl or thioacyl group is unsubstituted or substituted with one or more suitable substituents, or where any two of the R$^l$, R$^m$, R$^n$ and R$^o$, taken together with the atoms to which they are bonded, form a heterocycloalkyl group, which may be optionally substituted, or Z and R$^d$, together with the atoms to which they are bonded, form a cycloalkyl or heterocycloalkyl group, where Z and R$^d$ are as defined above except for moieties that cannot form the cycloalkyl or heterocycloalkyl group, or Z and $Z^1$, together with the atoms to which they are bonded, form a cycloalkyl or heterocycloalkyl group, where Z and $Z^1$ are as defined above (except for moieties that cannot form the cycloalkyl or heterocycloalkyl group);

or a prodrug, pharmaceutically acceptable salt, pharmaceutically active metabolite, or pharmaceutically acceptable solvate of said compound.

In another embodiment of the compounds of the above Formula I, $A_1$ is CH or N;

$A_2$ is $C(R^g)(R^h)$, $N(R^i)$, S, S(O), S(O)$_2$, or O, where each $R^g$, $R^h$ and $R^i$ is independently H or a lower alkyl group;

each $A_3$ present is independently $C(R^g)(R^h)$, $N(R^i)$, S, S(O), S(O)$_2$, or O, where each $R^g$, $R^h$ and $R^i$ is independently H or a lower alkyl group;

when p is 1, 2, 3, 4, or 5, $A_4$ is $N(R^j)$, $C(R^g)(R^h)$, or O, and when p is 0, $A_4$ is $N(R^j)(R^k)$, $C(R^g)(R^h)(R^i)$, and $O(R^k)$, where each $R^g$, $R^h$ and $R^i$ is independently H or a lower alkyl group, each $R^j$ is H, an alkyl, aryl, or acyl group, and each $R^k$ is H or an alkyl or aryl group;

provided that no more than two heteroatoms occur consecutively in the above-depicted ring formed by $A_1$, $(A_2)_m$, $(A_3)_p$, $A_4$, and C=O, where each dotted line in the ring depicts a single bond when $A_2$ is present and a hydrogen atom when $A_2$ is absent; and Z and $Z^1$ are each independently H, F, an alkyl, cycloalkyl, heterocycloalkyl, aryl or heteroaryl group, where the alkyl, cycloalkyl, heterocycloalkyl, aryl or heteroaryl group is unsubstituted or substituted with one or more suitable substituents, —C(O)R$^l$, —CO$_2$R$^l$, —CN, —C(O)NR$^l$R$^m$, —C(O)NR$^l$OR$^m$, —C(S)R$^l$, —C(S)NR$^l$R$^m$, —NO$_2$, —SOR$^m$, —SO$_2$R$^l$, —SO$_2$NR$^l$R$^m$, —SO$_2$(NR$^l$)(OR$^m$), —SONR$^l$, —SO$_3$R$^l$, —PO(OR$^l$)$_2$, —PO(OR$^l$)(OR$^m$), —PO(NR$^l$R$^m$)(OR$^n$), —PO(NR$^l$R$^m$)(NR$^n$R$^o$), —C(O)NR$^l$NR$^m$R$^n$, —C(S)NR$^l$NR$^m$R$^n$, where R$^l$, R$^m$, R$^n$ and R$^o$ are each independently H, an alkyl, cycloalkyl, aryl, heterocycloalkyl, acyl or thioacyl group, where the alkyl, cycloalkyl, aaryl, heterocycloalkyl, acyl or thioacyl group is unsubstituted or substituted with one or more suitable substituents, or where any two of the R$^l$, R$^m$, R$^n$ and R$^o$, taken together with the atoms to which they are bonded, form a heterocycloalkyl group, which is unsubstituted or substituted with one or more suitable substituents, or Z and $Z^1$, together with the atoms to which they are bonded, form a cycloalkyl or heterocycloalkyl group, where Z and $Z^1$ are as defined above.

One embodiment of this invention relates to compounds useful for inhibiting the activity of picornaviral 3C proteases having the following general Formula II:

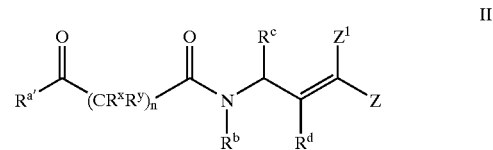

II wherein $R^{a'}$ is an alkyl, cycloalkyl, aryl or heteroaryl group, where the alkyl, cycloalkyl, aryl or heteroaryl group is unsubstituted or substituted with one or more suitable substituents, n is 1, 2 or 3, m is 1, $R^x$ and $R^y$ are each independently selected from H and an alkyl group, unsubstituted or substituted with one or more suitable substituents, and $R^b$, $R^c$, $R^d$, Z and $Z^1$ are as defined above, provided that $R^{a'}$ is not an amino-substituted alkyl group.

Another embodiment of this invention relates to compounds useful for inhibiting the activity of picornaviral 3C proteases having the following general Formula III:

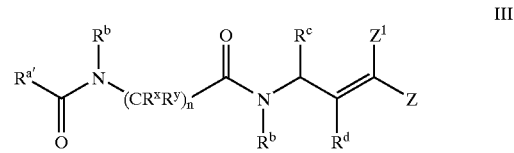

III wherein $R^{a'}$ is an alkyl, cycloalkyl, aryl or heteroaryl group, where the alkyl, cycloalkyl, aryl or heteroaryl group is unsubstituted or substituted with one or more suitable substituents, n is 1, 2 or 3, m is 1, $R^x$ and $R^y$ are each independently selected from H and an alkyl group, unsubstituted or substituted with one or more suitable substituents, and $R^b$, $R^c$, $R^d$, Z and $Z^1$ are as defined above, provided that $R^{a'}$ is not an amino-substituted alkyl group.

This invention also relates to compounds useful for inhibiting the activity of picornaviral 3C proteases having the following general Formula IV:

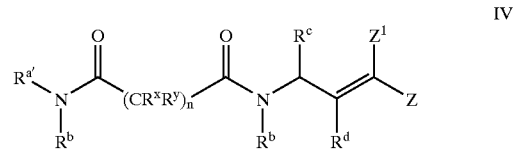

IV wherein $R^{a'}$ is an alkyl, aryl, cycloalkyl, heterocycloalkyl or heteroaryl group, where the alkyl, aryl, cycloalkyl, heterocycloalkyl and heteroaryl group is unsubstituted or substituted with one or more suitable substituents, n is 1, 2 or 3, $R^x$ and $R^y$ are each independently selected from H and an alkyl group, unsubstituted or substituted with one or more suitable substituents, and $R^b$, $R^c$, $R^d$, Z and $Z^1$ are as defined above.

This invention relates to compounds useful for inhibiting the activity of picornaviral 3C proteases having the general Formula V:

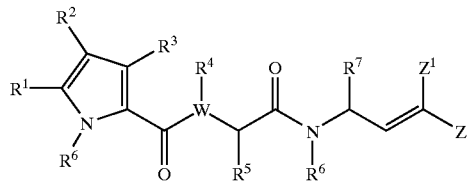

wherein:

W is CH or N;

$R^1$ is H, halo or an alkoxy, alkyl, aryl, cycloalkyl, heterocycloalkyl or heteroaryl group, where the alkoxy, alkyl, aryl, cycloalkyl, heterocycloalkyl and heteroaryl group is unsubstituted or substituted with one or more suitable substituents;

$R^2$ and $R^3$ are each independently H, halo or an alkoxy or lower alkyl group, where the alkoxy or lower alkyl group is unsubstituted or substituted with a suitable substituent;

or $R^1$ together with $R^2$ form a cycloalkyl, heterocycloalkyl, aryl or heteroaryl ring, where the cycloalkyl, heterocycloalkyl, aryl or heteroaryl ring is unsubstituted or substituted with a suitable substituent;

$R^4$ and $R^6$ are each independently H or a lower alkyl group, unsubstituted or substituted with a suitable substituent;

$R^5$ is H or an alkyl group, unsubstituted or substituted with a suitable substituent;

$R^7$ is a moiety having the formula:

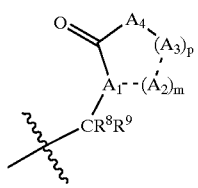

wherein:

$R^8$ and $R^9$ are each independently H or a lower alkyl group;

m is 0 or 1, provided that when W is N, m is 0 and $R^1$ together with $R^2$ form an aryl ring, the aryl ring is unsubstituted (e.g., $R^1$ together with $R^2$ and the pyrrole to which they are bound do not form a substituted indole);

p is an integer of from 0 to 5;

$A_1$ is CH or N;

when p is 1, 2, 3, 4, or 5, $A_2$ is $C(R^{10})(R^{11})$, $N(R^{12})$, S, S(O), S(O)$_2$, or O, and when p is 0, $A_2$ is $C(R^{10})(R^{11})(R^{12})$, $N(R^{10})(R^{12})$, $S(R^{10})$, $S(O)(R^{10})$, $S(O)_2(R^{10})$, or $O(R^{10})$ where each $R^{10}$, $R^{11}$ and $R^{12}$ is independently H or a lower alkyl group;

each $A_3$ present is independently $C(R^{10})(R^{11})$, $N(R^{12})$, S, S(O), S(O)$_2$, or O, where each $R^{10}$, $R^{11}$ and $R^{12}$ is independently H or a lower alkyl group;

when p is 1, 2, 3, 4, or 5, $A_4$ is $N(R^{13})$, $C(R^{10})(R^{11})$, or O, and when p is 0, $A_4$ is $N(R^{13})(R^{14})$, $C(R^{10})(R^{11})(R^{12})$, and $O(R^{14})$, where each $R^{10}$, $R^{11}$ and $R^{12}$ is independently H or a lower alkyl group, each $R^{13}$ is H or an alkyl, aryl, or acyl group, and each $R^{14}$ is H or an alkyl or aryl group;

provided that no more than two heteroatoms occur consecutively in the above-depicted ring formed by $A_1$, $(A_2)_m$, $(A_3)_p$, $A_4$, and C=O, where each dotted line in the ring depicts a single bond when $A_2$ is present and a hydrogen atom when $A_2$ is absent; and Z and $Z^1$ are each independently H, F, an alkyl, cycloalkyl, heterocycloalkyl, aryl or heteroaryl group, where the alkyl, cycloalkyl, heterocycloalkyl, aryl or heteroaryl group is unsubstituted or substituted with one or more suitable substituents, —C(O)$R^{15}$, —CO$_2R^{15}$, —CN, —C(O)NR$^{15}$R$^{16}$, —C(O)NR$^{15}$OR$^{16}$, —C(S)R$^{15}$, —C(S)OR$^{15}$, —C(S)NR$^{15}$R$^{16}$, —C(=NR$^{15}$)R$^{16}$, —C(=NR$^{15}$)OR$^{16}$, —NO$_2$, —SOR$^{16}$, —SO$_2R^{15}$, —SO$_2$NR$^{15}$R$^{16}$, —SO$_2$(NR$^{15}$)(OR$^{16}$), —SONR$^{15}$, —SO$_3R^{15}$, —PO(OR$^{15}$)$_2$, —PO(OR$^{15}$)(OR$^{16}$), —PO(NR$^{15}$R$^{16}$)(OR$^{17}$), —PO(NR$^{15}$R$^{16}$)(NR$^{17}$R$^{18}$), —C(O)NR$^{15}$NR$^{16}$R$^{17}$, —C(S)NR$^{15}$NR$^{16}$R$^{17}$, where $R^{15}$, $R^{16}$, $R^{17}$ and $R^{18}$ are each independently H or an alkyl, cycloalkyl, aryl, heterocycloalkyl, acyl or thioacyl group, where the alkyl, cycloalkyl, aryl, heterocycloalkyl, acyl or thioacyl group is unsubstituted or substituted with one or more suitable substituents, or where any two of the $R^{15}$, $R^{16}$, $R^{17}$ and $R^{18}$, taken together with the atoms to which they are bonded, form a heterocycloalkyl group, which is unsubstituted or substituted with one or more suitable substituents, or Z and $Z^1$, together with the atoms to which they are bonded, form a cycloalkyl or heterocycloalkyl group, where Z and $Z^1$ are as defined above (except for moieties that cannot form the cycloalkyl or heterocycloalkyl group).

In another embodiment of the compounds of Formula V, $A_1$ is CH or N;

$A_2$ is $C(R^{10})(R^{11})$, $N(R^{12})$, S, S(O), S(O)$_2$, or O, where each $R^{10}$, $R^{11}$ and $R^{12}$ is independently H or a lower alkyl group;

each $A_3$ present is independently $C(R^{10})(R^{11})$, $N(R^{12})$, S, S(O), S(O)$_2$, or O, where each $R^{10}$, $R^{11}$ and $R^{12}$ is independently H or a lower alkyl group;

when p is 1, 2, 3, 4, or 5, $A_4$ is $N(R^{13})$, $C(R^{10})(R^{11})$, or O, and when p is 0, $A_4$ is $N(R^{13})(R^{14})$, $C(R^{10})(R^{11})(R^{12})$, and $O(R^{14})$, where each $R^{10}$, $R^{11}$ and $R^{12}$ is independently H or a lower alkyl group, each $R^{13}$ is H or an alkyl, aryl, or acyl group, and each $R^{14}$ is H or an alkyl or aryl group;

provided that no more than two heteroatoms occur consecutively in the above-depicted ring formed by $A_1$, $(A_2)_m$, $(A_3)_p$, $A_4$, and C=O, where each dotted line in the ring depicts a single bond when $A_2$ is present and a hydrogen atom when $A_2$ is absent; and Z and $Z^1$ are each independently H, F, an alkyl, cycloalkyl, heterocycloalkyl, aryl or heteroaryl group, where the alkyl, cycloalkyl, heterocycloalkyl, aryl or heteroaryl group is unsubstituted or substituted with one or more suitable substituents, —C(O)R$^{15}$, —CO$_2R^{15}$, —CN, —C(O)NR$^{15}$R$^{16}$, —C(O)NR$^{15}$OR$^{16}$, —C(S)R$^{15}$, —C(S)NR$^{15}$R$^{16}$, —NO$_2$, —SOR$^{16}$, —SO$_2R^{15}$, —SO$_2$NR$^{15}$R$^{16}$, —SO$_2$(NR$^{15}$)(OR$^{16}$), —SONR$^{15}$, —SO$_3R^{15}$, —PO(OR$^{15}$)$_2$, —PO(OR$^{15}$)(OR$^{16}$), —PO(NR$^{15}$R$^{16}$)(OR$^{17}$), —PO(NR$^{15}$R$^{16}$)(NR$^{17}$R$^{18}$), —C(O)NR$^{15}$NR$^{16}$R$^{17}$, —C(S)NR$^{15}$NR$^{16}$R$^{17}$, where $R^{15}$, $R^{16}$, $R^{17}$ and $R^{18}$ are each independently H or an alkyl, cycloalkyl, aryl, heterocycloalkyl, acyl or thioacyl group, where the alkyl, cycloalkyl, aryl, heterocycloalkyl, acyl or thioacyl group is unsubstituted or substituted with one or more suitable substituents, or where any two of the $R^{15}$, $R^{16}$, $R^{17}$ and $R^{18}$, taken together with the atoms to which they are bonded, form a heterocycloalkyl group, which is unsubstituted or substituted with one or more suitable substituents, or Z and $Z^1$, together with the atoms to which they are bonded, form a cycloalkyl or heterocycloalkyl group, where Z and $Z^1$ are as defined above.

In the compounds of the above-described Formulas I–V, $R^c$ and $R^7$ are defined to provide structures where m is 1 and p is 1–5 (i.e., both $A_2$ and $A_3$ are present), m is 0 and p is 0 (i.e, both $A_2$ and $A_3$ are absent), m is 0 and p is 1–5 (i.e, $A_2$ is absent and $A_3$ is present) and m is 1 and p is 0 (i.e, $A_2$ is present and $A_3$ is absent). Accordingly, one of ordinary skill in the are will recognize that when both $A_2$ and $A_3$ are present (m is 1 and p is 1–5), the dotted line between $A_1$ and $A_2$ represents a bond and the dotted line between $A_2$ and $A_3$ represents a bond. Wwhen both $A_2$ and $A_3$ are absent (m is 0 and p is 0) $A_2$, $A_3$ and the dotted line between these substituents are not present and the remaining dotted line in the structure between $A_1$ and $A_2$ represents a hydrogen (e.g., $A_1$ is $CH_2$ or NH). In embodiments of this invention when $A_2$ is absent and $A_3$ is present (m is 0 and p is 1–5), the dotted line between $A_1$ and $A_2$ represents a hydrogen and the dotted line between $A_2$ and $A_3$ represents a hydrogen (e.g., $A_1$ is $CH_2$ or NH and $A_3$ is $CH(R^g)(R^h)$, $NH(R^i)$, SH, S(O)H, $S(O)_2H$, or OH or $CH(R^{10})(R^{11})$, $NH(R^{12})$, SH, S(O)H, $S(O)_2H$, or OH); and when $A_2$ is present and $A_3$ is absent (m is 1 and p is 0), the dotted line between $A_1$ and $A_2$ represents a bond and $A_2$ is $C(R^g)(R^h)(R^i)$, $N(R^g)(R^i)$, $S(R^g)$, $S(O)(R^g)$, $S(O)_2(R^g)$, or $O(R^g)$ or $A_2$ is $C(R^{10})(R^{11})(R^{12})$, $N(R^{10})(R^{12})$, $S(R^{10})$, $S(O)(R^{10})$, $S(O)_2(R^{10})$, or $O(R^{10})$ or the dotted line between $A_2$ and $A_3$ represents a hydrogen and $A_2$ is $CH(R^g)$ $(R^h)$, $NH(R^i)$, SH, S(O)H, $S(O)_2H$, or OH or $A_2$ is $CH(R^{10})$ $(R^{11})$, $NH(R^{12})$, SH, S(O)H, $S(O)_2H$, or OH. In preferred embodiments of the compounds of Formula I–V of this invention, m is 1 and p is 1 or 2 or m is 0 and p is 0 or m is 1 and p is 0. More preferably, when m is 1 and p is 1 or 2, $A_2$ and $A_3$ are both $C(R^g)(R^h)$ or $C(R^{10})(R^{11})$, respectively. More preferably, m is 1 and p is 1.

In addition to compounds of the Formulas I–V, antipicornaviral agents of the invention include prodrugs, pharmaceutically active metabolites, and pharmaceutically acceptable salts and solvates of such compounds.

DETAILED DESCRIPTION OF INVENTION

In accordance with a convention used in the art,

is used in structural formulas herein to depict the bond that is the point of attachment of the moiety or substituent to the core or backbone structure.

As used herein, the term "alkyl" represents a straight- or branched-chain saturated or unsaturated hydrocarbon, containing 1 to 10 carbon atoms which may be unsubstituted or substituted by one or more of the substituents described below. A $C_1$–$C_6$ alkyl represents an alkyl substituent containing 1 to 6 carbon atoms. Exemplary alkyl substituents include, but are not limited to methyl (Me), ethyl (Et), propyl, isopropyl, butyl, isobutyl, t-butyl, ethenyl, propenyl, butenyl, pentenyl, ethynyl, butynyl, propynyl (propargyl, isopropynyl), pentynyl, hexynyl and the like. The term "lower alkyl" refers to an alkyl group containing from 1 to 4 carbon atoms.

"Cycloalkyl" represents a group comprising a non-aromatic monocyclic, bicyclic, or tricyclic hydrocarbon containing from 3 to 14 carbon atoms which may be unsubstituted or substituted by one or more of the substituents described below and may be saturated or unsaturated. Exemplary cycloalkyls include monocyclic rings having from 3–7, preferably 3–6, carbon atoms, such as cyclopropyl, cyclobutyl, cyclopentyl, cyclohexyl, cycloheptyl and the like, that may be fully saturated or partially unsaturated. Illustrative examples of cycloalkyl groups include the following:

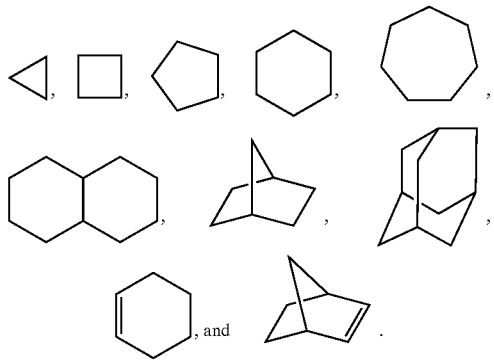

"Heterocycloalkyl" represents a group comprising a non-aromatic, monovalent monocyclic, bicyclic, or tricyclic radical, which is saturated or partially unsaturated, containing 3 to 18 ring atoms, which includes 1 to 5 heteroatoms selected from nitrogen, oxygen and sulfur, and which may be unsubstituted or substituted by one or more of the substituents described below. Illustrative examples of heterocycloalkyl groups include, but are not limited to, azetidinyl, pyrrolidyl, piperidyl, piperazinyl, morpholinyl, tetrahydro-2H-1,4-thiazinyl, tetrahydrofuryl, dihydrofuryl, tetrahydropyranyl, dihydropyranyl, 1,3-dioxolanyl, 1,3-dioxanyl, 1,4-dioxanyl, 1,3-oxathiolanyl, 1,3-oxathianyl, 1,3-dithianyl, azabicyclo[3.2.1]octyl, azabicyclo[3.3.1] nonyl, azabicyclo[4.3.0]nonyl, oxabicyclo[2.2.1]heptyl, 1,5,9-triazacyclododecyl, and the like. Illustrative examples of heterocycloalkyl groups include the following moieties:

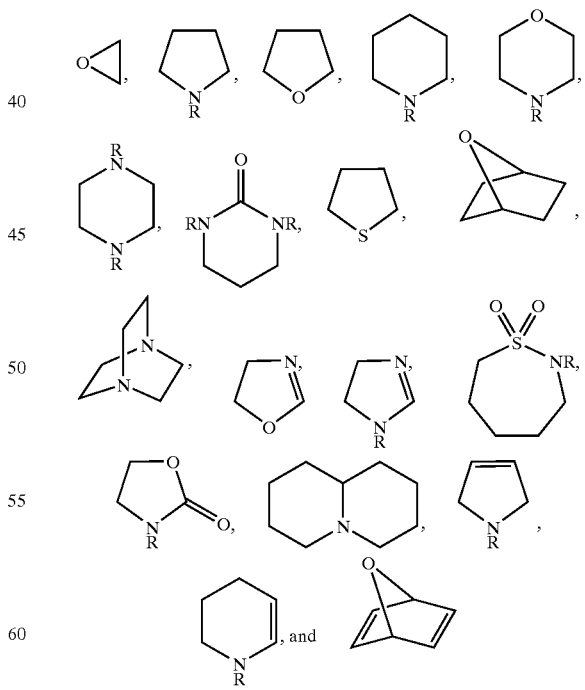

wherein R is H, alkyl or hydroxyl.

"Aryl" represents a group comprising an aromatic, monovalent monocyclic, bicyclic, or tricyclic radical containing from 6 to 18 carbon ring atoms, which may be unsubstituted or substituted by one or more of the substituents described below, and to which may be fused one or more cycloalkyl groups, heterocycloalkyl groups or heteroaryl groups, which themselves may be unsubstituted or substituted by one or more suitable substituents. Illustrative examples of aryl groups include the following moieties:

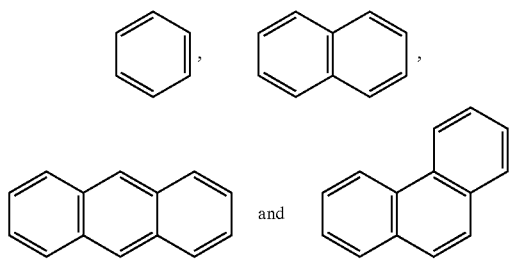

"Heteroaryl" represents a group comprising an aromatic monovalent monocyclic, bicyclic, or tricyclic radical, containing 5 to 18 ring atoms, including 1 to 5 heteroatoms selected from nitrogen, oxygen and sulfur, which may be unsubstituted or substituted by one or more of the substituents described below. As used herein, the term "heteroaryl" is also intended to encompass the N-oxide derivative (or N-oxide derivatives, if the heteroaryl group contains more than one nitrogen such that more than one N-oxide derivative may be formed) of the nitrogen-containing heteroaryl groups described herein. Illustrative examples of heteroaryl groups include, but are not limited to, thienyl, pyrrolyl, imidazolyl, pyrazolyl, furyl, isothiazolyl, furazanyl, isoxazolyl, thiazolyl, pyridyl, pyrazinyl, pyrimidinyl, pyridazinyl, triazinyl, benzo[b]thienyl, naphtho[2,3-b]thianthrenyl, isobenzofuranyl, chromenyl, xanthenyl, phenoxathienyl, indolizinyl, isoindolyl, indolyl, indazolyl, purinyl, isoquinolyl, quinolyl, phthalazinyl, naphthyridinyl, quinoxyalinyl, quinzolinyl, benzothiazolyl, benzimidazolyl, tetrahydroquinolinyl, cinnolinyl, pteridinyl, carbazolyl, beta-carbolinyl, phenanthridinyl, acridinyl, perimidinyl, phenanthrolinyl, phenazinyl, isothiazolyl, phenothiazinyl, and phenoxazinyl. Illustrative examples of N-oxide derivatives of heteroaryl groups include, but are not limited to, pyridyl N-oxide, pyrazinyl N-oxide, pyrimidinyl N-oxide, pyridazinyl N-oxide, triazinyl N-oxide, isoquinolyl N-oxide, and quinolyl N-oxide. Further examples of heteroaryl groups include the following moieties:

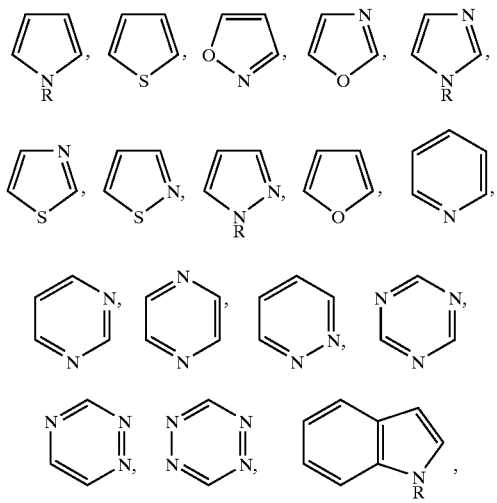

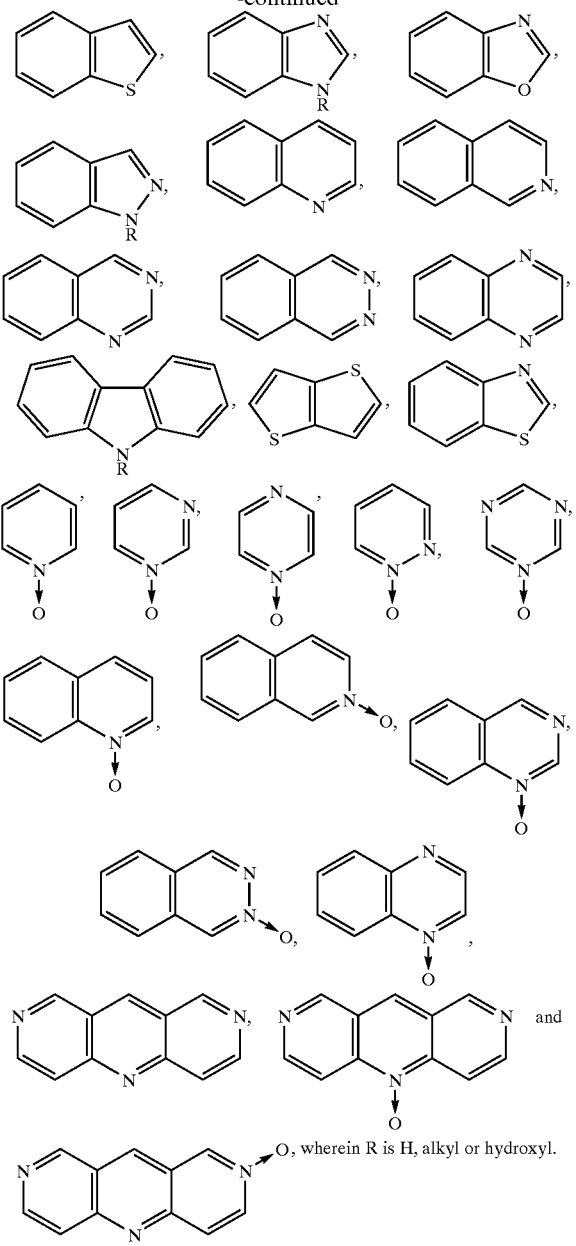

The term "suitable substituent" represents a substituent that is optionally present on any of the above alkyl, aryl, cycloalkyl, heterocycloalkyl or heteroaryl groups, described herein, and is selected from alkyl (except for alkyl) haloalkyl, haloaryl, halocycloalkyl, haloheterocycloalkyl, aryl, cycloalkyl, heterocycloalkyl, heteroaryl, nitro, amino, hydroxamino, cyano, halo, hydroxyl, alkoxy, alkylenedioxy, aryloxy, cycloalkoxy, heterocycloalkoxy, heteroaryloxy, alkylcarbonyl, alkyloxycarbonyl, alkylcarbonyloxy, arylcarbonyl, arylcarbonyloxy, aryloxycarbonyl, cycloalkylcarbonyl, cycloalkylcarbonyloxy, cycloalkyoxycarbonyl, heteroarylcarbonyl, heteroarylcarbonyloxy, heteroaryloxycarbonyl, heterocycloalkylcarbonyl, heterocycloalkylcarbonyloxy, heterocycloalkyoxycarbonyl, carboxyl, carbamoyl, formyl, keto (oxo), thioketo, sulfo, alkylamino, cycloalkylamino, arylamino, heterocycloalkylamino, heteroarylamino, dialkylamino, alkylaminocarbonyl, cycloalkylaminocarbonyl, arylaminocarbonyl, heterocycloalkylaminocarbonyl, heteroarylaminocarbonyl, dialkylaminocarbonyl, alkylaminothiocarbonyl, cycloalkylaminothiocarbonyl, arylaminothiocarbonyl, heterocycloalkylaminothiocarbonyl, heteroarylaminothiocarbonyl, dialkylaminothiocarbonyl, alkylsulfonyl, arylsulfonyl, alkylsulfenyl, arylsulfenyl, alkylcarbonylamino, cycloalkylcarbonylamino, arylcarbonylamino, heterocycloalkylcarbonylamino, heteroarylcarbonylamino, alkylthiocarbonylamino, cycloalkylthiocarbonylamino, arylthiocarbonylamino, heterocycloalkylthiocarbonylamino, heteroarylthiocarbonylamino, alkylsulfonyloxy, arylsulfonyloxy, alkylsulfonylamino, arylsulfonylamino, mercapto, alkylthio, arylthio, and heteroarylthio groups, where any of the alkyl, alkylene, aryl, cycloalkyl, heterocycloalkyl, heteroaryl moieties present in the above substituents may be further substituted with one or more substituents selected from nitro, amino, cyano, halo, haloalkyl, haloaryl, hydroxyl, keto, hydroxamino, alkylamino, dialkylamino, mercapto, and unsubstituted alkyl, aryl, cycloalkyl, heterocycloalkyl, heteroaryl, alkoxy, aryloxy, alkylthio or arylthio groups and where any of the aryl or heteroaryl moieties may be substituted with alkylenedioxy. Preferred "suitable substituents" include alkyl, aryl, cycloalkyl, heterocycloalkyl, heteroaryl, halo, hydroxyl, alkoxy, alkylenedioxy, aryloxy, cycloalkoxy, heteroaryloxy, and carboxyl. The alkyl, alkylene, cycloalkyl, heterocycloalkyl, aryl, and heteroaryl moieties of any of the above substituents may be optionally substituted by one or more of alkyl (except for alkyl), halo, haloalkyl, aryl or heteroaryl, where the aryl or heteroaryl is unsubstituted or substituted with one or more subsituents, (e.g., haloaryl), independently selected from alkyl, haloalkyl, alkylenedioxy, nitro, amino, hydroxamino, alkylamino, dialkylamino, halo, hydroxyl, alkoxy, haloalkoxy, aryloxy, mercapto, alkylthio or arylthio groups.

The terms "halogen" and "halo" represent chloro, fluoro, bromo or iodo substituents. "Heterocycle" is intended to mean a heteroaryl or heterocycloalkyl group. "Acyl" is intended to mean a —C(O)—R radical, wherein R is an alkyl, cycloalkyl, aryl, heterocycloalkyl or heteroaryl group. "Acyloxy" is intended to mean an —OC(O)—R radical, wherein R is an alkyl, cycloalkyl, aryl, heterocycloalkyl or heteroaryl group. "Thioacyl" is intended to mean a —C(S)—R radical, wherein R is an alkyl, cycloalkyl, aryl, heterocycloalkyl or heteroaryl group. "Sulfonyl" is intended to mean an —SO$_2$— biradical. "Sulfenyl" is intended to mean an —SO— biradical. "Sulfo" is intended to mean an —SO$_2$H radical. Sulfoxide is intended to mean a —SO$_3^-$ radical "Hydroxy" is intended to mean the radical —OH. "Amine" or "amino" is intended to mean the radical —NH$_2$. "Alkylamino" is intended to mean the radical —NHR$_a$, wherein R$_a$ is an alkyl group. "Dialkylamino" is intended to mean the radical —NR$_a$R$_b$, wherein R$_a$ and R$_b$ are each independently an alkyl group, and is intended to include heterocycloalkyl groups, wherein R$_a$ and R$_b$, taken together, form a heterocyclic ring that includes the amine nitrogen. "Hydroxamino" is intended to mean the radical —N—OH. "Alkoxy" is intended to mean the radical —OR$_a$, wherein R$_a$ is an alkyl group. Exemplary alkoxy groups include methoxy, ethoxy, propoxy, and the like. "Lower alkoxy" groups have alkyl moieties having from 1 to 4 carbons. "Alkylenedioxy" is intended to mean the divalent radical —OR$_a$O— which is bonded to adjacent atoms on an aryl or heteroaryl moiety (e.g., adjacent atoms on a phenyl or naphthyl ring), wherein R$_a$ is a lower alkyl group. "Alkoxycarbonyl" is intended to mean the radical —C(O)OR$_a$, wherein R$_a$ is an alkyl group. "Alkylsulfonyl" is intended to mean the radical —SO$_2$R$_a$, wherein R$_a$ is an alkyl group. "Alkylaminocarbonyl" is intended to mean the radical —C(O)NHR$_a$, wherein R$_a$ is an alkyl group. "Dialkylaminocarbonyl" is intended to mean the radical —C(O)NR$_a$R$_b$, wherein R$_a$ and R$_b$ are each independently an alkyl group. "Mercapto" is intended to mean the radical —SH. "Alkylthio" is intended to mean the radical —SR$_a$, wherein R$_a$ is an alkyl group. "Carboxyl" is intended to mean the radical —C(O)OH. "Keto" or "oxo" is intended to mean the radical =O. "Thioketo" is intended to mean the radical =S. "Carbamoyl" is intended to mean the radical —C(O)NH$_2$. "Cycloalkylalkyl" is intended to mean the radical -alkylcycloalkyl, wherein alkyl and cycloalkyl are defined as above, and is exemplified by the bonding arrangement present in the groups —CH$_2$-cyclohexane or —CH$_2$-cyclohexene. "Arylalkyl" is intended to mean the radical-alkylaryl, wherein alkyl and aryl are defined as above, and is exemplified by the bonding arrangement present in a benzyl group. "Aminocarbonylalkyl" is intended to mean the radical-alkylC(O) NH$_2$ and is exemplified by the bonding arrangement present in the group —CH$_2$CH$_2$C(O)NH$_2$. "Alkylaminocarbonylalkyl" is intended to mean the radical-alkylC(O)NHR$_a$, wherein R$_a$ is an alkyl group and is exemplified by the bonding arrangement present in the group —CH$_2$CH$_2$C(O)NHCH$_3$. "Alkylcarbonylaminoalkyl is intended to mean the radical-alkylNHC(O)-alkyl and is exemplified by the bonding arrangement present in the group —CH$_2$NHC(O)CH$_3$. "Dialkylaminocarbonylalkyl" is intended to mean the radical-alkylC(O)NR$_a$R$_b$, wherein R$_a$ and R$_b$ are each independently an alkyl group. "Aryloxy" is intended to mean the radical —OR$_c$, wherein R$_c$ is an aryl group. "Heteroaryloxy" is intended to mean the radical —OR$_d$, wherein R$^d$ is a heteroaryl group. "Arylthio" is intended to mean the radical —SR$_c$, wherein R$_c$ is an aryl group. "Heteroarylthio" is intended to mean the radical —SR$_d$, wherein R$_d$ is a heteroaryl group.

The alkyl, cycloalkyl, aryl, heterocycloalkyl and heteroaryl groups and the substituents containing these groups, as defined hereinabove, may be optionally substituted by at least one other substituent. The term "optionally substituted" is intended to expressly indicate that the specified group is unsubstituted or substituted by one or more suitable substituents. Various groups may be unsubstituted or substituted (i.e., they are optionally substituted) as indicated.

If the substituents themselves are not compatible with the synthetic methods of this invention, the substituent may be protected with a suitable protecting group that is stable to the reaction conditions used in these methods. The protecting group may be removed at a suitable point in the reaction sequence of the method to provide a desired intermediate or target compound. Suitable protecting groups and the methods for protecting and de-protecting different substituents using such suitable protecting groups are well known to those skilled in the art; examples of which may be found in T. Greene and P. Wuts, Protecting Groups in Chemical Synthesis (3rd ed.), John Wiley & Sons, NY (1999), which is incorporated herein by reference in its entirety. In some instances, a substituent may be specifically selected to be reactive under the reaction conditions used in the methods of this invention. Under these circumstances, the reaction conditions convert the selected substituent into another substituent that is either useful in an intermediate compound in the methods of this invention or is a desired substituent in a target compound.

Particular embodiments of this invention comprise the compounds of Formulas II and III, wherein n is 2 or 1, respectively, depicted by the formula:

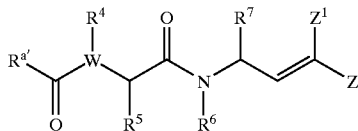

VI wherein:

W is CH or N;

$R^{a'}$ is an alkyl, cycloalkyl, aryl or heteroaryl group, where the alkyl, cycloalkyl, aryl, and heteroaryl group is unsubstituted or substituted with one or more suitable substituents, provided that $R^{a'}$ is not an amino-substituted alkyl group;

$R^4$ and $R^6$ are each independently H or a lower alkyl group;

$R^5$ is H or an alkyl group;

$R^7$ is a substituent having the formula:

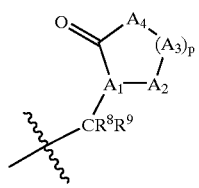

wherein:

$R^8$ and $R^9$ are each independently H or lower alkyl;

p is an integer of from 1 to 5;

$A_1$ is CH or N;

when p is 1, 2, 3, 4, or 5, $A_2$ is $C(R^{10})(R^{11})$, $N(R^{12})$, S, S(O), $S(O)_2$, or O, and when p is 0, $A_2$ is $C(R^{10})(R^{11})(R^{12})$, $N(R^{10})(R^{12})$, $S(R^{10})$, $S(O)(R^{10})$, $S(O)_2(R^{10})$, or $O(R^{10})$ where each $R^{10}$, $R^{11}$ and $R^{12}$ is independently H or a lower alkyl group;

each $A_3$ present is independently $C(R^{10})(R^{11})$, $N(R^{12})$, S, S(O), $S(O)_2$, or O, where each $R^{10}$, $R^{11}$ and $R^{12}$ is independently H or a lower alkyl group;

when p is 1, 2, 3, 4, or 5, $A_4$ is $N(R^{13})$, $C(R^{10})(R^{11})$, or O, and when p is 0, $A_4$ is $N(R^{13})(R^{14})$, $C(R^{10})(R^{11})(R^{12})$, and $O(R^{14})$, where each $R^{10}$, $R^{11}$ and $R^{12}$ is independently H or a lower alkyl group, each $R^{13}$ is H or an alkyl, aryl, or acyl group, and each $R^{14}$ is H or an alkyl or aryl group;

provided that no more than two heteroatoms occur consecutively in the above-depicted ring formed by $A_1$, $(A_2)_m$, $(A_3)_p$, $A_4$, and C=O, where each dotted line in the ring depicts a single bond when $A_2$ is present and a hydrogen atom when $A_2$ is absent; and Z and $Z^1$ are each independently H, F, an alkyl, cycloalkyl, heterocycloalkyl, aryl or heteroaryl group, where the alkyl, cycloalkyl, heterocycloalkyl, aryl or heteroaryl group is unsubstituted or substituted with one or more suitable substituents, —C(O)$R^{15}$, —CO$_2R^{15}$, —CN, —C(O)NR$^{15}R^{16}$, —C(O)NR$^{15}$OR$^{16}$, —C(S)R$^{15}$, —C(S)OR$^5$, —C(S)NR$^{15}R^{16}$, —C(=NR$^{15}$)R$^{16}$, —C(=NR$^{15}$)OR$^{16}$, —NO$_2$, —SOR$^{16}$, —SO$_2R^{15}$, —SO$_2$NR$^{15}R^{16}$, —SO$_2$(NR$^{15}$)(OR$^{16}$), —SONR$^{15}$, —SO$_3R^{15}$, —PO(OR$^{15}$)$_2$, —PO(OR$^{15}$)(OR$^{16}$), —PO(NR$^{15}R^{16}$)(OR$^{17}$), —PO(NR$^{15}R^{16}$)(NR$^{17}R^{18}$), —C(O)NR$^{15}$NR$^{16}R^{17}$, —C(S)NR$^{15}$NR$^{16}R^{17}$, where $R^{15}$, $R^{16}$, $R^{17}$ and $R^{18}$ are each independently H or an alkyl, cycloalkyl, aryl, heterocycloalkyl, acyl or thioacyl group, where the alkyl, cycloalkyl, aryl, heterocycloalkyl, acyl or thioacyl group is unsubstituted or substituted with one or more suitable substituents, or where any two of the $R^{15}$, $R^{16}$, $R^{17}$ and $R^{18}$, taken together with the atoms to which they are bonded, form a heterocycloalkyl group, which is unsubstituted or substituted with one or more suitable substituents, or Z and $Z^1$, together with the atoms to which they are bonded, form a cycloalkyl or heterocycloalkyl group, where Z and $Z^1$ are as defined above (except for moieties that cannot form the cycloalkyl or heterocycloalkyl group);

or a prodrug, pharmaceutically acceptable salt, pharmaceutically active metabolite, or pharmaceutically acceptable solvate thereof of said compound.

More specifically, preferred embodiments of Formula VI of this invention comprise the compounds depicted by the formula:

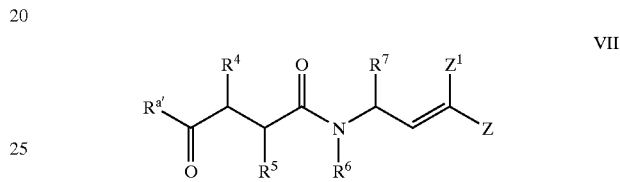

VII wherein $R^{a'}$, $R^4$, $R^5$, $R^6$, $R^7$, Z and $Z^1$ are as defined above; and the compounds depicted by the formula:

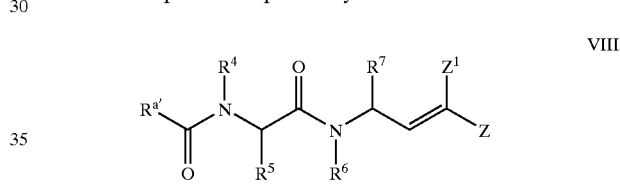

VIII wherein $R^{a'}$, $R^4$, $R^5$, $R^6$, $R^7$, Z and $Z^1$ are as defined above.

In particular, this invention comprises the compounds depicted by the formula:

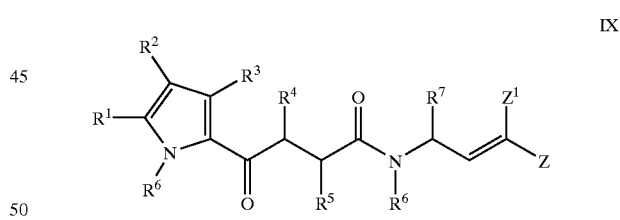

IX wherein:

$R^1$ is H, halo or an alkoxy, alkyl, aryl, cycloalkyl, heterocycloalkyl or heteroaryl group, where the alkoxy, alkyl, aryl, cycloalkyl, heterocycloalkyl, or heteroaryl group is unsubstituted or substituted with one or more suitable substituents;

$R^2$ and $R^3$ are each independently H, halo or an alkoxy or lower alkyl group, where the alkoxy or lower alkyl group is unsubstituted or substituted with one or more suitable substituents;

or $R^1$ together with $R^2$ form a cycloalkyl, heterocycloalkyl, aryl or heteroaryl ring, where the cycloalkyl, heterocycloalkyl, aryl or heteroaryl ring is unsubstituted or substituted with one or more suitable substituents;

$R^4$ and $R^6$ are each independently H or a lower alkyl group, unsubstituted or substituted with one or more suitable substituents;

$R^5$ is H or an alkyl group, unsubstituted or substituted with one or more suitable substituents;

$R^7$ is a moiety having the formula:

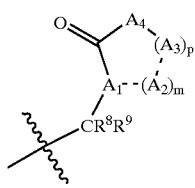

wherein:

$R^8$ and $R^9$ are each each independently H or a lower alkyl group;

m is 0 or 1;

p is an integer of from 0 to 5;

$A_1$ is CH or N;

when p is 1, 2, 3, 4, or 5, $A_2$ is $C(R^{10})(R^{11})$, $N(R^{12})$, S, S(O), S(O)$_2$, or O, and when p is 0, $A_2$ is $C(R^{10})(R^{11})(R^{12})$, $N(R^{10})(R^{12})$, $S(R^{10})$, $S(O)(R^{10})$, $S(O)_2(R^{10})$, or $O(R^{10})$ where each $R^{10}$, $R^{11}$ and $R^{12}$ is independently H or a lower alkyl group;

each $A_3$ present is independently $C(R^{10})(R^{11})$, $N(R^{12})$, S, S(O), S(O)$_2$, or O, where each $R^{10}$, $R^{11}$ and $R^{12}$ is independently H or a lower alkyl group;

when p is 1, 2, 3, 4, or 5, $A_4$ is $N(R^{13})$, $C(R^{10})(R^{11})$, or O, and when p is 0, $A_4$ is $N(R^{13})(R^{14})$, $C(R^{10})(R^{11})(R^{12})$, and $O(R^{14})$, where each $R^{10}$, $R^{11}$ and $R^{12}$ is independently H or a lower alkyl group, each $R^{13}$ is H or an alkyl, aryl, or acyl group, and each $R^{14}$ is H or an alkyl or aryl group;

provided that no more than two heteroatoms occur consecutively in the above-depicted ring formed by $A_1$, $(A_2)_m$, $(A_3)_p$, $A_4$, and C=O, where each dotted line in the ring depicts a single bond when $A_2$ is present and a hydrogen atom when $A_2$ is absent; and Z and $Z^1$ are each independently H, F, an alkyl, cycloalkyl, heterocycloalkyl, aryl or heteroaryl group, where the alkyl, cycloalkyl, heterocycloalkyl, aryl or heteroaryl group is unsubstituted or substituted with one or more suitable substituents, —C(O)R$^{15}$, —CO$_2$R$^{15}$, —CN, —C(O)NR$^{15}$R$^{16}$, —C(O)NR$^{15}$OR$^{16}$, —C(S)R$^{15}$, —C(S)OR$^{15}$, —C(S)NR$^{15}$R$^{16}$, —C(=NR$^{15}$)R$^{16}$, —C(=NR$^{15}$)OR$^{16}$, —NO$_2$, —SOR$^{16}$, —SO$_2$R$^{15}$, —SO$_2$NR$^{15}$R$^{16}$, —SO$_2$(NR$^{15}$)(OR$^{16}$), —SONR$^{15}$, —SO$_3$R$^{15}$, —PO(OR$^{15}$)$_2$, —PO(OR$^{15}$)(OR$^{16}$), —PO(NR$^{15}$R$^{16}$)(OR$^{17}$), —PO(NR$^{15}$R$^{16}$)(NR$^{17}$R$^{18}$, —C(O)NR$^{15}$NR$^{16}$R$^{17}$, —C(S)NR$^{15}$NR$^{16}$R$^{17}$, where R$^{15}$, R$^{16}$, R$^{17}$ and R$^{18}$ are each independently H or an alkyl, cycloalkyl, aryl, heterocycloalkyl, acyl or thioacyl group, where the alkyl, cycloalkyl, aryl, heterocycloalkyl, acyl or thioacyl group is unsubstituted or substituted with one or more suitable substituents, or where any two of the R$^{15}$, R$^{16}$, R$^{17}$ and R$^{18}$, taken together with the atoms to which they are bonded, form a heterocycloalkyl group, which is unsubstituted or substituted with one or more suitable substituents, or Z and $Z^1$, together with the atoms to which they are bonded, form a cycloalkyl or heterocycloalkyl group, where Z and $Z^1$ are as defined above (except for moieties that cannot form the cycloalkyl or heterocycloalkyl group);

or a prodrug, pharmaceutically acceptable salt, pharmaceutically active metabolite, or pharmaceutically acceptable solvate of said compound.

Another embodiment of this invention comprises the compounds depicted by the formula:

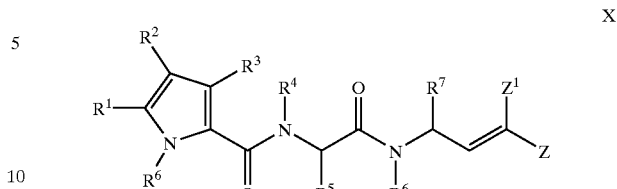

wherein:

$R^1$ is H, halo or an alkoxy, alkyl, aryl, cycloalkyl, heterocycloalkyl, or heteroaryl group, where the alkoxy, alkyl, aryl, cycloalkyl, heterocycloalkyl, or heteroaryl group is unsubstituted or substituted with one or more suitable substituents;

$R^2$ and $R^3$ are each independently H, halo or an alkoxy or lower alkyl group, where the alkoxy or lower alkyl group is unsubstituted or substituted with one or more suitable substituents;

or $R^1$ together with $R^2$ form a cycloalkyl, heterocycloalkyl, aryl or heteroaryl ring, where the cycloalkyl, heterocycloalkyl, aryl or heteroaryl ring is unsubstituted or substituted with one or more suitable substituents;

$R^4$ and $R^6$ are each independently H or lower alkyl, unsubstituted or substituted with one or more suitable substituents;

$R^5$ is H or an alkyl group, unsubstituted or substituted with one or more suitable substituents;

$R^7$ is a moiety having the formula:

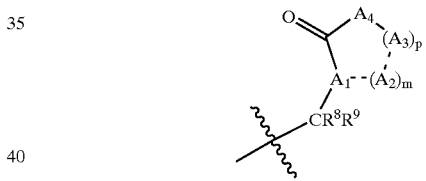

wherein:

$R^8$ and $R^9$ are each independently H or a lower alkyl group;

m is 0 or 1, provided that when m is 0 and $R^1$ together with $R^2$ form an aryl ring, the aryl ring is unsubstituted (e.g., $R^1$ together with $R^2$ and the pyrrole to which they are bound do not form a substituted indole);

p is an integer of from 0 to 5;

$A_1$ is CH or N;

when p is 1, 2, 3, 4, or 5, $A_2$ is $C(R^{10})(R^{11})$, $N(R^{12})$, S, S(O), S(O)$_2$, or O, and when p is 0, $A_2$ is $C(R^{10})(R^{11})(R^{12})$, $N(R^{10})(R^{12})$, $S(R^{10})$, $S(O)(R^{10})$, $S(O)_2(R^{10})$, or $O(R^{10})$ where each $R^{10}$, $R^{11}$ and $R^{12}$ is independently H or a lower alkyl group;

each $A_3$ present is independently $C(R^{10})(R^{11})$, $N(R^{12})$, S, S(O), S(O)$_2$, or O, where each $R^{10}$, $R^{11}$ and $R^{12}$ is independently H or a lower alkyl group;

when p is 1, 2, 3, 4, or 5, $A_4$ is $N(R^{13})$, $C(R^{10})(R^{11})$, or O, and when p is 0, $A_4$ is $N(R^{13})(R^{14})$, $C(R^{10})(R^{11})(R^{12})$, and $O(R^{14})$, where each $R^{10}$, $R^{11}$ and $R^{12}$ is independently H or a lower alkyl group, each $R^{13}$ is H or an alkyl, aryl, or acyl group, and each $R^{14}$ is H or an alkyl or aryl group;

provided that no more than two heteroatoms occur consecutively in the above-depicted ring formed by $A_1$, $(A_2)_m$, $(A_3)_p$, $A_4$, and C=O, where each dotted line in the ring depicts a single bond when $A_2$ is present and a hydrogen atom when $A_2$ is absent; and Z and $Z^1$ are each independently H, F, an alkyl, cycloalkyl, heterocycloalkyl, aryl or heteroaryl group, where the alkyl, cycloalkyl, heterocycloalkyl, aryl or heteroaryl group is unsubstituted or substituted with one or more suitable substituents, —C(O)R$^{15}$, —CO$_2$R$^{15}$, —CN, —C(O)NR$^{15}$R$^{16}$, —C(O)NR$^{15}$OR$^{16}$, —C(S)R$^{15}$, —C(S)OR$^{15}$, —C(S)NR$^{15}$R$^{16}$, —C(=NR$^{15}$)R$^{16}$, —C(=NR$^{15}$)OR$^{16}$, —NO$_2$, —SOR$^{16}$, —SO$_2$R$^{15}$, —SO$_2$NR$^{15}$R$^{16}$, —SO$_2$(NR$^{15}$)(OR$^{16}$), —SONR$^{15}$, —SO$_3$R$^{15}$, —PO(OR$^{15}$)$_2$, —PO(OR$^{15}$)(OR$^{16}$), —PO(NR$^{15}$R$^{16}$)(OR$^{17}$), —PO(NR$^{15}$R$^{16}$)(NR$^{17}$R$^{18}$), —C(O)NR$^{15}$NR$^{16}$R$^{17}$, —C(S)NR$^{15}$NR$^{16}$R$^{17}$, where R$^{15}$, R$^{16}$, R$^{17}$ and R$^{18}$ are each independently H or an alkyl, cycloalkyl, aryl, heterocycloalkyl, acyl or thioacyl group, where the alkyl, cycloalkyl, aryl, heterocycloalkyl, acyl or thioacyl group is unsubstituted or substituted with one or more suitable substituents, or where any two of the R$^{15}$, R$^{16}$, R$^{17}$ and R$^{18}$, taken together with the atoms to which they are bonded, form a heterocycloalkyl group, which is unsubstituted or substituted with one or more suitable substituents, or Z and $Z^1$, together with the atoms to which they are bonded, form a cycloalkyl or heterocycloalkyl group, where Z and $Z^1$ are as defined above (except for moieties that cannot form the cycloalkyl or heterocycloalkyl group);

or a prodrug, pharmaceutically acceptable salt, pharmaceutically active metabolite, or pharmaceutically acceptable solvate of said compound.

In another embodiment of the compounds of the above formulas, $A_1$ is CH or N;

$A_2$ is C(R$^{10}$)(R$^{11}$), N(R$^{12}$), S, S(O), S(O)$_2$, or O, where each R$^{10}$, R$^{11}$ and R$^{12}$ is independently H or a lower alkyl group;

each $A_3$ present is independently C(R$^{10}$)(R$^{11}$), N(R$^{12}$), S, S(O), S(O)$_2$, or O, where each R$^{10}$, R$^{11}$ and R$^{12}$ is independently H or a lower alkyl group;

when p is 1, 2, 3, 4, or 5, $A_4$ is N(R$^{13}$), C(R$^{10}$)(R$^{11}$), or O, and when p is 0, $A_4$ is N(R$^{13}$)(R$^{14}$), C(R$^{10}$)(R$^{11}$)(R$^{12}$), and O(R$^{14}$), where each R$^{10}$, R$^{11}$ and R$^{12}$ is independently H or a lower alkyl group, each R$^{13}$ is H or an alkyl, aryl, or acyl group, and each R$^{14}$ is H or an alkyl or aryl group;

provided that no more than two heteroatoms occur consecutively in the above-depicted ring formed by $A_1$, $(A_2)_m$, $(A_3)_p$, $A_4$, and C=O, where each dotted line in the ring depicts a single bond when $A_2$ is present and a hydrogen atom when $A_2$ is absent; and Z and $Z^1$ are each independently H, F, an alkyl, cycloalkyl, heterocycloalkyl, aryl or heteroaryl group, where the alkyl, aryl, cycloalkyl, heterocycloalkyl, aryl or heteroaryl group is unsubstituted or substituted with one or more suitable substituents, —C(O)R$^{15}$, —CO$_2$R$^{15}$, —CN, —C(O)NR$^{15}$R$^{16}$, —C(O)NR$^{15}$OR$^{16}$, —C(S)R$^{15}$, —C(S)NR$^{15}$R$^{16}$, —NO$_2$, —SOR$^{16}$, —SO$_2$R$^{15}$, —SO$_2$NR$^{15}$R$^{16}$, —SO$_2$(NR$^{15}$)(OR$^{16}$), —SONR$^{15}$, —SO$_3$R$^{15}$, —PO(OR$^{15}$)$_2$, —PO(OR$^{15}$)(OR$^{16}$), —PO(NR$^{15}$R$^{16}$)(OR$^{17}$), —PO(NR$^{15}$R$^{16}$)(NR$^{17}$R$^{18}$), —C(O)NR$^{15}$NR$^{16}$R$^{17}$, —C(S)NR$^{15}$NR$^{16}$R$^{17}$, where R$^{15}$, R$^{16}$, R$^{17}$ and R$^{18}$ are each independently H or an alkyl, cycloalkyl, aryl, heterocycloalkyl, acyl or thioacyl group, where the alkyl, aryl, cycloalkyl, aryl, heterocycloalkyl, acyl or thioacyl group is unsubstituted or substituted with one or more suitable substituents, or where any two of the R$^{15}$, R$^{16}$, R$^{17}$ and R$^{18}$, taken together with the atoms to which they are bonded, form a heterocycloalkyl group, which is unsubstituted or substituted with one or more suitable substituents, or Z and $Z^1$, together with the atoms to which they are bonded, form a cycloalkyl or heterocycloalkyl group, where Z and $Z^1$ are as defined above. Preferably, in the compounds of Formulas IX and X, R$^1$ may be selected from H and a lower alkyl, phenyl, naphthyl, pyridyl, quinoyl, isoquinoyl or isoxazoyl group, where the lower alkyl, phenyl, naphthyl, pyridyl, quinoyl, isoquinoyl or isoxazoyl group is unsubstituted or substituted with one or more substituents selected from alkyl (but not as a substituent for alkyl), hydroxy, halo, haloalkyl, alkoxy, haloalkoxy and alkylenedioxy moiety. Exemplary R$^1$ groups include, but are not limited to H, phenyl, α-naphthyl, β-naphthyl, 2-chlorophenyl, 2-α,α,α-trifluoromethylphenyl, 3-chloro-6-methoxyphenyl, 2,3-dichlorophenyl, 4-isoquinoyl, 3-iso-propylphenyl, 2,5-dimethoxyphenyl, 2-methoxyphenyl, 2-methylphenyl (o-tolyl), 2-bromophenyl, 3-pyridyl, 4-pyridyl, 3-methylisoxazol-5-yl, 3,3,3-trifluoroprop-1-yl, and 2,3-benzo[d]dioxolyl. Preferably, in the compounds of Formulas IX and X, R$^2$ and R$^3$ may be each independently selected from H, halo, alkoxy, unsubstituted lower alkyl, haloalkyl, and lower alkoxyalkyl. R$^4$ and R$^6$ may be each independently selected from H, unsubstituted lower alkyl, haloalkyl and lower alkoxyalkyl.

Yet another preferred embodiment of this invention comprises the compounds depicted by the formula:

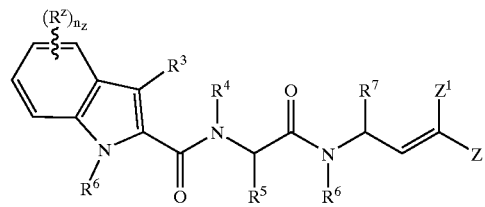

XI wherein:

each R$^2$ is H or a suitable substituent and $n_Z$ is an integer from 1 to 4;

R$^7$ is a moiety having the formula:

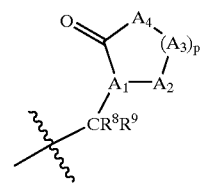

wherein:

R$^8$ and R$^9$ are each independently H or a lower alkyl group;

p is an integer of from 1 to 5;

$A_1$ is CH or N;

when p is 1, 2, 3, 4, or 5, $A_2$ is C(R$^{10}$)(R$^{11}$), N(R$^{12}$), S, S(O), S(O)$_2$, or O, and when p is 0, $A_2$ is C(R$^{10}$)(R$^{11}$)(R$^{12}$), N(R$^{10}$)(R$^{12}$), S(R$^{10}$), S(O)(R$^{10}$), S(O)$_2$(R$^{10}$), or O(R$^{10}$) where each R$^{10}$, R$^{11}$ and R$^{12}$ is independently H or a lower alkyl group;

each $A_3$ present is independently C(R$^{10}$)(R$^{11}$), N(R$^{12}$), S, S(O), S(O)$_2$, or O, where each R$^{10}$, R$^{11}$ and R$^{12}$ is independently H or a lower alkyl group;

$A_4$ is N(R$^{13}$), C(R$^{10}$)(R$^{11}$), or O, where R$^{10}$ and R$^{11}$ are each independently H or a lower alkyl group, and R$^{13}$ is H or an alkyl, aryl or acyl group;

provided that no more than two heteroatoms occur consecutively in the above-depicted ring formed by $A_1$, $(A_2)_m$, $(A_3)_p$, $A_4$, and C=O; and each R$^3$, R$^4$, R$^5$, R$^6$, Z and $Z^1$ are as defined above.

Preferably, in the compounds of Formula XI, each $R^z$ is independently selected from H, halo, alkoxy, unsubstituted lower alkyl, haloalkyl, and lower alkoxyalkyl. $R^3$ may be independently selected from H, halo, alkoxy, unsubstituted lower alkyl, haloalkyl and lower alkoxyalkyl and $R^4$ and $R^6$ may be each independently selected from H, unsubstituted lower alkyl, haloalkyl and lower alkoxyalkyl.

Another preferred embodiment of this invention comprise the compounds of Formula IV, wherein n is 1, depicted by the formula:

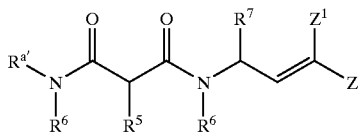

XII wherein:

$R^{a'}$ is an alkyl, aryl, cycloalkyl, heterocycloalkyl or heteroaryl, where the alkyl, aryl, cycloalkyl, heterocycloalkyl, or heteroaryl group is unsubstituted or substituted with one or more suitable substituents;

$R^5$ is H or an alkyl group, unsubstituted or substituted with one or more suitable substituents;

each $R^6$ is independently H or a lower alkyl group, unsubstituted or substituted with one or more suitable substituents;

$R^7$ is a moiety having the formula:

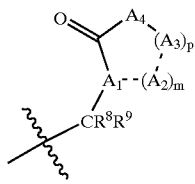

wherein:

$R^8$ and $R^9$ are each independently H or a lower alkyl group;

m is 0 or 1;

p is an integer of from 0 to 5;

$A_1$ is CH or N;

when p is 1, 2, 3, 4, or 5, $A_2$ is $C(R^{10})(R^{11})$, $N(R^{12})$, S, S(O), $S(O)_2$, or O, and when p is 0, $A_2$ is $C(R^{10})(R^{11})(R^{12})$, $N(R^{10})(R^{12})$, $S(R^{10})$, $S(O)(R^{10})$, $S(O)_2(R^{10})$, or $O(R^{10})$ where each $R^{10}$, $R^{11}$ and $R^{12}$ is independently H or a lower alkyl group;

each $A_3$ present is independently $C(R^{10})(R^{11})$, $N(R^{12})$, S, S(O), $S(O)_2$, or O, where each $R^{10}$, $R^{11}$ and $R^{12}$ is independently H or a lower alkyl group;

when p is 1, 2, 3, 4, or 5, $A_4$ is $N(R^{13})$, $C(R^{10})(R^{11})$, or O, and when p is 0, $A_4$ is $N(R^{13})(R^{14})$, $C(R^{10})(R^{11})(R^{12})$, and $O(R^{14})$, where each $R^{10}$, $R^{11}$ and $R^{12}$ is independently H or a lower alkyl group, each $R^{13}$ is H or an alkyl, aryl, or acyl group, and each $R^{14}$ is H or an alkyl or aryl group;

provided that no more than two heteroatoms occur consecutively in the above-depicted ring formed by $A_1$, $(A_2)_m$, $(A_3)_p$, $A_4$, and C=O, where each dotted line in the ring depicts a single bond when $A_2$ is present and a hydrogen atom when $A_2$ is absent; and Z and $Z^1$ are each independently H, F, an alkyl, cycloalkyl, heterocycloalkyl, aryl or heteroaryl group, where the alkyl, cycloalkyl, heterocycloalkyl, aryl or heteroaryl group is unsubstituted or substituted with one or more suitable substituents, $—C(O)R^{15}$, $—CO_2R^{15}$, $—CN$, $—C(O)NR^{15}R^{16}$, $—C(O)NR^{15}OR^{16}$, $—C(S)R^{15}$, $—C(S)OR^{15}$, $—C(S)NR^{15}R^{16}$, $—C(=NR^{15})R^{16}$, $—C(=NR^{15})OR^{16}$, $—NO_2$, $—SOR^{16}$, $—SO_2R^{15}$, $—SO_2NR^{15}R^{16}$, $—SO_2(NR^{15})(OR^{16})$, $—SONR^{15}$, $—SO_3R^{15}$, $—PO(OR^{15})_2$, $—PO(OR^{15})(OR^{16})$, $—PO(NR^{15}R^{16})(OR^{17})$, $—PO(NR^{15}R^{16})(NR^{17}R^{18})$, $—C(O)NR^{15}NR^{16}R^{17}$, $—C(S)NR^{15}NR^{16}R^{17}$, where $R^{15}$, $R^{16}$, $R^{17}$ and $R^{18}$ are each independently H or an alkyl, cycloalkyl, aryl, heterocycloalkyl, acyl or thioacyl group, where the alkyl, cycloalkyl, aryl, heterocycloalkyl, acyl or thioacyl group is unsubstituted or substituted with one or more suitable substituents, or where any two of the $R^{15}$, $R^{16}$, $R^{17}$ and $R^{18}$, taken together with the atoms to which they are bonded, form a heterocycloalkyl group, which is unsubstituted or substituted with one or more suitable substituents, or Z and $Z^1$, together with the atoms to which they are bonded, form a cycloalkyl or heterocycloalkyl group, where Z and $Z^1$ are as defined above (except for moieties that cannot form the cycloalkyl or heterocycloalkyl group);

or a prodrug, pharmaceutically acceptable salt, pharmaceutically active metabolite, or pharmaceutically acceptable solvate of said compound.

In another embodiment of the compounds of the above formulas, Z and $Z^1$ are each independently H, F, an alkyl, cycloalkyl, heterocycloalkyl, aryl or heteroaryl group, where the alkyl, cycloalkyl, heterocycloalkyl, aryl or heteroaryl group is unsubstituted or substituted with one or more suitable substituents, $—C(O)R^{15}$, $—CO_2R^{15}$, $—CN$, $—C(O)NR^{15}R^{16}$, $—C(O)NR^{15}OR^{16}$, $—C(S)R^{15}$, $—C(S)NR^{15}R^{16}$, $—NO_2$, $—SOR^{16}$, $—SO_2R^{15}$, $—SO_2NR^{15}R^{16}$, $—SO_2(NR^{15})(OR^{16})$, $—SONR^{15}$, $—SO_3R^{15}$, $—PO(OR^{15})_2$, $—PO(OR^{15})(OR^{16})$, $—PO(NR^{15}R^{16})(OR^{17})$, $—PO(R^{15}R^{16})(NR^{17}R^{18})$, $—C(O)NR^{15}NR^{16}R^{17}$, $—C(S)NR^{15}NR^{16}R^{17}$, where $R^{15}$, $R^{16}$, $R^{17}$ and $R^{18}$ are independently H or an alkyl, cycloalkyl, aryl, heterocycloalkyl, acyl or thioacyl group, where the alkyl, cycloalkyl, aryl, heterocycloalkyl, acyl or thioacyl group is unsubstituted or substituted with one or more suitable substituents, or where any two of the $R^{15}$, $R^{16}$, $R^{17}$ and $R^{18}$, taken together with the atoms to which they are bonded, form a heterocycloalkyl group, which is unsubstituted or substituted with one or more suitable substituents, or Z and $Z^1$, together with the atoms to which they are bonded, form a cycloalkyl or heterocycloalkyl group, where Z and $Z^1$ are as defined above.

Preferably, in the compounds of Formula XII, $R^{a'}$ may be selected from H, lower alkyl, phenyl, naphthyl, pyridyl, quinoyl, isoquinoyl and isoxazoyl, each of which may be substituted by alkyl (but not as a substituent for alkyl), hydroxy, halo, haloalkyl, alkoxy, haloalkoxy and alkylenedioxy. Each $R^6$ may be independently selected from H, unsubstituted lower alkyl, haloalkyl and loweralkoxyalkyl.

If an inventive compound is a base, a desired salt may be prepared by any suitable method known in the art, including treatment of the free base with an inorganic acid, such as hydrochloric acid, hydrobromic acid, sulfuric acid, nitric acid, phosphoric acid, and the like, or with an organic acid, such as acetic acid, maleic acid, succinic acid, mandelic acid, fumaric acid, malonic acid, pyruvic acid, oxalic acid, glycolic acid, salicylic acid, pyranosidyl acid, such as glucuronic acid or galacturonic acid, alpha-hydroxy acid, such as citric acid or tartaric acid, amino acid, such as aspartic acid or glutamic acid, aromatic acid, such as benzoic acid or cinnamic acid, sulfonic acid, such as p-toluenesulfonic acid or ethanesulfonic acid, or the like.

If an inventive compound is an acid, a desired salt may be prepared by any suitable method known to the art, including treatment of the free acid with an inorganic or organic base, such as an amine (primary, secondary, or tertiary); an alkali metal or alkaline earth metal hydroxide; or the like. Illustrative examples of suitable salts include organic salts derived from amino acids such as glycine and arginine; ammonia; primary, secondary, and tertiary amines; and cyclic amines, such as piperidine, morpholine, and piperazine; as well as inorganic salts derived from sodium, calcium, potassium, magnesium, manganese, iron, copper, zinc, aluminum, and lithium.

All compounds of this invention contain at least one chiral center and may exist as single stereoisomers (e.g., single enantiomers or diastereomers), any mixture of stereosisomers (e.g., any mixture of enantiomers or diastereomers) or racemic mixtures thereof. All such single stereoisomers, mixtures and racemates are intended to be encompassed within the broad scope of the present invention. Where the stereochemistry of the chiral carbons present in the chemical structures illustrated herein is not specified, the chemical structure is intended to encompass compounds containing either stereoisomer of each chiral carbon. When used describe a particular compound, the term "optically pure" is used herein to indicate that the compound is substantially enantiomerically or diastereomerically pure. Compounds that are substantially enatiomerically pure contain at least 90% of a single isomer and preferably contain at least 95% of a single isomer. Compounds that are substantially diastereomerically pure contain at least 90% of a single isomer of each chiral carbon center present in the diastereomer, and preferably contain at least 95% of a single isomer of each chiral carbon. More preferably, when an optically active compound is desired, it contains at least 97.5% of a single isomer and, most preferably, at least 99% of the single isomer. Compounds identified herein as single stereoisomers are meant to describe compounds that are present in a form that contains at least 90% of a single isomer. The term "racemic" or "racemic mixture" refers to a mixture of equal amounts of enantiomeric compounds, which encompasses mixtures of enantiomers and mixtures of enantiomeric diastereomers. The compounds of this invention may be obtained in stereochemically (e.g., enantiomerically or diastereomerically) pure or substantially stereochemically pure form. Such compounds may be obtained synthetically, according to the procedures described herein using optically pure or substantially optically pure materials. Alternatively, these compounds may be obtained by resolution/separation of a mixture of stereoisomers, including racemic mixtures, using conventional procedures. Exemplary methods that may be useful for the resolution/separation of stereoisomeric mixtures include chromatography and crystallization/recrystallization. Other useful methods may be found in "Enantiomers, Racemates, and Resolutions," J. Jacques et al., 1981, John Wiley and Sons, New York, N.Y. Preferred stereoisomers of the compounds of this invention are described herein.

In especially preferred embodiments of Formulas V, VI, VII, VIII, IX, X, XI and XII, $R^5$ (or $R^x$ or $R^y$ in Formulas II, III and VI) is H or an unsubstituted alkyl group or an optionally substituted lower alkyl group, where these groups are comprised of a straight- or branched-chain saturated hydrocarbon group, a straight- or branched-chain substituted saturated hydrocarbon group, or group comprised of a straight- or branched-chain saturated hydrocarbon moiety and an unsaturated hydrocarbon moiety. When $R^5$ or $R^x/R^y$ is a substituted alkyl group, the point of attachment of $R^5$ or $R^x/R^y$ is via a saturated hydrocarbon moiety. When $R^5$ or $R^x/R^y$ is a substituted saturated hydrocarbon group, the saturated hydrocarbon group may be optionally substituted with a cycloalkyl group, a heterocycloalkyl group, an aryl group, a heteroaryl group, an alkoxy group, an aryloxy group, an alkylthio group, an arylthio group, where each alkyl, cycloalkyl, aryl, heterocycloalkyl or heteroaryl moiety thereof may be optionally substituted. When $R^5$ or $R^x/R^y$ is comprised of a saturated hydrocarbon moiety and an unsaturated hydrocarbon moiety, the saturated hydrocarbon moiety may be bound to an unsaturated hydrocarbon moiety containing one or more double-bonds or triple-bonds, the terminal positions of which may be substituted by the substituents described above, or may contain additional straight- or branched-chain saturated hydrocarbon moieties. Preferably, the unsaturated hydrocarbon moiety contains one double-bond or one triple-bond, the terminal position(s) of which may optionally contain a straight- or branched-chain saturated hydrocarbon moiety. Preferably, if the unsaturated hydrocarbon moiety contains a double-bond, both terminal positions of the double bond contain a straight- or branched-chain saturated hydrocarbon moiety. In especially preferred embodiments, $R^5$ or $R^x/R^y$ is H or a lower alkyl, arylalkyl, heteroarylalkyl, cycloalkylalkyl group, or a group comprised of a straight-chain saturated hydrocarbon moiety and an unsaturated hydrocarbon moiety, where the alkyl, arylalkyl, heteroarylalkyl, cycloalkylalkyl group is unsubstituted or substituted with one or more suitable substituents. Preferably, $R^5$ or $R^x/R^y$ is H or substituted or unsubstituted methyl, ethyl, n-propyl, iso-propyl, n-butyl, sec-butyl, iso-butyl, 2-propen-1-yl, 2-propen-2-yl, 2-propyn-1-yl, 3-methyl-3-buten-1-yl, -methylcyclohexyl, substituted or unsubstituted-methylthienyl or substituted or unsubstituted benzyl, where the methyl, ethyl, propyl, propenyl, butenyl or cyclohexyl moiety thereof is optionally substituted with one or more substituents independently selected from lower alkoxy, hydroxy, amino, alkylamino or dialkylamino and halogen, the phenyl moiety of the substituted benzyl is substituted by one or more substituents independently selected from lower alkyl, lower alkoxy, hydroxy, amino, alkylamino or dialkylamino and halogen and the thienyl moiety of the substituted -methylthienyl is substituted by one or more substituents independently selected from lower alkyl, lower alkoxy, hydroxy, amino, alkylamino, dialkylamino and halogen. When $R^5$ or $R^x/R^y$ is substituted methyl, the methyl (methylene) moiety may be substituted with an alkoxy group, an aryloxy group, an alkylthio group or an arylthio group. Most preferably, $R^5$ or $R^x/R^y$ is H, ethyl, 2-propyn-1-yl, -methylcyclohexyl, or substituted or unsubstituted benzyl, where the phenyl moiety of the substituted benzyl is substituted by one or more substituents independently selected from lower alkyl, lower alkoxy and halogen.

In the especially preferred embodiments of Formulas V, VI, VII, VIII, XI, X XI and XII, $R^5$ (or $R^x$ or $R^y$ in Formulas II, III and VI) is selected from H and:

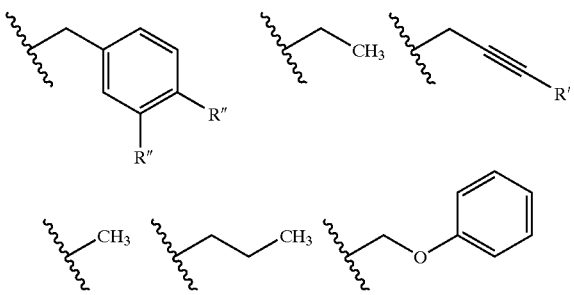

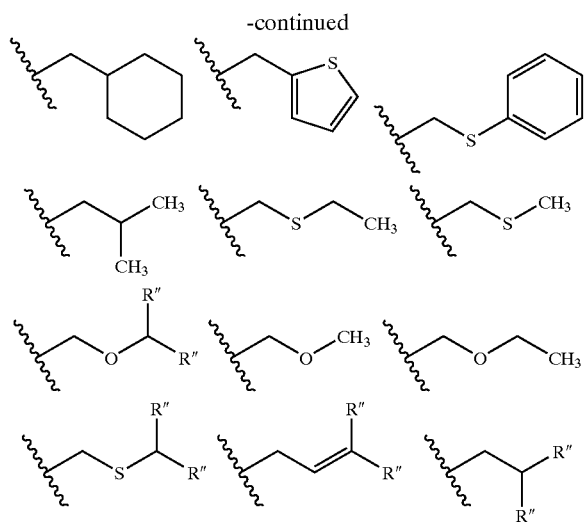

wherein R' may be H or alkyl and each R" may be H or independently selected from lower alkyl, lower alkoxy, hydroxy, amino, alkylamino or dialkylamino, and halogen.

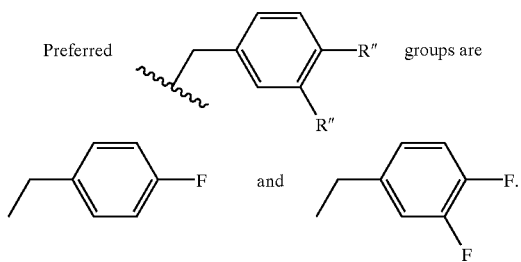

In especially preferred embodiments of Formulas V, VI, VII, VIII, IX, X, XI and XII, $R^7$ (or $R^c$ in Formulas I, II, III and VI) is selected from —$CH_2CH_2C(O)NH_2$; —$CH_2CH_2C(O)NH$-alkyl; —$CH_2NHC(O)CH_3$; and

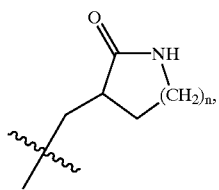

where n is 1 or 2. More preferably, $R^7$ is

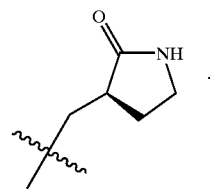

Preferably, in each of the formulas described herein, Z and $Z^1$ are each independently H, alkyl, where the alkyl is unsubstituted or substituted with one or more suitable substituents, —$CO_2R^{15}$ (in Formulas V to XII) or —$CO_2R^1$ (in Formulas I to VI), where $R^1$ and $R^{15}$ are as defined above, or Z and $Z^1$, taken together with the atom to which they are attached, form a heterocycloalkyl group, as defined above, which may be optionally substituted. In one useful embodiment of the compounds of this invention, Z and/or $Z^1$ may be —C(S)OR" or —C(S)O$R^{19}$, where R" and $R^{19}$ are as defined above. Such compounds may be prepared using procedures described in K. Hartke, et al., *Leibigs Ann. Chem.*, 321–330 (1989) and K. Hartke, et al., *Synthesis*, 960–961 (1985). More preferably, the heterocycloalkyl group may optionally contain O, N, S and/or P and may be substituted by one or more of oxo (keto) or thioketo. In another preferred embodiment of this invention, Z and $Z^1$ are each independently selected from H, lower alkyl which is unsubstituted or substituted with one or more suitable substituents, —$CO_2H$, —$CO_2$-alkyl and —$CO_2$-cycloalkyl, or taken together with the atom to which they are attached form a heterocycloalkyl group, which is optionally substituted with one or more of keto or thioketo. In other preferred embodiments of this invention, Z and $Z^1$ are not both H. Most preferably, $Z^1$ is H or lower alkyl and Z is a —$CO_2H$, —$CO_2$-alkyl, —$CO_2$-alkylaryl, —$CO_2$-alkylheteroaryl, —$CO_2$-cycloalkyl group, where the lower alkyl, -alkyl, -cycloalkyl, -alkylaryl and -alkylheteroaryl moieties thereof are unsubstituted or substituted with one or more suitable substituents, or $Z^1$ and Z taken together with the atom to which they are attached form a heterocycloalkyl group, which may be optionally substituted. Exemplary Z groups include, but are not limited to: substituted and unsubstituted —$CO_2$-alkyl groups, which include straight- and branched-chain alkyl groups such as ethoxycarbonyl, t-butoxycarbonyl, isopropoxycarbonyl and (2,2-dimethylpropyl)-oxycarbonyl, where the ethoxy, t-butoxy, isopropoxy, and (2,2-dimethylpropyl)-oxy moieties thereof are unsubstituted or substituted with one or more suitable substituents; and include substituted and unsubstituted straight and branched-chain arylalkyl and heteroarylalkyl groups, such as benzyloxycarbonyl and pyridylmethyleneoxycarbonyl, where the benzyl and pyridylmethylene moieties thereof are unsubstituted or substituted with one or more suitable substituents; and include substituted and unsubstituted —$CO_2$-cycloalkyl groups such as cyclobutyloxycarbonyl, cyclopentyloxycarbonyl, cyclohexyloxycarbonyl and cycloheptyloxycarbonyl groups, where the cyclobutyl, cyclopentyl, cyclohexyl and cycloheptyl moieties thereof are unsubstituted or substituted with one or more suitable substituents, or $Z^1$ and Z taken together with the atom to which they are attached form

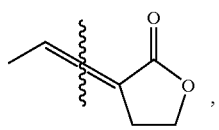

in Formulas V to XII

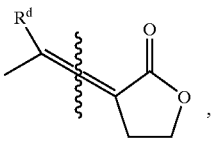

in Formulas I to VI).

In another embodiment of this invention, $Z^1$ is H and Z is —$CO_2CH_2CH_3$, —$CO_2(CH(CH_3)_2)$, —$CO_2(C(CH_3)_3)$, —CO$_2$CH$_2$(C(CH$_3$)$_3$), —CO$_2$(cyclo-C$_5$H$_9$) or Z$^1$ and Z taken together with the atom to which they are attached form

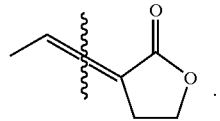

In yet another embodiment of this invention, Z$^1$ is H and Z is selected from ethoxycarbonyl, t-butoxycarbonyl, isopropoxycarbonyl, (2,2-dimethylpropyl)-oxycarbonyl, benzyloxycarbonyl, pyridylmethyleneoxycarbonyl, cyclobutyloxycarbonyl, cyclopentyloxycarbonyl, cyclohexyloxycarbonyl and cycloheptyloxycarbonyl, or Z$^1$ and Z taken together with the atom to which they are attached form

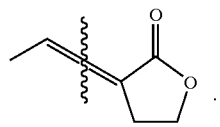

In the compounds of each of the above-described Formulas, R$^c$ and R$^7$ are defined to provide structures where m is 1 and p is 1–5 (i.e., both A$_2$ and A$_3$ are present), m is 0 and p is 0 (i.e, both A$_2$ and A$_3$ are absent), m is 0 and p is 1–5 (i.e, A$_2$ is absent and A$_3$ is present) and m is 1 and p is 0 (i.e, A$_2$ is present and A$_3$ is absent). Accordingly, one of ordinary skill in the are will recognize that when both A$_2$ and A$_3$ are present (m is 1 and p is 1–5), the dotted line between A$_1$ and A$_2$ represents a bond and the dotted line between A$_2$ and A$_3$ represents a bond and when both A$_2$ and A$_3$ are absent (m is 0 and p is 0); A$_2$, A$_3$ and the dotted line between these substituents are not present), the remaining dotted line in the structure between A$_1$ and A$_2$ represents a hydrogen (e.g., A$_1$ is CH$_2$ or NH). In embodiments of this invention when A$_2$ is absent and A$_3$ is present (m is 0 and p is 1–5), the dotted line between A$_1$ and A$_2$ represents a hydrogen and the dotted line between A$_2$ and A$_3$ represents a hydrogen (e.g., A$_1$ is CH$_2$ or NH and A$_3$ is CH(R$^g$)(R$^h$), NH(R$^i$), SH, S(O)H, S(O)$_2$H, or OH or CH(R$^{10}$)(R$^{11}$), NH(R$^{12}$), SH, S(O)H, S(O)$_2$H, or OH); and when A$_2$ is present and A$_3$ is absent (m is 1 and p is 0), the dotted line between A$_1$ and A$_2$ represents a bond and A$_2$ is C(R$^g$)(R$^h$)(R$^i$), N(R$^g$)(R$^i$), S(R$^g$), S(O)(R$^g$), S(O)$_2$(R$^g$), or O(R$^g$) or A$_2$ is C(R$^{10}$)(R$^{11}$)(R$^{12}$), N(R$^{10}$)(R$^{12}$), S(R$^{10}$), S(O)(R$^{10}$), S(O)$_2$(R$^{10}$), or O(R$^{10}$) or the dotted line between A$_2$ and A$_3$ represents a hydrogen and A$_2$ is CH(R$^g$)(R$^h$), NH(R$^i$), SH, S(O)H, S(O)$_2$H, or OH or A$_2$ is CH(R$^{10}$)(R$^{11}$), NH(R$^{12}$), SH, S(O)H, S(O)$_2$H, or OH. In preferred embodiments of the compounds of each of the above-described Formulas, m is 1 and p is 1 or 2 or m is 0 and p is 0 or m is 1 and p is 0. More preferably, when m is 1 and p is 1 or 2, A$_2$ and A$_3$ are both C(R$^g$)(R$^h$) or C(R$^{10}$)(R$^{11}$), respectively. More preferably, m is 1 and p is 1.

In the compounds of Formulas I to IV, R$^d$ and each R$^b$ are preferably H, in the compounds of Formulas V to XI, each R$^4$ and R$^6$ are preferably H and in the compounds of Formula XIII, each R$^6$ is preferably H.

Other embodiments of this invention comprise compounds having the formula:

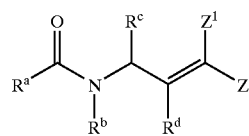

I wherein:

R$^a$ is (C$_1$–C$_4$)alkylcarbonyl-(C$_1$–C$_4$)alkyl, (C$_3$–C$_8$) cycloalkylcarbonyl-(C$_1$–C$_4$)alkyl, arylcarbonyl-(C$_1$–C$_4$) alkyl, heteroarylcarbonyl-(C$_1$–C$_4$)alkyl, (C$_1$–C$_4$) alkylcarbonylamino-(C$_1$–C$_4$)alkyl, (C$_3$–C$_8$) cycloalkylcarbonylamino-(C$_1$–C$_4$)alkyl, heterocycloalkylcarbonylamino-(C$_1$–C$_4$)alkyl, arylcarbonylamino-(C$_1$–C$_4$)alkyl, heteroarylcarbonylamino-(C$_1$–C$_4$)alkyl, (C$_1$–C$_4$ alkylaminocarbonyl-(C$_1$–C$_4$)alkyl, (C$_3$–C$_8$) cycloalkylaminocarbonyl-(C$_1$–C$_4$)alkyl, heterocycloalkylaminocarbonyl-(C$_1$–C$_4$)alkyl, arylaminocarbonyl-(C$_1$–C$_4$)alkyl, heteroarylaminocarbonyl-(C$_1$–C$_4$)alkyl, wherein each (C$_1$–C$_4$)alkyl, (C$_3$–C$_8$)cycloalkyl, heterocycloalkyl, aryl and heteroaryl moiety thereof is unsubstituted or substituted with one or more suitable substituents; preferably R$^3$ is (C$_1$–C$_4$)alkylcarbonyl-(C$_1$–C$_4$) alkyl, (C$_5$–C$_6$)cycloalkylcarbonyl-(C$_1$–C$_4$)alkyl, arylcarbonyl-(C$_1$–C$_4$)alkyl, heteroarylcarbonyl-(C$_1$–C$_4$) alkyl, (C$_1$–C$_4$)alkylcarbonylamino-(C$_1$–C$_4$)alkyl, C$_3$–C$_8$ cycloalkylcarbonylamino-(C$_1$–C$_4$)alkyl, heterocycloalkylcarbonylamino-(C$_1$–C$_4$)alkyl, arylcarbonylamino-(C$_1$–C$_4$)alkyl, heteroarylcarbonylamino-(C$_1$–C$_4$)alkyl, (C$_1$–C$_4$alkylaminocarbonyl-(C$_1$–C$_4$)alkyl, (C$_5$–C$_6$) cycloalkylaminocarbonyl-(C$_1$–C$_4$)alkyl, heterocycloalkylaminocarbonyl-(C$_1$–C$_4$)alkyl, arylaminocarbonyl-(C$_1$–C$_4$)alkyl, heteroarylaminocarbonyl-(C$_1$–C$_4$)alkyl, wherein each (C$_1$–C$_4$)alkyl, (C$_3$–C$_8$)cycloalkyl, heterocycloalkyl, aryl and heteroaryl moiety thereof is unsubstituted or substituted with one or more suitable substituents; more preferably, R$^a$ is (C$_1$–C$_4$)alkylcarbonyl-(C$_1$–C$_4$)alkyl, phenylcarbonyl-(C$_1$–C$_4$)alkyl, naphthylcarbonyl-(C$_1$–C$_4$)alkyl, pyrrolylcarbonyl-(C$_1$–C$_4$) alkyl, indolylcarbonyl-(C$_1$–C$_4$)alkyl, (C$_1$–C$_4$) alkylcarbonylamino-(C$_1$–C$_4$)alkyl, pyrrolylcarbonylamino-(C$_1$–C$_4$)alkyl, indolylcarbonylamino-(C$_1$–C$_4$)alkyl, phenylcarbonylamino-(C$_1$–C$_4$)alkyl, naphthylcarbonylamino-(C$_1$–C$_4$)alkyl, (C$_1$–C$_4$)alkylaminocarbonyl-(C$_1$–C$_4$) alkyl, pyrrolylaminocarbonyl-(C$_1$–C$_4$)alkyl, phenylaminocarbonyl-(C$_1$–C$_4$)alkyl, naphthylaminocarbonyl-(C$_1$–C$_4$)alkyl, wherein each (C$_1$–C$_4$)alkyl, phenyl, naphthyl, pyrrolyl, and indolyl moiety thereof is unsubstituted or substituted with one or more substituents independently selected from halo, C$_1$–C$_4$ alkyl, C$_1$–C$_4$ haloalkyl, C$_1$–C$_4$ alkoxy, C$_1$–C$_4$ haloalkoxy, methylenedioxy, aryl, heterocycloalkyl, and heteroaryl, where the aryl, heterocycloalkyl or heteroaryl is unsubstituted or substituted by one or more substituents independently selected from halo, C$_1$–C$_4$ alkyl, C$_1$–C$_4$ haloalkyl, C$_1$–C$_4$ alkoxy, C$_1$–C$_4$ haloalkoxy and methylenedioxy; and preferably, where said indolyl moiety thereof is substituted with one or two substituents independently selected from halo, C$_1$–C$_4$ alkoxy, unsubstituted C$_1$–C$_4$ alkyl and C$_1$–C$_4$ haloalkyl;

R$^b$ and R$^d$ are each independently H or C$_1$–C$_4$ alkyl; preferably R$^b$ and R$^d$ are each H;

$R^c$ is selected from —CH$_2$CH$_2$C(O)NH$_2$; —CH$_2$CH$_2$C(O)NH-alkyl; —CH$_2$NHC(O)CH$_3$; and

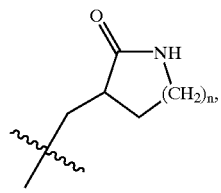

where n is 1 or 2; preferably $R^c$ is —CH$_2$CH$_2$C(O)NH$_2$ or

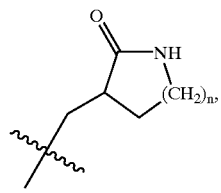

where n is 1; more preferably, $R^c$ is —CH$_2$CH$_2$C(O)NH$_2$ or

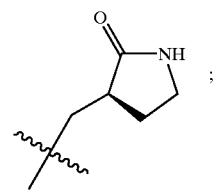

and $Z^1$ is H or $C_1$–$C_4$ alkyl and Z is —CO$_2$-alkyl, —CO$_2$-cycloalkyl, —CO$_2$-alkylaryl or —CO$_2$-alkylheterocycloaryl, or $Z^1$ and Z taken together with the atom to which they are attached form

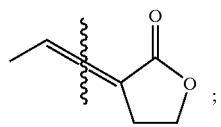

preferably, $Z^1$ is H and Z is —CO$_2$CH$_2$CH$_3$, —CO$_2$(CH(CH$_3$)$_2$), —CO$_2$(C(CH$_3$)$_3$), —CO$_2$CH$_2$(C(CH$_3$)$_3$), —CO$_2$(cyclo-C$_5$H$_9$) or $Z^1$ and Z taken together with the atom to which they are attached form

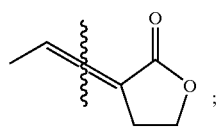

more preferably $Z^1$ is H and Z is —CO$_2$CH$_2$CH$_3$ or $Z^1$ and Z taken together with the atom to which they are attached form

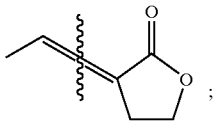

provided that $R^c$ is

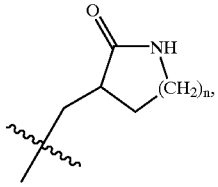

where n is 1 or 2, when $R^a$ is an indolylcarbonylamino-(C$_1$–C$_4$)alkyl group where the indolyl moiety thereof is substituted with one or more suitable substituents or $R^a$ is is not an amino-substituted (C$_1$–C$_4$)alkylcarbonylamino-(C$_1$–C$_4$)alkyl or $R^a$ is is not an amino-substituted (C$_1$–C$_4$)alkylcarbonyl-(C$_1$–C$_4$)alkyl; and $R^c$ is selected from —CH$_2$CH$_2$C(O)NH$_2$; —CH$_2$CH$_2$C(O)NH-alkyl; —CH$_2$NHC(O)CH$_3$; and

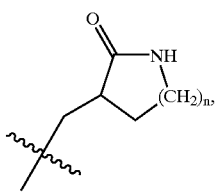

where n is 1 or 2, when $R^a$ is an indolylcarbonylamino-(C$_1$–C$_4$)alkyl group where the indolyl moiety thereof is unsubstituted or $R^a$ is a (C$_1$–C$_4$) alkylaminocarbonyl-(C$_1$–C$_4$)alkyl, (C$_3$–C$_8$)cycloalkylaminocarbonyl-(C$_1$–C$_4$)alkyl, heterocycloalkylaminocarbonyl-(C$_1$–C$_4$)alkyl, arylaminocarbonyl-(C$_1$–C$_4$)alkyl, heteroarylaminocarbonyl-(C$_1$–C$_4$)alkyl, or heteroarylcarbonylamino-(C$_1$–C$_4$)alkyl group, wherein each (C$_1$–C$_4$)alkyl, (C$_3$–C$_8$)cycloalkyl, heterocycloalkyl, aryl and heteroaryl moiety thereof is unsubstituted or substituted with one or more suitable substituents;

or a prodrug, pharmaceutically acceptable salt, pharmaceutically active metabolite, or pharmaceutically acceptable solvate of said compound.

Preferably, in the compounds of Formula I, as defined above, $R^c$ is

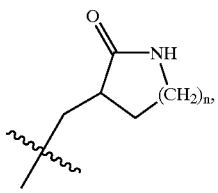

where n is 1, when $R^a$ is an indolylcarbonylamino-(C$_1$–C$_4$) alkyl group where the indolyl moiety thereof is substituted with one or two substituents independently selected from halo, C$_1$–C$_4$ alkoxy, unsubstituted C$_1$–C$_4$ alkyl and C$_1$–C$_4$ haloalkyl, C$_1$–C$_4$ haloalkoxy, methylenedioxy, aryl, heterocycloalkyl, and heteroaryl where the aryl, heterocycloalkyl and heteroaryl is unsubstituted or substituted by one ore more substituents independently selected from halo, $C_1$–$C_4$ alkyl, $C_1$–$C_4$ haloalkyl, $C_1$–$C_4$ alkoxy, $C_1$–$C_4$ haloalkoxy and methylenedioxy; and $R^c$ is selected from —$CH_2CH_2C(O)NH_2$; —$CH_2CH_2C(O)NH$-alkyl; —$CH_2NHC(O)CH_3$; and

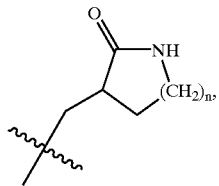

where n is 1, when $R^a$ is $(C_1$–$C_4)$alkylcarbonyl-$(C_1$–$C_4)$alkyl, $(C_5$–$C_6)$cycloalkyl carbonyl-$(C_1$–$C_4)$alkyl, arylcarbonyl-$(C_1$–$C_4)$alkyl, heteroarylcarbonyl-$(C_1$–$C_4)$alkyl, $(C_1$–$C_4)$alkylcarbonylamino-$(C_1$–$C_4)$alkyl, $C_3$–$C_8$ cycloalkylcarbonylamino-$(C_1$–$C_4)$alkyl, heterocycloalkylcarbonylamino-$(C_1$–$C_4)$alkyl, arylcarbonylamino-$(C_1$–$C_4)$alkyl, heteroarylcarbonylamino-$(C_1$–$C_4)$alkyl, $(C_1$–$C_4$alkylaminocarbonyl-$(C_1$–$C_4)$alkyl, $(C_3$–$C_8)$cycloalkylaminocarbonyl-$(C_1$–$C_4)$alkyl, heterocycloalkylaminocarbonyl-$(C_1$–$C_4)$alkyl, arylaminocarbonyl-$(C_1$–$C_4)$alkyl, heteroarylaminocarbonyl-$(C_1$–$C_4)$alkyl, wherein each $(C_1$–$C_4)$alkyl, $(C_3$–$C_8)$ cycloalkyl, heterocycloalkyl, aryl and heteroaryl moiety thereof unsubstituted or substituted with one or more suitable substituents.

More preferably, in the compounds of Formula I, as defined above, $R^c$ is

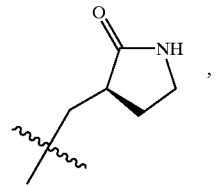

when $R^a$ is an indolylcarbonylamino-$(C_1$–$C_4)$alkyl group where the indolyl moiety thereof is substituted with one or two substituents independently selected from halo, $C_1$–$C_4$ alkoxy, unsubstituted $C_1$–$C_4$ alkyl and $C_1$–$C_4$ haloalkyl; and and $R^c$ is —$CH_2CH_2C(O)NH_2$ or

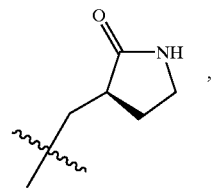

when $R^a$ is $(C_1$–$C_4)$alkylcarbonyl-$(C_1$–$C_4)$alkyl, phenylcarbonyl-$(C_1$–$C_4)$alkyl, naphthylcarbonyl-$(C_1$–$C_4)$alkyl, pyrrolylcarbonyl-$(C_1$–$C_4)$alkyl, indolylcarbonyl-$(C_1$–$C_4)$alkyl, $(C_1$–$C_4)$alkylcarbonylamino-$(C_1$–$C_4)$alkyl, pyrrolylcarbonylamino-$(C_1$–$C_4)$alkyl, indolylcarbonylamino-$(C_1$–$C_4)$alkyl, phenylcarbonylamino-$(C_1$–$C_4)$alkyl, naphthylcarbonylamino-$(C_1$–$C_4)$alkyl, $(C_1$–$C_4)$ alkylaminocarbonyl-$(C_1$–$C_4)$alkyl, phenylaminocarbonyl-$(C_1$–$C_4)$alkyl, naphthylaminocarbonyl-$(C_1$–$C_4)$alkyl, wherein each $(C_1$–$C_4)$alkyl, phenyl, naphthyl and pyrrolyl moiety thereof is group is unsubstituted or substituted with one or more substituents independently selected from halo, $C_1$–$C_4$ alkyl, $C_1$–$C_4$ haloalkyl, $C_1$–$C_4$ alkoxy, $C_1$–$C_4$ haloalkoxy, methylenedioxy, aryl, heterocycloalkyl, and heteroaryl, where the aryl, heterocycloalkyl and heteroaryl is unsubstituted or substituted by one ore more substituents independently selected from halo, $C_1$–$C_4$ alkyl, $C_1$–$C_4$ haloalkyl, $C_1$–$C_4$ alkoxy, $C_1$–$C_4$ haloalkoxy and methylenedioxy; and said indolyl moiety is unsubstituted.

Other specific compounds of this invention have the formula:

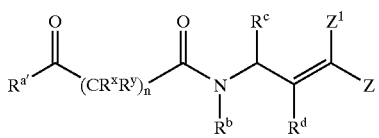

II $R^{a'}$ is a $(C_1$–$C_4)$alkyl, $(C_3$–$C_8)$cycloalkyl, aryl or heteroaryl group, wherein the $(C_1$–$C_4)$alkyl, $(C_3$–$C_8)$ cycloalkyl, aryl and heteroaryl group is unsubstituted or substituted with one or more substituents independently selected from $(C_1$–$C_4)$alkyl, aryl, $(C_3$–$C_8)$cycloalkyl, heterocycloalkyl, heteroaryl, halo, hydroxyl, $(C_1$–$C_4)$ alkoxy, alkylenedioxy (as a substituent for aryl or heteroaryl), aryloxy, $(C_3$–$C_8)$cycloalkoxy, heteroaryloxy, and carboxyl where the $(C_1$–$C_4)$alkyl, aryl, $(C_3$–$C_8)$ cycloalkyl, heterocycloalkyl, heteroaryl moieties thereof are optionally substituted by one or more of $(C_1$–$C_4)$alkyl (except for alkyl), halo, $(C_1$–$C_4)$haloalkyl, $(C_1$–$C_4)$alkoxy, $(C_1$–$C_4)$haloalkoxy, alkylenedioxy, aryl or heteroaryl, where the aryl or heteroaryl is unsubstituted or substituted with one or more substituents independently selected from alkyl, haloalkyl, alkylenedioxy, nitro, amino, hydroxamino, alkylamino, dialkylamino, halo, hydroxyl, alkoxy, haloalkoxy, aryloxy, mercapto, alkylthio or arylthio groups; preferably, $R^{a'}$ is a $(C_1$–$C_4)$alkyl, pyrrolyl, indolyl, phenyl or naphthyl group, where the $(C_1$–$C_4)$alkyl group is unsubstituted or substituted with one or more substituents independently selected from halo, $C_1$–$C_4$ alkoxy or $C_1$–$C_4$ haloalkoxy and the pyrrolyl, indolyl, phenyl or naphthyl group is unsubstituted or substituted with one or more substituents independently selected from halo, $C_1$–$C_4$ alkyl, $C_1$–$C_4$ haloalkyl, $C_1$–$C_4$ alkoxy, $C_1$–$C_4$ haloalkoxy, methylenedioxy, aryl, heterocycloalkyl and heteroaryl, where the aryl, heterocycloalkyl and heteroaryl is unsubstituted or substituted by one or more substituents independently selected from halo, $C_1$–$C_4$ alkyl, $C_1$–$C_4$ haloalkyl, $C_1$–$C_4$ alkoxy, $C_1$–$C_4$ haloalkoxy and methylenedioxy; more preferably, $R^{a'}$ is an unsubstituted $(C_1$–$C_4)$alkyl, or a pyrrolyl, indolyl, phenyl or naphthyl group, where the pyrrolyl, indolyl, phenyl or naphthyl group is unsubstituted or substituted by one or more substituents independently selected from halo, $C_1$–$C_4$ alkyl, $C_1$–$C_4$ haloalkyl or a phenyl, naphthyl, isoxazolyl, pyridyl, quinoyl or isoquinoyl group, where the phenyl, naphthyl, isoxazolyl, pyridyl, quinoyl or isoquinoyl group is unsubstituted or substituted with one or more substituents independently selected from halo, $C_1$–$C_4$ alkyl, $C_1$–$C_4$ haloalkyl, $C_1$–$C_4$ alkoxy, $C_1$–$C_4$ haloalkoxy and methylenedioxy; in specific embodiments, $R^{a'}$ is an unsubstituted $(C_1$–$C_4)$alkyl, pyrrolyl, indolyl, phenyl or naphthyl group or a pyrrolyl group substituted by phenyl, α-naphthyl, β-naphthyl, 2-chlorophenyl, 2-α,α,α-trifluoromethylphenyl, 3-chloro-6-methoxyphenyl, 2,3-dichlorophenyl, 4-isoquinoyl, 3-iso-propylphenyl, 2,5- dimethoxyphenyl, 2-methoxyphenyl, 2-methylphenyl (o-tolyl), 2-bromophenyl, 3-pyridyl, 4-pyridyl, 3-methylisoxazol-5-yl, 3,3,3-trifluoroprop-1-yl, or 2,3-benzo[d]dioxolyl or an indolyl group substituted by halo, $C_1$–$C_4$ alkoxy, unsubstituted $C_1$–$C_4$ alkyl, $C_1$–$C_4$ haloalkyl, and $C_1$–$C_4$ alkoxyalkyl;

n is 1, 2 or 3; preferably n is 1 or 2; more preferably, n is 2;

$R^x$ is H and $R^y$ is H, $C_1$–$C_4$ alkyl, $C_1$–$C_4$ haloalkyl or an arylalkyl, heteroarylalkyl, cycloalkylalkyl group or a straight-chain saturated hydrocarbon moiety or an unsaturated hydrocarbon moiety, where the arylalkyl, heteroarylalkyl, cycloalkylalkyl group is unsubstituted or substituted with one or more suitable substituents; preferably, $R^x$ is H and $R^y$ is substituted or unsubstituted methyl, ethyl, n-propyl, iso-propyl, n-butyl, sec-butyl, iso-butyl, 2-propen-1-yl, 2-propen-2-yl, 2-propyn-1-yl, 3-methyl-3-buten-1-yl, -methylcyclohexyl, -methylthienyl or benzyl, where the substituted methyl, ethyl, n-propyl, iso-propyl, n-butyl, sec-butyl, iso-butyl, 2-propen-1-yl, 2-propen-2-yl, 2-propyn-1-yl, 3-methyl-3-buten-1-yl, and -methylcyclohexyl is substituted by one or more substituents independently selected from halo, alkoxy, aryloxy, alkylthio and arylthio; the subsituted thienyl is substituted by one or more substituents independently selected from lower alkyl, lower alkoxy, hydroxy, amino, alkylamino, dialkylamino and halo; and the phenyl moiety of the substituted benzyl is substituted by one or more substituents independently selected from lower alkyl, lower alkoxy, alkylenedioxy, hydroxy, amino, alkylamino, dialkylamino and halo; more preferably, $R^x$ is H and $R^y$ is ethyl, n-propyl, iso-propyl, n-butyl, sec-butyl, iso-butyl, 2-propen-1-yl, 2-propen-2-yl, 2-propyn-1-yl, 3-methyl-3-buten-1-yl, -methylcyclohexyl, benzyl or substituted benzyl, wherein the phenyl moiety of the substituted benzyl comprises one or more substituents independently selected from $C_1$–$C_4$ alkyl, $C_1$–$C_4$ alkoxy and halo; even more preferably, where $R^x$ is H and $R^y$ is H, ethyl, 2-propyn-1-yl, methylcyclohexyl or benzyl;

$R^c$ is

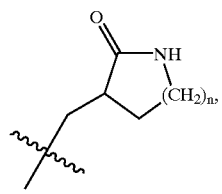

where n is 1 or 2; preferably $R^c$ is

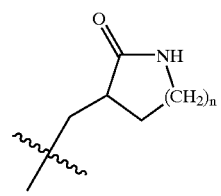

where n is 1; more preferably, $R^c$ is

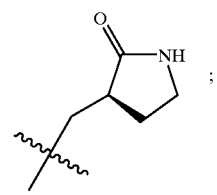

and $R^b$, $R^d$, Z and $Z^1$ are defined as in Formula I, above.

Yet other specific compounds of this invention have the formula:

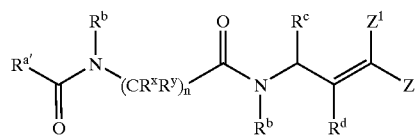

III wherein:

$R^{a'}$ is a ($C_1$–$C_4$)alkyl, ($C_3$–$C_8$)cycloalkyl, aryl or heteroaryl group, wherein the ($C_1$–$C_4$)alkyl, ($C_3$–$C_8$)cycloalkyl, aryl and heteroaryl group is unsubstituted or substituted with one or more suitable substituents provided that $R^{a'}$ is not an amino-substituted ($C_1$–$C_4$)alkyl group; preferably, $R^{a'}$ is a ($C_1$–$C_4$)alkyl, phenyl, naphthyl, pyrrolyl or indolyl group, where the ($C_1$–$C_4$)alkyl group is unsubstituted or substituted with one or more substituents independently selected from halo, $C_1$–$C_4$ alkoxy or $C_1$–$C_4$ haloalkoxy and the phenyl, naphthyl, pyrrolyl or indolyl group is unsubstituted or substituted with one or more substituents independently selected from halo, $C_1$–$C_4$ alkyl, $C_1$–$C_4$ haloalkyl, $C_1$–$C_4$ alkoxy, $C_1$–$C_4$ haloalkoxy, methylenedioxy, aryl, heterocycloalkyl, and heteroaryl, where the aryl, heterocycloalkyl or heteroaryl is unsubstituted or substituted by one ore more substituents independently selected from halo, $C_1$–$C_4$ alkyl, $C_1$–$C_4$ haloalkyl, $C_1$–$C_4$ alkoxy, $C_1$–$C_4$ haloalkoxy and methylenedioxy; more preferably, $R^{a'}$ is a pyrrolyl or indolyl group, where the pyrrolyl or indolyl group is unsubstituted or substituted by one or more substituents independently selected from halo, $C_1$–$C_4$ alkyl, $C_1$–$C_4$ haloalkyl or a phenyl, naphthyl, isoxazolyl, pyridyl, quinoyl or isoquinoyl group, where the phenyl, naphthyl, isoxazolyl, pyridyl, quinoyl or isoquinoyl group is unsubstituted or substituted with one or more substituents independently selected from halo, $C_1$–$C_4$ alkyl, $C_1$–$C_4$ haloalkyl, $C_1$–$C_4$ alkoxy, $C_1$–$C_4$ haloalkoxy and methylenedioxy; even more preferably, $R^{a'}$ is a pyrrolyl group that is unsubstituted or substituted by phenyl, α-naphthyl, β-naphthyl, 2-chlorophenyl, 2-α,α,α-trifluoromethylphenyl, 3-chloro-6-methoxyphenyl, 2,3-dichlorophenyl, 4-isoquinoyl, 3-iso-propylphenyl, 2,5-dimethoxyphenyl, 2-methoxyphenyl, 2-methylphenyl (o-tolyl), 2-bromophenyl, 3-pyridyl, 4-pyridyl, 3-methylisoxazol-5-yl, 3,3,3-trifluoroprop-1-yl, or 2,3-benzo[d]dioxolyl;

n is 1, 2 or 3; preferably n is 1;

$R^x$ is H and $R^y$ is H, $C_1$–$C_4$ alkyl, $C_1$–$C_4$ haloalkyl or an arylalkyl, heteroarylalkyl, cycloalkylalkyl group or a straight-chain saturated hydrocarbon moiety or an unsaturated hydrocarbon moiety, where the arylalkyl, heteroarylalkyl, cycloalkylalkyl group is unsubstituted or substituted with one or more suitable substituents; preferably, $R^x$ is H and $R^y$ is substituted or unsubstituted methyl, ethyl, n-propyl, iso-propyl, n-butyl, sec-butyl, iso-butyl, 2-propen-1-yl, 2-propen-2-yl, 2-propyn-1-yl, 3-methyl-3-buten-1-yl, -methylcyclohexyl, -methylthienyl or benzyl, where the substituted methyl, ethyl, n-propyl, iso-propyl, n-butyl, sec-butyl, iso-butyl, 2-propen-1-yl, 2-propen-2-yl, 2-propyn-1-yl, 3-methyl-3-buten-1-yl, and -methylcyclohexyl is substituted by one or more substituents independently selected from halo, alkoxy, aryloxy, alkylthio and arylthio; the subsituted thienyl is substituted by one or more substituents independently selected from lower alkyl, lower alkoxy, hydroxy, amino, alkylamino, dialkylamino and halo; and the phenyl moiety of the substituted benzyl is substituted by one or more substituents independently selected from lower alkyl, lower alkoxy, alkylenedioxy, hydroxy, amino, alkylamino, dialkylamino and halo; more preferably, $R^x$ is H and $R^y$ is ethyl, n-propyl, iso-propyl, n-butyl, sec-butyl, iso-butyl, 2-propen-1-yl, 2-propen-2-yl, 2-propyn-1-yl, 3-methyl-3-buten-1-yl, -methylcyclohexyl, benzyl or substituted benzyl, wherein the phenyl moiety of the substituted benzyl comprises one or more substituents independently selected from $C_1$–$C_4$ alkyl, $C_1$–$C_4$ alkoxy and halo; even more preferably, where $R^x$ is H and $R^y$ is H, ethyl, 2-propyn-1-yl, methylcyclohexyl or benzyl;

$R^c$ is

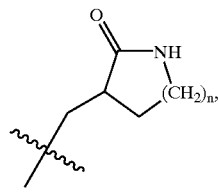

where n is 1 or 2; preferably $R^c$ is

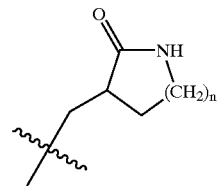

where n is 1; more preferably, $R^c$ is

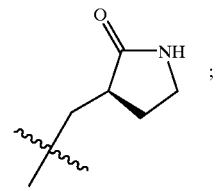

and $R^b$, $R^d$, Z and $Z^1$ are defined as in Formula I, above.

Another embodiment of this invention comprises compounds having the formula:

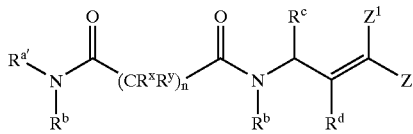

IV wherein:

$R^{a'}$ is a $(C_1$–$C_4)$alkyl, $(C_3$–$C_8)$cycloalkyl, heterocycloalkyl, aryl or heteroaryl group, wherein the $(C_1$–$C_4)$alkyl, $(C_3$–$C_8)$cycloalkyl, heterocycloalkyl, aryl and heteroaryl group is unsubstituted or substituted with one or more suitable substituents; preferably, $R^{a'}$ is a $(C_1$–$C_4)$alkyl, phenyl or naphthyl group, where the $(C_1$–$C_4)$alkyl group is unsubstituted or substituted with one or more substituents independently selected from halo, $C_1$–$C_4$ alkoxy or $C_1$–$C_4$ haloalkoxy and the phenyl or naphthyl group is unsubstituted or substituted with one or more substituents independently selected from halo, $C_1$–$C_4$ alkyl, $C_1$–$C_4$ haloalkyl, $C_1$–$C_4$ alkoxy, $C_1$–$C_4$ haloalkoxy, methylenedioxy and phenyl, where the phenyl is unsubstituted or substituted by one or more substituents independently selected from halo, $C_1$–$C_4$ alkyl, $C_1$–$C_4$ haloalkyl, $C_1$–$C_4$ alkoxy, $C_1$–$C_4$ haloalkoxy and methylenedioxy; in specific embodiments, $R^{a'}$ is a halo-substituted phenyl group;

n is 1, 2 or 3; preferably, n is 1 or 2; more preferably, n is 1;

$R^x$ is H and $R^y$ is H, $C_1$–$C_4$ alkyl, $C_1$–$C_4$ haloalkyl or an arylalkyl, heteroarylalkyl, cycloalkylalkyl group or a straight-chain saturated hydrocarbon moiety or an unsaturated hydrocarbon moiety, where the arylalkyl, heteroarylalkyl, cycloalkylalkyl group is unsubstituted or substituted with one or more suitable substituents; preferably, $R^x$ is H and $R^y$ is substituted or unsubstituted methyl, ethyl, n-propyl, iso-propyl, n-butyl, sec-butyl, iso-butyl, 2-propen-1-yl, 2-propen-2-yl, 2-propyn-1-yl, 3-methyl-3-buten-1-yl, -methylcyclohexyl, -methylthienyl or benzyl, where the substituted methyl, ethyl, n-propyl, iso-propyl, n-butyl, sec-butyl, iso-butyl, 2-propen-1-yl, 2-propen-2-yl, 2-propyn-1-yl, 3-methyl-3-buten-1-yl, and -methylcyclohexyl is substituted by one or more substituents independently selected from halo, alkoxy, aryloxy, alkylthio and arylthio; the subsituted thienyl is substituted by one or more substituents independently selected from lower alkyl, lower alkoxy, hydroxy, amino, alkylamino, dialkylamino and halo; and the phenyl moiety of the substituted benzyl is substituted by one or more substituents independently selected from lower alkyl, lower alkoxy, alkylenedioxy, hydroxy, amino, alkylamino, dialkylamino and halo; more preferably, $R^x$ is H and $R^y$ is ethyl, n-propyl, iso-propyl, n-butyl, sec-butyl, iso-butyl, 2-propen-1-yl, 2-propen-2-yl, 2-propyn-1-yl, 3-methyl-3-buten-1-yl, -methylcyclohexyl, benzyl or substituted benzyl, wherein the phenyl moiety of the substituted benzyl comprises one or more substituents independently selected from $C_1$–$C_4$ alkyl, $C_1$–$C_4$ alkoxy and halo; even more preferably, where $R^x$ is H and $R^y$ is H, ethyl, 2-propyn-1-yl, methylcyclohexyl or benzyl; and and $R^b$, $R^c$, $R^d$, Z and $Z^1$ are defined as in Formula I, above.

Other specific embodiments of this invention comprise the compounds having the formula:

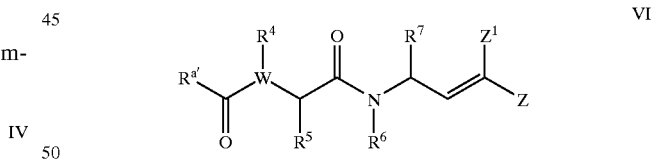

VI wherein:

W is CH or N;

$R^{a'}$ is a $C_1$–$C_4$ alkyl, $C_3$–$C_8$ cycloalkyl, aryl or heteroaryl group, where the $C_1$–$C_4$ alkyl, $C_3$–$C_8$ cycloalkyl, aryl, and heteroaryl group is unsubstituted or substituted with one or more suitable substituents, provided that $R^{a'}$ is not an amino-substituted alkyl group; preferably, $R^{a'}$ is a $C_1$–$C_4$ alkyl, $C_5$–$C_6$ cycloalkyl, phenyl, naphthyl or heteroaryl group, where the phenyl, naphthyl or heteroaryl group is unsubstituted or substituted with one or more substituents independently selected from halo, $C_1$–$C_4$ alkyl, $C_1$–$C_4$ haloalkyl, $C_1$–$C_4$ alkoxy, $C_1$–$C_4$ haloalkoxy, methylenedioxy, aryl, heterocycloalkyl, and heteroaryl, where the aryl, heterocycloalkyl and heteroaryl is unsubstituted or substituted by one ore more substituents independently selected from halo, $C_1$–$C_4$ alkyl, $C_1$–$C_4$ haloalkyl, $C_1$–$C_4$ alkoxy, $C_1$–$C_4$ haloalkoxy and methylenedioxy; more preferably, $R^{a'}$ is a $C_1$–$C_4$ alkyl, $C_5$–$C_6$ cycloalkyl, phenyl, naphthyl, pyrrolyl or indolyl, group, where the phenyl, naphthyl, pyrrolyl or indolyl, group is unsubstituted or substituted with one or more substituents independently selected from halo, $C_1$–$C_4$ alkyl, $C_1$–$C_4$ haloalkyl, $C_1$–$C_4$ alkoxy, $C_1$–$C_4$ haloalkoxy, methylenedioxy and a phenyl, naphthyl, isoquinoyl, pyridyl or isoxazolyl group, wherein the phenyl, naphthyl, isoquinoyl, pyridyl and isoxazolyl group is unsubstituted or substituted by one ore more substituents independently selected from halo, $C_1$–$C_4$ alkyl, $C_1$–$C_4$ haloalkyl, $C_1$–$C_4$ alkoxy, $C_1$–$C_4$ haloalkoxy and methylenedioxy;

$R^4$ and $R^6$ are each independently H or $C_1$–$C_4$ alkyl; preferably $R^4$ and $R^6$ are each H;

$R^5$ is H, $C_1$–$C_4$ alkyl, $C_1$–$C_4$ haloalkyl or an arylalkyl, heteroarylalkyl, cycloalkylalkyl group or a straight-chain saturated hydrocarbon moiety or an unsaturated hydrocarbon moiety, where the arylalkyl, heteroarylalkyl, cycloalkylalkyl group is unsubstituted or substituted with one or more suitable substituents; preferably, $R^5$ is H or substituted or unsubstituted methyl, ethyl, n-propyl, iso-propyl, n-butyl, sec-butyl, iso-butyl, 2-propen-1-yl, 2-propen-2-yl, 2-propyn-1-yl, 3-methyl-3-buten-1-yl, -methylcyclohexyl, -methylthienyl or benzyl, where the substituted methyl, ethyl, n-propyl, iso-propyl, n-butyl, sec-butyl, iso-butyl, 2-propen-1-yl, 2-propen-2-yl, 2-propyn-1-yl, 3-methyl-3-buten-1-yl, and -methylcyclohexyl is substituted by one or more substituents independently selected from halo, alkoxy, aryloxy, alkylthio and arylthio; the subsituted thienyl is substituted by one or more substituents independently selected from lower alkyl, lower alkoxy, hydroxy, amino, alkylamino, dialkylamino and halo; and the phenyl moiety of the substituted benzyl is substituted by one or more substituents independently selected from lower alkyl, lower alkoxy, alkylenedioxy, hydroxy, amino, alkylamino, dialkylamino and halo; more preferably, $R^5$ is H, ethyl, n-propyl, iso-propyl, n-butyl, sec-butyl, iso-butyl, 2-propen-1-yl, 2-propen-2-yl, 2-propyn-1-yl, 3-methyl-3-buten-1-yl, -methylcyclohexyl, benzyl or substituted benzyl, wherein the phenyl moiety of the substituted benzyl comprises one or more substituents independently selected from $C_1$–$C_4$ alkyl, $C_1$–$C_4$ alkoxy and halo; even more preferably, $R^5$ is H, ethyl, 2-propyn-1-yl, methylcyclohexyl or benzyl;

$R^7$ is

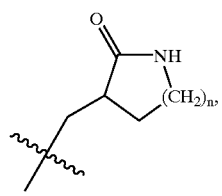

where n is 1 or 2; preferably, $R^7$ is

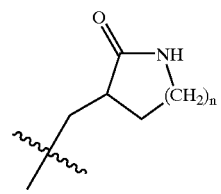

where n is 1; most preferably, $R^7$ is

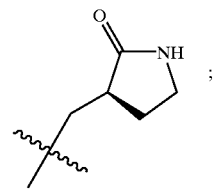

and $Z^1$ is H or $C_1$–$C_4$ alkyl and Z is —$CO_2$-alkyl, —$CO_2$-cycloalkyl, —$CO_2$-alkylaryl or —$CO_2$-alkylheterocycloaryl, or $Z^1$ and Z taken together with the atom to which they are attached form

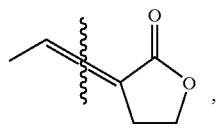

preferably, $Z^1$ is H and Z is —$CO_2CH_2CH_3$, —$CO_2(CH(CH_3)_2)$, —$CO_2(C(CH_3)_3)$, —$CO_2CH_2(C(CH_3)_3)$, —$CO_2$(cyclo-$C_5H_9$) or $Z^1$ and Z taken together with the atom to which they are attached form

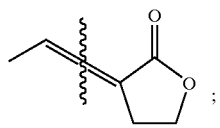

most preferably, $Z^1$ is H and Z is —$CO_2CH_2CH_3$ or $Z^1$ and Z taken together with the atom to which they are attached form

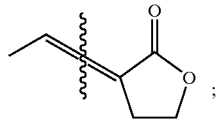

or a prodrug, pharmaceutically acceptable salt, pharmaceutically active metabolite, or pharmaceutically acceptable solvate of said compound.

Specific embodiments of Formula VI of this invention comprise the compounds depicted by the formula:

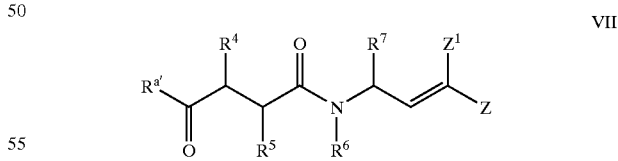

VII and the compounds depicted by the formula:

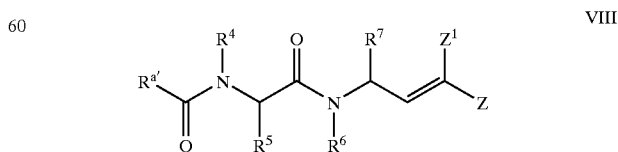

VIII wherein $R^{a'}$, $R^4$, $R^5$, $R^6$, $R^7$, Z and $Z^1$ are as defined above.

In addition, specific embodiments of this invention comprise the compounds depicted by the formula:

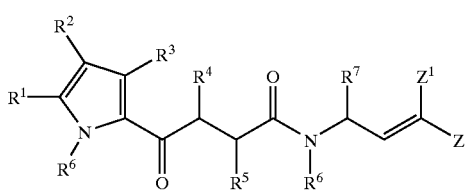

IX wherein:

$R^1$ is H, halo, $C_1$–$C_4$ alkyl, $C_1$–$C_4$ haloalkyl, or an aryl or heteroaryl group, where the aryl or heteroaryl group is unsubstituted or substituted with one or more suitable substituents; preferably, $R^1$ is H, halo, $C_1$–$C_4$ alkyl, $C_1$–$C_4$ haloalkyl or a phenyl, naphthyl, isoxazolyl, pyridyl, quinoyl or isoquinoyl group, where the phenyl, naphthyl, isoxazolyl, pyridyl, quinoyl or isoquinoyl group is unsubstituted or substituted with one or more substituents independently selected from: halo, $C_1$–$C_4$ alkyl, $C_1$–$C_4$ haloalkyl, $C_1$–$C_4$ alkoxy, $C_1$–$C_4$ haloalkoxy and methylenedioxy; more preferably, $R^1$ is H, phenyl, α-naphthyl, β-naphthyl, 2-chlorophenyl, 2-α,α,α-trifluoromethylphenyl, 3-chloro-6-methoxyphenyl, 2,3-dichlorophenyl, 4-isoquinoyl, 3-isopropylphenyl, 2,5-dimethoxyphenyl, 2-methoxyphenyl, 2-methylphenyl (o-tolyl), 2-bromophenyl, 3-pyridyl, 4-pyridyl, 3-methyl-isoxazol-5-yl, 3,3,3-trifluoroprop-1-yl, or 2,3-benzo[d]dioxolyl;

$R^2$ and $R^3$ are each independently H or $C_1$–$C_4$ alkyl; preferably $R^2$ and $R^3$ are each H; or $R^1$ together with $R^2$ form a cycloalkyl, heterocycloalkyl, aryl or heteroaryl ring, where the cycloalkyl, heterocycloalkyl, aryl or heteroaryl ring is unsubstituted or substituted with one or more suitable substituents; or preferably, $R^1$ together with $R^2$ form a phenyl ring, which is unsubstituted or substituted with one or more suitable substituents and $R^3$ is H;

$R^4$ and $R^6$ are each independently H or $C_1$–$C_4$ alkyl; preferably $R^4$ and $R^6$ are each H;

$R^5$ is H, $C_1$–$C_4$ alkyl, $C_1$–$C_4$ haloalkyl or an arylalkyl, heteroarylalkyl, cycloalkylalkyl group or a straight-chain saturated hydrocarbon moiety or an unsaturated hydrocarbon moiety, where the arylalkyl, heteroarylalkyl, cycloalkylalkyl group is unsubstituted or substituted with one or more suitable substituents; preferably, $R^5$ is H or substituted or unsubstituted methyl, ethyl, n-propyl, iso-propyl, n-butyl, sec-butyl, iso-butyl, 2-propen-1-yl, 2-propen-2-yl, 2-propyn-1-yl, 3-methyl-3-buten-1-yl, -methylcyclohexyl, -methylthienyl or benzyl, where the substituted methyl, ethyl, n-propyl, iso-propyl, n-butyl, sec-butyl, iso-butyl, 2-propen-1-yl, 2-propen-2-yl, 2-propyn-1-yl, 3-methyl-3-buten-1-yl, and -methylcyclohexyl is substituted by one or more substituents independently selected from halo, alkoxy, aryloxy, alkylthio and arylthio; the subsituted thienyl is substituted by one or more substituents independently selected from lower alkyl, lower alkoxy, hydroxy, amino, alkylamino, dialkylamino and halo; and the phenyl moiety of the substituted benzyl is substituted by one or more substituents independently selected from lower alkyl, lower alkoxy, alkylenedioxy, hydroxy, amino, alkylamino, dialkylamino and halo; more preferably, $R^5$ is H, ethyl, n-propyl, iso-propyl, n-butyl, sec-butyl, iso-butyl, 2-propen-1-yl, 2-propen-2-yl, 2-propyn-1-yl, 3-methyl-3-buten-1-yl, -methylcyclohexyl, benzyl or substituted benzyl, wherein the phenyl moiety of the substituted benzyl comprises one or more substituents independently selected from $C_1$–$C_4$ alkyl, $C_1$–$C_4$ alkoxy and halo; even more preferably, $R^5$ is H, ethyl, 2-propyn-1-yl, methylcyclohexyl or benzyl;

$R^7$ is selected from —$CH_2CH_2C(O)NH_2$; —$CH_2CH_2C(O)NH$-alkyl; —$CH_2NHC(O)CH_3$; and

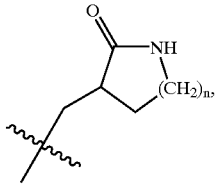

where n is 1 or 2; preferably, $R^7$ is —$CH_2CH_2C(O)NH_2$ or

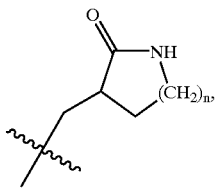

where n is 1; most preferably, $R^7$ is —$CH_2CH_2C(O)NH_2$ or

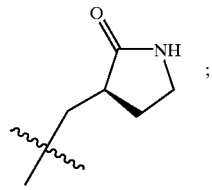

and $Z^1$ is H or $C_1$–$C_4$ alkyl and Z is —$CO_2$-alkyl, —$CO_2$-cycloalkyl, —$CO_2$-alkylaryl or —$CO_2$-alkylheterocycloaryl, or $Z^1$ and Z taken together with the atom to which they are attached form

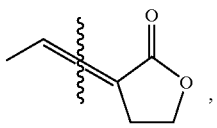

preferably, $Z^1$ is H and Z is —$CO_2CH_2CH_3$, —$CO_2(CH(CH_3)_2)$, —$CO_2(C(CH_3)_3)$, —$CO_2CH_2(C(CH_3)_3)$, —$CO_2$(cyclo-$C_5H_9$) or $Z^1$ and Z taken together with the atom to which they are attached form

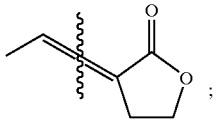

most preferably, $Z^1$ is H and Z is —$CO_2CH_2CH_3$ or $Z^1$ and Z taken together with the atom to which they are attached form

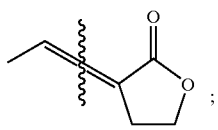

or a prodrug, pharmaceutically acceptable salt, pharmaceutically active metabolite, or pharmaceutically acceptable solvate of said compound.

Another specific embodiment of this invention comprises the compounds depicted by the formula:

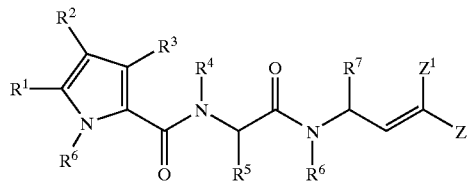

wherein:

$R^1$ is H, halo, $C_1$–$C_4$ alkyl, $C_1$–$C_4$ haloalkyl, or an aryl or heteroaryl group, where the aryl or heteroaryl group is unsubstituted or substituted with one or more suitable substituents; preferably, $R^1$ is H, halo, $C_1$–$C_4$ alkyl, $C_1$–$C_4$ haloalkyl or a phenyl, naphthyl, isoxazolyl, pyridyl, quinoyl or isoquinoyl group, where the phenyl, naphthyl, isoxazolyl, pyridyl, quinoyl or isoquinoyl group is unsubstituted or substituted with one or more substituents independently selected from: halo, $C_1$–$C_4$ alkyl, $C_1$–$C_4$ haloalkyl, $C_1$–$C_4$ alkoxy, $C_1$–$C_4$ haloalkoxy and methylenedioxy; more preferably, $R^1$ is H, phenyl, α-naphthyl, β-naphthyl, 2-chlorophenyl, 2-α,α,α-trifluoromethylphenyl, 3-chloro-6-methoxyphenyl, 2,3-dichlorophenyl, 4-isoquinoyl, 3-isopropylphenyl, 2,5-dimethoxyphenyl, 2-methoxyphenyl, 2-methylphenyl (o-tolyl), 2-bromophenyl, 3-pyridyl, 4-pyridyl, 3-methyl-isoxazol-5-yl, 3,3,3-trifluoroprop-1-yl, or 2,3-benzo[d]dioxolyl;

$R^2$ and $R^3$ are each independently H or $C_1$–$C_4$ alkyl; preferably $R^2$ and $R^3$ are each H; or $R^1$ together with $R^2$ form a cycloalkyl, heterocycloalkyl, aryl or heteroaryl ring, where the cycloalkyl, heterocycloalkyl, aryl or heteroaryl ring is unsubstituted or substituted with one or more suitable substituents; or preferably, $R^1$ together with $R^2$ form an unsubstituted phenyl ring and $R^3$ is H;

$R^4$ and $R^6$ are each independently H or $C_1$–$C_4$ alkyl; preferably $R^4$ and $R^6$ are each H;

$R^5$ is H, $C_1$–$C_4$ alkyl, $C_1$–$C_4$ haloalkyl or an arylalkyl, heteroarylalkyl, cycloalkylalkyl group or a straight-chain saturated hydrocarbon moiety or an unsaturated hydrocarbon moiety, where the arylalkyl, heteroarylalkyl, cycloalkylalkyl group is unsubstituted or substituted with one or more suitable substituents; preferably, $R^5$ is H or substituted or unsubstituted methyl, ethyl, n-propyl, iso-propyl, n-butyl, sec-butyl, iso-butyl, 2-propen-1-yl, 2-propen-2-yl, 2-propyn-1-yl, 3-methyl-3-buten-1-yl, -methylcyclohexyl, -methylthienyl or benzyl, where the substituted methyl, ethyl, n-propyl, iso-propyl, n-butyl, sec-butyl, iso-butyl, 2-propen-1-yl, 2-propen-2-yl, 2-propyn-1-yl, 3-methyl-3-buten-1-yl, and -methylcyclohexyl is substituted by one or more substituents independently selected from halo, alkoxy, aryloxy, alkylthio and arylthio; the subsituted thienyl is substituted by one or more substituents independently selected from lower alkyl, lower alkoxy, hydroxy, amino, alkylamino, dialkylamino and halo; and the phenyl moiety of the substituted benzyl is substituted by one or more substituents independently selected from lower alkyl, lower alkoxy, alkylenedioxy, hydroxy, amino, alkylamino, dialkylamino and halo; more preferably, $R^5$ is H, ethyl, n-propyl, iso-propyl, n-butyl, sec-butyl, iso-butyl, 2-propen-1-yl, 2-propen-2-yl, 2-propyn-1-yl, 3-methyl-3-buten-1-yl, -methylcyclohexyl, benzyl or substituted benzyl, wherein the phenyl moiety of the substituted benzyl comprises one or more substituents independently selected from $C_1$–$C_4$ alkyl, $C_1$–$C_4$ alkoxy and halo; even more preferably, $R^5$ is H, ethyl, 2-propyn-1-yl, methylcyclohexyl or benzyl;

$R^7$ is selected from —$CH_2CH_2C(O)NH_2$; —$CH_2CH_2C(O)NH$-alkyl; —$CH_2NHC(O)CH_3$; and

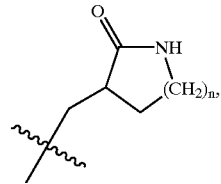

where n is 1 or 2; preferably, $R^7$ is —$CH_2CH_2C(O)NH_2$ or

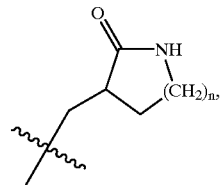

where n is 1; most preferably, $R^7$ is —$CH_2CH_2C(O)NH_2$ or

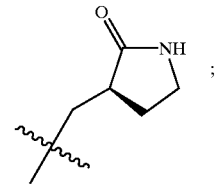

provided that when $R^1$ together with $R^2$ form a phenyl ring and the phenyl ring is substituted, $R^7$ is selected from

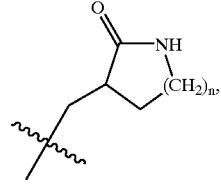

where n is 1 or 2,

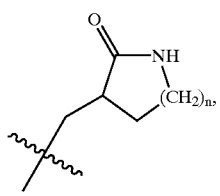

where n is 1, or

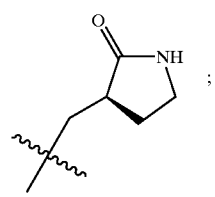

and $Z^1$ is H or $C_1$–$C_4$ alkyl and Z is —$CO_2$-alkyl, —$CO_2$-cycloalkyl, —$CO_2$-alkylaryl or —$CO_2$-alkylheterocycloaryl, or $Z^1$ and Z taken together with the atom to which they are attached form

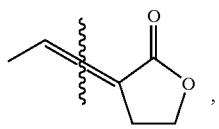

preferably, $Z^1$ is H and Z is —$CO_2CH_2CH_3$, —$CO_2$(CH($CH_3$)$_2$), —$CO_2$(C($CH_3$)$_3$), —$CO_2CH_2$(C($CH_3$)$_3$), —$CO_2$(cyclo-$C_5H_9$) or $Z^1$ and Z taken together with the atom to which they are attached form

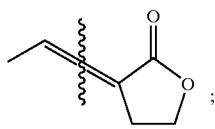

most preferably, $Z^1$ is H and Z is —$CO_2CH_2CH_3$ or $Z^1$ and Z taken together with the atom to which they are attached form

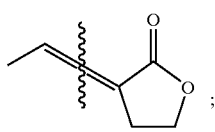

or a prodrug, pharmaceutically acceptable salt, pharmaceutically active metabolite, or pharmaceutically acceptable solvate of said compound.

Yet another specific embodiment of this invention comprises the compounds depicted by the formula:

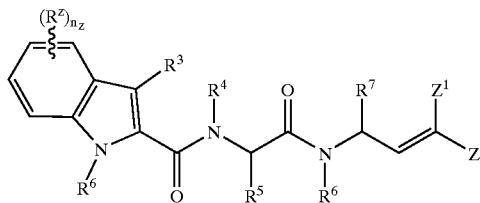

XI wherein:

each $R^z$ is independently selected from halo and a $C_1$–$C_4$ alkoxy, $C_1$–$C_4$ alkyl, aryl, heterocycloalkyl or heteroaryl group where the $C_1$–$C_4$ alkoxy or $C_1$–$C_4$ alkyl group is unsubstituted or substituted with one or more substituents independently selected from halo, $C_1$–$C_4$ alkoxy or $C_1$–$C_4$ haloalkoxy and the aryl, heterocycloalkyl or heteroaryl group is unsubstituted or substituted by one ore more substituents independently selected from halo, $C_1$–$C_4$ alkyl, $C_1$–$C_4$ haloalkyl, $C_1$–$C_4$ alkoxy, $C_1$–$C_4$ haloalkoxy and methylenedioxy and $n_z$ is an integer from 1 to 4; preferably, each $R^z$ is independently selected from halo, $C_1$–$C_4$ alkoxy, unsubstituted $C_1$–$C_4$ alkyl, $C_1$–$C_4$ haloalkyl, and $C_1$–$C_4$ alkoxyalkyl and $n_z$ is an integer from 1 to 2; more preferably, each $R^z$ is independently selected from halo, $C_1$–$C_4$ alkoxy, unsubstituted $C_1$–$C_4$ alkyl and $C_1$–$C_4$ haloalkyl, and $n_z$ is 1 or 2;

$R^3$ is H, halo, $C_1$–$C_4$ alkoxy, unsubstituted $C_1$–$C_4$ alkyl, $C_1$–$C_4$ haloalkyl and $C_1$–$C_4$ alkoxyalkyl; preferably, $R^3$ is H or $C_1$–$C_4$ alkyl; more preferably, $R^3$ is H;

$R^4$ and each $R^6$ are independently selected from H, unsubstituted lower alkyl, haloalkyl and lower alkoxyalkyl, preferably, $R^4$ and each $R^6$ are independently H or $C_1$–$C_4$ alkyl; more preferably $R^4$ and $R^6$ are each H;

$R^5$ is H, $C_1$–$C_4$ alkyl, $C_1$–$C_4$ haloalkyl or an arylalkyl, heteroarylalkyl, cycloalkylalkyl group or a straight-chain saturated hydrocarbon moiety or an unsaturated hydrocarbon moiety, where the arylalkyl, heteroarylalkyl, cycloalkylalkyl group is unsubstituted or substituted with one or more suitable substituents; preferably, $R^5$ is H or substituted or unsubstituted methyl, ethyl, n-propyl, iso-propyl, n-butyl, sec-butyl, iso-butyl, 2-propen-1-yl, 2-propen-2-yl, 2-propyn-1-yl, 3-methyl-3-buten-1-yl, -methylcyclohexyl, -methylthienyl or benzyl, where the substituted methyl, ethyl, n-propyl, iso-propyl, n-butyl, sec-butyl, iso-butyl, 2-propen-1-yl, 2-propen-2-yl, 2-propyn-1-yl, 3-methyl-3-buten-1-yl, and -methylcyclohexyl is substituted by one or more substituents independently selected from halo, alkoxy, aryloxy, alkylthio and arylthio; the subsituted thienyl is substituted by one or more substituents independently selected from lower alkyl, lower alkoxy, hydroxy, amino, alkylamino, dialkylamino and halo; and the phenyl moiety of the substituted benzyl is substituted by one or more substituents independently selected from lower alkyl, lower alkoxy, alkylenedioxy, hydroxy, amino, alkylamino, dialkylamino and halo; more preferably, $R^5$ is H, ethyl, n-propyl, iso-propyl, n-butyl, sec-butyl, iso-butyl, 2-propen-1-yl, 2-propen-2-yl, 2-propyn-1-yl, 3-methyl-3-buten-1-yl, -methylcyclohexyl, benzyl or substituted benzyl, wherein the phenyl moiety of the substituted benzyl comprises one or more substituents independently selected from $C_1$–$C_4$ alkyl, $C_1$–$C_4$ alkoxy and halo; even more preferably, $R^5$ is H, ethyl, 2-propyn-1-yl, methylcyclohexyl or benzyl;

$R^7$ is

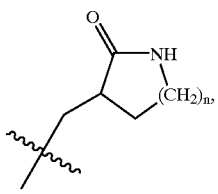

where n is 1 or 2; preferably, $R^7$ is

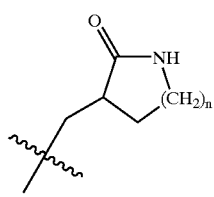

where n is 1; most preferably, $R^7$ is

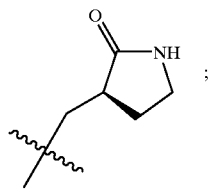

and $Z^1$ is H or $C_1$–$C_4$ alkyl and Z is —$CO_2$-alkyl, —$CO_2$-cycloalkyl, —$CO_2$-alkylaryl or —$CO_2$-alkylheterocycloaryl, or $Z^1$ and Z taken together with the atom to which they are attached form

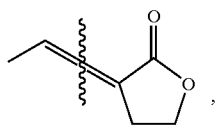

preferably, $Z^1$ is H and Z is —$CO_2CH_2CH_3$, —$CO_2(CH(CH_3)_2)$, —$CO_2(C(CH_3)_3)$, —$CO_2CH_2(C(CH_3)_3)$, —$CO_2$(cyclo-$C_5H_9$) or $Z^1$ and Z taken together with the atom to which they are attached form

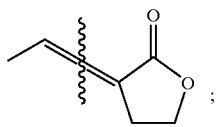

most preferably, $Z^1$ is H and Z is —$CO_2CH_2CH_3$ or $Z^1$ and Z taken together with the atom to which they are attached form

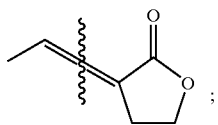

or a prodrug, pharmaceutically acceptable salt, pharmaceutically active metabolite, or pharmaceutically acceptable solvate of said compound.

Another preferred embodiment of this invention comprises the compounds of Formula XII, depicted by the formula:

XII

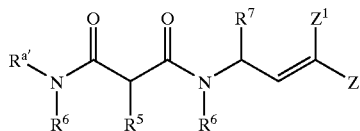

wherein:

$R^{a'}$ is a $C_1$–$C_4$ alkyl, aryl, $C_3$–$C_7$ cycloalkyl, heterocycloalkyl or heteroaryl group, where the $C_1$–$C_4$ alkyl, aryl, $C_3$–$C_7$ cycloalkyl, heterocycloalkyl or heteroaryl group is unsubstituted or substituted with one or more substituents independently selected from alkyl, haloalkyl, alkylenedioxy (as a substituent for aryl or heteroaryl), nitro, amino, hydroxamino, alkylamino, dialkylamino, halo, hydroxyl, alkoxy, haloalkoxy, aryloxy, mercapto, alkylthio or arylthio, aryl or heteroaryl, where the aryl or heteroaryl group is unsubstituted or substituted with one or more substituents independently selected from halo, $C_1$–$C_4$ alkyl, $C_1$–$C_4$ haloalkyl, $C_1$–$C_4$ alkoxy, $C_1$–$C_4$ haloalkoxy and methylenedioxy; preferably, $R^{a'}$ is a $C_1$–$C_4$ alkyl, $C_1$–$C_4$ haloalkyl, phenyl, naphthyl, $C_5$–$C_6$ cycloalkyl, isoquinoyl, pyridyl or pyrrolyl group, where the phenyl, naphthyl, isoquinoyl, pyridyl or pyrrolyl group is unsubstituted or substituted with one or more substituents independently selected from halo, $C_1$–$C_4$ alkyl, $C_1$–$C_4$ haloalkyl, $C_1$–$C_4$ alkoxy, $C_1$–$C_4$ haloalkoxy and methylenedioxy; more preferably, $R^{a'}$ is a phenyl group, where the phenyl group is unsubstituted or substituted with one or more substituents independently selected from halo, $C_1$–$C_4$ alkyl, $C_1$–$C_4$ haloalkyl or $C_1$–$C_4$ alkoxy;

each $R^6$ is independently H or $C_1$–$C_4$ alkyl; preferably, each $R^6$ is H;

$R^5$ is H, $C_1$–$C_4$ alkyl, $C_1$–$C_4$ haloalkyl or an arylalkyl, heteroarylalkyl, cycloalkylalkyl group or a straight-chain saturated hydrocarbon moiety or an unsaturated hydrocarbon moiety, where the arylalkyl, heteroarylalkyl, cycloalkylalkyl group is unsubstituted or substituted with one or more suitable substituents; preferably, $R^5$ is H or substituted or unsubstituted methyl, ethyl, n-propyl, iso-propyl, n-butyl, sec-butyl, iso-butyl, 2-propen-1-yl, 2-propen-2-yl, 2-propyn-1-yl, 3-methyl-3-buten-1-yl, -methylcyclohexyl, -methylthienyl or benzyl, where the substituted methyl, ethyl, n-propyl, iso-propyl, n-butyl, sec-butyl, iso-butyl, 2-propen-1-yl, 2-propen-2-yl, 2-propyn-1-yl, 3-methyl-3-buten-1-yl, and -methylcyclohexyl is substituted by one or more substituents independently selected from halo, alkoxy, aryloxy, alkylthio and arylthio; the subsituted thienyl is substituted by one or more substituents independently selected from lower alkyl, lower alkoxy, hydroxy, amino, alkylamino, dialkylamino and halo; and the phenyl moiety of the substituted benzyl is substituted by one or more substituents independently selected from lower alkyl, lower alkoxy, alkylenedioxy, hydroxy, amino, alkylamino, dialkylamino and halo; more preferably, $R^5$ is H, ethyl, n-propyl, iso-propyl, n-butyl, sec-butyl, iso-butyl, 2-propen-1-yl, 2-propen-2-yl, 2-propyn-1-yl, 3-methyl-3-buten-1-yl, -methylcyclohexyl, benzyl or substituted benzyl, wherein the phenyl moiety of the substituted benzyl comprises one or more substituents independently selected from $C_1$–$C_4$ alkyl, $C_1$–$C_4$ alkoxy and halo; even more preferably, $R^5$ is H, ethyl, 2-propyn-1-yl, methylcyclohexyl or benzyl;

$R^7$ is selected from —$CH_2CH_2C(O)NH_2$; —$CH_2CH_2C(O)NH$-alkyl; —$CH_2NHC(O)CH_3$; and

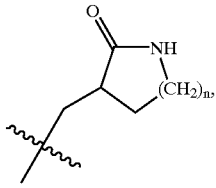

where n is 1 or 2; preferably, $R^7$ is —$CH_2CH_2C(O)NH_2$ or

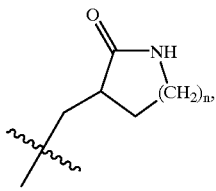

where n is 1; most preferably, $R^7$ is —$CH_2CH_2C(O)NH_2$ or

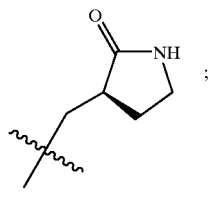

and $Z^1$ is H or $C_1$–$C_4$ alkyl and Z is —$CO_2$-alkyl, —$CO_2$-cycloalkyl, —$CO_2$-alkylaryl or —$CO_2$-alkylheterocycloaryl, or $Z^1$ and Z taken together with the atom to which they are attached form

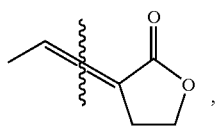

preferably, $Z^1$ is H and Z is —$CO_2CH_2CH_3$, —$CO_2(CH(CH_3)_2)$, —$CO_2(C(CH_3)_3)$, —$CO_2CH_2(C(CH_3)_3)$, —$CO_2$(cyclo-$C_5H_9$) or $Z^1$ and Z taken together with the atom to which they are attached form

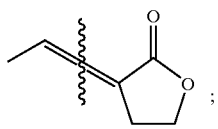

most preferably, $Z^1$ is H and Z is —$CO_2CH_2CH_3$ or $Z^1$ and Z taken together with the atom to which they are attached form

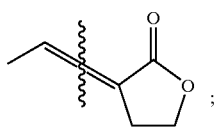

or a prodrug, pharmaceutically acceptable salt, pharmaceutically active metabolite, or pharmaceutically acceptable solvate of said compound.

Preferred embodiments of this invention comprise the compounds depicted by the formula:

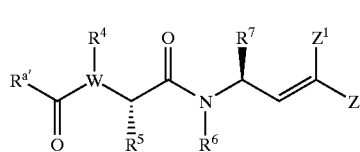

VI-a wherein $R^{a'}$ is an alkyl, cycloalkyl, aryl or heteroaryl group, where said alkyl, cycloalkyl, aryl, and heteroaryl group is unsubstituted or substituted with one or more suitable substituents, and each W, $R^4$, $R^5$, $R^6$, $R^7$, Z and $Z^1$ are as defined in VI above, provided that $R^{a'}$ is not amino-substituted alkyl.

Particularly preferred embodiments of the compounds of Formula VI-a comprise the compounds depicted by the formula:

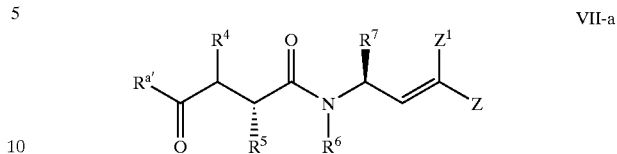

VII-a wherein $R^{a'}$ is an alkyl, cycloalkyl, aryl or heteroaryl group, where said alkyl, cycloalkyl, aryl, and heteroaryl group is unsubstituted or substituted with one or more suitable substituents, and each $R^4$, $R^5$, $R^6$, $R^7$, Z and $Z^1$ are as defined above, provided that $R^{a'}$ is not amino-substituted alkyl.

Other preferred embodiments of the compounds of Formula VI-a comprise the compounds depicted by the formula:

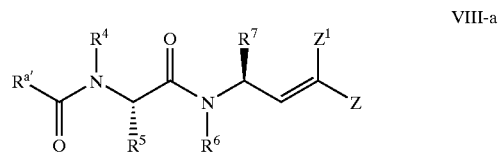

VIII-a wherein $R^{a'}$ is an alkyl, cycloalkyl, aryl or heteroaryl group, where said alkyl, cycloalkyl, aryl, and heteroaryl group is unsubstituted or substituted with one or more suitable substituents, and each $R^4$, $R^5$, $R^6$, $R^7$, Z and $Z^1$ are as defined above, provided that $R^{a'}$ is not amino-substituted alkyl.

More preferably, the compounds of this invention have the formula:

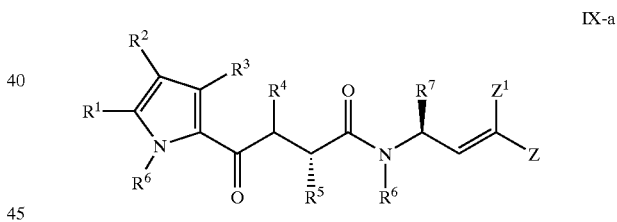

IX-a wherein $R^1$ is an alkyl, cycloalkyl, heterocycloalkyl, aryl or heteroaryl group, where the alkyl, cycloalkyl, heterocycloalkyl, aryl, and heteroaryl group is unsubstituted or substituted with one or more suitable substituents, and each $R^2$, $R^3$, $R^4$, $R^5$, $R^6$, $R^7$, Z and $Z^1$ are as defined above for IX.

In another preferred embodiment, the compounds of this invention have the formula:

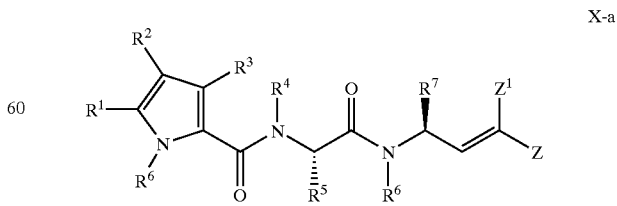

X-a wherein each $R^1$, $R^2$, $R^3$, $R^4$, $R^5$, $R^6$, $R^7$, Z and $Z^1$ are as defined above.

Yet another preferred embodiment of this invention comprises the compounds depicted by the formula:

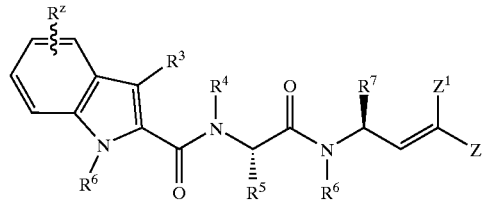

XI-a wherein each $R^z$, $R^3$, $R^4$, $R^5$, $R^6$, Z and $Z^1$ are as defined above and $R^7$ is a moiety having the formula:

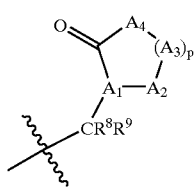

wherein each $R^8$, $R^9$, $A_1$, $A_2$, $A_3$, $A_4$ and p are as defined above.

Another particularly preferred embodiment of this invention comprises the compounds depicted by the formula:

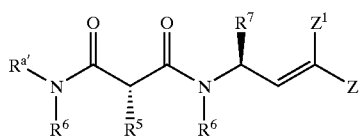

XII-a wherein each $R^{a'}$, $R^5$, $R^6$, $R^7$, Z and $Z^1$ are as defined above. More preferably, $R^5$ is H and the invention comprises the compounds depicted by the formula:

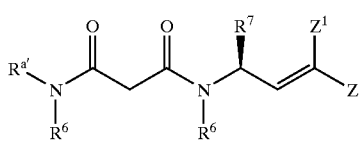

XII-b wherein each $R^{a'}$, $R^6$, $R^7$, Z and $Z^1$ are as defined above.

In the compounds of Formulas VI-a to XII-b, $R^6$ is preferably H. In the compounds of Formulas VI-a to XI-a, each $R^4$ and $R^6$ is preferably H.

Preferred specific compounds include those of any of the Examples below, especially:

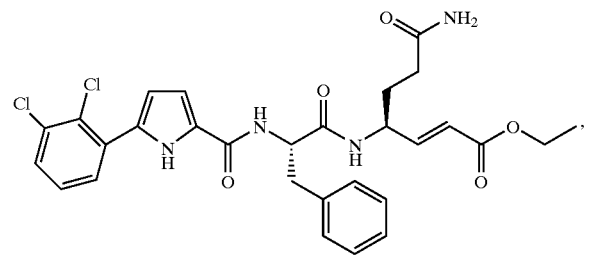

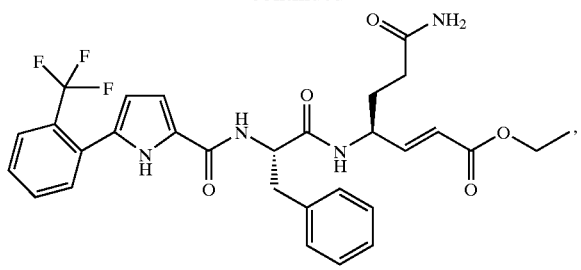

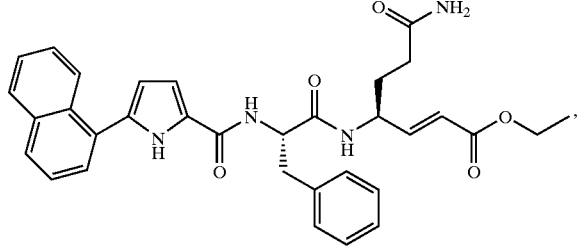

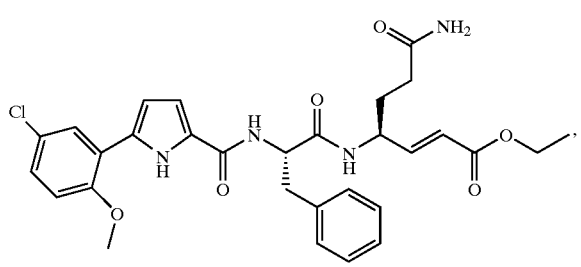

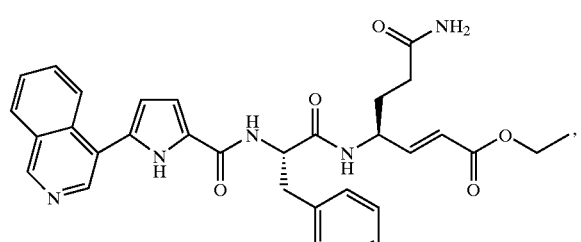

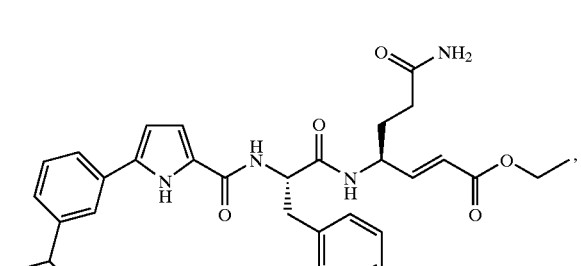

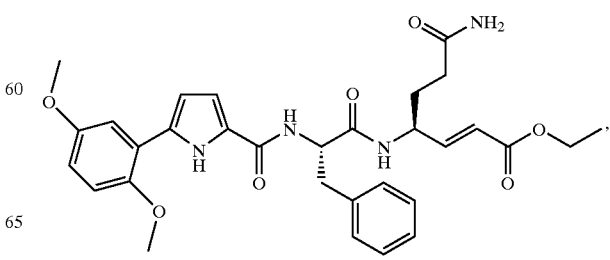

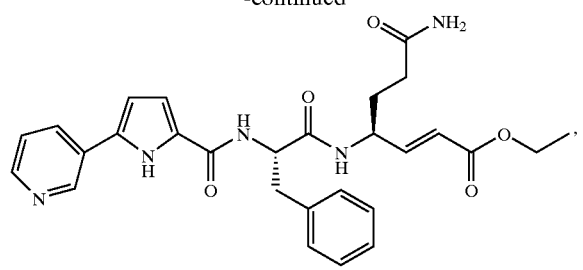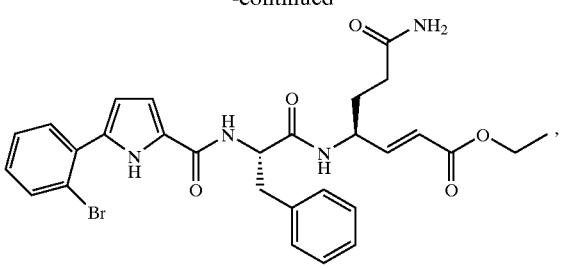

51
-continued
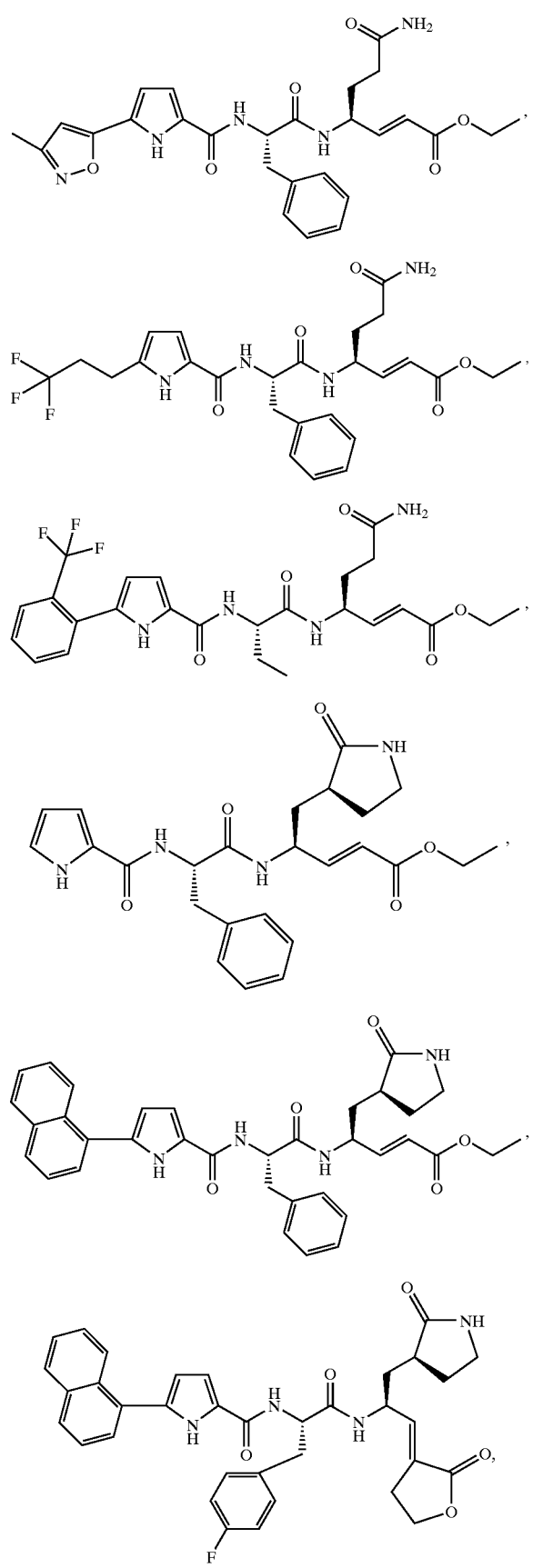
52
-continued
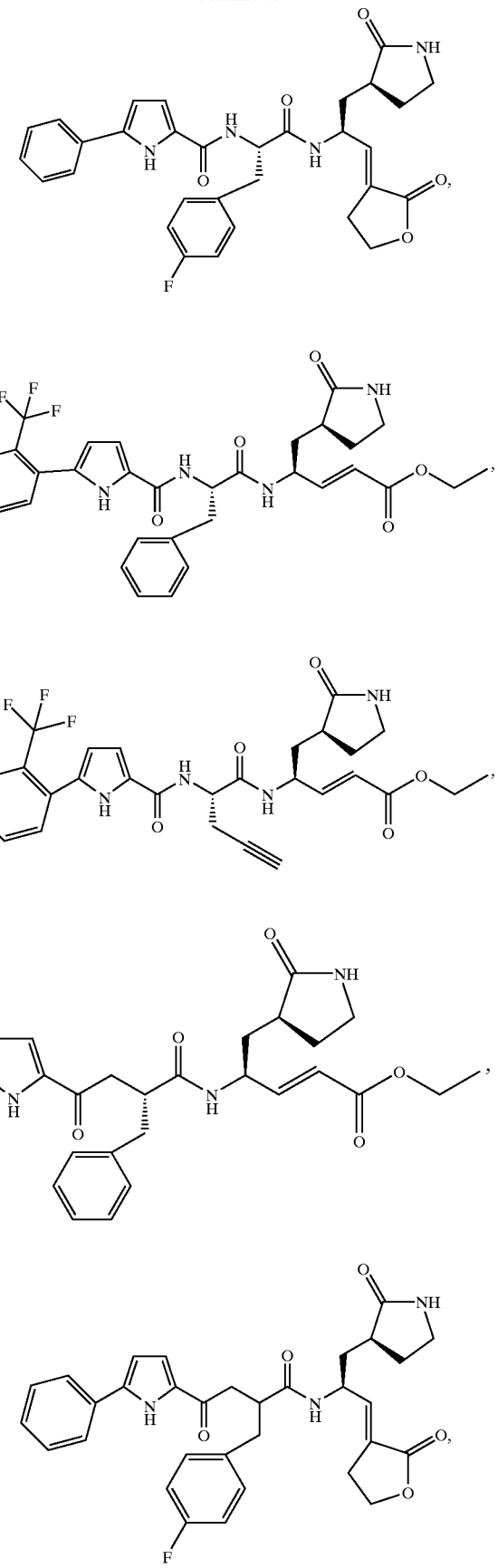

53
-continued
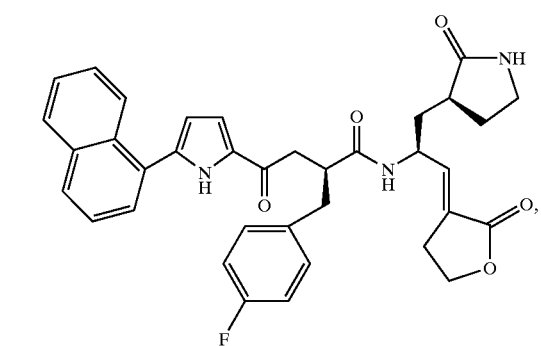
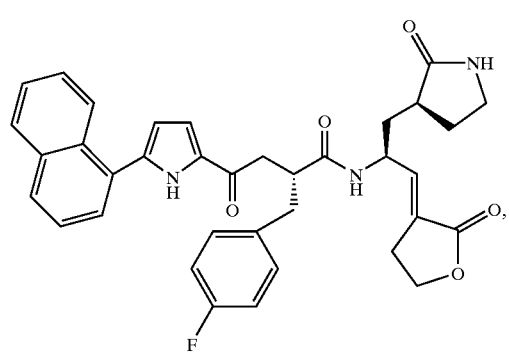
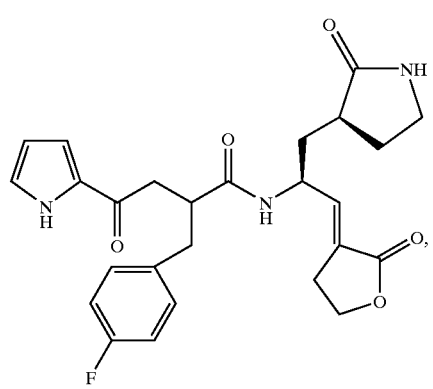
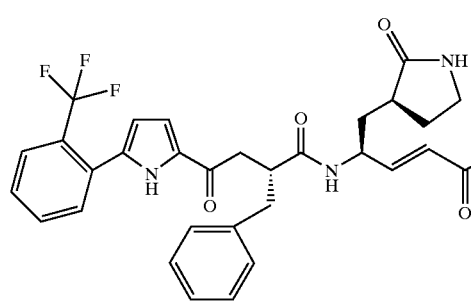
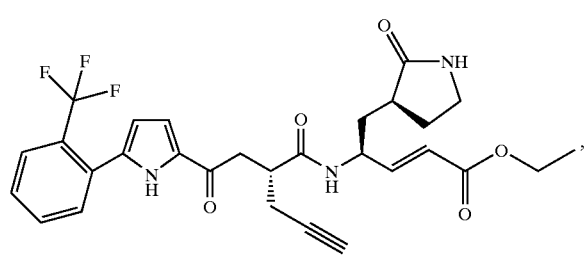
54
-continued
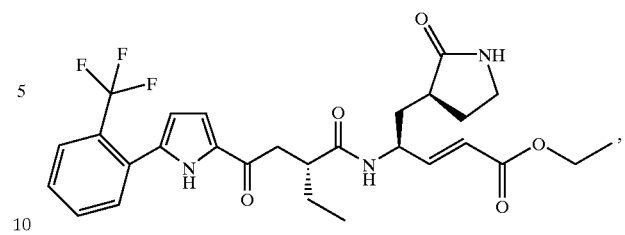
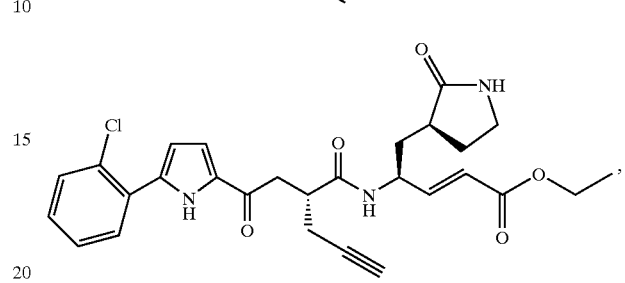
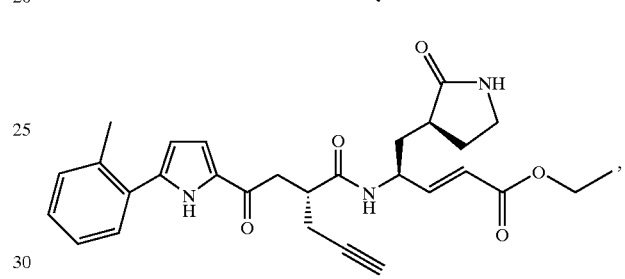
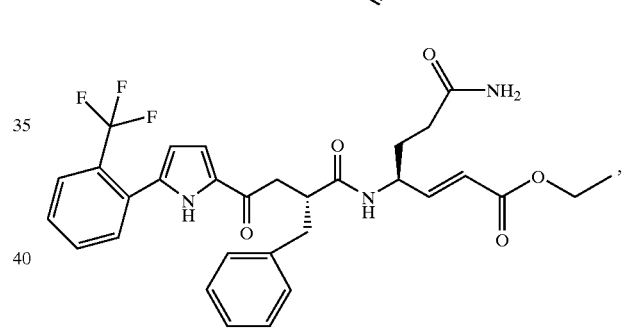
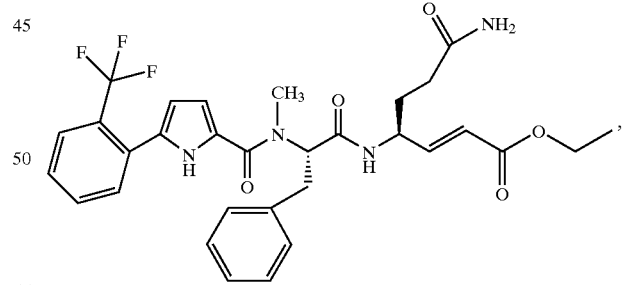
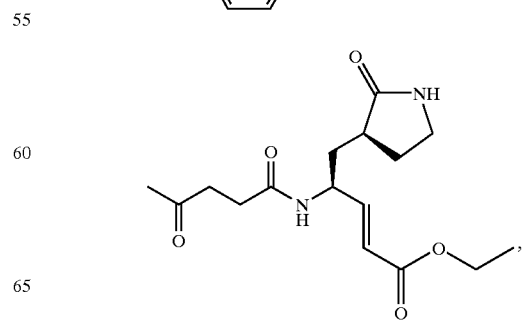

55
-continued
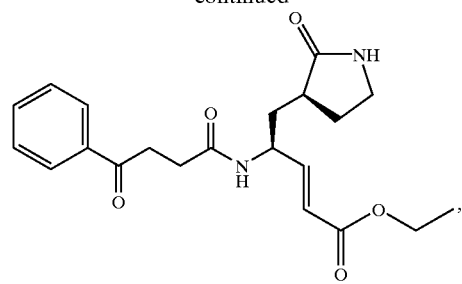
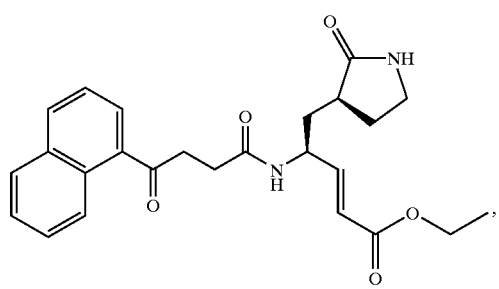
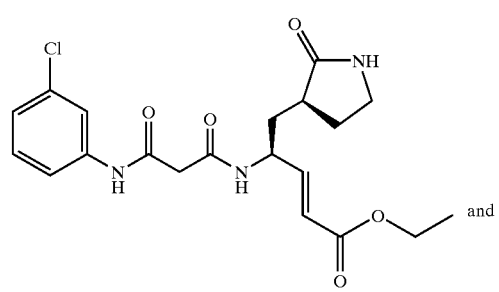
and
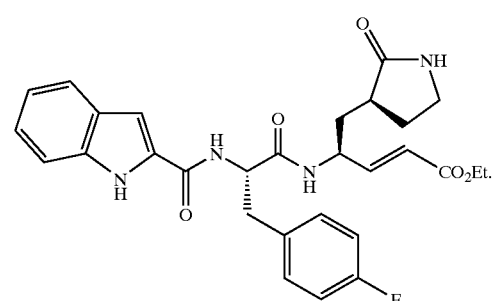
Preferred specific embodiments of the compounds of this invention include any one of the following:
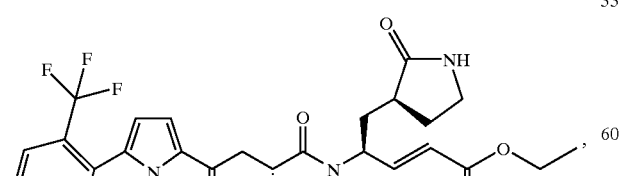
56
-continued
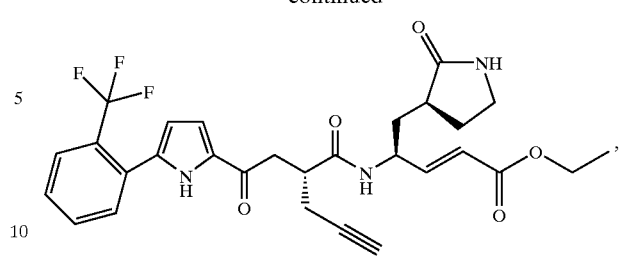
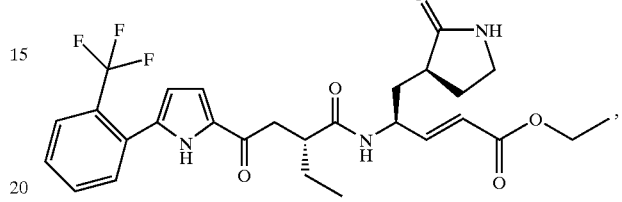
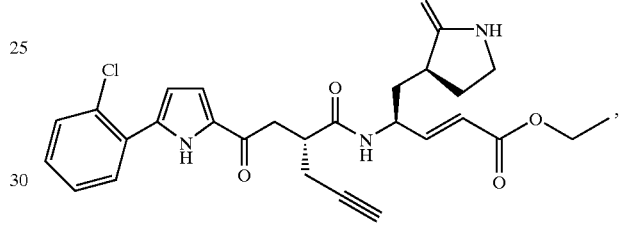
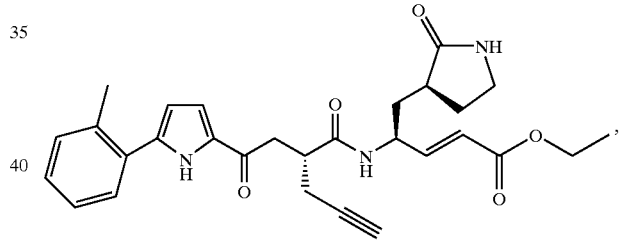
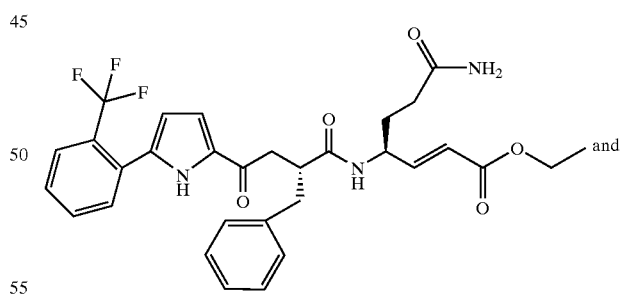
and
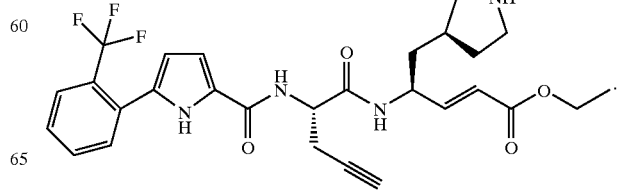

The invention is also directed to intermediate compounds of Formula XIII which are useful in the synthesis of certain compounds of Formulas I–XII:

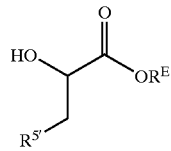

XIII wherein $R^{5'}$ is a lower alkyl or aryl group, where the lower alkyl or aryl group is unsubstituted or substituted with one or more suitable substituents, (where —$CH_2$—$R^{5'}$ represents $R^5$ as defined above) and $R^E$ is H or an alkyl or aryl group, where the alkyl or aryl group is unsubstituted or substituted with one or more suitable substituents.

The invention is also directed to pharmaceutically acceptable salts of the compounds of Formulas XIII. Preferred examples of the compounds of Formula XIII, include the following:

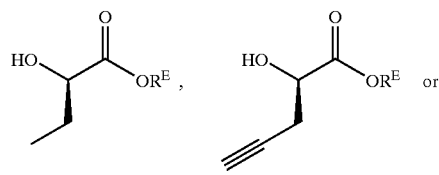

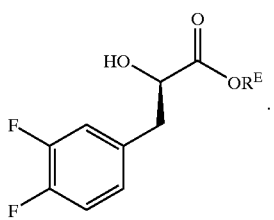

and pharmaceutically acceptable salts thereof. Exemplary preferred $R^E$ groups include, but are not limited to, H, methyl, tert-butyl, allyl, and benzyl, as illustrated in the following:

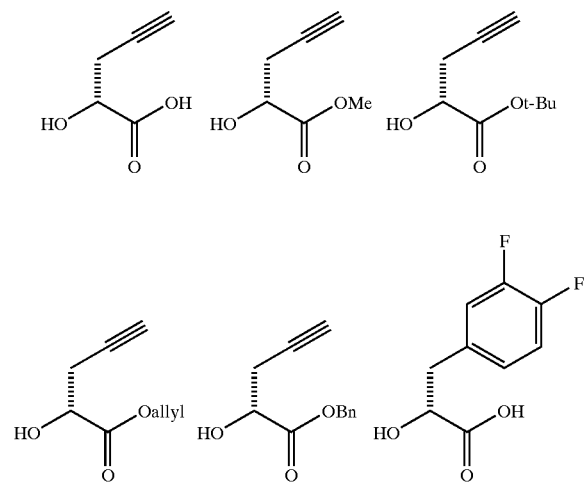

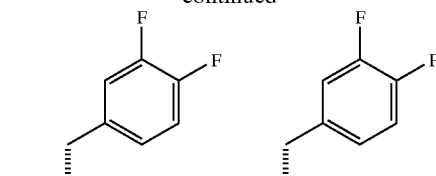

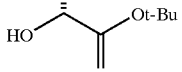

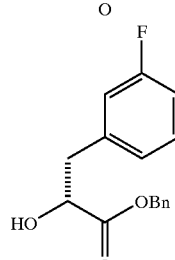

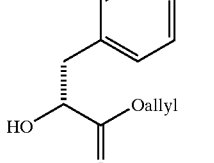

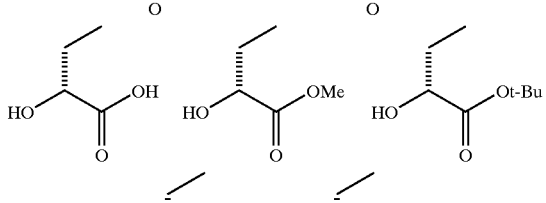

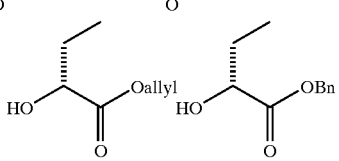

The antipicornaviral compounds of this invention include prodrugs, the pharmaceutically active metabolites, and the pharmaceutically acceptable salts and solvates thereof. In preferred embodiments, the compounds of Formulas I to XII, prodrugs, pharmaceutically acceptable salts, and pharmaceutically active metabolites and solvates thereof have an antipicornaviral activity, more preferably antirhinoviral activity, corresponding to an $EC_{50}$ less than or equal to 100 $\mu M$ in the H1-HeLa cell culture assay.

A "prodrug" is intended to mean a compound that is converted under physiological conditions or by solvolysis or metabolically to a specified compound that is pharmaceutically active. A prodrug may be a derivative of one of the compounds of this invention that contains a moiety, such as for example —$CO_2R$, —$PO(OR)_2$ or —C=NR, that may be cleaved under physiological conditions or by solvolysis. Any suitable R substituent may be used that provides a pharmaceutically acceptable solvolysis or cleavage product. A prodrug containing such a moiety may be prepared according to conventional procedures by treatment of a compound of this invention containing, for example, an amido, carboxylic acid, or hydroxyl moiety with a suitable reagent. A "pharmaceutically active metabolite" is intended to mean a pharmacologically active compound produced through metabolism in the body of a specified compound. Prodrugs and active metabolites of compounds of this invention of the above-described Formulas may be determined using techniques known in the art, for example, through metabolic studies. See, e.g., "Design of Prodrugs," (Bundgaard, ed.), 1985, Elsevier Publishers B.V., Amsterdam, The Netherlands. A "pharmaceutically acceptable salt" is intended to mean a salt that retains the biological effectiveness of the free acids and bases of a specified compound and that is not biologically or otherwise undesirable. Examples of pharmaceutically acceptable salts include sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycollates, tartrates, methanesulfonates (mesylates), propanesulfonates, naphthalene-1-sulfonates, naphthalene-2-sulfonates, and mandelates. A "solvate" is intended to mean a pharmaceutically acceptable solvate form of a specified compound that retains the biological effectiveness of such compound. Examples of solvates include compounds of the invention in combination with water, isopropanol, ethanol, methanol, DMSO, ethyl acetate, acetic acid, or ethanolamine. In the case of compounds, salts, or solvates that are solids, it is understood by those skilled in the art that the inventive compounds, salts, and solvates may exist in different crystal forms, all of which are intended to be within the scope of the present invention and specified formulas.

The present invention is also directed to a method of inhibiting picornaviral 3C protease activity, comprising contacting the protease with an effective amount of a compound of Formulas I to XII, or a pharmaceutically acceptable salt, prodrug, pharmaceutically active metabolite, or solvate thereof. For example, picornaviral 3C protease activity may be inhibited in mammalian tissue by administering a compound of Formulas I to XII or a pharmaceutically acceptable salt, prodrug, pharmaceutically active metabolite, or solvate thereof. More preferably, the present method is directed at inhibiting rhinoviral protease activity. "Treating" or "treatment" is intended to mean at least the mitigation of a disease condition in a mammal, such as a human, that is alleviated by the inhibition of the activity of one or more picornaviral 3C proteases, including, but not limited to human rhinoviruses, human poliovirus, human coxsackieviruses, encephalomyocarditis viruses, meningitis virus, and hepatitis A virus. The methods of treatment for mitigation of a disease condition include the use of the compounds in this invention in any conventionally acceptable manner, for example, as a prophylactic. The activity of the inventive compounds as inhibitors of picornaviral 3C protease activity may be measured by any of the suitable methods known to those skilled in the art, including in vivo and in vitro assays. An example of a suitable assay for activity measurements is the antiviral H1-HeLa cell culture assay described herein.

Administration of the compounds of the Formulas I to XII and their pharmaceutically acceptable prodrugs, salts, active metabolites, and solvates may be performed according to any of the generally accepted modes of administration available to those skilled in the art. Illustrative examples of suitable modes of administration include oral, nasal, parenteral, topical, transdermal, and rectal.

An inventive compound of Formulas I to XII or a pharmaceutically acceptable salt, prodrug, active metabolite, or solvate thereof may be administered as a pharmaceutical composition in any pharmaceutical form recognizable to the skilled artisan as being suitable. Suitable pharmaceutical forms include solid, semisolid, liquid, or lyophilized formulations, such as tablets, powders, capsules, suppositories, suspensions, liposomes, and aerosols. Pharmaceutical compositions of the invention may also include suitable excipients, diluents, vehicles, and carriers, as well as other pharmaceutically active agents, depending upon the intended use or mode of administration. In preferred embodiments, the inventive pharmaceutical compositions are delivered orally, or intranasally in the form of suspensions. Acceptable methods of preparing suitable pharmaceutical forms of the pharmaceutical compositions may be routinely determined by those skilled in the art. For example, pharmaceutical preparations may be prepared following conventional techniques of the pharmaceutical chemist involving steps such as mixing, granulating, and compressing when necessary for tablet forms, or mixing, filling, and dissolving the ingredients as appropriate, to give the desired products for oral, parenteral, topical, intravaginal, intranasal, intrabronchial, intraocular, intraaural, and/or rectal administration.

The compounds (active ingredients) may be formulated into solid oral dosage forms which may contain, but are not limited to, the following inactive ingredients: diluents (i.e., lactose, corn starch, microcrystalline cellulose), binders (i.e., povidone, hydroxypropyl methylcellulose), disintegrants (i.e., crospovidone, croscarmellose sodium), lubricants (i.e., magnesium stearate, stearic acid), and colorants (FD&C lakes or dyes). Alternatively, the compounds may be formulated into other oral dosage forms including liquids, suspensions, emulsions, or soft gelatin capsules, with each dosage form having a unique set of ingredients.

Solid or liquid pharmaceutically acceptable carriers, diluents, vehicles, or excipients may be employed in the pharmaceutical compositions. Illustrative solid carriers include starch, lactose, calcium sulfate dihydrate, terra alba, sucrose, talc, gelatin, pectin, acacia, magnesium stearate, and stearic acid. Illustrative liquid carriers include syrup, peanut oil, olive oil, saline solution, and water. The carrier or diluent may include a suitable prolonged-release material, such as glyceryl monostearate or glyceryl distearate, alone or with a wax. When a liquid carrier is used, the preparation may be in the form of a syrup, elixir, emulsion, soft gelatin capsule, sterile injectable liquid (e.g., solution), or a nonaqueous or aqueous liquid suspension. A dose of the pharmaceutical composition contains at least a therapeutically effective amount of the active compound (i.e., a compound of Formulas I to XII or a pharmaceutically acceptable salt, prodrug, active metabolite, or solvate thereof), and preferably is made up of one or more pharmaceutical dosage units. The selected dose may be administered to a mammal, for example, a human patient, in need of treatment mediated by inhibition of picornaviral 3C protease activity, by any known or suitable method of administering the dose, including: topically, for example, as an ointment or cream; orally; rectally, for example, as a suppository; parenterally by injection; or continuously by intravaginal, intranasal, intrabronchial, intraaural, or intraocular infusion. A "therapeutically effective amount" is intended to mean the amount of an inventive agent that, when administered to a mammal in need thereof, is sufficient to effect treatment for disease conditions alleviated by the inhibition of the activity of one or more picornaviral 3C proteases, such as human rhinoviruses, human poliovirus, human coxsackieviruses, encephalomyocarditis viruses, menigovirus, and hepatitis A virus. The amount of a given compound of the invention that will be therapeutically effective will vary depending upon factors such as the particular compound, the disease condition and the severity thereof, the identity of the mammal in need thereof, which amount may be routinely determined by artisans.

General Synthetic Methods

Preferably, compounds of the general formulas are prepared by the methods of the present invention, including the General Methods below, where the $R^1$, $R^4$, $R^5$, $R^6$, Z and $Z^1$ substituents present in the compounds illustrated in the General and Specific Methods are as defined above. Abbreviations used herein include: DCC (1,3-dicyclohexyl-carbodiimide), HOBT (1-hydroxybenzotriazole hydrate), HATU (O-(7-azabenzotriazol-1-yl)-N,N,N',N'-tetramethyluronium hexafluorophosphate), IBX (2-iodoxybenzoic acid), FMOC (9-fluorenylmethoxycarbonyl), Boc (t-butoxycarbonyl), DIEA (diisopropylethylamine), DMSO (dimethylsulfoxide), TMSOTf (trimethylsilyl trifluoromethanesulfonate), TFA (trifluoroacetic acid), LiHMDS (lithium bis(trimethylsilyl) amide).

General Method 1

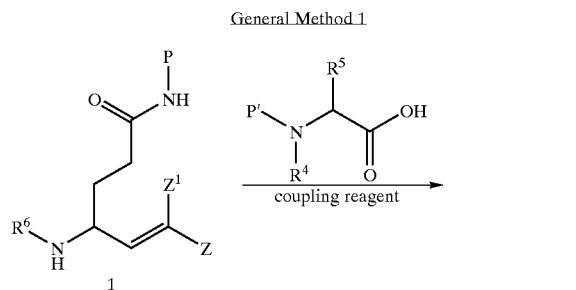

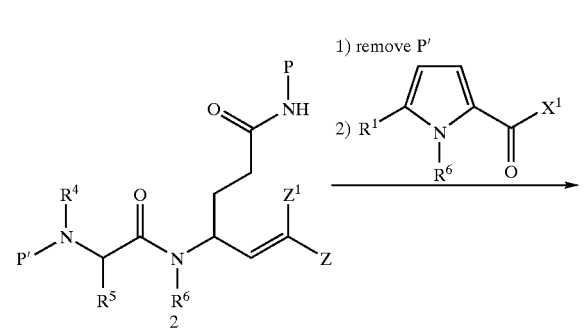

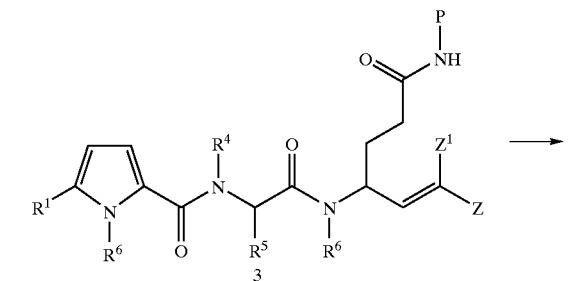

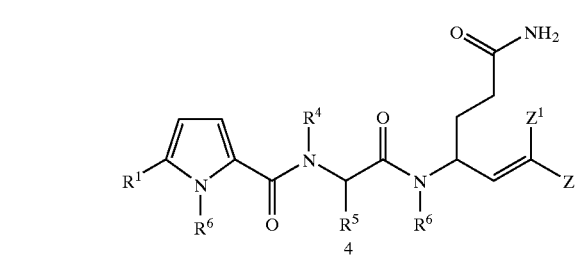

In General Method 1, a sidechain protected (P) compound 1 (Dragovich, et al., *J. Med. Chem.* 1998, 41, 2819), is coupled using standard peptide coupling methods, to another amino acid with a different protecting group (P') on the alpha-nitrogen, to give di-peptide compound 2. The P' protecting group is then selectively removed, and the resulting amine is coupled to a substituted pyrrole-2-carboxylic acid (prepared as described in General Methods 4, 5, and 6), or a suitably activated analog of this acid, such as an acid chloride, ester or amide ($X^1$=OH, halo, etc.), to give 3. The sidechain-protecting group P is then removed to give 4. These compounds may also be made using solid phase synthetic techniques (Dragovich, et al., *Bioorg. Med. Chem.*, 1999 7, 589), where protecting group P constitutes a linker (such as the Rink linker) attached to solid phase resin.

General Method 2

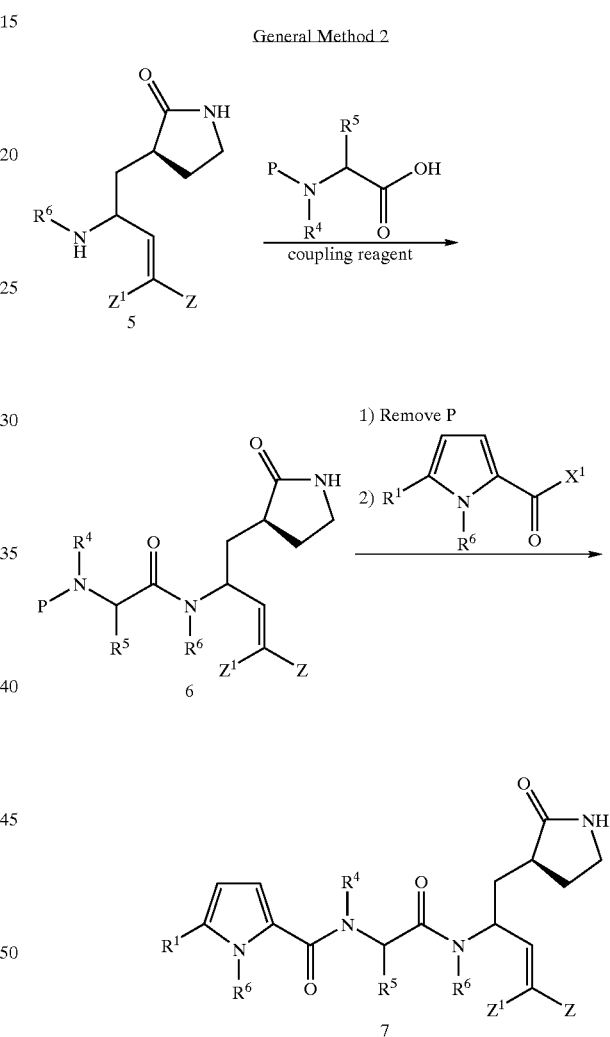

In General Method 2, compound 5 (prepared by a method analogous to that described in Tian, et al., U.S. Provisional Patent Application No. 60/150,358, filed Aug. 24, 1999 (now U.S. patent application Ser. No. 09/643,864) and also Baldwin et al., *J. Org. Chem.*, 1971, 36, 1441) is coupled to another amino acid with sidechain protecting group P to give 6. The protecting group of 6 is removed, and the liberated amine is coupled to a 5-substituted pyrrole-2-carboxylic acid (prepared as described in General Methods 4, 5, and 6) via a suitably activated analog of this acid, such as an acid chloride, ester or amide ($X^1$=OH, halo, etc.), to give compound 7.

General Method 3

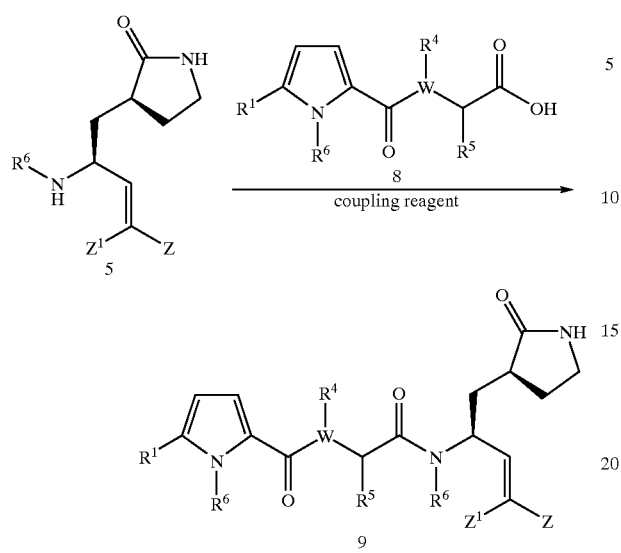

In General Method 3, compound 5 is coupled to carboxylic acids of the type 8 (prepared as described in General Methods 7 and 8), where W=N or CH, to give compound 9.

General Method 4

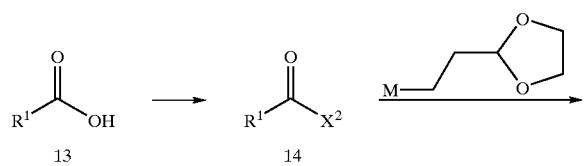

In General Method 4,2, 5-disubstituted pyrroles are prepared by bromination of pyrrole-2-carboxylic acid ester 10, where R is an alkyl or aryl group, which is unsubstituted or substituted with one or more suitable substituents, to give 11, followed by a transition-metal mediated carbon-carbon bond forming reaction (for example, using Pd⁰ with an appropriate ligand such as triphenylphosine or triphenylarsine) with an organometallic species, $R^1M$ (for example, an organoboronic acid or an organotin compound) to give 12.

General Method 5

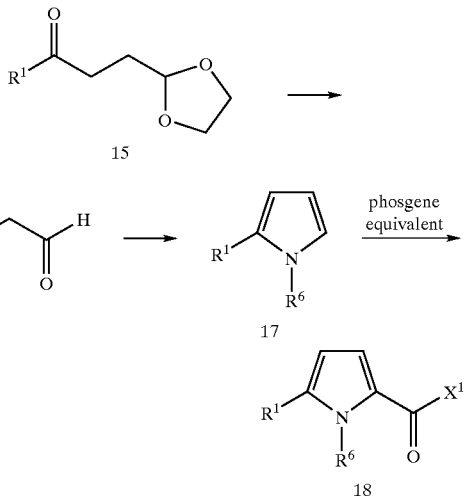

General Method 5 depicts another method used to make 2,5-disubstituted pyrroles, analogous to the method described by Kruse, et al., *Heterocycles*, 1987, 26, 3141. A carboxylic acid 13 is converted to a suitably activated species 14 ($X^2$=a Weinreb amide (—N(OCH$_3$)CH$_3$), halo, etc.) then reacted with a nucleophilic organometallic compound containing a protected aldehyde to provide 15. The aldehyde is deprotected to give 16, then is condensed with an ammonia equivalent such as ammonium chloride, to provide pyrrole 17. This pyrrole is then reacted with a phosgene-type equivalent such as trichloroacetyl chloride (analogous to the method described by Bailey, et al., *Org. Synth.*, 1971, 51, 100), to provide the 2, 5-disubstituted pyrrole 18. ($X^1$=OH, halo, etc.).

General Method 6

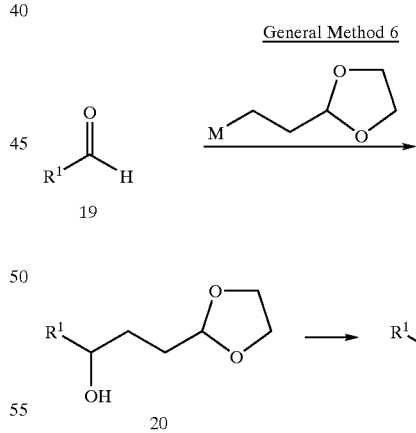

General Method 6 shows an alternate method to make 2, 5-disubstituted pyrroles. Aldehyde 19 is reacted with a nucleophilic organometallic compound containing a protected aldehyde to provide alcohol 20. The alcohol is then oxidized to ketone 15 using standard methodology such as a Swern oxidation. Ketone 15 is carried on to pyrrole 18 using the same method as shown in General Method 5.

General Method 7

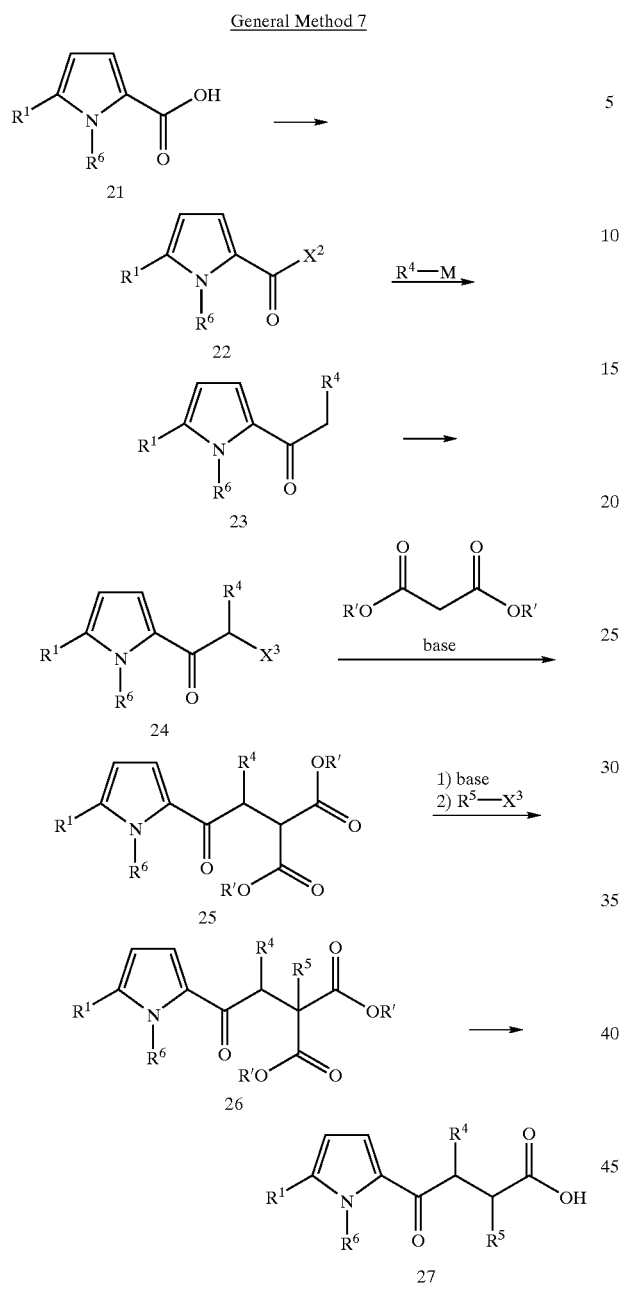

General Method 8

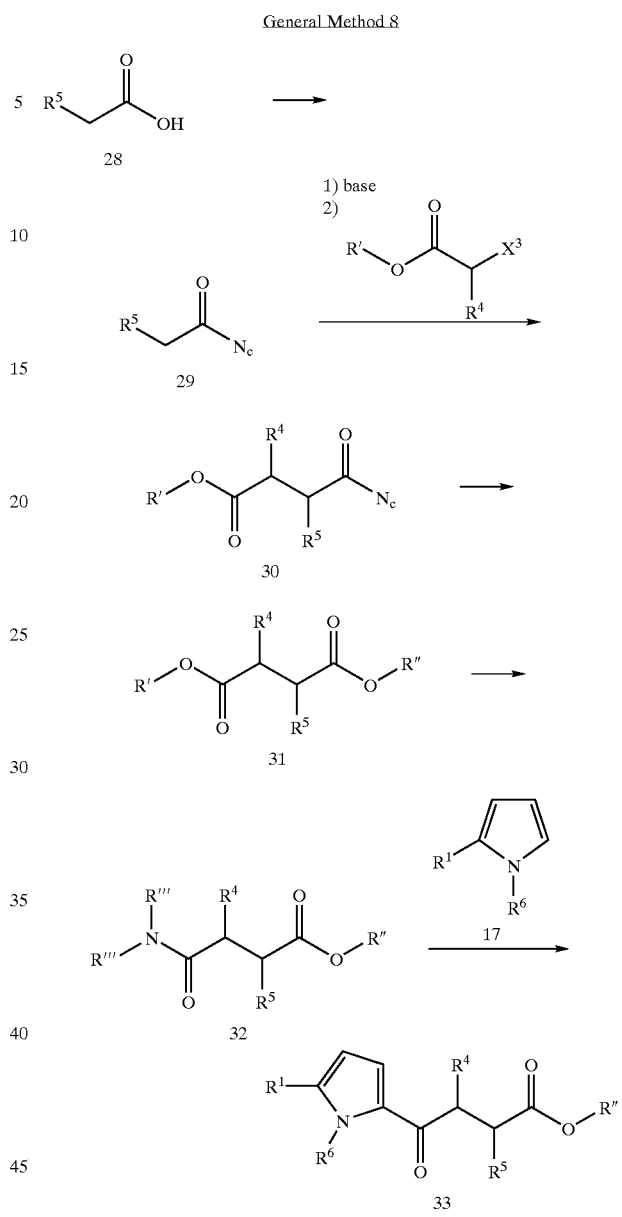

General Method 7 depicts the preparation of a pyrrole containing the keto-methylene moiety, 27, analogous to the method described by Gonzalez-Muniz et. al. (Gonzalez-Muniz, et al., *Tetrahedron*, 1992, 48, 5191; Garcia-Lopez, et al., *Tetrahedron Lett.*, 1988, 29, 1577; Garcia-Lopez, et al., *Tetrahedron*, 1988, 44, 5138). Carboxylic acid 21 is converted to a suitably reactive intermediate 22 such as a Weinreb amide, acid chloride or ester ($X^2=N(OCH_3)CH_3$, halo, etc.), then reacted with an organometallic reagent ($R^4M$, such as methyllithium) to give pyrrole-acetone compound 23. This compound is then halogenated to give 24 (where $X^3$=halo), then reacted with a malonate salt (R'= alkyl) to give 25. This compound is deprotonated by treatment with a strong base, then reacted with an electrophile ($R^5$—$X^3$) to give 26. Decarboxylation of compound 26 gives product 27.

General Method 8 shows the preparation of an optically active pyrrole containing the keto-methylene moiety, compound 33. Carboxylic acid 28 is converted to chiral amide 29, by coupling to a chiral amine or oxazolidinone, $N_c$, that is known to control enolate alkylation diastereoselectivity. Compound 29 is deprotonated, then reacted with an electrophile such as t-butyl bromoacetate, analogous to the method described by Charlton, et al., *Can. J. Chem*. 1997, 75, 1076, to give 30. The chiral auxiliary is removed, and the resulting acid is esterified to give 31. The R' ester of 31 is selectively removed, and the resulting acid is converted to the disubstituted amide 32, by coupling to a secondary amine. Compound 32 is reacted with pyrrole 17, under typical Vilsmeier reaction conditions (Silverstein, et al., *Org. Synth.*, 1963, *Coll. Vol. IV*, 831) to give pyrrole 33. As used herein, R', R" and R''' are each independently lower alkyl, which is unsubstituted or substituted with one or more suitable substituents,

General Method 9

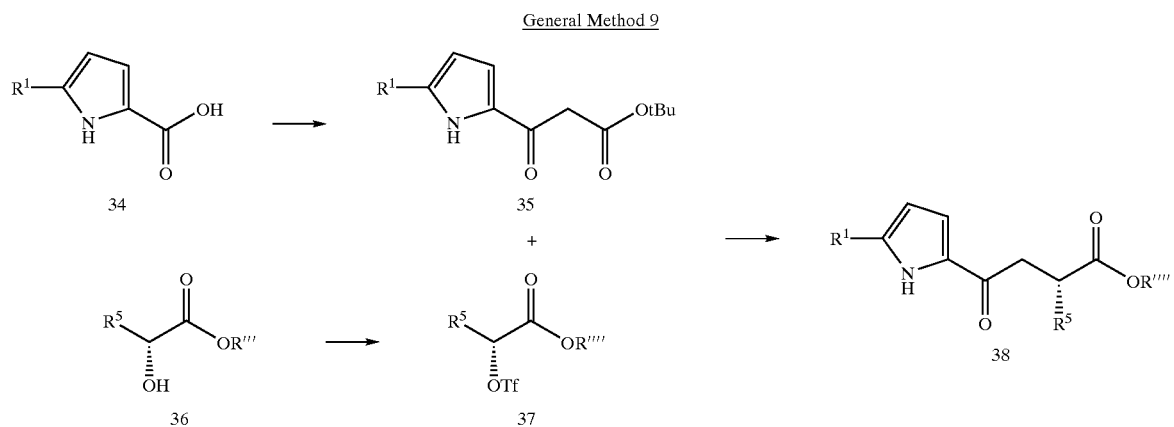

In General Method 9, a pyrrole-carboxylic acid 34 (commercially available or prepared by methods described in the chemical literature or as prepared as described in General Methods 4, 5 and 6), where $R^1$ is as defined above, is transformed into ketoester 35. Compound 35 is subsequently deprotonated and coupled with triflate 37 (which incorporates $R^5$ and which can be prepared from hydroxyester 36, where R'''' is alkyl or cycloalkyl, e.g., lower alkyl, allyl, benzyl, or $C_3$–$C_6$ cycloalkyl, which are unsubstituted or substituted with one or more suitable substituents) to afford intermediate 38 after acid-effected decarboxylation. Intermediate 38 is related to compound 32 (General Method 8) and may be utilized in any of the previously described general syntheses where appropriate. Note that the NH present in pyrrole-carboxylic acid 34 may also be protected with a suitable protecting group which may be removed at any time during the synthesis of 38. The methodology for converting pyrrole-carboxylic acid 34 to intermediate 38 is generally described in: Hoffman, R. V.; Tao, J. *Tetrahedron* 1997, 53, 7119–7126.

General Method 10

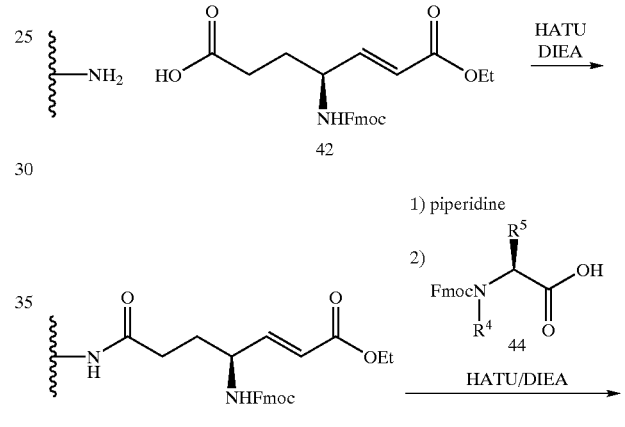

In General Method 10, an amino acid 39 (or salt thereof) which incorporates $R^5$ is transformed into hydroxy acid 40. This intermediate is subsequently converted to hydroxy ester 41 which may be utilized in General Method 9 above for the preparation of the compounds described in this invention.

Specific Methods

Specific Method 1

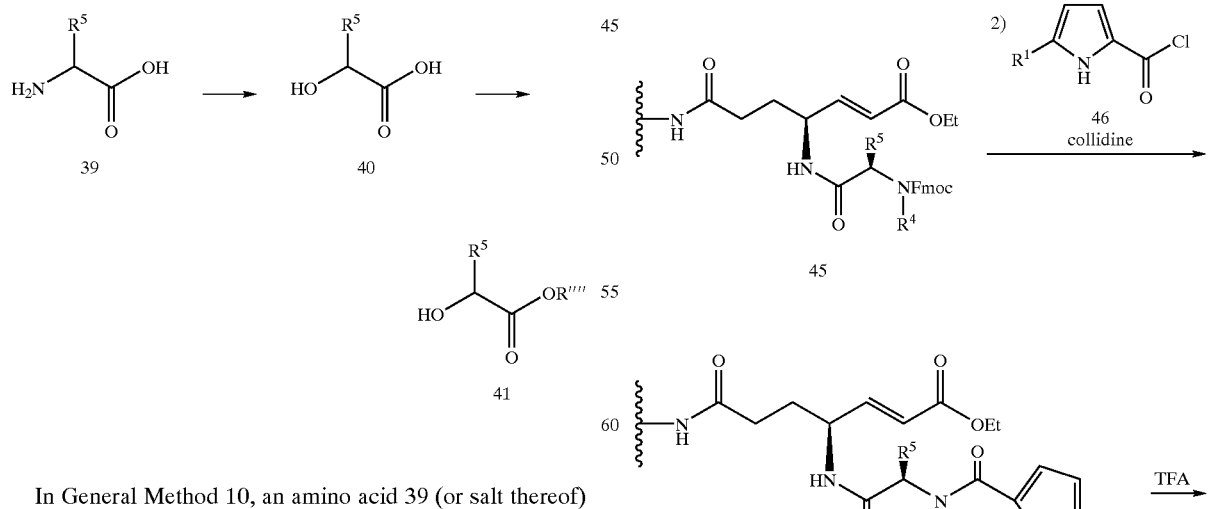

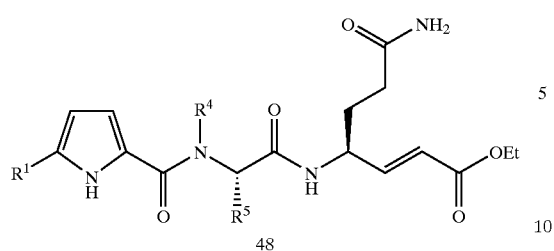

48

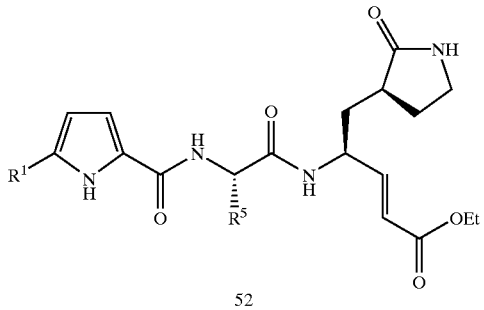

52

Specific Method 1 describes the preparation of compounds containing a glutamine residue in the P-1 position. FMOC-4-amino-hept-2(trans)-enedioic acid -1 ethyl ester 42 (Dragovich, et al., *J. Med. Chem.* 1998, 41, 2819) was coupled to Rink polystyrene utilizing HATU as a coupling reagent to get 43. The FMOC protecting group was removed with piperidine, and the liberated amine was then coupled to an FMOC-protected amino acid 44 to get compound 45. The FMOC of 45 was again removed with piperidine, and the free amine was acylated with a 5-substituted-2-pyrrole carboxylic acid chloride 46 (prepared as described in Specific Methods 4, 5, and 6). The final compound, 37, was cleaved from the resin with trifluoroacetic acid, to give compound 48.

Specific Method 2 describes the synthesis of compounds containing the oxo-pyrrolidine sidechain in the P-1 position. Boc-protected 4S-amino-5-(2-oxo-pyrrolidin-3S-yl)-pent-2 (trans)-enoic acid ethyl ester 49 (prepared by a method analogous to that described in Tian, et al., U.S. Provisional Patent Application No. 60/150,358, filed Aug. 24, 1999 and also Baldwin et al., *J. Org. Chem.*, 1971, 36, 1441) was deprotected with HCl, then coupled using HATU to a Boc-protected amino acid 50. The Boc-protected product 51 was treated with HCl, then coupled to a 5-substituted-pyrrole-2-carboxylic acid chloride 46 (prepared as described in Specific Methods 4, 5, and 6), to produce product 52.

Specific Method 2

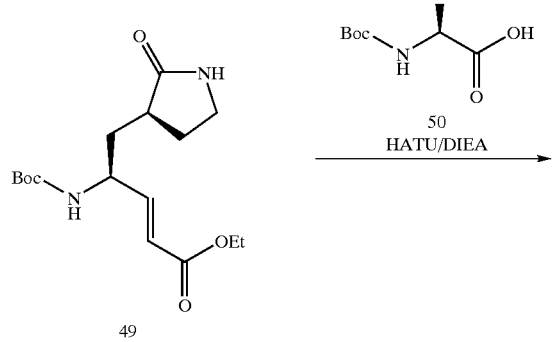

Specific Method 3

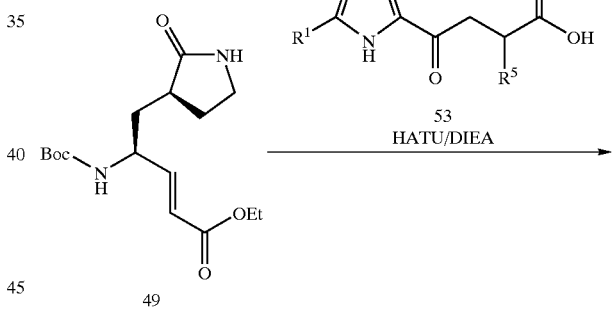

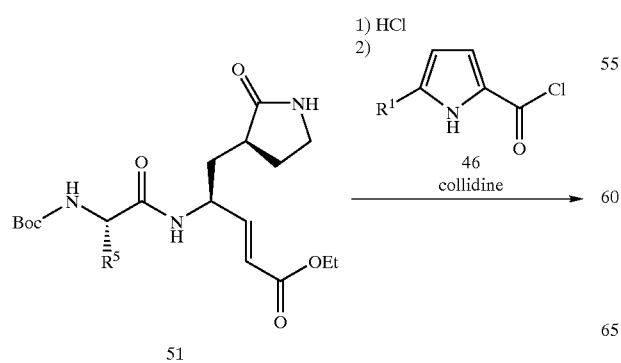

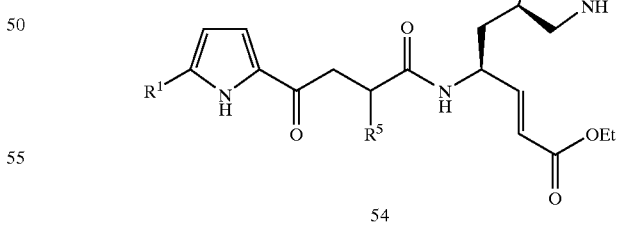

Specific Method 3 describes the preparation of compounds containing the pyrrole-ketomethylene moiety. Boc-protected 4S-amino-5-(2-oxo-pyrrolidin-3S-yl)-pent-2 (trans)-enoic acid ethyl ester 49 was deprotected with HCl, then coupled to acid 53 (prepared as described in Specific Method 7 and 8), using HATU, to provide compound 54.

Specific Method 4

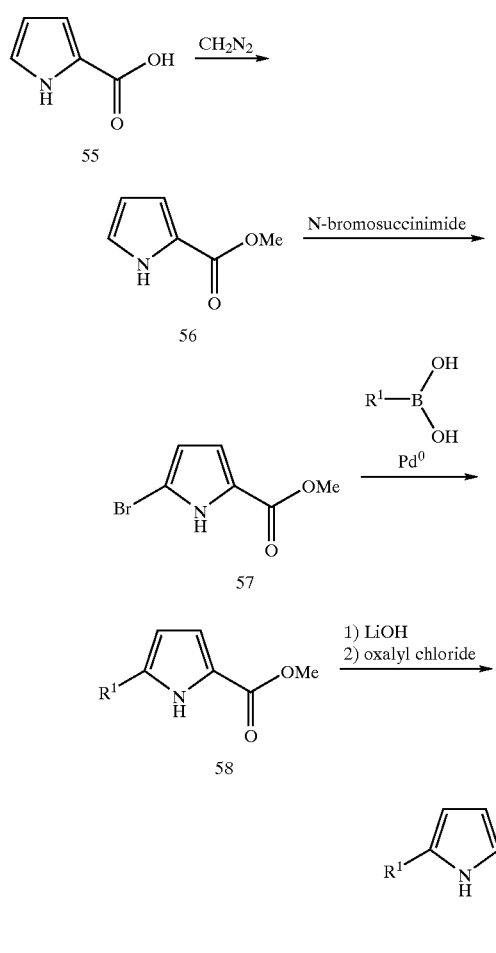

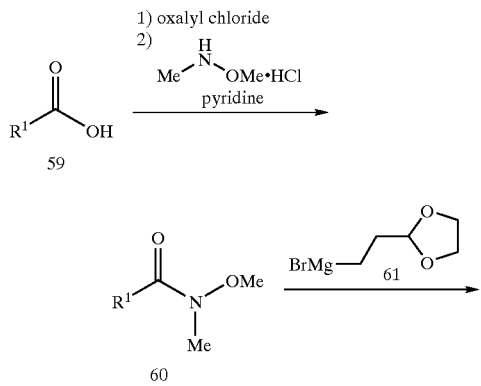

Specific Method 4 describes the synthesis of 5-substituted-pyrrole-2-carboxylic acid chlorides. Pyrrole-2-carboxylic acid 55 was esterified with diazomethane, to give methyl ester 56, then brominated with N-bromosuccinimide to give 5-bromopyrrole 57. The bromide was reacted with a boronic acid using standard Suzuki coupling conditions to give 58. The methyl ester was cleaved with lithium hydroxide, and the resulting acid was converted to the acid chloride 46 using oxalyl chloride.

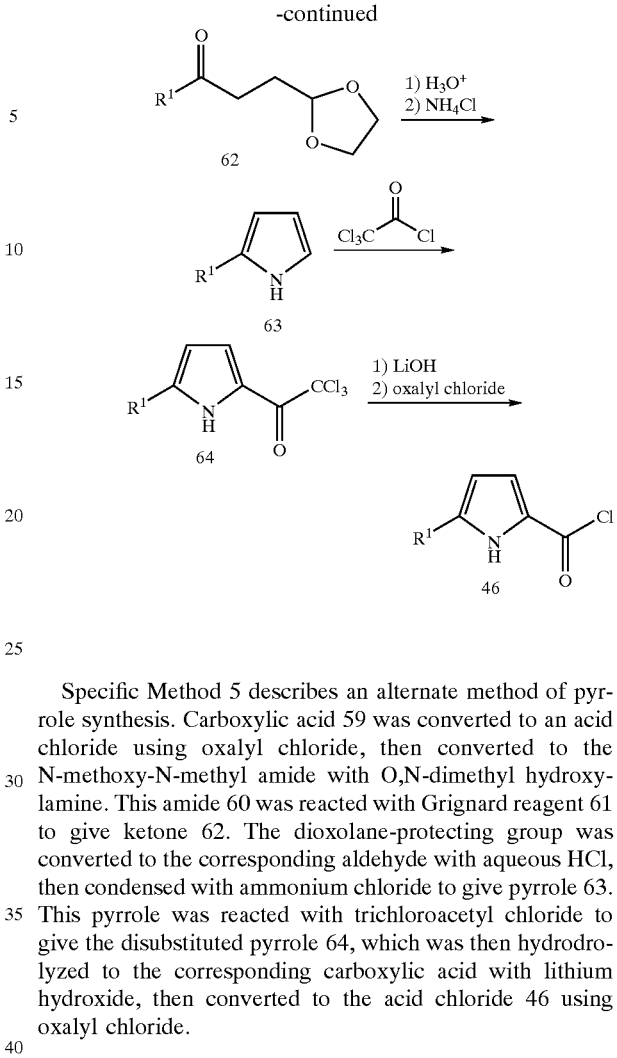

Specific Method 5 describes an alternate method of pyrrole synthesis. Carboxylic acid 59 was converted to an acid chloride using oxalyl chloride, then converted to the N-methoxy-N-methyl amide with O,N-dimethyl hydroxylamine. This amide 60 was reacted with Grignard reagent 61 to give ketone 62. The dioxolane-protecting group was converted to the corresponding aldehyde with aqueous HCl, then condensed with ammonium chloride to give pyrrole 63. This pyrrole was reacted with trichloroacetyl chloride to give the disubstituted pyrrole 64, which was then hydrodrolyzed to the corresponding carboxylic acid with lithium hydroxide, then converted to the acid chloride 46 using oxalyl chloride.

Specific Method 6

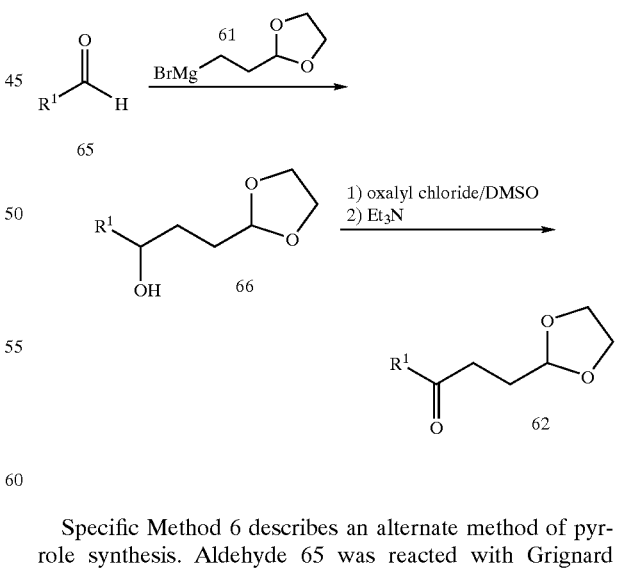

Specific Method 6 describes an alternate method of pyrrole synthesis. Aldehyde 65 was reacted with Grignard reagent 61 to give alcohol 66. This alcohol was subjected to Swern oxidation conditions to provide ketone 62, which was converted to the acid chloride 46 according to Specific Method 5.

Specific Method 7

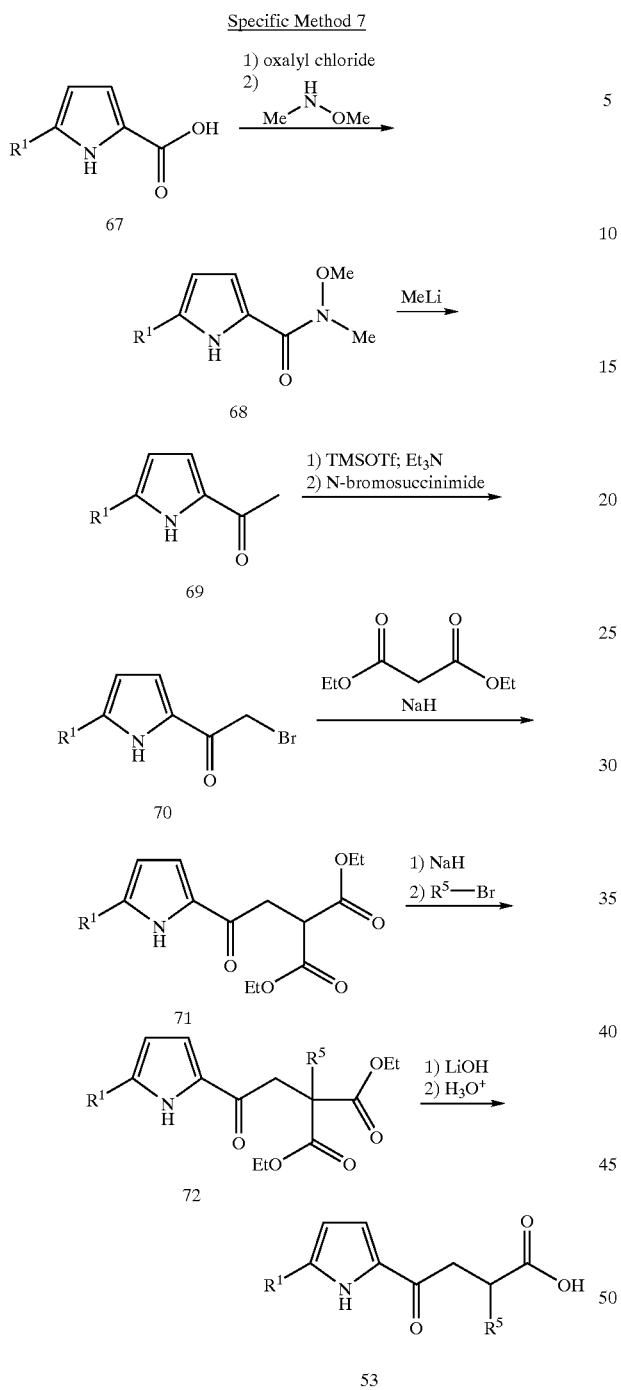

Specific Method 8

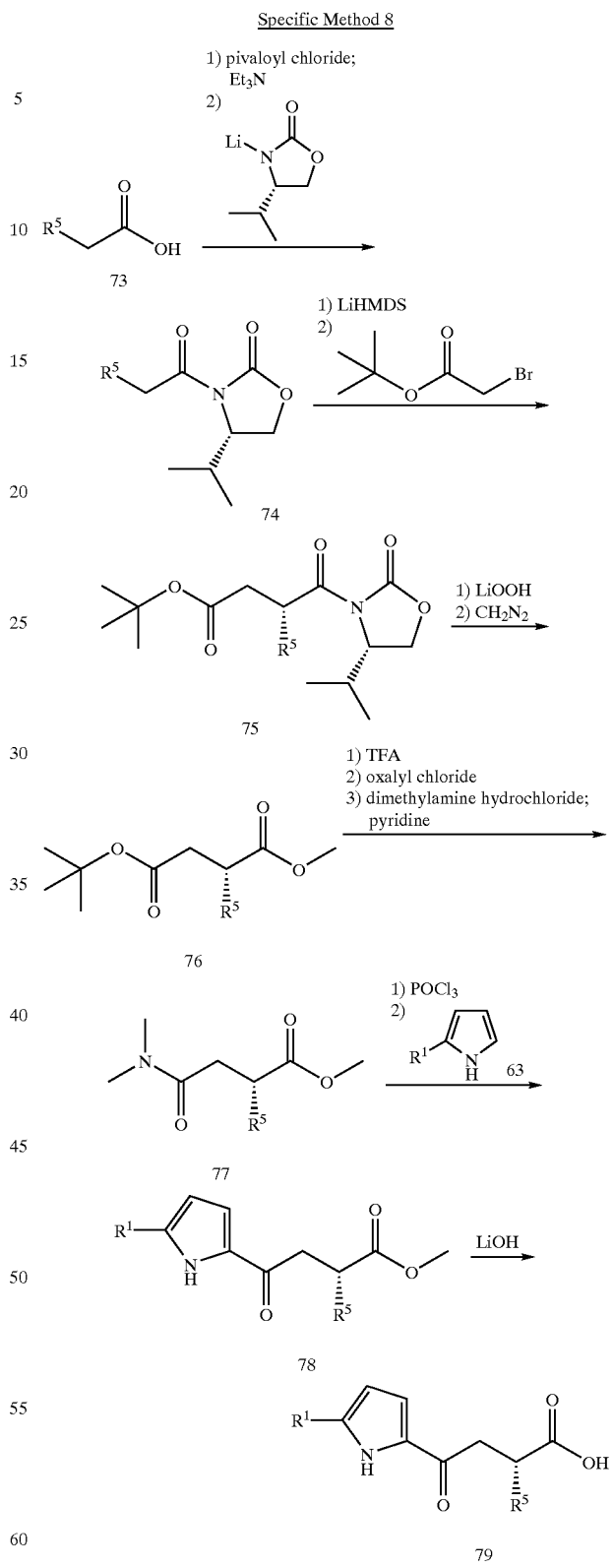

Specific Method 7 describes the synthesis of a racemic pyrrole-ketomethylene compound. 5-Substituted-pyrrole-2-carboxylic acid 67 (prepared as described in Specific Methods 4, 5 and 6) was converted to the Weinreb amide 68 using standard conditions, then treated with methyllithium to give pyrrole-acetone 69. This ketone was converted to its silyl-enol ether with trimethylsilyl triflate, then brominated with N-bromosuccinimide to give bromide 70. The bromide was displaced with sodium diethylmalonate to give malonate 71. The sodium enolate of this compound was alkylated to give 72, which was then de-esterified and de-carboxylated to give carboxylic acid 53.

Specific Method 8 describes the enantioselective preparation of a pyrrole-ketomethylene compound. Carboxylic acid 73 was converted to the chiral amide 74 using standard conditions, then converted to its lithium enolate and alkylated with t-butylbromoacetate to give 75. The chiral auxiliary was removed with lithium hydroperoxide, and the resulting acid was esterified with diazomethane to give ester 76. The t-butylester was selectively removed with trifluoroacetic acid, and the resulting acid was converted to dimethyl amide 77 by treatment of the acid chloride (formed using oxalyl chloride) with dimethylamine hydrochloride. Amide 77 was reacted with pyrrole 63 (prepared as described in Specific Methods 4, 5 and 6) using standard Vilsmeier conditions to give pyrrole-ketomethylene 78. The methyl ester was cleaved with lithium hydroxide to give carboxylic acid 79.

Specific Method 9

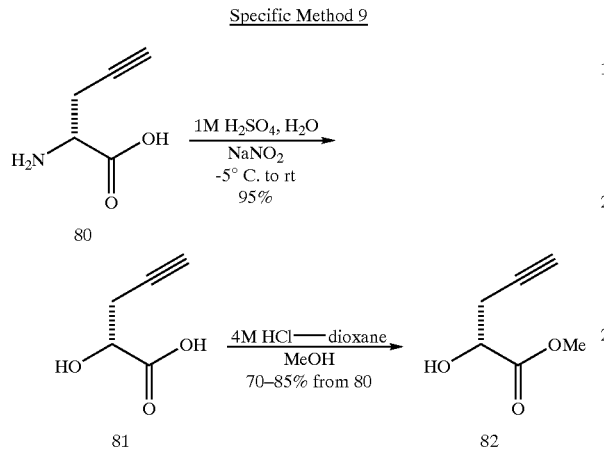

In Specific Method 9, H-D-propargyl glycine (80) (or a suitable salt thereof) is treated with sodium nitrite under mildly acidic aqueous conditions to provide hydroxy acid 81 in good yield. This material is esterified by exposure to acidic methanol to give hydroxy ester 82.

In Specific Method 10, Boc-D-3,4-difluorophenylalanine 83 is deprotected by treatment with trifluoroacetic acid in $CH_2Cl_2$ to afford amino acid TFA salt 84. This intermediate is treated with sodium nitrite under mildly acidic aqueous conditions to provide hydroxy acid 85 in good yield. Compound 85 is esterified by exposure to either methanol or benzyl alcohol under acidic conditions to give hydroxy esters 86 and 87, respectively.

Specific Method 11

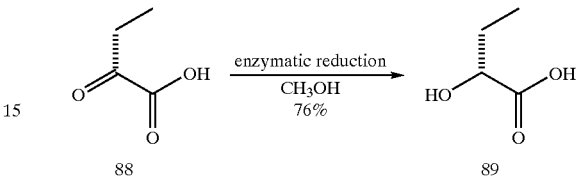

In Specific Method 11, 2-ketobutyric acid (88) is subjected to an enzyme-mediated reduction process to afford hydroxy acid 89 in good yield.

EXAMPLES

Examples of the processes used to make several of the compounds of Formulas I and II are set forth below. The structures of the compounds of the following examples were confirmed by one or more of the following: proton magnetic resonance spectroscopy, infrared spectroscopy, elemental microanalysis and melting point. Proton magnetic resonance ($^1$H NMR) spectra were determined using either a Varian UNITYplus 300 or a General Electric QE-300 spectrometer operating at a field strength of 300 megahertz (MHz). Chemical shifts are reported in parts per million (ppm, δ) downfield from an internal tetramethylsilane standard.

Specific Method 10

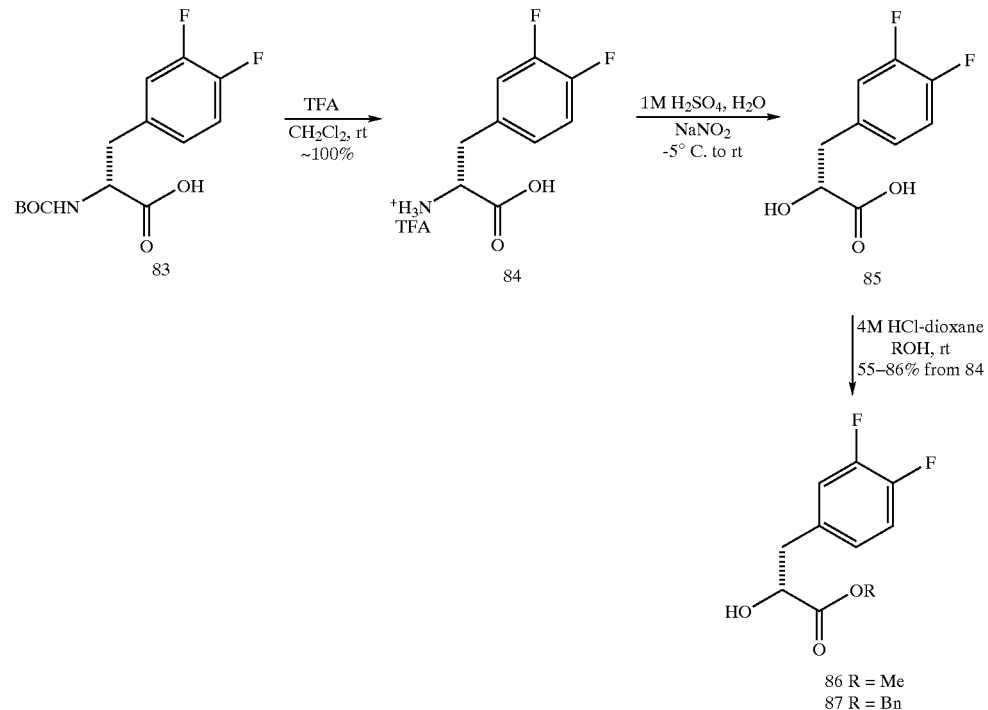

Alternatively, $^1$H NMR spectra were referenced to residual protic solvent signals as follows: $CHCl_3$=7.26 ppm; DMSO=2.49 ppm, $C_6HD_5$=7.15 ppm. Peak multiplicities are designated as follows: s, singlet; d, doublet; dd, doublet of doublets; t, triplet; q, quartet; br, broad resonance; m, multiplet. Coupling constants are given in Hertz. Infrared absorption (IR) spectra were obtained using a Perkin-Elmer 1600 series FTIR spectrometer. Elemental microanalyses were performed by Atlantic Microlab Inc., Norcross, Ga. and gave results for the elements stated within ±0.4% of the theoretical values. Flash column chromatography was conducted using Silica gel 60 (Merck Art 9385). Analytical thin layer chromatography (TLC) was conducted using precoated sheets of Silica 60 $F_{254}$ (Merck Art 5719). Melting points were determined on a Mel-Temp apparatus and are uncorrected. All reactions were conducted in septum-sealed flasks under a slight positive pressure of argon unless otherwise noted. All commercial reagents were used as received from their respective suppliers with the following exceptions. Tetrahydrofuran (THF) was distilled from sodium-benzophenone ketyl prior to use. Dichloromethane ($CH_2Cl_2$) was distilled from calcium hydride prior to use. The abbreviations used herein include: $Et_2O$ (diethyl ether), DMF (N,N-dimethylformamide), DMSO (dimethylsulfoxide), MTBE (tert-butyl methyl ether), $CH_3OH$ (methanol), EtOH (ethanol), EtOAc (ethyl acetate), DME (ethylene glycol dimethyl ether) Ac (acetyl), Me (methyl), Ph (phenyl), Tr (triphenylmethyl), Cbz (benzyloxycarbonyl), Boc (tert-butoxycarbonyl), TFA (trifluoroacetic acid), DIEA (N,N-diisopropylethylamine), TMEDA (N,N,N',N'-tetramethylethylenediamine), AcOH (acetic acid), $Ac_2O$ (acetic anhydride), NMM (4-methylmorpholine), HOBt (1-hydroxybenzotriazole hydrate), HATU (O-(7-azabenzotriazol-1-yl)-N,N,N',N'-tetramethyluronium hexafluorophosphate), EDC (1-(3-dimethylaminopropyl)-3-ethylcarbarbodiimide hydrochloride), DCC (dicyclohexyl-carbodiimide), DDQ (2,3-dichloro-5,6-dicyano-1,4-benzoquinone), DMAP (4-dimethylaminopyridine), Gln (glutamine), Leu (leucine), Phe (phenylalanine), Phe(4-F) (4-fluorophenylalanine), Val (valine), amino-Ala (2,3-diaminopropionic acid), and (S)-Pyrrol-Ala((2S,3'S)-2-amino-3-(2'-oxopyrrolidin-3'-yl)-propionic acid). Additionally, "L" represents the configuration of naturally occurring amino acids.

Example 1

Preparation of Gln-resin and Phe-Gln Resin

Fmoc-Rink polystyrene resin (1.58 mmol, 2.40 g) was treated with a 1:1 solution of DMF-piperidine (25 ml) in a shaker vessel, to remove the Fmoc. The resulting slurry was agitated for 15 min, then washed with DMF (3×10 ml). The resin was then treated with a solution of Fmoc-4-amino-hept-2(trans)-enedioic acid-1-ethyl ester[1a,b] (2.37 mmol, 1.00 g), DIEA (4.74 mmol, 0.82 ml), and HATU (2.37 mmol, 0.90 g) in DMF (25 ml). The resulting mixture was agitated for 1 h, then washed with DMF (3×10 ml). The Fmoc was then removed by treatment with a solution of 20% piperidine-DMF (25 ml), and agitation for 10 min. The resulting resin was washed with DMF (3×10 ml), MeOH (3×10 ml), and $CH_2Cl_2$ (3×10 ml). (The resin at this stage will be hereafter referred to as Gln-resin) The Gln-resin was then treated with a solution of Fmoc-phenylalanine (4.74 mmol, 1.84 g), DIEA (9.48 mmol, 1.65 ml), and HATU (4.74 mmol, 1.80 g) in DMF (25 ml). The resulting mixture was agitated for 1 h, then washed with DMF (3×25 ml). The Fmoc was removed by treatment with a solution of 20% piperidine-DMF (25 ml), then agitation for 10 min. The resin was washed with DMF (3×10 ml), MeOH (3×10 ml), and $CH_2Cl_2$ (3×10 ml). The resin was then dried in a vacuum desiccator. (The resin at this stage will be hereafter referred to as Phe-Gln-resin).

Example 2

6-Carbamoyl-4S-{2S-[(5-naphthalen-1-yl-1H-pyrrole-2-carbonyl)-amino-3-phenyl-propionylamino}-hex-2(trans)-enoic acid ethyl ester. (Compound 3)

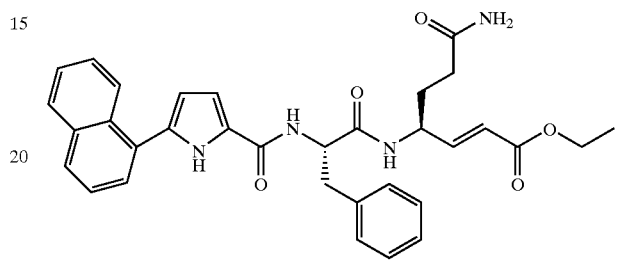

5-Naphthalen-1-yl-1H-pyrrole-2-carboxylic Acid Chloride

Method 4 General Experimental: Pyrrole-2-carboxylic acid (90.0 mmol, 10.0 g) in diethyl ether (200 ml) was treated with diazomethane (270 mmol, generated from N-nitroso-N-methyl urea), then back titrated with acetic acid until the yellow color dissipated. The solution was washed with saturated aqueous sodium bicarbonate (3×20 ml) and brine (3×20 ml), then concentrated under reduced pressure to provide 10 g (88%) of pyrrole-2-carboxylic acid methyl ester. $^1$H NMR ($CDCl_3$) δ 9.14 (1H, s), 6.98–6.65 (1H, m), 6.94–6.91 (1H, m), 6.29–6.26 (1H, m), 3.86 (3H, s).

A solution of pyrrole-2-carboxylic acid methyl ester (79.9 mmol, 10.0 g) in carbon tetrachloride (300 ml) was heated to 70° C., then treated dropwise with a solution of bromine (99.9 mmol, 126.0 ml) in carbon tetrachloride (200 ml). The reaction was initiated by the addition of iodine (40 mg). After the addition was complete, the reaction was held at 70° C. for 10 min, then cooled to room temperature using an ice bath. The mixture was washed with 10% aqueous sodium carbonate (100 ml), followed by water (100 ml). The organics were concentrated under reduced pressure and the residue was purified by silica gel chromatography to provide 4.5 g (27%) of 5-bromo-1H-pyrrole-2-carboxylic acid methyl ester. $^1$H NMR ($CDCl_3$) δ 9.29 (1H, s), 6.80 (1H, dd, J=3.9, 2.7), 6.23 (1H, dd, J=3.8, 2.6), 3.88 (3H, s).

Argon gas was bubbled 15 min through a solution of 5-bromo-1H-pyrrole-2-carboxylic acid methyl ester (10.0 mmol, 2.04 g), 1-naphthylboronic acid (30.0 mmol, 5.16 g), 2M aqueous sodium carbonate (20 ml), and DMF (150 ml). The mixture was then treated with tris (dibenzylidienacetone)dipalladium (0) (0.50 mmol, 0.46 g), and triphenylarsine (2.0 mmol, 0.61 g), then heated to reflux under argon for 12 h. The mixture was partitioned between ethyl acetate (500 ml) and water (150 ml). The organics were filtered through celite, washed with brine (3×50 ml), then concentrated under reduced pressure and the residue was purified by silica gel chromatography to provide 2.05 g (81%) of 5-naphthalen-1-yl-1H-pyrrole-2-carboxylic acid methyl ester. $^1$H NMR ($CDCl_3$) δ 9.37 (1H, s), 8.22–8.17 (1H, m), 8.16–7.89 (2H, m), 7.59–7.50 (4H, m), 7.88 (1H, dd, J=3.9, 2.7), 6.22 (1H, dd, J=3.8. 2.6), 3.88 (3H, s).

5-Naphthalen-1-yl-1H-pyrrole-2-carboxylic acid methyl ester was diluted with 1:1 dioxane-water (30 ml), and treated with lithium hydroxide hydrate (24.4 mmol, 1.02 g), then heated to reflux for 15 min. The solution was acidified with 20% aqueous citric acid (30 ml), then extracted with ethyl acetate (75 ml). The organics were washed with brine (2×20 ml), then concentrated under reduced pressure. The residue was diluted with $CH_2Cl_2$, (30 ml), and treated with oxalyl chloride (24.0 mmol, 2.10 ml), and DMF (one drop), then heated to reflux for 30 min. The solution was concentrated under reduced pressure to provide 1.95 g of 5-naphthalen-1-yl-1H-pyrrole-2-carboxylic acid chloride.

Method 1 General Experimental: 5-Naphthalen-1-yl-1H-pyrrole-2-carboxylic acid chloride (0.75 mmol, 0.19 g, prepared as described above) in $CH_2Cl_2$ (10 ml) and collidine (3.75 mmol, 0.50 ml) was added to Phe-Gln-resin, prepared as described in Example 1, (0.38 mmol, 0.51 g), and agitated for 1 h. The resin was then washed with $CH_2Cl_2$ (3×10 ml), then suspended in a solution of 95:5 TFA—$CH_2Cl_2$ (10 ml) and stirred vigorously. The resin was separated by filtration, and the filtrate was concentrated under reduced pressure. The resulting oil was purified by preparative reverse phase chromatography ($H_2O$—$CH_3CN$ gradient) to provide 21 mg (10%) of the title product. $^1$H NMR ($CDCl_3$) δ 10.55 (1H, br s), 8.16–8.08 (1H, m), 7.83–7.73 (2H, m), 7.48–7.36 (4H, m), 7.27–7.11 (5H, m), 6.88 (1H, dd, J=3.7, 2.5), 6.54 (1H, dd, J=15.7, 5.4), 6.41 (1H, dd, J=3.7, 2.5), 5.46 (1H, dd, J=15.7, 1.6), 4.62 (1H, t, J=7.2), 4.45–4.35 (1H, m), 4.09 (2H, q, J=7.2), 3.05–2.99 (2H, m), 2.19–2.11 (2H, m), 1.92–1.80 (1H, m), 1.68–1.54 (1H, m), 1.21 (3H, t, J=7.2). HRMS (FAB) 589.2427 (MNa$^+$, calcd. 589.2447).

Example 3

6-Carbamoyl-4S-(2S-{[5-(2,3-dichloro-phenyl)-1H-pyrrole-2-carbonyl]-amino}-3-phenyl-propionylamino-hex-2(trans)-enoic acid ethyl ester. (Compound 1)

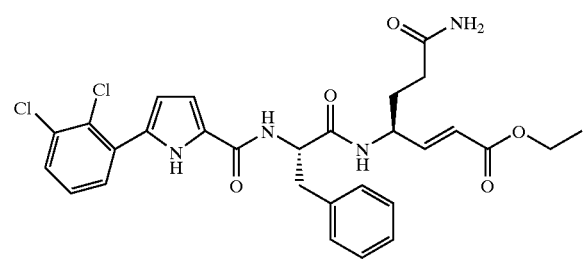

5-(2,3-Dichloro-phenyl)-1H-pyrrole-2-carboxylic acid chloride was prepared according to the procedure described in Method 4 of Example 2, starting with 2,3-dichlorophenyl boronic acid. This material was coupled to Phe-Gln resin and converted to the title compound according to the procedure described in Method 1 of Example 2. $^1$H NMR ($CD_3OD$) δ 7.52–7.44 (2H, m), 7.36–7.16 (6H, m), 6.83 (1H, d, J=3.9), 6.64 (1H, dd, J=15.8, 5.7), 6.54 (1H, d, J=3.9), 5.57 (1H, d, J=6.0), 4.68 (1H, t, J=7.7), 4.53–4.42 (1H, m), 4.17 (2H, q, J=7.1), 3.19–3.03 (2H, m), 2.28 (2H, t, J=7.9), 1.99–1.85 (1H, m), 1.78–1.65 (1H, m), 1.28 (3H, t, J=7.1). HRMS (MALDI) 607.1501 (MNa$^+$, calcd. 607.1491).

Example 4

6-Carbamoyl-4S-{3-phenyl-2S-[(5-(2-trifluoromethyl-phenyl)-1H-pyrrole-2-carbonyl)-amino]-propionylamino}-hex-2(trans)-enoic acid ethyl ester. (Compound 2)

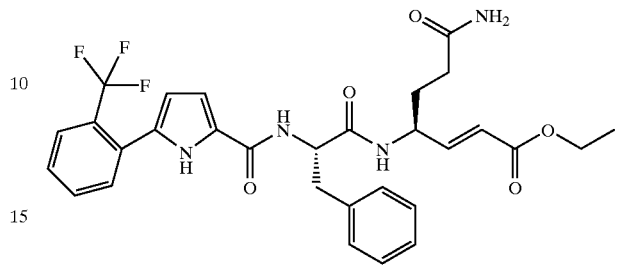

5-(2-Trifluoromethyl-phenyl)-1H-pyrrole-2-carboxylic acid chloride.

Method 6 General Experimental: Magnesium (230.0 mmol, 5.6 g) in THF (200 ml), under an argon atmosphere, was treated with 2-(2-bromoethyl)-1,3-dioxolane (200.0 mmol, 23.5 ml), slowly, keeping the internal temperature below 35° C. with the aid of an ice bath. After completion of the addition, the mixture was held at room temperature for an additional 1 h. 2-Trifluoromethyl benzaldehyde (100 mmol, 13.2 ml) in THF (100 ml) was cooled to −78° C. under an argon atmosphere, then treated with the freshly formed Grignard reagent prepared above. After completion of the addition, the solution was allowed to warm to room temperature, then held at room temperature overnight. The reaction mixture was then poured into saturated aqueous $NH_4Cl$ (200 ml), and extracted with ethyl acetate (2×150 ml). The combined organics were washed with brine (2×75 ml), then concentrated under reduced pressure to give 32.8 g of 3-[1,3]dioxolan-2-yl-1-(2-trifluoromethyl-phenyl)-propan-1-ol, which may be used without further purification. $^1$H NMR ($CDCl_3$) δ 7.78 (1H, d, J=7.7), 7.62–7.52 (2H, m), 7.34 (1H, t, J=7.6), 4.92 (1H, t, J=4.0), 4.00–3.81 (5H, m), 1.90–1.80 (4H, m).

Oxalyl chloride (115.0 mmol, 10.0 ml) in $CH_2Cl_2$ (200 ml) was cooled to −78° C. under an argon atmosphere. DMSO (240.0 mmol, 17.0 ml) was then added slowly, keeping the internal temperature below −50° C. After completing the addition, the solution was held 20 minutes at −78° C. 3-[1,3]Dioxolan-2-yl-1-(2-trifluoromethyl-phenyl)-propan-1-ol (32.8 g of crude material prepared above) in $CH_2Cl_2$ (30 ml) was added slowly, keeping the internal temperature below −50° C. The mixture was held at −78° C. for 30 minutes, then treated with $Et_3N$ (480 mmol, 70.0 ml). The mixture was allowed to warm to room temperature, then washed with water (2×75 ml), then concentrated under reduced pressure to give crude 3-[1,3]dioxolan-2-yl-1-(2-trifluoromethyl-phenyl)-propan-1-one, which may be used without further purification. $^1$H NMR ($CDCl_3$) δ 7.00 (1H, d, J=7.7), 7.63–7.50 (2H, m), 7.44 (1H, d, J=7.4), 4.99 (1H, t, J=4.3), 3.97–3.82 (4H, m), 2.98 (2H, t, J=7.3) 2.12 (2H, dt, J=7.4, 4.3).

The crude product 3-[1,3]dioxolan-2-yl-1-(2-trifluoromethyl-phenyl)-propan-1-one, in its entirety, was treated with 1:1 2N HCl:dioxane (150 ml), then heated to reflux for 20 minutes. The resulting mixture was extracted with ethyl acetate (2×150 ml). The combined organics were washed with brine (2×75 ml), then concentrated under reduced pressure to give crude 4-oxo-4-(2-trifluoromethyl-phenyl)-butyrylaldehyde, which may be used without further purification. 1H NMR (CDCl₃) δ 9.89 (1H, s), 7.71 (1H, d, J=7.5), 7.66–7.52 (3H, m), 3.15 (2H, t, J=6.1), 3.01–2.92 (2H, m).

The above prepared 4-oxo-4-(2-trifluoromethyl-phenyl)-butyrylaldehyde was diluted with ethanol (300 ml), and treated with ammonium acetate (1.00 mol, 53.5 g), then heated to reflux for 1 h. This mixture was diluted with ethyl acetate (500 ml) and washed with brine (2×75 ml). The organics were concentrated under reduced pressure and the residue was purified by silica gel chromatography to provide 7.8 g (37% from 2-trifluoromethyl benzaldehyde) of 2-(2-trifluoromethyl-phenyl)-1H-pyrrole. ¹H NMR (CDCl₃) δ 8.51 (1H, br s), 7.74 (1H, d, J=7.9), 7.60–7.54 (2H, m), 7.44–7.36 (1H, m), 6.95–6.91 (1H, m), 6.44–6.41 (1H, m), 6.33 (1H, dd, J=6.0, 2.6).

This material was treated with trichloroacetyl chloride, hydrolyzed with lithium hydroxide, and converted to the corresponding acid chloride using oxalyl chloride, as described in Method 5 of Example 12, to give 5-(2-trifluoromethyl-phenyl)-1H-pyrrole-2-carboxylic acid chloride. ¹H NMR (CDCl₃) δ 9.35 (1H, s), 7.80 (1H, d, J=7.4), 7.68–7.52 (3H, m), 7.26–7.23 (1H, m), 7.53–7.49 (1H, m).

5-(2-Trifluoromethyl-phenyl)-1H-pyrrole-2-carboxylic acid chloride was coupled to Phe-Gln-resin, and converted to the title compound according to the procedure described in Method 1 of Example 2. ¹H NMR (CDCl₃) δ 10.10 (1H, br s), 7.21 (1H, d, J=7.8), 7.59–7.40 (3H, m), 7.32–7.16 (5H, m), 6.82–6.76 (1H, m), 6.61 (1H, dd, J=15.8, 5.2), 6.39–6.33 (1H, m), 5.55 (1H, d, J=15.7), 4.69 (1H, t, J=7.2), 4.54–4.43 (1H, m), 4.16 (2H, q, J=7.1), 3.09 (2H, d, J=7.0), 2.25–2.15 (2H, m), 2.20–1.85 (1H, m), 1.78–1.52 (1H, m), 1.27 (3H, t, J=7.1). HRMS (FAB) 607.2128 (MNa⁺, calcd. 607.2144).

Example 5

6-Carbamoyl-4S-(2S-{[5-(5-chloro-2-methoxy-phenyl)-1H-pyrrole-2-carbonyl]amino}-3-phenyl-propionylamino)-hex-2(trans)-enoic acid ethyl ester. (Compound 4)

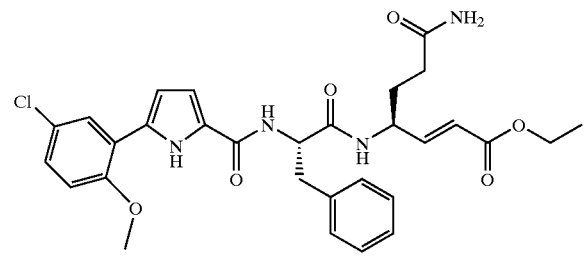

5-(5-Chloro-2-methoxy-phenyl)-1H-pyrrole-2-carboxylic acid chloride was prepared according to the procedure described in Method 4 of Example 2, starting with 5-chloro-2-methoxyphenyl boronic acid. This material was coupled to Phe-Gln resin, and converted to the title compound according to the procedure described in Method 1 of Example 2. ¹H NMR (CDCl₃) δ 10.50 (1H, br s), 7.56 (1H, d, J=2.6), 7.30–7.12 (6H, m), 6.88 (1H, d, J=8.9), 6.79–6.75 (1H, m), 6.60 (1H, dd, J=15.7, 5.3), 6.58–6.55 (1H, m), 5.54 (1H, dd, J=15.7, 1.5), 4.73–4.65 (1H, m), 4.53–4.43 (1H, m), 4.16 (2H, q, J=7.1), 3.93 (3H, s,), 3.14–3.04 (2H, m), 2.23–2.15 (2H, m), 1.99–1.84 (1H, m), 1.78–1.62 (1H, m), 1.27 (3H, t, J=7.1). HRMS (FAB) 603.1963 (MNa⁺, calc. 603.1986).

Example 6

6-Carbamoyl-4S-{2S-[(5-isoquinolin-4-yl-1H-pyrrole-2-carbonyl)-amino]-3-phenyl-propionylamino}-hex-2(trans)-enoic acid ethyl ester. (Compound 5)

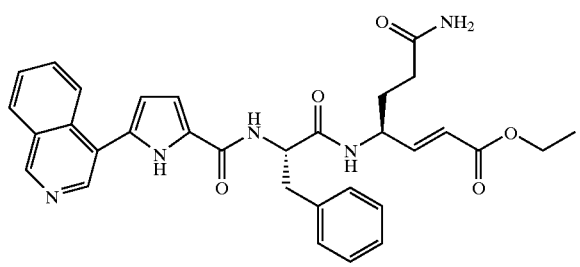

4-Bromoisoquinoline (4.10 mmol, 0.85 g) in toluene (15 ml) was treated with hexamethylditin (5.6 mmol, 2.00 g), and tetrakis(triphenylphosphine)-palladium(0) (0.20 mmol, 0.24 g), then heated to reflux overnight under an argon atmosphere. The resulting mixture was concentrated under reduced pressure, then purified by silica gel chromatography to provide 1.03 g (87%) of 4-(trimethylstannyl)-isoquinoline. ¹H NMR (CDCl₃) δ 9.23 (1H, s), 8.52 (1H, s), 8.00 (1H, d, J=8.1), 7.78–7.62 (3H, m), 0.5 (9H, s).

5-Bromo-1H-pyrrole-2-carboxylic acid methyl ester (1.49 mmol, 0.30 g, prepared according to the procedure described in Method 4 of Example 2) in NMP (10 ml) was treated with triphenylarsine (0.30 mmol, 91 mg), tris(dibenzylideneacetone) dipalladium(0) (0.07 mmol, 68 mg), and 4-(trimethylstannyl)-isoquinoline (2.22 mmol, 0.65 g), then heated to reflux under an argon atmosphere overnight. The resulting mixture was concentrated under reduced pressure, then purified by silica gel chromatography to provide 0.21 g (55%) of 5-isoquinolin-4-yl-1H-pyrrole-2-carboxylic acid methyl ester. ¹H NMR (CDCl₃) δ 9.81 (1H, br s), 9.35 (1H, s), 8.66 (1H, s), 8.31 (1H, d, J=8.5), 8.10 (1H, d, J=8.1), 7.91 (1H, t, J=15.2), 7.79 (1H, t, J=15.2), 7.11 (1H, dd, J=3.8, 2.5), 6.64 (1H, dd, J=3.7, 2.7), 3.90 (3H, s).

This material was converted to 5-isoquinolin-4-yl-1H-pyrrole-2-carboxylic acid chloride according to the procedures described in Method 4 of Example 2. This material was then coupled to Phe-Gln resin, and converted to the title compound according to the procedure of Method 1 of Example 2. ¹H NMR (CD₃OD) δ 9.20 (1H, br s), 8.51 (1H, s), 8.27 (1H, d, J=8.6), 8.17 (1H, d, J=8.1), 7.85 (1H, t, J=8.4), 7.74 (1H, t, J=8.2), 7.30–7.17 (9H, m), 7.07 (1H, d, J=3.8), 6.65 (1H, dd, J=15.8, 5.6), 6.56 (1H, d, J=3.8), 5.58 (1H, d, J=15.8), 4.55–4.46 (1H, m), 4.18 (2H, q, J=7.1), 3.17 (2H, t, J=7.8), 2.29 (2H, q, J=7.9), 2.24–1.68 (4H, m), 1.31 (3H, t, J=7.1). HRMS (FAB) 590.2363 (MNa⁺, calcd. 590.2379).

Example 7

6-Carbamoyl-4S-(2S-{[5-(3-isopropyl-phenyl)-1H-pyrrole-2-carbonyl]-amino}-3-phenyl-propionylamino)-hex-2(trans)-enoic acid ethyl ester. (Compound 6)

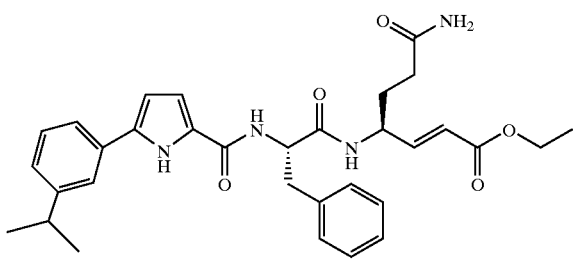

5-(3-iso-Propyl-phenyl)-1H-pyrrole-2-carboxylic acid chloride was prepared according to the procedure described in Method 4 of Example 2, starting with 3-isopropylphenyl boronic acid. This product was coupled to Phe-Gln resin, according to the procedure described in Method 1 of Example 2. $^1$H NMR (CD$_3$OD) δ 11.13 (1H, br s), 7.53 (1H, s), 7.47 (1H, d, J=7.9), 7.32–7.26 (5H, m), 7.25–7.18 (1H, m), 7.14 (1H, d, J=7.8), 6.93 (1H, dd, J=3.7, 2.3), 6.65 (1H, dd, J=15.7, 5.6), 6.53 (1H, dd, J=3.8, 2.4), 5.58 (1H, dd, J=15.7, 1.5), 4.71 (1H, t, J=7.7), 4.53–4.44 (1H, m), 4.18 (2H, q, J=7.1), 3.20–3.06 (2H, m), 2.94 (1H, d, J=6.9), 2.30 (2H, t, J=7.2), 2.00–1.87 (1H, m), 1.80–1.66 (1H, m), 1.29 (3H, t, J=7.0), 1.28 (6H, d, J=7.0). HRMS (FAB) 581.2761 (MNa$^+$, calcd. 581.2740). Anal. (C$_{32}$H$_{38}$N$_4$O$_5$·0.7H$_2$O) C, H, N.

Example 8

6-Carbamoyl-4S-(2S-{[5-(2,5-dimethoxy-phenyl)-1H-pyrrole-2-carbonyl]-amino}-3-phenyl-propionylamino)-hex-2-enoic acid ethyl ester. (Compound 7)

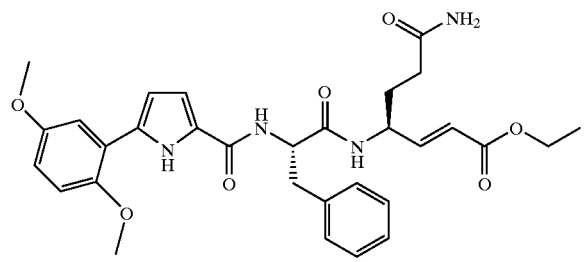

5-(2,5-Dimethoxy-phenyl)-1H-pyrrole-2-carboxylic acid chloride was prepared according to the procedure described in Method 4 of Example 2, starting with 2,5-dimethoxyphenyl boronic acid. This material was coupled to Phe-Gln resin, and converted to the title compound according to the procedure described in Method 1 of Example 2. $^1$H NMR (CDCl$_3$) δ 10.55 (1H, br s), 7.37–7.20 (7H, m), 6.90 (1H, d, J=9.0), 6.81 (1H, d, J=3.0), 6.65 (1H, dd, J=15.7, 5.3), 6.63–6.57 (1H, m), 5.61 (1H, dd, J=15.7, 1.5), 4.73–4.65 (1H, m), 4.53–4.43 (1H, m), 4.16 (2H, q, J=7.1), 3.89 (3H, s), 3.80 (3H, s), 3.14–3.04 (2H, m), 2.35–2.20 (2H, m), 2.10–1.85 (1H, m), 1.80–1.70 (1H, m), 1.27 (3H, t, J=7.1). HRMS (FAB) 599.2499 (MNa$^+$, calcd. 599.2482).

Example 9

6-Carbamoyl-4S-{3-phenyl-2S-[(5-o-tolyl-1H-pyrrole-2-carbonyl)-amino]-propionylamino}-hex-2(trans)-enoic acid ethyl ester. (Compound 9)

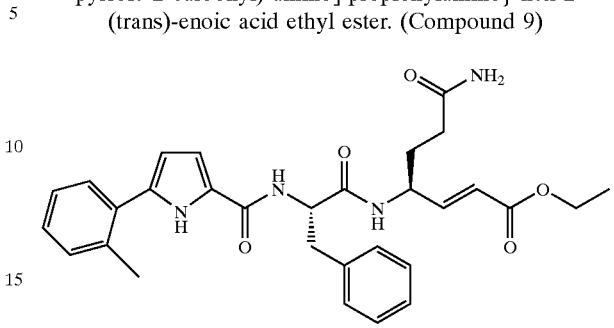

5-(o-Tolyl)-1H-pyrrole-2-carboxylic acid chloride was prepared according to the procedure described in Method 4 of Example 2, starting with o-tolyl boronic acid. This material was coupled to Phe-Gln resin, and converted to the title compound according to the procedure described in Method 1 of Example 2. $^1$H NMR (CDCl$_3$) δ 10.10 (1H, br s), 7.38–7.15 (7H, m), 6.81 (1H, d, J=7.2), 6.77–6.70 (1H, m), 6.65–6.55 (2H, m), 6.29 (1H, s), 5.58 (1H, d, J=15.5), 4.76–4.65 (1H, m), 4.58–4.45 (1H, m), 4.18 (2H, q, J=7.1), 3.20–3.03 (2H, m), 2.20–2.00 (5H, m), 1.93–1.77 (1H, m), 1.72–1.57 (1H, m), 1.90 (3H, t, J=7.1). HRMS (FAB) 553.2438 (MNa$^+$, calcd. 553.2427). Anal. (C$_{30}$H$_{34}$N$_4$O$_5$·1.0H$_2$O) C, H, N.

Example 10

6-Carbamoyl-4S-{3-phenyl-2S-[(5-phenyl-1H-pyrrole-2-carbonyl)-amino]-propionylamino}-hex-2(trans)-enoic acid ethyl ester. (Compound 10)

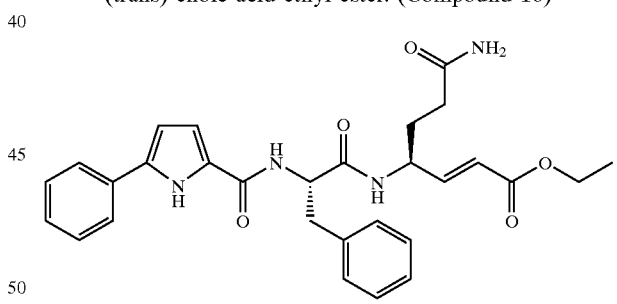

5-Phenyl-1H-pyrrole-2-carboxylic acid chloride was prepared according to the procedure described in Method 4 of Example 2, starting with phenyl boronic acid. This material was coupled to Phe-Gln resin, and converted to the title compound according to the procedure described in Method 1 of Example 2. $^1$H NMR (CDCl$_3$) δ 11.15 (1H, br s), 8.27 (I1H, d, J=4.8), 7.67 (2H, d, J=7.3), 7.39 (2H, t, J=7.8), 7.33–7.19 (5H, m), 7.76–7.71 (1H, m), 6.66 (1H, dd, J=15.7, 5.7), 6.57–6.53 (1H, m), 5.59 (1H, d, J=15.7), 4.71 (1H, t, J=7.6), 4.55–4.45 (1H, m), 4.19 (2H, q, J=7.2), 3.33 (2H, q, J=8.3), 2.30 (2H, t, J=7.3), 2.03–1.87 (1H, m), 1.80–1.68 (1H, m), 1.21 (3H, t, J=7.1). HRMS (FAB) 539.2283 (MNa$^+$, calcd. 539.2270). Anal. (C$_{29}$H$_{32}$N$_4$O$_5$·0.7H$_2$O+0.1 TFA), C, H, N.

Example 11

6-Carbamoyl-4S-(2S-{[5-(2-methoxy-phenyl)-1H-pyrrole-2-carbonyl]-amino}-3-phenyl-propionylamino)-hex-2(trans)-enoic acid ethyl ester. (Compound 11)

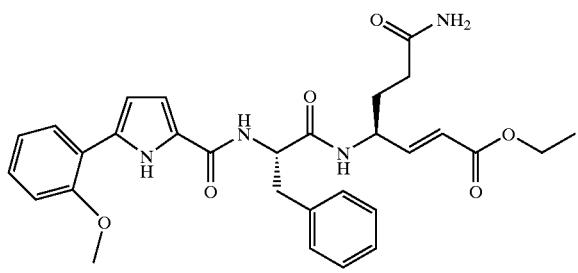

5-(2-Methoxy-phenyl)-1H-pyrrole-2-carboxylic acid chloride was prepared according to the procedure described in Method 4 of Example 2, starting with 2-methoxyphenyl boronic acid. This material was coupled to Phe-Gln resin, and converted to the title compound according to the procedure described in Method 1 of Example 2. $^1$H NMR (CDCl$_3$) δ 10.73 (1H, s), 8.27 (1H, d, J=8.3), 7.69 (1H, d, J=7.6), 7.33–7.19 (5H, m), 7.10 (1H, d, J=8.3), 7.01 (1H, t, J=7.7), 6.95 (1H, br s), 6.72–6.62 (2H, m), 5.61 (1H, d, J=15.8), 4.72 (1H, t, J=7.2), 4.57–4.46 (1H, m), 4.20 (2H, q, J=7.1), 3.99 (3H, s), 3.22–3.06 (2H, m), 2.32 (2H, t, J=7.4), 2.03–1.88 (1H, m), 1.82–1.70 (1H, m), 1.32 (3H, t, J=7.1). HRMS (MALDI) 569.2398 (MNa$^+$, calcd. 569.2376). Anal. (C$_{30}$H$_{34}$N$_4$O$_6$.0.9H$_2$O.0.4 TFA) C, H, N.

Example 12

6-Carbamoyl-4S-(3-phenyl-2S-{[5-(3,3,3-trifluoro-propyl)-1H-pyrrole-2-carbonyl]-amino}-propionylamino)-hex-2(trans)-enoic acid ethyl ester. (Compound 22)

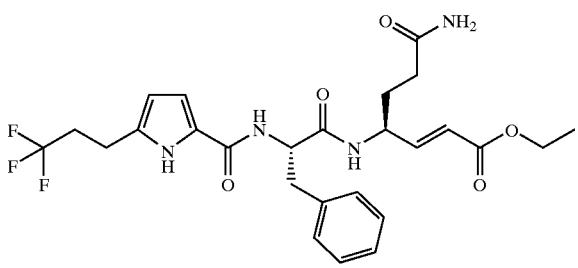

5-(3,3,3-Trifluoro-propyl)-1H-pyrrole-2-carboxylic acid chloride

Method 5 General Experimental: 4,4,4-Trifluorobutyric acid (70.0 mmol, 10.0 g) in CH$_2$Cl$_2$ (190 ml) was treated with oxalyl chloride (140 mmol, 12.3 ml) and DMF (1 drop), then heated to reflux for 1 h. Solvent and excess oxalyl chloride were removed from the volatile product by simple distillation of the reaction mixture at atmospheric pressure to provide crude 4,4,4-trifluorobutyric acid chloride (6.4 g). $^1$H NMR (CDCl$_3$) δ 3.20 (2H, t, J=7.2), 2.65–2.45 (2H, m).

4,4,4-Trifluorobutyric acid chloride (6.4 g from above) in CH$_2$Cl$_2$ (80 ml) was treated with O,N-dimethylhydroxylamine hydrochloride (60.0 mmol, 5.85 g). The mixture was cooled to 0° C., then treated with pyridine (160.0 mmol, 12.9 ml), then allowed to warm to room temperature overnight. The mixture was diluted with CH$_2$Cl$_2$ (200 ml), then washed with brine(2×50 ml). Solvent was removed from the volatile product by simple distillation at atmospheric pressure to provide 20 g of 4,4,4-trifluoro-N-methoxy-N-methyl butyramide, which may be used without further purification. $^1$H NMR (CDCl$_3$) δ 3.70 (3H, s), 3.19 (3H, s), 2.78–2.65 (2H, m), 2.57–2.40 (2H, m). Mg (92.0 mmol, 2.2 g) in THF (80 ml), under an argon atmosphere, was treated with 2-(2-bromoethyl)-[1,3]dioxolane (80 mmol, 9.4 ml), while keeping the internal temperature below 35° C. with the aid of an ice bath. After the addition was complete, the mixture was stirred for 2 h at room temperature, then cooled to −78° C. Crude 4,4,4-trifluoro-N-methoxy-N-methyl butyramide (20 g, prepared above) in THF (40 ml) was cooled to −78° C., then the freshly prepared Grignard reagent was transferred via cannula into the amide solution at −78° C. The resulting mixture was allowed to warm to room temperature, held at room temperature overnight, then poured into saturated aqueous ammonium chloride (200 ml). The mixture was extracted with ethyl acetate (3×75 ml). The combined organics were washed with brine (2×75 ml) and concentrated under reduced pressure to provide crude 1-[1,3]dioxolan-2-yl-6,6,6-trifluoro-hexan-3-one (18 g) $^1$H NMR (CDCl$_3$) δ 4.91 (1H, t, J=4.1), 3.97–3.82 (4H, m), 2.70 (2H, t, J=7.3), 2.57 (2H, t, J=7.2), 2.49–2.34 (2H, m), 2.01 (2H, dt, J=7.3, 4.1).

Crude 1-[1,3]dioxolan-2-yl-6,6,6-trifluoro-hexan-3-one (18 g, prepared above) in 1:1 2N HCl-dioxane (80 ml) was heated to reflux for 20 minutes, then neutralized with aqueous sodium bicarbonate (100 ml), then extracted with ethyl acetate (3×75 ml). The combined organics were washed with brine (2×50 ml), then concentrated under reduced pressure to provide crude 7,7,7-trifluoro-4-oxo-heptanal (10 g), which may be used without further purification. $^1$H NMR (CDCl$_3$) δ 9.80 (1H, s), 2.85–2.70 (6H, m), 2.47–2.35 (2H, m).

Crude 7,7,7-trifluoro-4-oxo-heptanal (10 g, prepared above) in ethanol (100 ml) was treated with ammonium chloride (400 mmol, 21 g), then heated to reflux for 1 h. The resulting solution was diluted with ethyl acetate (300 ml) and washed with brine (2×50 ml). The organics were concentrated under reduced pressure. Purification of the residue by silica gel chromatography provided 1.3 g (21% overall from 4,4,4-trifluorobutyric acid) of 2-(3,3,3-trifluoro-propyl)-1H-pyrrole. $^1$H NMR (CDCl$_3$) δ 7.98 (1H, br s), 6.71 (1H, dd, J=4.1, 2.6), 6.15 (1H, dd, J=5.9, 2.8), 5.99–5.94 (1H, m), 2.92–2.85 (2H, m), 2.52–2.35 (2H, m).

2-(3,3,3-Trifluoro-propyl)-1H-pyrrole (8.15 mmol, 1.33 g) was added to a solution of trichloroacetyl chloride (8.15 mmol, 0.91 ml) in diethyl ether (10 ml). The resulting solution was held at room temperature for 1 h, then concentrated under reduced pressure. The resulting solid was dissolved in 1:1 dioxane-water (20 ml), treated with lithium hydroxide (24.5 mmol, 0.59 g), and heated to reflux for 30 minutes. After cooling to room temperature, the solution was acidified with saturated aqueous citric acid (20 ml), then extracted with ethyl acetate (2×50 ml). The combined organics were concentrated under reduced pressure. Purification of the resulting solid by silica gel chromatography provided 1.15 g (68%) of 5-(3,3,3-trifluoropropyl)-1H-pyrrole-2-carboxylic acid. $^1$H NMR (CDCl$_3$) δ 9.33 (1H, br s), 6.99 (1H, dd, J=3.7, 2.5), 6.07 (1H, t, J=3.3), 2.96–2.89 (2H, m), 2.55–2.39 (2H, m).

5-(3,3,3-trifluoropropyl)-1H-pyrrole-2-carboxylic acid (5.55 mmol, 1.15 g) in CH$_2$Cl$_2$ (10 ml) was treated with oxalyl chloride (16.7 mmol, 1.5 ml), then DMF (1 drop). The solution was heated to reflux for 1 h, then concentrated under reduced pressure to provide 5-(3,3,3-trifluoropropyl)-1H-pyrrole-2-carboxylic acid chloride (1.04 g). $^1$H NMR (CDCl$_3$) δ 10.25 (1H, br s), 7.12 (1H, dd, J=4.0, 2.6), 6.12 (1H, dd, J=3.8, 2.7), 3.05–2.88 (2H, m), 2.59–2.41 (2H, m).

The 5-(3,3,3-trifluoro-propyl)-1H-pyrrole-2-carboxylic acid chloride was coupled to Phe-Gln resin, and converted to the title compound according to the procedure described in Method 1 of Example 2. $^1$H NMR (CDCl$_3$) δ 10.30 (1H, br s), 7.41 (1H, d, J=8.5), 7.29–7.13 (4H, m), 6.61 (1H, dd, J=15.7, 5.3), 6.63 (1H, m), 5.93 (1H, br s), 5.53 (1H, dd, J=15.7, 1.3), 4.65 (1H, t, J=7.1), 4.53–4.42 (1H, m), 4.15 (2H, q, J=7.1), 3.05–3.00 (2H, m), 2.88–2.79 (2H, m), 2.45–2.30 (2H, m), 2.20–2.10 (2H, m), 1.86–1.83 (1H, m), 1.75–1.66 (1H, m), 1.27 (3H, t, J=7.1). HRMS (MALDI) 559.2131 (MNa$^+$, calcd. 559.2144).

Example 13

6-Carbamoyl-4S-{3-phenyl-2S-[(5-pyridin-3-yl-1H-pyrrole-2-carbonyl)-amino]-propionylamino}-hex-2(trans)-enoic acid ethyl ester. (Compound 8)

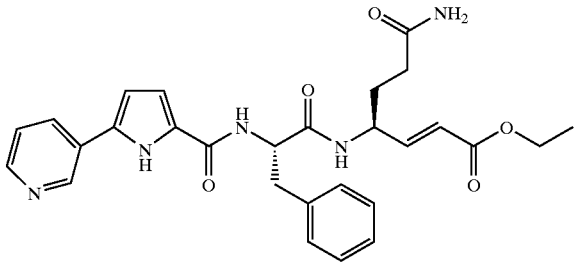

5-Pyridin-3-yl-1H-pyrrole-2-carboxylic acid chloride was prepared according to the procedure described in Method 5 of Example 12, starting with 3-pyridine carboxylic acid. This material was coupled to Phe-Gln resin, and converted to the title compound according to the procedure described in Method 1 of Example 2. $^1$H NMR (CD$_3$OD) δ 8.88 (1H, s), 8.41 (1H, d, J=3.4), 8.11 (1H, d, J=7.9), 7.46 (1H, dd, J=8.0, 4.5), 7.29–7.19 (5H, m), 6.90 (1H, d, J=3.9), 6.68 (1H, d, J=3.9), 6.66 (1H, dd, J=15.6, 5.6), 5.59 (1H, d, J=15.6), 4.71 (1H, t, J=7.7), 4.51–4.48 (1H, m), 4.19 (2H, q, J=7.1), 3.11 (2H, t, J=8.5), 2.25–2.10 (2H, m), 1.96–1.82 (1H, m), 1.75–1.60 (1H, m), 1.28 (3H, t, J=7.1). HRMS (MALDI) 540.2217 (MNa$^+$, calcd. 540.2223).

Example 14

4S-{2S-[(5-Benzo{1,3}dioxol-4-yl-1H-pyrrole-2-carbonyl)-amino-3-phenyl-propionylamino}-6-carbamoyl-hex-2(trans)-enoic acid ethyl ester. (Compound 12)

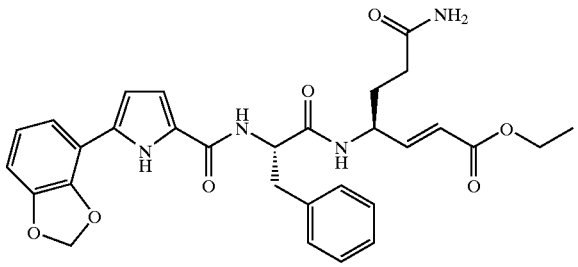

5-Benzo[1,3]dioxol-4-yl-1H-pyrrole-2-carboxylic acid chloride was prepared according to the procedure described in Method 5 of Example 12, starting with benzo[1,3]dioxole-4-carboxylic acid. This material was coupled to Phe-Gln resin, and converted to the title compound according to the procedure described in Method 1 of Example 2. $^1$H NMR (CD$_3$OD) δ 7.32–7.24 (5H, m), 7.18 (1H, dd, J=7.1, 1.1), 6.95 (1H, d, J=3.9), 6.89 (1H, t, J=5.1), 6.75 (1H, dd, J=7.7, 1.1), 6.70–6.63 (2H, m), 6.08 (2H, s), 5.58 (1H, d, J=15.3), 4.70 (1H, t, J7.7), 4.55–4.42 (1H, m), 4.18 (2H, q, J=7.2), 3.10 (2H, t, J=8.0), 2.31 (2H, t, J=8.5), 1.96–1.82 (1H, m), 1.75–1.60 (1H, m), 1.27 (3H, t, J=7.1). HRMS (FAB) 583.2148 (MNa$^+$, calcd. 583.2169).

Example 15

6-Carbamoyl-4S-(3-phenyl-2S-{[5-(3,3,3-trifluoro-1methyl-propyl)-1H-pyrrole-2-carbonyl]-amino}-propionylamino)-hex-2(trans)-enoic acid ethyl ester. (Compound 13)

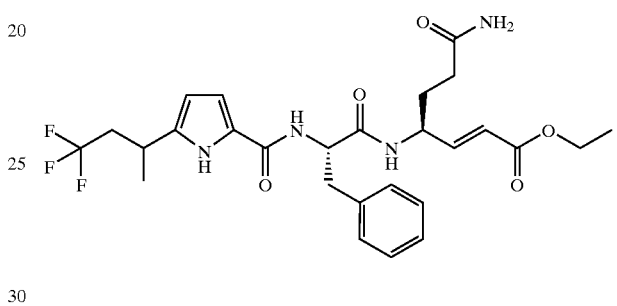

5-(3,3,3-trifluoro-1-methyl-propyl)-1H-pyrrole-2-carboxylic acid chloride was prepared according to the procedure described in Method 5 of Example 12, starting with 4,4,4-trifluoro-2-methyl butyric acid. This material was coupled to Phe-Gln resin, and converted to the title compound according to the procedure described in Method 1 of Example 2. $^1$H NMR (CDCl$_3$) δ 10.00 (1H, br s), 7.32–7.16 (5H, m), 6.99 (1H, d, J=6.9), 6.77 (1H, br s), 6.67 (H, dd, J=15.7, 5.4), 6.62–6.58 (1H, m), 6.20–6.01 (2H, m), 5.97 (1H, t, J=3.0), 5.66 (1H, d, J=15.9), 4.86–4.75 (1H, m), 4.60–4.48 (1H, m), 4.17 (2H, q, J=7.1), 3.23–3.04 (3H, m), 2.52–2.38 (1H, m), 2.22–2.12 (3H, m), 1.83–1.70 (1H, m), 1.23 (3H, d, J=7.0), 1.30 (3H, t, J=7.2). HRMS (MALDI) 573.2295 (MNa$^+$, calcd. 573.2301). Anal. (C$_{27}$H$_{33}$N$_4$O$_5$F$_3$.0.1 TFA) C, H, N.

Example 16

4S-(2S-{[5-(2-Bromo-phenyl)-1H-pyrrole-2-carbonyl]-amino}-3-phenyl-propionylamino)-6-carbamoyl-hex-2(trans)-enoic acid ethyl ester. (Compound 14)

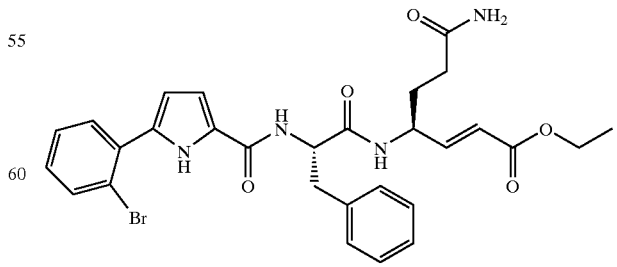

5-(2-bromo-phenyl)-1H-pyrrole-2-carboxylic acid chloride was prepared according to the procedure described in Method 5 of Example 12, starting with 2-bromobenzoic acid. This material was coupled to Phe-Gln resin, and converted to the title compound according to the procedure described in Method 1 of Example 2. ¹H NMR (CDCl₃) δ 10.30 (1H, br s), 7.56 (1H, d, J=7.9), 7.41 (1H, dd, J=7.7, 1.5), 7.31–7.13 (7H, m), 7.08 (1H, dt, J=7.8, 1.2), 7.01 (1H, d, J=8.6), 6.80–6.74 (1H, m), 6.64 (1H, dd, J=15.7, 5.3), 6.54–6.49 (1H, m), 6.26 (1H, br s), 6.14 (1H, br s), 5.63 (1H, dd, J=15.7, 1.2), 4.83–4.72 (1H, m), 4.58–4.46 (1H, m), 4.37 (2H, q, J=7.1), 3.20–3.02 (2H, m), 2.25–2.10 (2H, m), 1.96–1.82 (1H, m), 1.75–1.60 (1H, m), 1.29 (3H, t, J=7.1). HRMS (MALDI) 617.1365 (MNa⁺, calcd. 617.1376). Anal. (C₂₉H₃₁N₄O₅Br.0.2H₂O.0.3 TFA) C, H, N.

Example 17

6-Carbamoyl-4S-{3-phenyl-2S-[(5-pyridin-4-yl-1H-pyrrole-2-carbonyl)-amino]-propionylamino}-hex-2(trans)-enoic acid ethyl ester. (Compound 15)

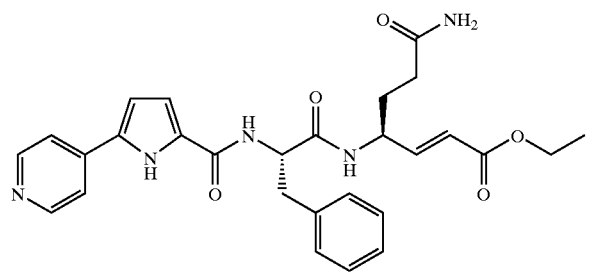

5-Pyridin-4-yl-1H-pyrrole-2-carboxylic acid chloride was prepared according to the procedure described in Method 5 of Example 12, starting with 4-pyridine carboxylic acid. This material was coupled to Phe-Gln resin, and converted to the title compound according to the procedure described in Method 1 of Example 2. ¹H NMR (CD₃OD) δ 8.50 (2H, d, J=6.7), 7.70 (2H, d, J=6.4), 7.30–7.19 (5H, m), 6.97 (1H, d, J=3.9), 6.84 (1H, d, J=4.0), 6.66 (1H, dd, J=15.8, 5.6), 5.59 (1H, d, J=15.7), 4.72 (1H, t, J=15.4), 4.60–4.40 (1H, m), 4.18 (2H, q, J=7.1), 3.17 (2H, t, J=7.9), 2.25–2.10 (2H, m), 1.96–1.82 (1H, m), 1.75–1.60 (1H, m), 1.28 (3H, t, J=7.1). HRMS (MALDI) 540.2217 (MNa⁺, calcd. 540.2223).

Example 18

6-Carbamoyl-4S-(2S-{[5-(2-trifluoromethyl-phenyl)-1H-pyrrole-2-carbonyl]-amino}-pent-4-ynoylamino)-hex-2(trans)-enoic acid ethyl ester. (Compound 16)

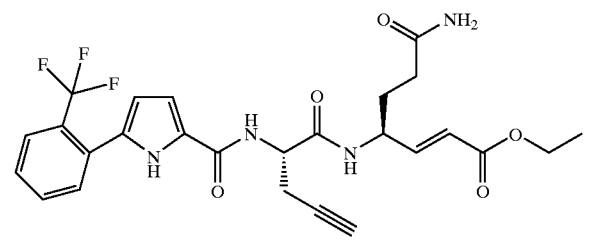

Gln-resin was coupled with Fmoc-propargyl glycine, deprotected, then coupled to 5-(2-trifluoromethyl-phenyl)-1H-pyrrole-2-carboxylic acid chloride (prepared according to the procedure described in Method 6 of Example 4), following Method 1 of Example 2. ¹H NMR (CDCl₃) δ 10.13 (1H, s), 7.73 (1H, d, J=7.8), 7.60–7.40 (4H, m), 7.15 (1H, d, J=7.6), 6.90–6.75 (2H, m), 6.38 (1H, s), 6.15 (2H, br s), 6.02 (1H, d, J=16.3), 4.78–4.68 (1H, m), 4.68–4.55 (1H, m), 4.15 (2H, q, J=7.1), 2.80–2.20 (4H, m), 2.12 (1H, s), 2.08–1.90 (1H, m), 1.90–1.75 (1H, m), 1.25 (3H, t, J=7.1). HRMS (MALDI) 555.1828 (MNa⁺, calcd. 555.1831). Anal. (C₂₆H₂₇F₃N₄O₅.0.8H₂O).

Example 19

6-Carbamoyl-4S-(4-methyl-2S-{[5-(2-trifluoromethyl-phenyl)-1H-pyrrole-2-carbonyl]-amino}-pentanoylamino)-hex-2(trans)-enoic acid ethyl ester. (Compound 17)

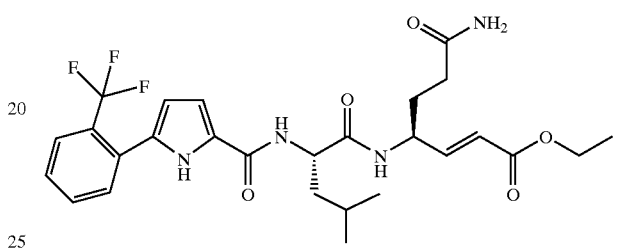

Gln-resin was coupled with Fmoc-leucine, deprotected, then coupled to 5-(2-trifluoromethyl-phenyl)-1H-pyrrole-2-carboxylic acid chloride (prepared according to the procedure described in Method 6 of Example 4), following Method 1 of Example 2. ¹H NMR (CDCl₃) δ 10.06 (1H, s), 7.70 (1H, d, J=7.6), 7.60–7.38 (4H, m), 7.13 (1H, d, J=7.8) 6.88–6.75 (2H, m), 6.36 (2H, br s), 6.19 (1H, br s), 5.91 (1H, d, J=15.5), 4.72–4.60 (1H, m), 4.60–4.45 (1H, m), 4.17 (2H, q, J=7.1), 2.28–2.15 (2H, m), 2.00–1.85 (1H, m), 1.80–1.60 (4H, m), 1.27 (3H, t, J=7.1), 0.92 (3H, d, J=5.5), 0.88 (3H, d, J=5.5). HRMS (MALDI) 573.2292 (MNa⁺, calcd. 573.2301). Anal. (C₂₇H₃₃N₄F₃O₅.0.2H₂O.0.2 TFA) C, H, N.

Example 20

6-Carbamoyl-4S-(2S-{[5-(2-trifluoromethyl-phenyl)-1H-pyrrole-2-carbonyl]-amino}-pentanoylamino)-hex-2(trans)-enoic acid ethyl ester. (Compound 18)

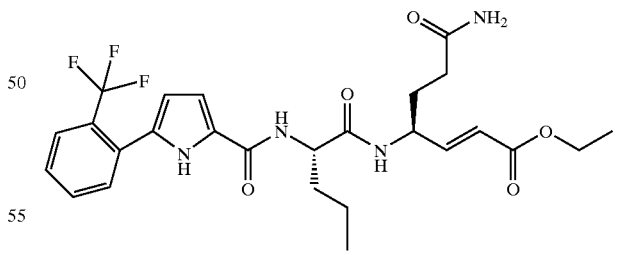

Gln-resin was coupled with Fmoc-norvaline, deprotected, then coupled to 5-(2-trifluoromethyl-phenyl)-1H-pyrrole-2-carboxylic acid chloride (prepared according to the procedure described in Method 6 of Example 4), following Method 1 of Example 2. ¹H NMR (CDCl₃) δ 10.21 (1H, s), 7.69 (1H, d, J=7.7), 7.64 (1H, d, J=8.0), 7.55–7.33 (4H, m), 6.88–6.75 (2H, m), 6.45–6.20 (3H, m), 5.91 (1H, d, J=15.7), 4.65–4.50 (2H, m), 4.15 (2H, q, J=7.1), 2.25–2.15 (2H, m), 2.00–1.60 (4H, m), 1.48–1.28 (2H, m), 1.25 (3H, t, J=7.1), 0.89 (3H, t, J=7.2). HRMS (MALDI) 559.2158 (MNa+, calcd. 559.2144).

Example 21

6-Carbamoyl-4S-(2S-{[5-(2-trifluoromethyl-phenyl)-1H-pyrrole-2-carbonyl]-amino}-hexanoylamino)-hex-2(trans)-enoic acid ethyl ester. (Compound 19)

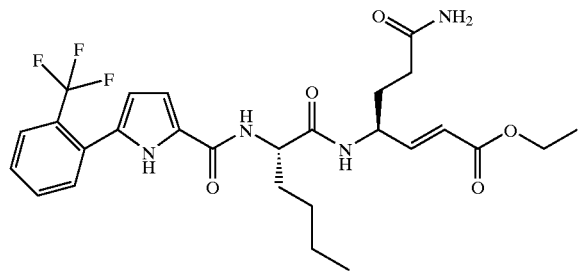

Gln-resin was coupled with Fmoc-norleucine, deprotected, then coupled to 5-(2-trifluoromethyl-phenyl)-1H-pyrrole-2-carboxylic acid chloride (prepared according to the procedure described in Method 6 of Example 4), following Method 1 of Example 2. $^1$H NMR (CDCl$_3$) δ 10.08 (1H, br s), 7.71 (1H, d, J=7.7), 7.56–7.38 (4H, m), 7.09 (1H, d, J=7.9), 6.88–6.76 (2H, m), 6.37 (1H, s), 6.32 (1H, br s), 6.18 (1H, br s), 5.92 (1H, d, J=15.0), 4.64–4.52 (2H, m), 4.16 (2H, q, J=7.1), 2.30–2.15 (2H, m), 2.00–1.65 (4H, m), 1.40–1.22 (7H, m), 0.87 (3H, t, J=6.3). HRMS (MALDI) 573.2307 (MNa+, calcd. 573.2301).

Example 22

6-Carbamoyl-4S-(2S-{[5-(2-trifluoromethyl-phenyl)-1H-pyrrole-2-carbonyl]-amino}-acetylamino)-hex-2(trans)-enoic acid ethyl ester. (Compound 20)

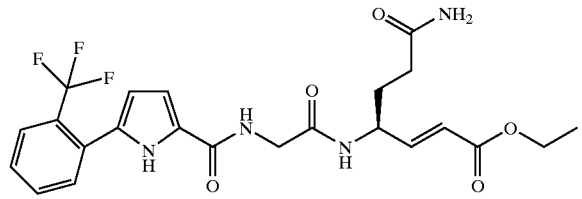

Gln-resin was coupled with Fmoc-glycine, deprotected, then coupled to 5-(2-trifluoromethyl-phenyl)-1H-pyrrole-2-carboxylic acid chloride (prepared according to the procedure described in Method 6 of Example 4), following Method 1 of Example 2. $^1$H NMR (CD$_3$OD) δ 11.18 (1H, s), 7.79 (1H, d, J=7.8), 7.70–7.50 (3H, m), 6.92–6.88 (1H, m), 6.85 (1H, d, J=5.5), 6.32 (1H, m), 5.97 (1H, dd, J=15.7, 1.7), 4.64–4.54 (1H, m), 4.17 (2H, q, J=7.1), 4.02 (2H, d, J=2.4), 2.35–2.27 (2H, m), 2.06–1.94 (1H, m), 1.90–1.75 (1H, m), 1.27 (3H, t, J=7.1). HRMS (MALDI) 495.1874 (MNa+, calcd. 495.1855).

Example 23

6-Carbamoyl-4S-(2S-{[5-(3-methyl-isoxazol-5-yl)-1H-pyrrole-2-carbonyl]-amino}-3-phenyl-propionylamino)-hex-2(trans)-enoic acid ethyl ester. (Compound 21)

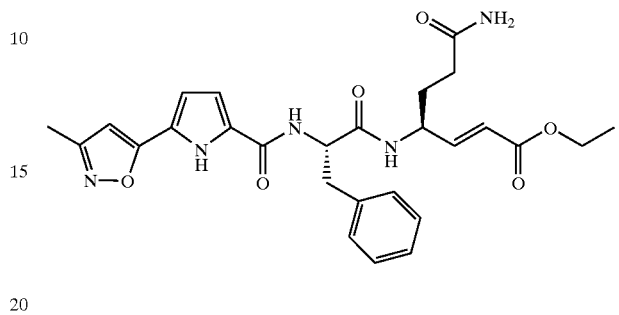

3-Methyl-5-(1H-pyrrol-2-yl)-isoxazole (Sundberg, et al., J. Org. Chem., 1985, 50, 425) was converted to 5-(3-methyl-isoxazol-5-yl)-1H-pyrrole-2-carboxylic acid chloride according to the procedure described in Method 5 of Example 12, then coupled to Phe-Gln resin following Method 1 of Example 2, then cleaved from resin to provide the title compound. $^1$H NMR (CD$_3$OD) δ 7.31–7.19 (6H, m), 6.93 (1H, d, J=3.9), 6.67 (1H, d, J=4.0), 6.64 (1H, dd, J=15.3, 5.7), 6.49 (1H, s), 5.57 (1H, dd, J=15.8, 0.9), 4.69 (1H, t, J=15.6), 4.55–4.46 (1H, m), 4.18 (2H, q, J=7.1), 3.12 (2H, t, J=7.6), 2.31 (2H, q, J=8.0), 2.05–1.94 (1H, m), 1.83–1.74 (1H, m), 1.28 (3H, t, J=7.1). HRMS 544.2163 (MNa+, calcd. 544.2172).

Example 24

6-Carbamoyl-4S-(2S-{[5-(2-trifluoromethyl-phenyl)-1H-pyrrole-2-carbonyl]-amino}-butyrlamino)-hex-2(trans)-enoic acid ethyl ester. (Compound 23)

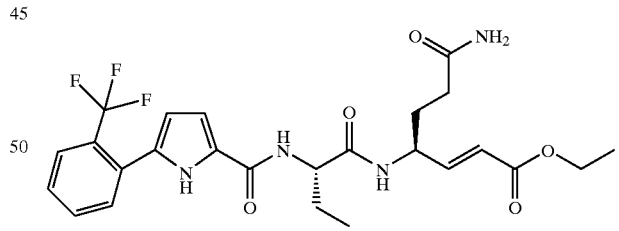

Gln-resin was coupled with Fmoc-aminobutyric acid, deprotected, then coupled to 5-(2-trifluoromethyl-phenyl)-1H-pyrrole-2-carboxylic acid chloride (prepared according to the procedure described in Method 6 of Example 4), following Method 1 of Example 2. $^1$H NMR (CDCl$_3$) δ 10.06 (1H, br s), 7.72 (1H, d, J=7.7), 7.63–7.37 (4H, m), 7.02 (1H, d, J=7.5), 6.88–6.76 (2H, m), 6.37 (1H, s), 6.28 (1H, br s), 6.18 (1H, br s), 5.92 (1H, d, J=15.8), 4.68–4.45 (2H, m), 4.16 (2H, q, J=7.1), 2.34–2.22 (2H, m), 2.04–1.65 (4H, m), 1.26 (3H, t, J=7.1), 0.95 (3H, t, J=7.1). HRMS (MALDI) 545.2002 (MNa+, calcd. 545.1988).

Example 25

5-Naphthalen-1-yl-1H-pyrrole-2-carboxylic acid-{1 S-[2-oxo-dihydrofuran-3-ylidine)-1-(2-oxo-pyrrolidin-3S-methyl)-ethyl carbamoyl]-2S-(4-fluoro-phenyl-ethyl)}-amide. (Compound 26)

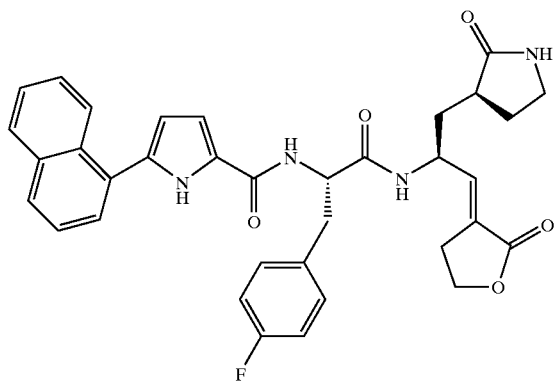

Method 2 General Experimental: Boc-protected 3S-[2S-amino-3-(2-oxo-dihydro-furan-3-ylidene)-propyl]-pyrrolidin-2-one, prepared by a method analogous to that described in Tian, et al., U.S. Provisional Patent Application No. 60/150,358, filed Aug. 24, 1999 and also Baldwin et al., J. Org. Chem., 1971, 36, 1441, (3.40 mmol, 1.10 g) in $CH_2Cl_2$ (10 ml) was treated with HCl (17.0 mmol, 4.3 ml of 4M in dioxane), and held at room temperature for 1 h, then concentrated under reduced pressure. The product was diluted with DMF (10 ml), treated with Boc-4-fluoro-phenylalanine (3.40 mmol, 0.96 g), DIEA (10.2 mmol, 1.8 ml), and HATU (3.40 mmol, 1.29 g), then held at room temperature for 1 h. The resulting solution was diluted with in ethyl acetate (75 ml), washed with brine (3×20 ml), then concentrated under reduced pressure. The residue was purified by silica gel chromatography to provide 0.84 g (51%) of 2-(4-fluorophenyl)-1S-[2-(2-oxodihydrofuran-3-ylidene)-1-(2-oxo-pyrrolidin-3S-ylmethyl)-ethyl carbamoyl]-ethyl-carbamic acid t-butyl ester. $^1$H NMR ($CDCl_3$) δ 7.82 (1H, br s), 7.15–7.07 (2H, m), 6.96 (2H, t, J=8.7), 6.32 (1H, d, J=8.2), 6.00 (1H, s), 5.22 (1H, d, J=7.8), 4.55–4.32 (4H, m), 3.40–3.28 (2H, m), 3.28–3.10 (1H, m), 3.05–2.95 (2H, m), 2.95–2.83 (1H, m), 2.50–2.20 (2H, m), 2.10–1.90 (1H, m), 1.90–1.70 (2H, m), 1.58–1.46 (1H, m), 1.39 (9H, s).

2-(4-Fluorophenyl)-1S-[2-(2-oxodihydrofuran-3-ylidine)-1-(2-oxo-pyrrolidin-3S-ylmethyl)-ethyl carbamoyl]-ethyl-carbamic acid t-butyl ester (0.96 mmol, 0.47 g) in $CH_2Cl_2$ (5 ml) was treated with HCl (4.8 mmol, 1.2 ml of 4M in dioxane), and held 1 h, then concentrated under reduced pressure. The product was diluted with $CH_2Cl_2$ (5 ml) and collidine (2.89 mmol, 0.38 ml), and treated with 5-naphthalene-1-yl-1H-pyrrole-2-carboxylic acid chloride (prepared according to the procedure described in Method 4 of Example 2, starting with 1-naphthalene boronic acid, 0.96 mmol, 0.25 g), then held at room temperature for 1 h. The resulting solution was diluted with ethyl acetate (75 ml), washed with saturated aqueous sodium bicarbonate (2×20 ml) and brine (2×20 ml), then concentrated under reduced pressure. Purification of the residue by silica gel chromatography gave 0.17 g (29%) of product. $^1$H NMR ($CDCl_3$) δ 10.05 (1H, s), 8.27–8.13 (2H, m) 7.92–7.80 (2H, m), 7.57–7.45 (4H, m), 7.20–7.11 (2H, m), 7.05–6.95 (3H, m), 6.73 (1H, d, J=9.6), 6.51 (1H, dd, J=3.7, 2.6), 6.32 (1H, DT, J=8.5, 2.9), 5.36 (1H, br s), 5.15–5.05 (1H, m), 4.46–4.32 (3H, m), 3.42–3.18 (4H, m), 3.02–2.82 (2H, m), 2.36–2.25 (1H, m), 1.90–1.65 (3H, m), 1.60–1.48 (1H, m). HRMS (FAB) 741.1466 ($MCs^+$, calcd. 741.1489).

Example 26

5-(2-Oxo-pyrrolidin-3S-yl)-4S-{3-phenyl-2S-[(1H-pyrrole-2-carbonyl)-amino]-propionylamino}-pent-2 (trans)-enoic acid ethyl ester. (Compound 24)

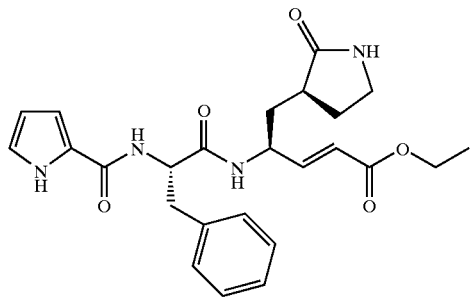

4S-Amino-5-(2-oxo-pyrrolidin-3S-yl)-pent-2(trans)-enoic acid ethyl ester was coupled to Boc-phenylalanine, then deprotected and coupled to pyrrole-2-carboxylic acid chloride, following Method 2 of Example 25. $^1$H NMR ($CD_3OD$) δ 7.23–7.08 (5H, m), 6.82 (1H, dd, J=2.5, 1.4), 6.71 (1H, dd, J=3.8, 1.4), 6.58 (1H, dd, J=10.2, 5.5), 6.13 (1H, dd, J=3.8, 2.5), 5.57 (1H, dd, J=15.8, 1.6), 4.74 (1H, t, J=6.8), 4.47–4.36 (1H, m), 4.10 (2H, q, J=7.1), 3.11–2.94 (2H, m), 2.27–2.13 (2H, m), 1.84–1.57 (1H, m), 1.49–1.38 (1H, m), 1.21 (3H, t, J=7.1). HRMS (FAB) 467.2299 ($MH^+$, calcd. 467.2294).

Example 27

4S-{2S-[(5-Naphthalen-1-yl-1H-pyrrole-2-carbonyl)-amino]-3-phenyl-propionylamino}-5-(2-oxo-pyrrolidin-3S-yl)-pent-2-enoic acid ethyl ester. (Compound 25)

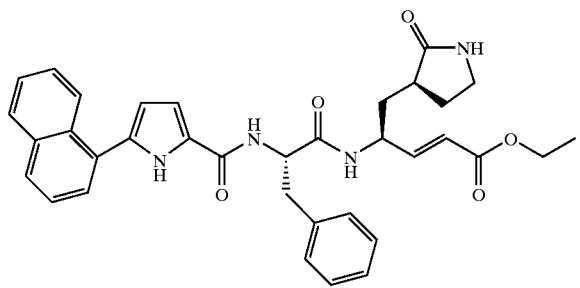

4S-Amino-5-(2-oxo-pyrrolidin-3S-yl)-pent-2(trans)-enoic acid ethyl ester was coupled to Boc-phenylalanine, then deprotected and coupled to 5-naphthalen-1-yl-pyrrole-2-carboxylic acid chloride (prepared according to the procedure described in Method 4 of Example 2, starting with 1-naphthyl boronic acid) following Method 2 of Example 25. $^1$H NMR ($CDCl_3$) δ 10.28 (1H, s), 8.21 (1H, d, J=9.0), 7.83–7.80 (3H, m), 7.57–7.44 (4H, m), 7.34–7.18 (5H, m), 7.02–6.96 (1H, m), 6.74 (1H, d, J=9.1), 6.67 (1H, dd, J=10.2, 5.4), 6.52–6.46 (1H, m), 5.75 (1H, d, J=15.6), 5.18 (1H, br s), 5.13–5.03 (1H, m), 4.47–4.36 (1H, m), 4.17 (2H, q, J=7.1), 3.41–3.31 (1H, m), 3.17–3.07 (2H, m), 3.06–2.97 (1H, m), 2.30–2.18 (1H, m), 2.05–1.92 (1H, m), 1.80–1.58

(2H, m), 1.55–1.45 (1H, m), 1.27 (3H, t, J=7.1). HRMS (FAB) 593.2750 (MH⁺, calcd. 593.2764).

Example 28

5-Phenyl-1H-pyrrole-2-carboxylic acid-{2S-(4-fluorophenyl)-1S-[1-(2-oxo-dihydrofuran-3-ylidinemethyl)-1-(2-oxo-pyrrolidin-3S-methyl)-ethyl carbamoyl]-2S-phenyl-ethyl}-amide. (Compound 27)

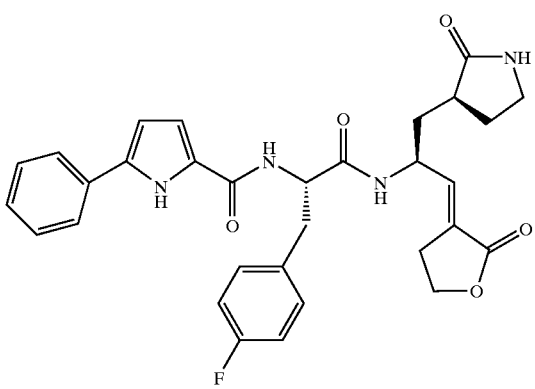

2-(4-Fluorophenyl)-1S-[2-(2-oxodihydrofuran-3-ylidine)-1-(2-oxo-pyrrolidin-3S-ylmethyl)-ethyl carbamoyl]-ethyl-carbamic acid t-butyl ester (prepared as described in Method 2 of Example 25) was deprotected, then coupled to 5-phenyl-1H-pyrrole-2-carboxylic acid chloride (prepared according to the procedure described in Method 5 of Example 12, starting with benzoic acid), following Method 2 of Example 25. ¹H NMR (CDCl₃) δ 10.48 (1H, s), 7.56 (2H, d, J=7.3), 7.36 (2H, t, J=7.7), 7.26–7.19 (1H, m), 7.14–7.06 (2H, m), 6.93 (2H, t, J=8.7), 6.85–6.81 (1H, m), 6.51–6.47 (1H, m), 6.28 (1H, dt, J=8.8, 3.9), 4.83 (1H, t, J=5.2), 4.50–4.39 (1H, m), 4.34 (2H, t, J=7.6), 3.30–3.27 (2H, m), 3.18–2.90 (3H, m), 2.91–2.76 (1H, m), 2.36–2.13 (2H, m), 1.98–1.85 (1H, m), 1.80–1.66 (1H, m), 1.53–1.43 (1H, m). HRMS (FAB) 581.2161 (MNa⁺, calcd. 581.2176).

Example 29

5-(2-Oxo-pyrrolidin-3S-yl)-4S-(3-phenyl-2S-{[5-(2-trifluoromethyl-phenyl)-1H-pyrrole-2-carbonyl]-amino}-propionylamino)-pent-2(trans)-enoic acid ethyl ester. (Compound 28)

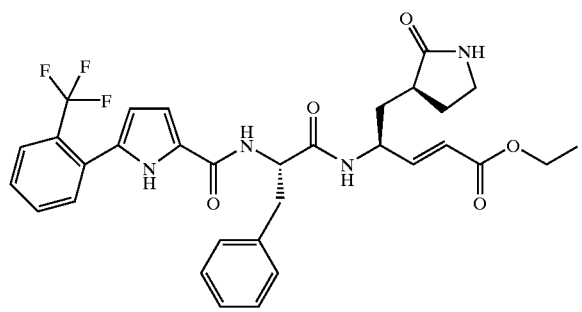

4S-Amino-5-(2-oxo-pyrrolidin-3S-yl)-pent-2(trans)-enoic acid ethyl ester was coupled to Boc-phenylalanine, then deprotected and coupled to 5-(2-trifluoromethyl-phenyl)-1H-pyrrole-2-carboxylic acid chloride (prepared according to the procedure described in Method 6 of Example 4, starting with 2-trifluoromethyl benzaldehyde) following Method 2 of Example 25. ¹H NMR (CDCl₃) δ 10.00 (1H, s), 7.75–7.65 (2H, m), 7.57–7.35 (3H, m), 7.30–7.13 (4H, m), 6.98 (1H, d, J=8.8), 6.84 (1H, br s), 6.65 (1H, dd, J=10.2, 5.4), 6.38 (1H, br s), 6.15 (1H, br s), 5.72 (1H, d, J=14.7), 5.10–4.98 (1H, m), 4.52–4.40 (1H, m), 4.17 (2H, q, J=7.1), 3.28–3.15 (3H, m), 3.00 (1H, dd, J=13.4, 7.0), 2.32–2.20 (1H, m), 2.18–2.05 (1H, m), 1.88–1.60 (2H, m), 1.58–1.48 (1H, m), 1.27 (3H, t, J=7.1). HRMS (MALDI) 611.2475 (MH⁺, calcd. 611.2481). Anal. (C₃₂H₃₃N₄O₅F₃.1.0 H₂O) C, H, N.

Example 30

5-(2-Oxo-pyrrolidin-3S-yl)-4S-(2S-{[5-(2-trifluoromethyl-phenyl)-1H-pyrrole-2-carbonyl]-amino}-pent-4-ynoylamino)-pent-2(trans)-enoic acid ethyl ester. (Compound 29)

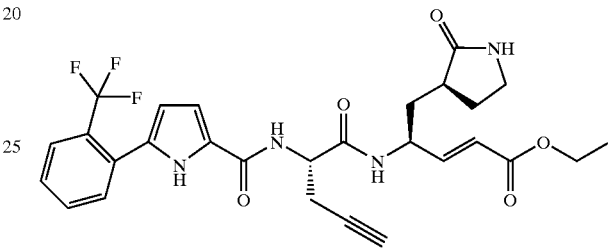

4S-Amino-5-(2-oxo-pyrrolidin-3S-yl)-pent-2(trans)-enoic acid ethyl ester was coupled to Boc-propargyl glycine, then deprotected and coupled to 5-(2-trifluoromethyl-phenyl)-1H-pyrrole-2-carboxylic acid chloride (prepared according to the procedure described in Method 6 of Example 4, starting with 2-trifluoromethyl benzaldehyde) following Method 2 of Example 25. ¹H NMR (CDCl₃) δ 10.13 (1H, s), 8.10 (1H, d, J=7.4), 7.73 (1H, d, J=7.8), 7.59–7.40 (3H, m), 7.19 (1H, d, J=8.4), 6.88 (1H, dd, J=3.8, 2.5), 6.83 (1H, dd, J=15.7, 5.0), 6.43–6.35 (1H, m), 6.03 (1H, dd, J=15.7, 1.6), 4.92–4.83 (1H, m), 4.65–4.54 (1H, m), 4.15 (2H, q, J=7.1), 3.32–3.23 (2H, m), 2.87–2.61 (2H, m), 2.50–2.22 (2H, m), 2.06 (1H, t, J=2.5), 2.00–1.92 (1H, m), 1.86–1.58 (2H, m), 1.25 (3H, t, J=7.1). HRMS (MALDI) 581.1992 (MNa⁺, calcd. 581.1988). Anal. (C₂₈H₂₉N₄O₅F₃.0.5H₂O) C, H, N.

Example 31

6-Carbamoyl-4S-(2S {methyl-[5-(2-trifluoromethyl-phenyl)-1H-pyrrole-2-carbonyl]-amino}-3–3-phenyl-propionylamino)-hex-2(trans)-enoic acid ethyl ester. (Compound 41)

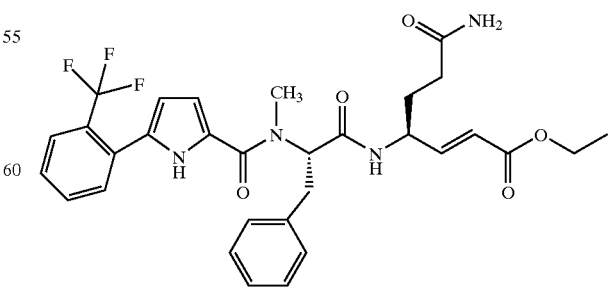

Gln-resin was coupled with Fmoc-N-methyl-phenylalanine, according to the procedure described in Method 1 of Example 2, then deprotected and coupled with 5-(2-trifluoromethyl-phenyl)-1H-pyrrole-2-carboxylic acid (prepared according to the procedure described in Method 6 of Example 4), according to the procedure described in Method 1 of Example 2. $^1$H NMR (CD$_3$OD) δ 7.90–7.50 (4H, m), 7.35–7.15 (5H, m), 6.88 (1H, dd, J=15.8, 5.4), 6.60–6.58 (1H, m), 6.38–6.32 (1H, m), 5.98 (1H, dd, J=15.8, 1.6), 5.32–5.20 (1H, m), 4.65–4.50 (1H, m), 4.25–4.10 (2H, m), 4.18 (2H, q, J=7.1), 3.50–3.10 (5H, m), 2.33–2.20 (2H, m), 2.03–1.72 (2H, m), 1.23 (3H, t, J=7.1). HRMS (MALDI) 621.2301 (MNa$^+$, calcd. 621.2301).

Example 32

4S-[2(R,S)-Benzyl-4-oxo-4-(1H-pyrrol-2-yl)-butyrylamino-5-(2-oxo-pyrrolidin-3S-yl)-pent-2 (trans)-enoic acid ethyl ester

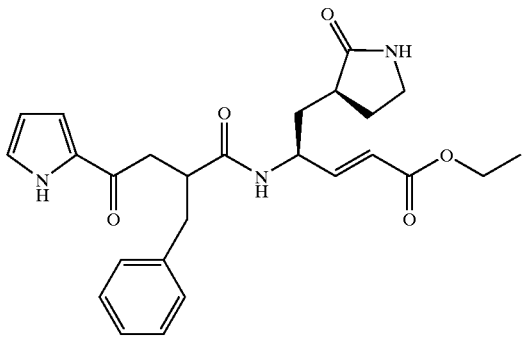

2(R,S)-Benzyl-4-oxo-4-(1H-pyrrol-2-yl)-butyric acid

Method 7 General Experimental: Pyrrole-2-carboxylic acid (27.0 mmol, 3.00 g) in CH$_2$Cl$_2$ (100 ml) was treated with oxalyl chloride (54.0 mmol, 4.70 ml) and DMF (1 drop), then heated to reflux for 1 h, then concentrated under reduced pressure. The residue was diluted with CH$_2$Cl$_2$ (100 ml) and pyridine (6.50 ml), and treated with O,N-dimethyl-hydroxylamine hydrochloride (27.0 mmol, 2.65 g), then held at room temperature overnight. The resulting solution was diluted with ethyl acetate (250 ml), washed with 10% aqueous citric acid (2×30 ml), saturated aqueous sodium bicarbonate (2×30 ml), then brine (2×30 ml). The organics were concentrated under reduced pressure. Purification of the residue by silica gel chromatography provided 3.42 g (82%) of 1H-pyrrole-2-carboxylic acid methoxy-methyl amide. $^1$H NMR (CDCl$_3$) δ 6.90–6.80 (1H, m), 6.79–6.60 (1H, m), 6.18 (1H, dd, J=3.7, 1.3), 3.81 (3H, s), 3.01 (3H, s).

1H-pyrrole-2-carboxylic acid methoxy-methyl amide (22.2 mmol, 3.42 g) in THF (100 ml) was cooled to −78° C., and treated with methyl lithium-lithium bromide complex (44.4 mmol, 29.6 ml of 1.5 M in Et$_2$O). The solution was held at −78° C. for 20 minutes, allowed to warm to 0° C., and held 30 minutes, then poured into saturated aqueous ammonium chloride (300 ml). The mixture was extracted with ethyl acetate (3×150 ml). The combined organic extracts were washed with brine (3×50 ml) and concentrated under reduced pressure. The residue was purified by silica gel chromatography to provide 2.28 g (94%) of 1-(1H-pyrrol-2-yl)-ethanone. $^1$H NMR (CDCl$_3$) δ 7.03 (1H, dt, J=2.7, 1.3), 6.91 (1H, ddd, J=3.8, 2.4, 1.3), 6.30–6.26 (1H, m), 2.44 (3H, s).

1-(1H-pyrrol-2-yl)-ethanone (2.67 mmol, 0.29 g) in CH$_2$Cl$_2$ (10 ml) and Et$_3$N (13.3 mmol, 1.90 ml) was cooled to 0° C. and treated with trimethylsilyl trifluoromethane-sulfonate (5.34 mmol, 1.00 ml). The solution was held at 0° C. for 30 minutes, then diluted with ethyl acetate (75 ml) and washed with saturated aqueous sodium bicarbonate (2×20 ml) then brine (30 ml). The solution was concentrated under reduced pressure to provide crude 2-[1-(trimethyl-silanyloxy)-vinyl]-1H-pyrrole. $^1$H NMR (CDCl$_3$) δ 6.77 (1H, dd, J=2.7, 1.6), 6.34 (1H, dd, J=3.2, 1.6), 6.15 (1H, t, J=2.8), 4.56 (1H, d, J=1.0), 4.31 (1H, d, J=1.0), 0.45 (9H, s), 0.25 (9H, s).

Crude 2-[1-(trimethyl-silanyloxy)-vinyl]-1H-pyrrole was diluted with CH$_2$Cl$_2$ (10 ml), cooled to 0° C., and treated with N-bromosuccinimide (1.94 mmol, 0.35 g). The resulting mixture was put in a −20° C. freezer overnight. After warming to room temperature, the mixture was diluted with ethyl acetate (75 ml), washed with saturated aqueous sodium bicarbonate (2×20 ml), brine (2×20 ml), and the organics concentrated under reduced pressure. Purification of the residue by silica gel chromatography provided 0.29 g (80%) of 2-bromo-1-(1H-pyrrol-2-yl)-ethanone. $^1$H NMR (CDCl$_3$) δ 7.12 (1H, dt, J=2.7, 1.3), 7.02 (1H, ddd, J=3.8, 2.4, 1.3), 6.36–6.31 (1H, m), 4.27 (2H, s).

2-Bromo-1-(1H-pyrrol-2-yl)-ethanone (1.00 mmol, 0.19 g) in DME (3 ml) was treated with NaI (1.00 mmol, 0.15 g), and stirred vigorously for 30 minutes. A solution of diethyl malonate (1.50 mmol, 0.2 ml), NaH (1.00 mmol, 40 mg of 60% in oil), and DME (3 ml) was added to the bromide-NaI mixture, and held at room temperature overnight. Saturated aqueous ammonium chloride (10 ml) was added, then the mixture was extracted with ethyl acetate (2×25 ml). The combined organic extracts washed with brine (25 ml), then concentrated under reduced pressure. Purification of the residue by silica gel chromatography provided 0.21 g (79%) of 2-(1H-pyrrole-2-carbonyl)-malonic acid diethyl ester. $^1$H NMR (CDCl$_3$) δ 9.76 (1H, s), 7.04 (1H, dt, J=2.7, 1.3), 7.00 (1H, ddd, J=3.8, 2.4, 1.3), 6.30–6.26 (1H, m), 4.21 (4H, m), 4.02 (1H, t, J=7.3), 3.45 (2H, d, J=7.3), 1.25 (6H, t, J=7.1).

2-(1H-Pyrrole-2-carbonyl)-malonic acid diethyl ester (0.79 mmol, 0.21 g) in DME (3 ml) was treated with lithium bis-trimethylsilylamide (0.79 mmol, 133 mg). The resulting solution was held at room temperature for 30 minutes, then treated with benzyl bromide (0.79 mmol, 0.10 ml). The resulting solution was held at room temperature overnight, then diluted with ethyl acetate (30 ml), and washed with saturated ammonium chloride (10 ml), followed by brine (20 ml). The organics were concentrated under reduced pressure and the residue was purified by silica gel chromatography to provide 0.23 g (84%) of 2-benzyl-2-(1H-pyrrole-2-carbonyl)-malonic acid diethyl ester. $^1$H NMR (CDCl$_3$) δ 10.01 (1H, s), 7.25–7.17 (4H, m), 7.14 (1H, dt, J=2.7, 1.3), 7.03–6.98 (1H, m), 6.86 (1H, ddd, J=3.8, 2.4, 1.3), 6.29–6.25 (1H, m), 4.22 (4H, q, J=7.1), 3.47 (2H, s), 3.39 (2H, s), 1.25 (6H, t, J=1.7).

2-Benzyl-2-(1H-pyrrole-2-carbonyl)-malonic acid diethyl ester (0.66 mmol, 0.23 g) in 1:1 dioxane-water (10 ml) was treated with lithium hydroxide (1.31 mmol, 31 mg), then heated to reflux for 30 minutes. The solution was treated with saturated aqueous citric acid (20 ml), extracted with ethyl acetate (30 ml). The organic extract was washed with brine (15 ml) then concentrated under reduced pressure. The residue was purified by silica gel chromatography to provide 0.11 g (64%) of 2(R,S)-benzyl-4-oxo-4-(1H-pyrrol-2-yl)-butyric acid. $^1$H NMR (CDCl$_3$) δ 7.18–7.04 (5H, m), 6.92 (1H, dd, J=2.4, 1.4), 6.80 (1H, dd, J=3.8, 1.3), 6.08 (1H, dd, J=3.8, 2.5), 3.20–2.85 (3H, m), 2.80–2.67 (2H, m).

Method 3 General Experimental: 2(R,S)-Benzyl-4-oxo-4-(1H-pyrrol-2-yl)-butyric acid (0.42 mmol, 0.11 g, prepared according to the procedure described in Example 7), 4S-amino-5-(2-oxo-pyrrolidin-3S-yl)-pent-2(trans)-enoic acid ethyl ester hydrochloride (0.42 mmol, 0.11 g), and DIEA (1.26 mmol, 0.22 ml) in DMF (2 ml) were treated with HATU (0.42 mmol, 0.16 g), then held at room temperature overnight. The resulting solution was diluted with ethyl acetate (30 ml), washed with brine (2×15 ml). The organics were concentrated under reduced pressure and the residue was purified by silica gel chromatography to provide 0.14 g (75%) of product. The diastereomers were separated by preparative reverse phase HPLC (CH$_3$CN-water gradient).

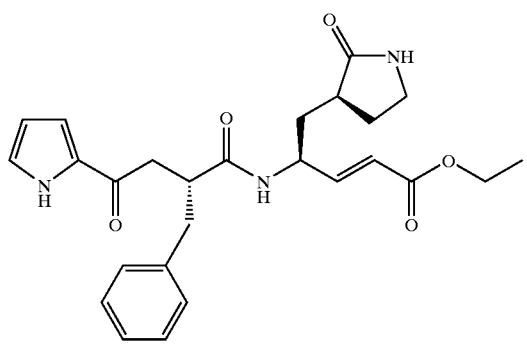

2R-Benzyl diastereomer (Compound 30): $^1$H NMR (CDCl$_3$) δ 11.05 (1H, s), 7.40 (1H, d, J=8.0), 7.32–7.15 (5H), 7.05 (1H, ddd, J=3.8, 2.4, 1.3), 7.00–6.96 (2H, m), 6.52 (1H, dd, J=15.7, 5.0), 6.27–6.23 (1H, m), 5.32 (1H, dd, J=15.7, 1.6), 4.44–4.32 (1H, m), 4.14 (2H, q, J=7.1), 3.53 (1H, dd, J=14.4, 10.9), 3.34–3.02 (4H, m), 2.85 (1H, dd, J=13.1, 4.9), 2.57 (1H, dd, J=14.5, 3.1), 2.20–2.08 (1H, m), 1.98–1.84 (1H, m), 1.72–1.60 (1H, m), 1.60–1.41 (1H, m), 1.40–1.28 (1H, m), 1.28 (3H, t, J=7.1). HRMS (FAB) 466.2234 (MH$^+$, calcd. 466.2342).

Example 33

2-(R,S)-(4-Fluorobenzyl)-4-oxo-N-[2-(2-oxo-dihydro-furan-3-ylidine)-1S-(2-oxo-pyrrolidin-3S-ylmethyl)-ethyl]-4-(5-phenyl-1H-pyrrol-2-yl)-butyramide. (Compound 31)

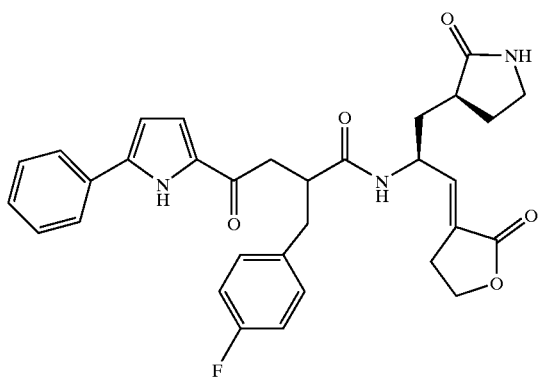

2-(R,S)-(4-Fluorobenzyl)-4-oxo-4-(5-phenyl-1H-pyrrol-2-yl)-butyric acid was prepared according to the procedure described in Example 7, starting with 5-phenyl-1H-pyrrole-2-carboxylic acid (prepared according to the procedure described in Example 4, starting with phenylboronic acid). This material was coupled to 3S-[2S-amino-3-(2-oxo-dihydro-furan-3-ylidene)-propyl]pyrrolidin-2-one hydrochloride according to the procedure described in Method 3 of Example 31, to provide the title compound as a 1:1 mixture of 2R-2S diastereomers. $^1$H NMR (CDCl$_3$) δ 10.24 (0.5H, br s), 9.90 (0.5H, br s), 7.70–6.85 (11H, m), 6.61–6.54 (1H, m), 6.37–6.27 (1H, m), 6.27–6.18 (1H, m), 4.50–4.13 (3H, m), 3.42–2.60 (9H, m), 2.25–1.20 (5H, m). HRMS (FAB) 580.2228 (MNa$^+$, calcd. 580.2224).

Example 34

2-(R,S)-(4-Fluorobenzyl)-4-(5-naphthalen-1-yl-1H-pyrrol-2-yl)-4-oxo-N-[2-(2-oxo-dihydro-furan-3-ylidine)-1S-(2-oxo-pyrrolidin-3S-ylmethyl)-ethyl]-butyramide

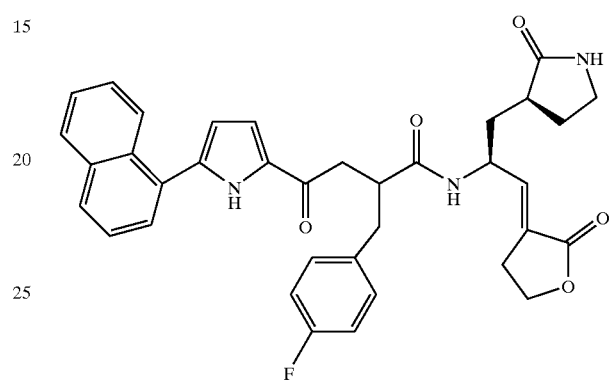

2-(R,S)-(4-Fluorobenzyl)-4-oxo-4-(5-naphthalen-1-yl-1H-pyrrol-2-yl)-butyric acid was prepared according to the procedure described in Example 7, starting with 5-naphthalen-1-yl-1H-pyrrole-2-carboxylic acid (prepared according to the procedure described in Example 4, starting with 1-naphthylboronic acid). This material was coupled to 3S-[2S-amino-3-(2-oxo-dihydro-furan-3-ylidene)-propyl] pyrrolidin-2-one hydrochloride according to the procedure described in Method 3 of Example 31, to provide the title compound as a 1:1 mixture of 2R-2S diastereomers. The diastereomers were separated by preparative reverse phase chromatography (acetonitrile-H$_2$O gradient).

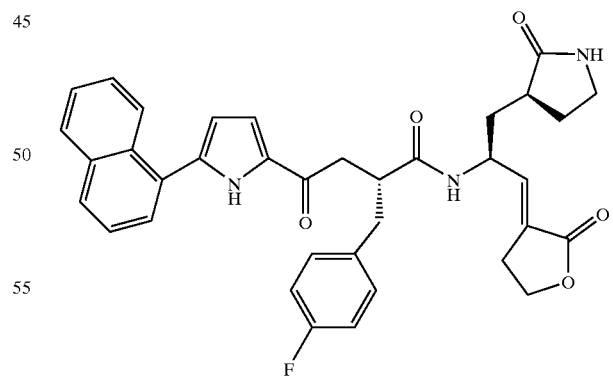

2R-(4-Fluorobenzyl) diastereomer (Compound 33): $^1$H NMR (CDCl$_3$) δ 10.48 (1H, s), 8.07 (1H, d, J=8.2), 7.87 (1H, d, J=7.8), 7.82 (1H, d, J=8.1), 7.70 (1H, d, J=5.6), 7.55–7.30 (4H, m), 7.15–7.02 (3H, m), 6.98–6.89 (2H, m), 6.55 (1H, br s), 6.48 (1H, br s), 6.22 (1H, d, J=8.5), 4.40–4.28 (3H, m), 3.80–1.30 (14H, m). HRMS (FAB) 740.1512 (MCs$^+$, calcd. 740.1537).

101

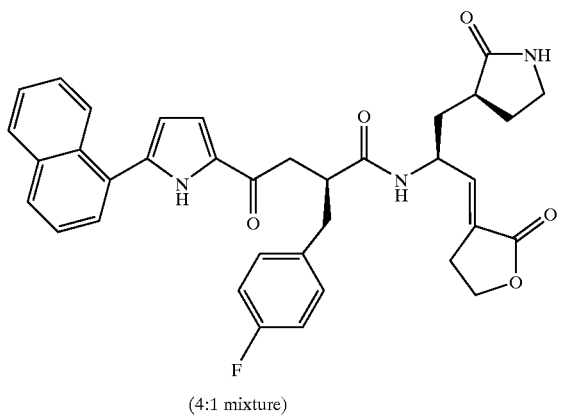

(4:1 mixture)

2S-(4-Fluorobenzyl) diastereomer (Compound 32): $^1$H NMR (CDCl$_3$) δ 9.81 (1H, br s), 8.04 (1H, d, J=8.6), 7.85–7.68 (3H, m), 7.52–7.35 (4H, m), 7.20–6.85 (5H, m), 6.50–6.25 (3H, m), 4.35–4.18 (3H, m), 3.28–2.60 (9H, m), 2.20–1.85 (2H, m), 1.70–1.55 (2H, m), 1.40–1.22 (1H, m). HRMS (FAB) 740.1512 (MCs$^+$, calcd. 740.1537).

Example 35

2-(R,S)-(4-Fluorobenzyl)-4-oxo-N-[2-(2-oxo-dihydro-furan-3-ylidine)-1S-(2-oxo-pyrrolidin-3S-ylmethyl)-ethyl]-4-(1H-pyrrol-2-yl)-butyramide. (Compound 34)

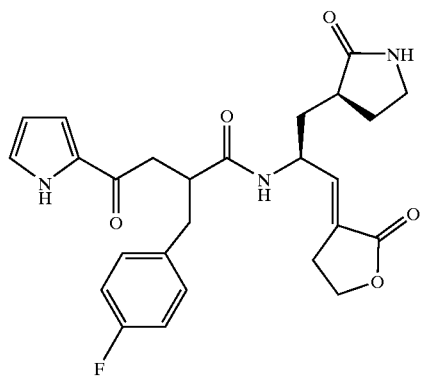

2-(R,S)-(4-Fluorobenzyl)-4-oxo-4-(1H-pyrrol-2-yl)-butyric acid was prepared according to the procedure described in Example 7, starting with 2-pyrrolecarboxylic acid. This material was coupled to 3S-[2S-amino-3-(2-oxo-dihydro-furan-3-ylidene)-propyl]pyrrolidin-2-one hydrochloride according to the procedure described in Method 3 of Example 31, to provide the title compound as a 1:1 mixture of 2R-2S diastereomers. $^1$H NMR (CDCl$_3$) δ 10.62 (0.5H, br s), 10.12 (0.5H, br s), 7.83 (0.5H, d, J=7.7), 7.62 (0.5H, d, J=7.1), 7.20–6.82 (6H, m), 6.65–6.20 (3H, m), 4.50–4.20 (3H, m), 3.45–2.60 (9H, m), 2.25–1.90 (3H, m), 1.68–1.50 (1H, m), 1.42–1.20 (1H, m). HRMS (FAB) 504.1932 (MNa$^+$, calcd. 504.1911).

102

Example 36

5-(2-Oxo-pyrrolidine-3S-yl)-4S-(2R-{2-oxo-2-[5-(2-trifluoromethyl-phenyl)-1H-pyrrol-2-yl]-ethyl}-pent-4-ynoylamino-pent-2(trans)-enoic acid ethyl ester. (Compound 36)

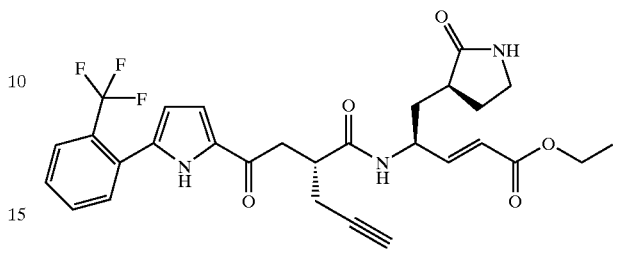

Method 8 General Experimental: 4-Pentynoic acid (60.1 mmol, 5.90 g) in THF (140 ml) was cooled to −78° C., then treated with Et$_3$N (69.1 mmol, 9.60 ml), followed by pivaloyl chloride (61.9 mmol, 7.6 ml). The resulting mixture was allowed to warm to 0° C., held 30 minutes, then recooled to −78° C. A solution of 4S-isopropyl-2-oxazolidinone (60.1 mmol, 7.76 g) in THF (140 ml) was cooled to −78° C. and treated with butyllithium (61.9 mmol, 24.8 ml of 2.5M in hexanes), held at −78° C. for 30 minutes, then transferred via cannula at −78° C. into the 4-pentynoic acid-pivaloyl chloride solution. The mixture was held at −78° C. for 1 h, then warmed to 0° C. and held 30 minutes, then poured into saturated aqueous ammonium chloride (200 ml). The solution was extracted with ethyl acetate (3×150 ml). The combined organic extracts were washed with brine (2×50 ml), then concentrated under reduced pressure to give 12.8 g of 4S-isopropyl-3-pent-4-ynoyl-oxazolidin-2-one, which may be used without further purification. $^1$H NMR (CDCl$_3$) δ 4.44–4.37 (1H, m), 4.29–4.15 (2H, m), 3.23–3.01 (2H, m), 2.50 (2H, dt, J=7.1, 2.6), 2.39–2.27 (1H, m), 1.93 (1H, t, J=2.6), 0.87 (3H, d, J=7.0), 0.82 (3H, d, J=6.9).

4S-Isopropyl-3-pent-4-ynoyl-oxazolidin-2-one (7.50 mmol, 2.11 g) in THF (25 ml) was cooled to −78° C. and treated with a solution of lithium bis(trimethylsilyl)amide (8.25 mmol, 1.38 g) in THF (5 ml). The resulting solution was allowed to warm to 0° C., held 15 minutes, then re-cooled to −78° C., then treated with t-butyl bromoacetate (22.5 mmol, 3.3 ml). The resulting solution was held at −78° C. for 15 minutes, then warmed to 0° C. and held for 2 h. The solution was then poured into saturated aqueous ammonium acetate (30 ml), then extracted with ethyl acetate (2×50 ml). The combined organic extracts were washed with brine (2×15 ml), then concentrated under reduced pressure. The residue was purified by silica gel chromatography to provide 1.23 g (43%) of 3R-(4S-isopropyl-2-oxo-oxazolidine-3-carbonyl)-hex-5-ynoic acid t-butyl ester. $^1$H NMR (CDCl$_3$) δ 4.46–4.39 (1H, m), 4.35–4.16 (3H, m), 2.87 (1H, dd, J=16.7, 9.8), 2.59–2.27 (4H, m), 2.00 (1H, t, J=2.6), 1.39 (9H, s), 0.90 (3H, d, J=3.9), 0.87 (3H, d, J=4.0).

3R-(4S-Isopropyl-2-oxo-oxazolidine-3-carbonyl)-hex-5-ynoic acid t-butyl ester (10.12 mmol, 3.27 g) in THF (100 ml) and H$_2$O (50 ml) was cooled to 0° C. and treated with lithium hydroxide hydrate (20.2 mmol, 0.85 g), followed by H$_2$O$_2$ (41.5 mmol, 4.7 ml of 30% aqueous). The resulting solution was held at 0° C. for 1 h, then allowed to warm to room temperature and held 3 h. The solution was then cooled to 0° C., and quenched with saturated aqueous sodium bisulfite (30 ml). The solution was acidified with saturated aqueous citric acid (30 ml), and extracted with ethyl acetate (75 ml). The organic extract was washed with brine (30 ml), then concentrated under reduced pressure. The residue was purified by silica gel chromatography to provide 2R-prop-2-ynyl-succinic acid-4-t-butyl ester. This material was treated with diazomethane (30 mmol, generated from N-nitroso-N-methyl urea), then concentrated under reduced pressure to give 1.95 g of 2R-prop-2-ynyl-succinic acid 4-t-butyl ester 1-methyl ester. This material was treated with 20% TFA—$CH_2Cl_2$ (30 ml), held 30 min, then concentrated under reduced pressure to give 1.47 g (85%) of 2R-prop-2-ynyl-succinic acid-1-methyl ester. $^1$H NMR (CDCl$_3$) δ 10.12 (1H, br s), 3.08–2.50 (5H, m), 3.73 (3H, s), 2.05 (1H, t, J=2.7).

2R-Prop-2-ynyl-succinic acid-1-methyl ester (8.63 mmol, 1.47 g) in $CH_2Cl_2$ (30 ml) was treated with oxalyl chloride (17.3 mmol, 1.50 ml) and DMF (1 drop), then heated to reflux for 30 minutes, then concentrated under reduced pressure. The residue was diluted with $CH_2Cl_2$ (30 ml), and pyridine (43.2 mmol, 3.5 ml), then treated with dimethylamine hydrochloride (25.9 mmol, 2.11 g), and held at room temperature overnight. The resulting mixture was diluted with ethyl acetate (150 ml) and washed with brine (3×30 ml). The organics were concentrated under reduced pressure. Purification of the residue by silica gel chromatography provided 0.83 g (49%) of 2R-dimethylcarbamoylmethyl-pent-4-ynoic acid methyl ester. $^1$H NMR (CDCl$_3$) δ 3.69 (3H, s), 3.18–2.52 (11H, m), 2.00 (1H, t, J=2.7).

2R-Dimethylcarbamoylmethyl-pent-4-ynoic acid methyl ester (4.20 mmol, 0.89 g) was cooled to 0° C. and treated with POCl$_3$ (4.2 mmol, 0.40 ml). The mixture was allowed to warm to room temperature, and held for 1 h then diluted with ethylene dichloride (10 ml), and re-cooled to 0° C. 2-(2-Trifluoromethyl-phenyl)-1H-pyrrole (4.2 mmol, 0.89 g, prepared according to the procedure described in Example 6) in ethylene dichloride (10 ml) was added, and the mixture was allowed to warm to room temperature, then heated to reflux for 2 h. The mixture was then allowed to cool to room temperature, then treated with saturated aqueous sodium acetate (10 ml), and heated to reflux for 15 minutes. The solution was then carefully neutralized with saturated aqueous sodium bicarbonate (20 ml), and extracted with ethyl acetate (75 ml). The organic extract was washed with brine (25 ml), then concentrated under reduced pressure. The residue was purified by silica gel chromatography to provide 1.11 g (72%) of 2R-(2-oxo-2-[5-(2-trifluoromethyl-phenyl)-1H-pyrrol-2-yl]-ethyl)-pent-4-ynoic acid methyl ester. $^1$H NMR (CDCl$_3$) δ 9.50 (1H, br s), 7.78 (1H, d, J=7.4), 7.64–7.46 (3H, m), 7.02 (1H, dd, J=3.9, 2.5), 6.45 (1H, t, J=3.0), 3.72 (3H, s), 3.45–3.14 (3H, m), 2.62 (1H, d, J=2.7), 2.59 (1H, d, J=2.6), 2.04 (1H, t, J=2.7). This material was diluted with 1:1H$_2$O-dioxane (40 ml), and treated with lithium hydroxide hydrate (9.18 mmol, 0.38 g), then heated to reflux for 30 minutes. The solution was acidified with saturated aqueous citric acid (20 ml), extracted with ethyl acetate (3×30 ml). The combined organic extracts were washed with brine (3×20 ml), then concentrated under reduced pressure. The residue was purified by silica gel chromatography to provide 0.67 g (60%) of 2R-(2-oxo-2-[5-(2-trifluoromethyl-phenyl)-1H-pyrrol-2-yl]-ethyl)-pent-4-ynoic acid.

2R-(2-oxo-2-[5-(2-trifluoromethyl-phenyl)-1H-pyrrol-2-yl]-ethyl)-pent-4-ynoic acid was coupled with 4S-amino-5-(2-oxo-pyrrolidin-3S-yl)-pent-2(trans)-enoic acid ethyl ester hydrochloride according to the procedure described in Method 3 of Example 31. $^1$H NMR (CD$_3$OD) δ 10.31 (1H, br s), 7.73 (1H, d, J=7.9), 7.61–7.42 (3H, m), 6.99 (1H, d, J=4.0), 6.82 (1H, dd, J=15.7, 4.6), 6.39 (1H, d, J=3.8), 6.04 (1H, dd, J=15.7, 1.6), 4.64–4.54 (1H, m), 4.13 (2H, q, J=7.1), 3.38–2.92 (5H, m), 2.62–2.38 (3H, m), 2.25–2.12 (1H, m), 2.10 (1H, t, J=2.6), 2.05–1.89 (1H, m), 1.75–1.60 (1H, m), 1.60–1.48 (1H, m), 1.24 (3H, t, J=7.1). HRMS (MALDI) 558.2221 (MH$^+$, calcd. 558.2216). Anal. (C$_{29}$H$_{30}$N$_3$O$_5$F$_3$.0.3H$_2$O) C, H, N.

Example 37

4S-{2R-Benzyl-4-oxo-4-[5-(2-trifluoromethyl-phenyl)-1H-pyrrol-2-yl]-butyrylamino}-5-(2-oxo-pyrrolidin-3S-yl)-pent-2(trans)-enoic acid ethyl ester. (Compound 35)

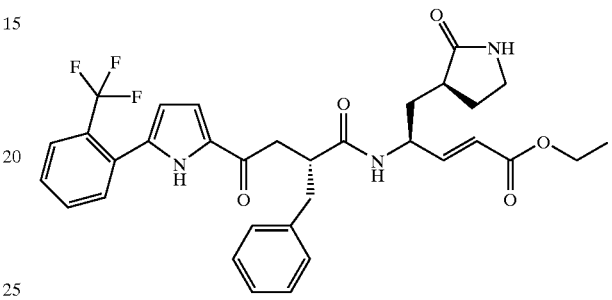

2R-Benzyl-N,N-dimethyl-succinamic acid was prepared according to the procedure described in Example 8, starting with hydrocinnamic acid. This material was reacted with 2-(2-trifluoromethyl-phenyl)-1H-pyrrole (prepared according to the procedure described in Example 6), then demethylated to give 2R-benzyl-4-oxo-4-[5-(2-trifluoromethyl-phenyl)-1H-pyrrol-2-yl]-butyric acid (all following Method 8). This material was coupled to 4S-amino-5-(2-oxo-pyrrolidin-3S-yl)-pent-2(trans)-enoic acid ethyl ester hydrochloride according to the procedure described in Method 3 of Example 31. $^1$H NMR (CDCl$_3$) δ 10.01 (1H, br s), 7.72 (1H, d, J=7.7), 7.5–7.40 (3H, m), 7.34–7.16 (5H, m), 6.98 (1H, dd, J=3.9, 2.4), 6.90 (1H, d, J=7.4), 6.62 (1H, dd, J=15.7, 5.1), 6.41 (1H, t, J=3.2), 6.13 (1H, br s), 5.49 (1H, dd, J=15.7, 1.6), 4.56–4.44 (1H, m), 4.16 (2H, q, J=7.1), 3.39 (1H, dd, J=16.1, 9.5), 3.25–2.96 (4H, m), 2.83–2.69 (2H, m), 2.42–2.28 (1H, m), 2.22–2.08 (1H, m), 1.94–1.78 (1H, m), 1.72–1.55 (1H, m), 1.52–1.40 (1H, m), 1.30 (3H, t, J=7.1). HRMS (MALDI) 610.2532 (MH$^+$, calcd. 610.2529). Anal. (C$_{33}$H$_{34}$F$_3$N$_3$O$_5$) C, H, N.

Example 38

4S-{2R-Ethyl-4-oxo-4-[5-(2-trifluoromethyl-phenyl)-1H-pyrrol-2-yl]-butyrylamino}-5-(2-oxo-pyrrolidin-3S-yl)-pent-2(trans)-enoic acid ethyl ester. (Compound 37)

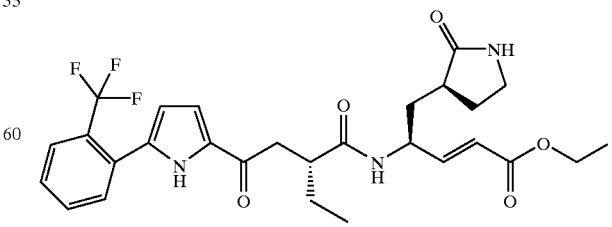

2R-Ethyl-N,N-dimethyl-succinamic acid methyl ester was prepared according to the procedure described in Example 8, starting with butyric acid. This was reacted with 2-(2-trifluoromethyl-phenyl)-1H-pyrrole (prepared according to the procedure described in Example 6), then demethylated to give 2R-ethyl-4-oxo-4-[5-(2-trifluoromethyl-phenyl)-1H-pyrrol-2-yl]-butyric acid (all following Method 8). This material was then coupled to 4S-amino-5-(2-oxo-pyrrolidin-3S-yl)-pent-2(trans)-enoic acid ethyl ester hydrochloride according to the procedure described in Method 3 of Example 31. $^1$H NMR (CDCl$_3$) δ 10.13 (1H, br s), 7.76 (1H, d, J=7.8), 7.62–7.46 (3H, m), 7.01 (1H, d, J=3.9), 6.84 (1H, dd, J=15.7, 5.2), 6.42 (1H, d, J=3.9), 5.93 (1H, dd, J=15.3, 1.6), 4.70–4.60 (1H, m), 4.17 (2H, q, J=7.1), 3.36–3.15 (3H, m), 2.86–2.70 (2H, m), 2.58–2.53 (1H, m), 2.33–2.23 (1H, m), 2.05–1.94 (1H, m), 1.83–1.74 (2H, m), 1.61–1.51 (2H, m), 1.27 (3H, t, J=7.1), 1.01 (3H, t, J=7.3). HRMS (MALDI) 548.2363 (MH$^+$, calcd. 548.2372). Anal. (C$_{28}$H$_{32}$N$_3$O$_5$F$_3$.0.7H$_2$O) C, H, N.

Example 39

4S-(2R-{2-[5-(2-Chloro-phenyl)-1H-pyrrol-2-yl]-2-oxo-ethyl}-pent-4-ynoylamino)-5-(2-oxo-pyrrolidin-3S-yl)-pent-2(trans)-enoic acid ethyl ester. (Compound 38)

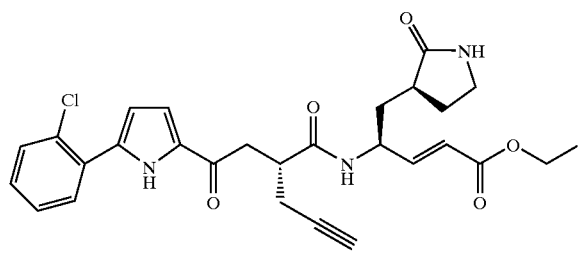

2R-Dimethylcarbamoylmethyl-pent-4-ynoic acid methyl ester was prepared according to the procedure described in Example 8, starting with 4-pentynoic acid. This material was reacted with 2-(2-chloro-phenyl)-1H-pyrrole (prepared according to the procedure described in Example 6, starting with 2-chlorobenzaldehyde). This product was demethylated to give 2R-{2-[5-(2-chloro-phenyl)-1H-pyrrol-2-yl]-2-oxo-ethyl}-pent-4-ynoic acid (all following Method 8), then coupled to 4S-amino-5-(2-oxo-pyrrolidin-3S-yl)-pent-2(trans)-enoic acid ethyl ester hydrochloride according to the procedure described in Method 3 of Example 31. $^1$H NMR (CDCl$_3$) δ 10.58 (1H, br s), 7.65 (1H, d, J=7.4), 7.56 (1H, dd, J=7.6, 1.8), 7.46 (1H, dd, J=7.7, 1.4), 7.37–7.23 (2H, m), 7.07 (1H, dd, J=4.0, 2.4), 6.83 (1H, dd, J=15.6, 4.7), 6.68 (1H, dd, J=4.0, 2.6), 6.28 (1H, br s), 6.05 (1H, dd, J=15.7, 1.6), 4.58–4.46 (1H, m), 4.15 (2H, q, J=7.1), 3.38 (1H, dd, J=15.3, 9.8), 3.15 (1H, t, J=9.1), 3.10–2.95 (2H, m), 2.87 (1H, dd, J=15.3, 3.7), 2.63 (1H, ddd, J=16.8, 7.3, 2.6), 2.47 (1H, ddd, J=16.8, 7.5, 2.6), 2.28–2.15 (1H, m), 2.10 (1H, t, J=2.5), 2.06–1.88 (2H, m), 1.73–1.50 (2H, m), 1.26 (3H, t, J=7.1). HRMS (MALDI) 546.1750 (MNa$^+$, calcd. 546.1722). Anal. (C$_{28}$H$_{30}$N$_3$O$_5$Cl.0.6H$_2$O) C, H, N.

Example 40

5-(2-Oxo-pyrrolidin-3S-yl)-4S-{2R-[2-oxo-2-(5-o-tolyl-1H-pyrrol-2-yl)-ethyl]-pent-4-ynoylamino}-pent-2(trans)-enoic acid ethyl ester. (Compound 39)

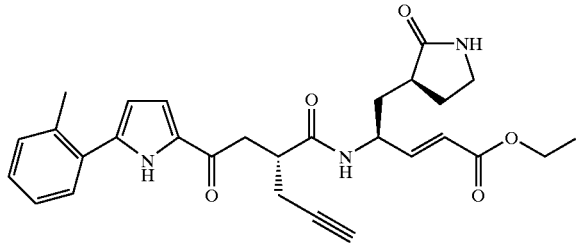

2R-Dimethylcarbamoylmethyl-pent-4-ynoic acid methyl ester was prepared according to the procedure described in Example 8, starting with 4-pentynoic acid. This material was reacted with 2-(o-tolyl)-1H-pyrrole (prepared according to the procedure described in Example 5, starting with o-toluic acid). This product was demethylated to give 2R-[2-oxo-2-(5-o-tolyl-1H-pyrrol-2-yl)-ethyl]-pent-4-ynoic acid (all following Method 8), then coupled to 4S-amino-5-(2-oxo-pyrrolidin-3S-yl)-pent-2(trans)-enoic acid ethyl ester hydrochloride according to the procedure described in Method 3 of Example 31. $^1$H NMR (CDCl$_3$) δ 10.65 (1H, br s), 7.50 (1H, d, J=7.6), 7.43–7.36 (1H, m), 7.30–7.21 (3H, m), 7.10–7.04 (1H, m), 6.82 (1H, dd, J=15.6, 5.4), 6.47 (1H, br s), 6.39–6.33 (1H, m), 6.04 (1H, d, J=15.6), 4.59–4.48 (1H, m), 4.15 (2H, q, J=7.1), 3.39 (1H, dd, J=15.4, 10.4), 3.12–2.95 (2H, m), 2.95–2.77 (2H, m), 2.68–2.55 (1H, m), 2.51–2.38 (1H, m), 2.40 (3H, s), 2.36–2.25 (1H, m), 2.12 (1H, br s), 2.03–1.90 (1H, m), 1.66–1.43 (2H, m), 1.26 (3H, t, J=7.1). HRMS (MALDI) 504.2497 (MH$^+$, calcd. 504.2498). Anal. (C$_{29}$H$_{33}$N$_3$O$_5$.0.7H$_2$O) C, H, N.

Example 41

4S-{2R-Benzyl-4-oxo-[5-(2-trifluoromethyl-phenyl)-1H-pyrrol-2-yl]-butyrylamino}-6-carbamoyl-hex-2(trans)-enoic acid ethyl ester. (Compound 40)

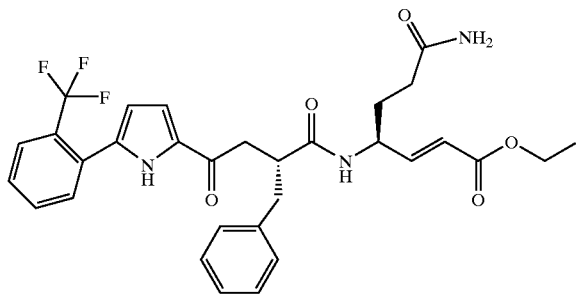

2R-Benzyl-N,N-dimethyl-succinamic acid (prepared according to the procedure described in Example 8, starting with hydrocinnamic acid) was reacted with 2-(2-trifluoromethyl-phenyl)-1H-pyrrole (prepared according to the procedure described in Example 6), then demethylated to give 2R-benzyl-4-oxo-4-[5-(2-trifluoromethyl-phenyl)-1H-pyrrol-2-yl]-butyric acid (all following Method 8), then coupled to Gln-resin, following Method 1. $^1$H NMR (CD$_3$OD) δ 7.70 (1H, d, J=7.3), 7.58–7.41 (3H, m), 7.25–7.11 (5H, m), 6.95 (1H, d, J=4.0), 6.53 (1H, dd, J=15.8, 5.1), 6.35 (1H, d, J=3.9) 5.38 (1H, dd, J=15.8, 1.7), 4.47–4.38 (1H, m), 4.12 (2H, q, J=7.1), 3.31 (1H, m), 3.08–2.70 (4H, m), 2.13 (2H, t, J=7.9), 1.92–1.78 (1H, m), 1.63–1.50 (1H, m), 1.25 (3H, t, J=7.1). HRMS (MALDI) 606.2194 (MNa+, calcd. 606.2192).

Example 42

4S-(4-oxo-pentanoylamino)-5-(2-oxo-pyrrolidin-3S-yl)-pent-2-enoic acid ethyl ester (Compound 43)

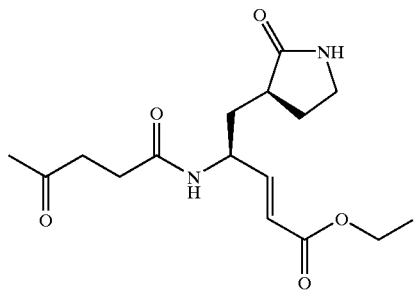

4S-Amino-5-(2-oxo-pyrrolidin-3S-yl)-pent-2-enoic acid ethyl ester (0.15 mmol, 35 mg) in DMF (1.5 ml) was treated with diisopropylethyl amine (0.30 mmol, 0.05 ml), 4-oxopentanoic acid (0.15 mmol, 27 mg), and HATU (0.15 mmol, 57 mg), and held at room temperature for 1 h. The solution was washed with brine (10 ml), and extracted with EtOAc (2×10 ml) and concentrated under reduced pressure to provide 40 mg of crude product. Purification by preparative reverse phase chromatography (CH$_3$CN—H$_2$O) provided 28 mg (48%) of the title product. $^1$H NMR (CDCl$_3$) δ 7.28 (1H, s), 6.83 (1H, dd, J=15.7, 5.2), 6.03 (1H, s), 5.92 (1H, dd, J=15.7, 1.5), 4.65–4.50 (1H, m), 4.17 (2H, q, J=7.1), 3.40–3.30 (2H, m), 2.92–2.65 (2H, m), 2.60–2.35 (4H, m), 2.17 (3H, m), 2.05–1.90 (1H, m), 1.90–1.72 (1H, m), 1.70–1.60 (1H, m), 1.27 (3H, t, J=7.1). MS (ES) 347 (MNa+), 323 (M–H)−.

Example 43

4S-(4-oxo-4-phenyl-butyrylamino)-5-(2-oxo-pyrrolidin-3S-yl)-pent-2-enoic acid ethyl ester. (Compound 44)

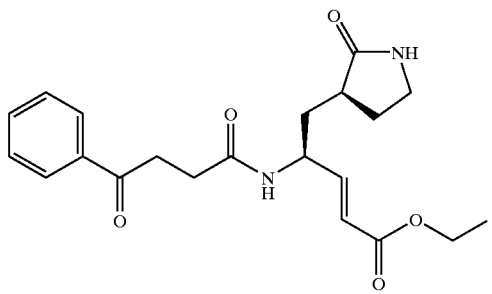

The title compound was prepared according to the method of Example 42, using 4-oxo-4-phenylbutyric acid. $^1$H NMR (CDCl$_3$) δ 8.10–7.95 (2H, m), 7.60–7.53 (1H, m), 7.50–7.42 (2H, m), 6.86 (1H, dd, J=15.6, 5.7), 5.97 (1H, d, J=15.6), 5.73 (1H, s), 4.65–4.61 (1H, m), 4.19 (2H, q, J=7.1), 3.50–3.20 (4H, m), 2.73–2.64 (2H, m), 2.62–2.35 (2H, m), 2.08–1.95 (1H, m), 1.92–1.65 (2H, m), 1.28 (3H, t, J=7.1). MS (ES) 387 (MH+), 409 (MNa+).

Example 44

4-S-(4-Naphthalen-1-yl-4-oxo-butyrylamino)-5-(2-oxo-pyrrolidin-3S-yl)-pent-2-enoic acid ethyl ester. (Compound 45)

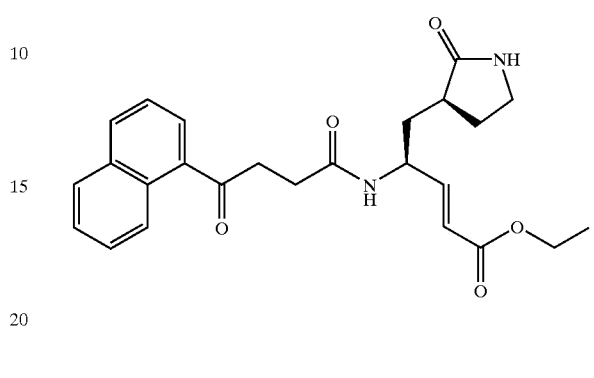

The title compound was prepared according to the method of Example 42, using as starting material gamma-oxo-1-naphthalene butyric acid. $^1$H NMR (CDCl$_3$) δ 8.57 (1H, d, J=8.6), 7.99–7.37 (7H, m), 6.88 (1H, dd, J=15.6, 5.4), 6.05 (1H, s), 6.01 (1H, d, J=15.6), 4.65–4.64 (1H, m), 4.17 (2H, q, J=7.2), 3.57–3.27 (4H, m), 2.86–2.39 (4H, m), 2.09–1.66 (3H, m), 1.25 (3H, t, J=7.2). MS (FAB) 437.2068 (MH+, calcd. 437.2076).

Example 45

4S-[2-(3-Chloro-phenylcarbamoyl)-acetylamino]-5-(2-oxo-pyrrolidin-3S-yl)-pent-2-enoic acid ethyl ester. (Compound 46)

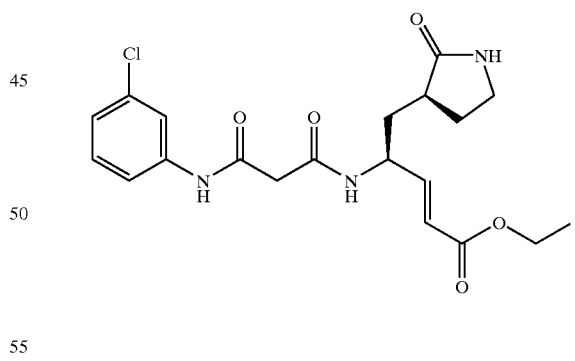

The title compound was prepared according to the method of Example 42, using as starting material N-(3-chlorophenyl)-malonamic acid. $^1$H NMR (CDCl$_3$) δ 9.89 (1H, s), 8.69 (1H, d, J=6.1), 7.69 (1H, s), 7.41–7.36 (1H, m), 7.22 (1H, t, J=8.1), 7.09–7.03 (1H, m), 6.84 (1H, dd, J=15.7, 5.7), 5.96 (1H, d, J=15.6), 5.97 (1H, s), 4.59–4.48 (1H, m), 4.18 (2H, q, J=7.1), 3.43–3.34 (4H, m), 2.57–2.37 (2H, m), 2.06–1.80 (2H, m), 1.74 (1H, dt, J=14.5, 4.3), 1.27 (3H, t, J=7.1). MS (FAB) 422.1494 (MH+, calcd 422.1483), 444 (MNa+).

Example 46

Preparation of Ethyl-3-{(Indole-2-carboxylic acid)-L-(4-F-Phe)-L-[(S)-Pyrrol-Ala]}-E-Propenoate. (Compound 42)

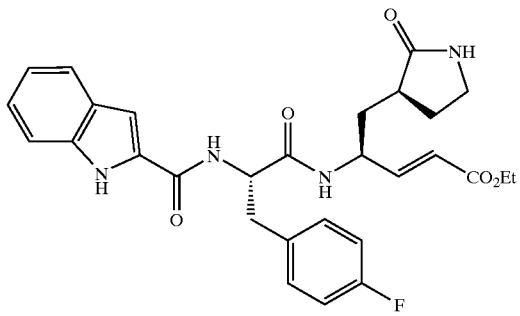

In this example, the following shorthand naming system employing amino acid abbreviations is used to identify some intermediates and final products. When naming compounds, italicized amino acid abbreviations represent modifications at the C-terminus of that residue where the following apply: (1) acrylic acid esters are reported as "E" (trans) propenoates; (2) substituted 3-methylene-dihydrofuran-2-ones are reported as "E" (trans) 2-(a-vinyl-g-butyrolactones); and (3) 5-vinylisoxazoles are reported as "E" (trans) propenisoxazoles.

Ethyl-3-{Boc-L-(4-F-Phe)-L-[(N-2,4-Dimethoxybenzyl)-(S)-Pyrrol-Ala]}-E-Propenoate

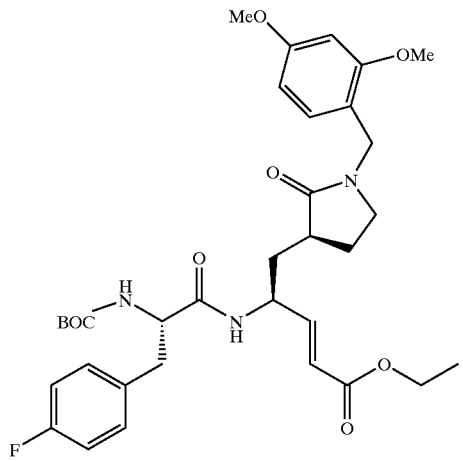

A solution of HCl in 1,4-dioxane (4.0 M, 12 ml) was added to a solution of ethyl-3-{Boc-L-[(N-2,4-dimethoxybenzyl)-(S)-Pyrrol-Ala]}-E-propenoate, prepared according to the procedure described in Dragovich, et al., *J. Med. Chem.* 1999, 42, 1213, (0.432 g, 0.906 mmol, 1 equiv) in the same solvent (12 ml). After stirring 1.5 h at 23° C., the solvent was concentrated under reduced pressure to give the crude amine salt. This material was dissolved in DMF (7 ml) and cooled to 0° C. Boc-L-(4-F-Phe)—OH (0.308 g, 1.09 mmol, 1.2 equiv), N,N-diisopropylethylamine (0.474 ml, 2.72 mmol, 3 equiv) and HATU (0.379 g, 0.997 mmol, 1.1 equiv) were added sequentially and the reaction mixture was allowed to warm to 23° C. After 1.5 h, the mixture was diluted with MTBE (200 ml), and washed with 5% KHSO$_4$ and brine (20 ml each), dried over MgSO$_4$ and concentrated. The residue was purified by flash column chromatography (60% EtOAc in hexanes) to provide ethyl-3-{Boc-L-(4-F-Phe)-L-[(N-2,4-dimethoxybenzyl)-(S)-Pyrrol-Ala]}-E-propenoate (0.447 g, 77%) as a white foam: R$_f$=0.34 (60% EtOAc in hexanes); IR (cm$^{-1}$) 3258, 1705, 1666; $^1$H NMR (CDCl$_3$) δ 1.28 (t, 3H, J=7.2), 1.45 (s, 9H), 1.51–1.66 (m, 2H), 1.78–1.90 (m, 1H), 2.06–2.23 (m, 2H), 2.99 (dd, 1H, J=13.7, 6.2), 3.11 (dd, 1H, J=13.7, 5.3), 3.17–3.23 (m, 2H), 3.80 (s, 3H), 3.81 (s, 3H), 4.18 (q, 2H, J=7.2), 4.35 (s, 2H), 4.38–4.51 (m, 2H), 5.29–5.37 (m, 1H), 5.76 (d, 1H, J=15.8), 6.43–6.47 (m, 2H), 6.72 (dd, 1H, J=15.8, 5.3), 6.83–6.91 (m, 2H), 7.09–7.17 (m, 3H), 7.92 (br, 1H); Anal. (C$_{34}$H$_{44}$FN$_3$O$_8$) C, H, N.

Preparation of Intermediate Ethyl-3-{Boc-L-(4-F-Phe)-L-[(S)-Pyrrol-Ala]}-E-Propenoate

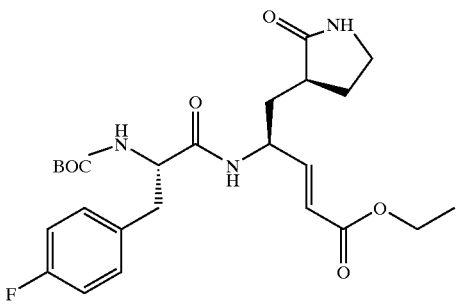

2,3-Dicholoro-5,6-dicyano-1,4-benzoquinone (0.14 g, 0.62 mmol, 1 equiv) was added to a solution of ethyl-3-{Boc-L-(4-F-Phe)-L-[(N-2,4-dimethoxybenzyl)-(S)-pyrrol-Ala]}-E-propenoate (0.39 g, 0.53 mmol, 1 equiv) in CHCl$_3$ (25 ml) and water (2.5 ml) and the reaction mixture was heated to reflux at 60° C. After 2 h, an additional equivalent of 2,3-dichloro-5,6-dicyano-1,4-benzoquinone was added to the mixture. After 2 h, one more equivalent of 2,3-dichloro-5,6-dicyano-1,4-benzoquinone was added to the mixture. The reaction mixture was diluted with EtOAc (150 ml) and washed sequentially with NaHCO$_3$ (100 ml) and brine (100 ml). The organic layers were dried over Na$_2$SO$_4$, concentrated, and the residue was purified by flash column chromatography (2% CH$_3$OH in CH$_2$Cl$_2$) to afford ethyl-3-{Boc-L-(4-F-Phe)-L-[(S)-pyrrol-Ala]}-E-propenoate (0.205 g, 79%) as a white solid: R$_f$=0.18 (5% CH$_3$OH in CH$_2$Cl$_2$); IR (cm$^{-1}$) 3281, 2981, 1690; $^1$H NMR (CDCl$_3$) δ 1.27–1.31 (t, 3H, J=7.2), 1.42 (s, 9H), 1.57–1.64 (m, 1H), 1.75–1.94 (m, 2H), 2.23–2.36 (m, 2H), 3.01–3.05 (m, 2H), 3.29–3.34 (m, 2H), 4.18 (q, 2H, J=7.2), 4.42–4.50 (m, 2H), 5.23 (m, 1H), 5.69–5.79 (m, 2H), 6.69–6.74 (m, 1H), 6.94–7.00 (m, 1H), 7.14–7.18 (m, 2H), 7.43 (m, 1H); Anal. Calcd for C$_{25}$H$_{34}$FN$_3$O$_6$·0.5H$_2$O C, 59.99; H, 7.05; N, 8.39. Found C, 59.63; H, 7.05; N, 8.14.

Ethyl-3-{(Indole-2-carboxylic acid)-L-(4-F-Phe)-L-[(S)-Pyrrol-Ala]}-E-Propenoate A solution of HCl in 1,4-dioxane (4.0 M, 2 ml) was added to ethyl-3-{Boc-L-(4-F-Phe)-L-[(S)-pyrrol-Ala]}-E-propenoate (0.19 g, 0.39 mmol, 1 equiv) in 2 ml of 1,4-dioxane at 23° C. After 2 h, the volatiles were removed under reduced pressure and CH$_2$Cl$_2$ (3 ml) and Et$_3$N (1 ml) were added sequentially to the residue. In a separate flask, N-hydroxysuccinimide (0.075 g, 0.65 mmol, 1.1 equiv) and 1,3-dicyclohexylcarbodiimide (0.13 g, 0.64 mmol, 1.1 equiv) were added to a solution of indole-2-carboxylic acid (0.99 g, 0.62 mmol, 1 equiv) in CH$_2$Cl$_2$ (3 ml) and DMF (1 ml) and stirred at 23° C. for 3 h. This solution was then filtered and added to the original reaction mixture described above. The resulting solution was stirred at 23° C. for 16 h. then was partitioned between water (25 ml) and $CH_2Cl_2$ (2×20 ml). The combined organic layers were dried over $Na_2SO_4$, concentrated, and the residue was purified by flash column chromatography (1 to 5% $CH_3OH$ in $CH_2Cl_2$) to afford ethyl-3-{(indole-2-carboxylic acid)-L-(4-F-Phe)-L-[(S)-pyrrol-Ala]}-E-propenoate (0.145 g, 70%) as a white powder: $R_f$=0.44 (10% $CH_3OH$ in $CH_2Cl_2$); IR ($cm^{-1}$) 3277, 1636, 1547; $^1H$ NMR (DMSO-$d_6$) δ 1.28 (t, 3H, J=7.2), 1.51–1.59 (m, 1H), 1.66–1.73 (m, 1H), 1.89–1.96 (m, 1H), 2.10–2.18 (m, 1H), 2.39–2.42 (m, 1H), 3.09–3.17 (m, 4H), 4.18 (q, 2H, J=7.5), 4.62 (m, 1H), 4.75–4.77 (m, 1H), 5.71–5.82 (m, 1H), 6.87 (dd, 1H, J=4.2, 15.9), 7.07–7.17 (m, 3H), 7.21–7.26 (m, 3H), 7.42–7.47 (m, 3H), 7.66–7.70 (m, 2H), 8.45 (d, 1H, J=8.7), 8.72 (d, 1H, J=7.8); Anal. Calcd for $C_{29}H_{31}FN_4O_5 \cdot 0.35H_2O$: C, 64.40; H, 5.91; N, 10.36. Found C, 64.12; H, 5.91; N, 10.14.

Results of tests conducted using exemplary compounds of the invention are described below.

Biochemical and Biological Evaluation
Inhibition of Rhinovirus 3C Protease:

Stock solutions (50 mM, in DMSO) of various compounds were prepared; dilutions were in the same solvent. Recombinant rhinovirus 3C proteases (see Birch et al., "Purification of recombinant human rhinovirus 14 3C protease expressed in *Escherichia coli*," Protein Expr. Pur. (1995), vol. 6(5), 609–618) from serotypes 14, 16, and 2 were prepared by the following standard chromatographic procedures: (1) ion exchange using Q Sepharose Fast Flow from Pharmacia; (2) affinity chromatography using Affi-Gel Blue from Biorad; and (3) sizing using Sephadex G-100 from Pharmacia. Each assay sample contained 2% DMSO, 50 mM tris pH 7.6, 1 mM EDTA, a test compound at the indicated concentration, approximately 1 μM substrate, and 50–100 nM protease. The $k_{obs/I}$ values were obtained from reactions initiated by addition of enzyme rather than substrate. RVP activity was measured in the fluorescence resonance energy transfer assay. The substrate was (N-terminal) DABCYL-(Gly-Arg-Ala-Val-Phe-Gln-Gly-Pro-Val-Gly)-EDANS. In the uncleaved peptide, the EDANS fluorescence was quenched by the proximal DABCYL moiety. When the peptide was cleaved, the quenching was relieved, and activity was measured as an increase in fluorescence signal. Data were analyzed using standard non-linear fitting programs (Enzfit), and are shown in the table below. The tabulated data in the column designated $k_{obs}/[I]$ were measured from progress curves in enzyme start experiments.

Antirhinoviral H1-HeLa Cell Culture Assay:

In this cell protection assay, the ability of compounds to protect cells against HRV infection was measured by the XTT dye reduction method, which is described in Weislow et al., J. Natl. Cancer Inst. (1989), vol. 81, 577–586. H1-HeLa cells were infected with HRV-14 at a multiplicity of infection (m.o.i.) of 0.13 (virus particles/cell) or mock-infected with medium only. Infected or mock-infected cells were resuspended at $8 \times 10^5$ cells per ml, and incubated with appropriate concentrations of the compounds to be tested. Two days later, XTT/PMS was added to test plates and the amount of formazan produced was quantified spectrophotometrically at 450/650 nm. The $EC_{50}$ value was calculated as the concentration of compound that increased the percentage of formazan production in compound-treated, virus-infected cells to 50% of that produced by compound-free, mock-infected cells. The 50% cytotoxic dose ($CC_{50}$) was calculated as the concentration of compound that decreased the percentage of formazan produced in compound-treated, mock-infected cells to 50% of that produced by compound-free, mock-infected cells. The therapeutic index (TI) was calculated by dividing the $CC_{50}$ value by the $EC_{50}$ value.

All strains of human rhinovirus (HRV) for use in this assay were purchased from American Type Culture Collection (ATCC), except for HRV serotype-14 (produced from the infectious cDNA clone constructed by Dr. Robert Rueckert, Institute for Molecular Virology, University of Wisconsin, Madison, Wis.). HRV stocks were propagated and viral assays were performed in H1-HeLa cells (ATCC). Cells were grown in minimal essential medium with 10% fetal bovine serum, available from Life Technologies (Gaithersburg, Md.). Test results for the HRV assay are shown in the table below.

Anticoxsackieviral Cell Culture Assay:

Coxsackievirus types A-21 (CAV-21) and B3 (CVB3) were purchased from American Type Culture Collection (ATCC, Rockville, Md.). Virus stocks were propagated and antiviral assays were performed in H1-HeLa cells (ATCC). Cells were grown in minimal essential medium with 10% fetal bovine serum (Life Technologies, Gaithersburg, Md.). The ability of the compounds of this invention to protect cells against either CAV-21 or CVB3 infection was measured by the XTT dye reduction method. This method is described in Weislow et al., J. Natl. Cancer Inst. (1989), vol. 81, 577–586. H1-HeLa cells were infected with CAV-21 or CVB3 at a multiplicity of infection (m.o.i.) of 0.025 or 0.075, respectively, or mock-infected with medium only. H1-HeLa cells were plated at $4 \times 10^4$ cells per well in a 96-well plate and incubated with appropriate concentrations of the test compound. One day (CVB3) or two days (CAV-21) later, XTT/PMS was added to test plates and the amount of formazan produced was quantified spectrophotometrically at 450/650 nm. The $EC_{50}$ was calculated as the concentration of compound that increased the formazan production in compound-treated, virus-infected cells to 50% of that produced by compound-free, uninfected cells. The 50% cytotoxic dose ($CC_{50}$) was calculated as the concentration of compound that decreased formazan production in compound-treated, uninfected cells to 50% of that produced in compound-free, uninfected cells. The therapeutic index (TI) was calculated by dividing the $CC_{50}$ by the $EC_{50}$.

Anti-Echoviral and Anti-Enteroviral Cell Culture Assays:

Echovirus type 11 (ECHO 11) was purchased from ATCC (Rockville, Md.). Virus stocks were propagated and antiviral assays were performed in MRC-5 cells (ATCC). Cells were grown in minimal essential medium with 10% fetal bovine serum (Life Technologies, Gaithersburg, Md.). The ability of the compounds of this invention to protect cells against ECHO 11 infection was measured by the XTT dye reduction method (Weislow et al., J. Natl. Cancer Inst. (1989), vol. 81, 577–586). MRC-5 cells were infected with ECHO 11 at an m.o.i. of 0.003 or 0.004, respectively, or mock-infected with medium only. Infected or uninfected cells were added at $1 \times 10^4$ cells per well and incubated with appropriate concentrations of compound. Four days later, XTT/PMS was added to test plates, and the amount of formazan produced was quantified spectrophotometrically at 450/650 nm. The $EC_{50}$ was calculated as the concentration of compound that increased the formazan production in compound-treated, virus-infected cells to 50% of that produced by compound-free, uninfected cells. The 50% cytotoxic dose ($CC_{50}$) was calculated as the concentration of compound that decreased formazan production in compound-treated, uninfected cells to 50% of that produced in compound-free, uninfected cells. The therapeutic index (TI) was calculated by dividing the $CC_{50}$ by the $EC_{50}$. Activity of the compounds against enterovirus type 70 (EV 70) may be measured by the same assay as described above in this section. Enterovirus type 70 (EV 70) may be obtained from the American Type Culture Collection ATCC (Rockville, Md.).

Antiviral data obtained for the test compounds are shown in the table below. The designation "ND" indicates that a value was not determined for that compound, and the designation "NA" means not applicable.

TABLE

| Compound # | Virus Serotype | $K_{obs}/I$ $(M^{-1}s^{-1})$ | $EC_{50}$ ($\mu$M) | $CC_{50}$ ($\mu$M) |
|---|---|---|---|---|
| 1 | HRV-14 | 20300 | 0.202 | >10 |
| 2 | HRV-14 | 32400 | 0.064 | >10 |
| 3 | HRV-14 | 30800 | 0.109 | >10 |
| 4 | HRV-14 | 5860 | ND | ND |
| 5 | HRV-14 | 12700 | 1.098 | >10 |
| 6 | HRV-14 | 2130 | 1.425 | >10 |
| 7 | HRV-14 | 5200 | 0.3 | >10 |
| 8 | HRV-14 | 1300 | 4.924 | >10 |
| 9 | HRV-14 | 12550 | ND | ND |
| 10 | HRV-14 | 2370 | ND | ND |
| 11 | HRV-14 | 5000 | 0.646 | >10 |
| 12 | HRV-14 | 2700 | 1.248 | >10 |
| 13 | HRV-14 | 6570 | 2.01 | >10 |
| 14 | HRV-14 | 34600 | 0.534 | >10 |
| 15 | HRV-14 | 980 | 27.0 | >100 |
| 16 | HRV-14 | 7100 | 1.321 | >10 |
| 17 | HRV-14 | 2900 | 2.186 | >10 |
| 18 | HRV-14 | 3140 | 1.597 | >10 |
| 19 | HRV-14 | 6650 | 1.527 | >10 |
| 20 | HRV-14 | 330 | 16.42 | >100 |
| 21 | HRV-14 | 1380 | ND | ND |
| 22 | HRV-14 | 4400 | 5.719 | >10 |
| 23 | HRV-14 | 3800 | 1.546 | >10 |
| 24 | HRV-14 | 5460 | 3.914 | >100 |
| 25 | HRV-14 | 690000 | 0.034 | >10 |
|  | HRV-1A | ND | 0.089 | >10 |
|  | HRV-10 | ND | 0.148 | >10 |
|  | CAV-21 | ND | 0.2 | >10 |
|  | ECHO-11 | ND | 0.044 | >10 |
|  | ENT-70 | ND | .003 | >10 |
| 26 | HRV-14 | 188000 | 0.073 | >10 |
| 27 | HRV-14 | 11700 | 1.585 | >10 |
| 28 | HRV-14 | 340000 | 0.059 | >1 |
|  | HRV-1A | ND | 0.213 | >1 |
|  | HRV-10 | ND | 0.066 | >1 |
| 29 | HRV-14 | 103000 | 0.15 | >10 |
|  | HRV-1A | ND | 0.054 | >10 |
|  | HRV-10 | ND | 0.027 | >10 |
|  | HRV-3 | ND | 0.065 | >10 |
|  | HRV-25 | ND | 0.316 | >10 |
|  | HRV-9 | ND | 0.119 | >10 |
|  | HRV-39 | ND | 0.180 | >10 |
| 30 | HRV-14 | 2500 | 3.336 | >10 |
| 31 | HRV-14 | 900 | ND | ND |
| 32 | HRV-14 | 8300 | ND | ND |
| 33 | HRV-14 | 100000 | 0.212 | >10 |
| 34 | HRV-14 | 520 | ND | ND |
| 35 | HRV-14 | 125000 | 0.143 | >10 |
| 36 | HRV-14 | 59300 | 0.17 | >10 |
|  | HRV-1A | ND | 0.145 | >10 |
|  | HRV-10 | ND | 0.330 | >10 |
|  | HRV-3 | ND | 0.145 | >10 |
|  | HRV-25 | ND | 0.329 | >10 |
|  | HRV-9 | ND | 0.144 | >10 |
|  | HRV-39 | ND | 0.235 | >10 |
|  | HRV-14 | 27900 | 0.541 | >10 |
| 37 | HRV-14 | 26400 | 0.266 | >10 |
| 38 | HRV-1A | ND | 0.537 | >10 |
|  | HRV-10 | ND | 0.446 | >10 |
|  | HRV-39 | ND | 0.593 | >10 |
|  | HRV-87 | ND | 0.097 | >10 |
|  | HRV-2 | ND | 0.353 | >10 |
|  | HRV-3 | ND | 0.605 | >10 |
|  | HRV-9 | ND | 0.885 | >10 |
|  | HRV-16 | ND | 1.49 | >10 |
|  | HRV-25 | ND | 1.51 | >10 |
|  | HRV-14 | 33000 | 0.136 | >10 |

TABLE-continued

| Compound # | Virus Serotype | $K_{obs}/I$ $(M^{-1}s^{-1})$ | $EC_{50}$ ($\mu$M) | $CC_{50}$ ($\mu$M) |
|---|---|---|---|---|
| 39 | HRV-1A | ND | 0.338 | >10 |
|  | HRV-10 | ND | 0.428 | >10 |
|  | HRV-39 | ND | 0.518 | >10 |
|  | HRV-87 | ND | 0.083 | >10 |
|  | HRV-2 | ND | 0.214 | >10 |
|  | HRV-3 | ND | 0.595 | >10 |
|  | HRV-9 | ND | 0.665 | >10 |
|  | HRV-16 | ND | 0.952 | >10 |
|  | HRV-25 | ND | 1.32 | >10 |
|  | HRV-14 | 20100 | 0.214 | >10 |
| 40 | HRV-14 | 3175 | 1.656 | >10 |
| 41 | HRV-14 | 10700 | 0.50 | >10 |
| 42 | HRV-14 | 42 | ND | ND |
| 43 | HRV-14 | 85 | ND | ND |
| 44 | HRV-14 | 1031 | ND | ND |
| 45 | HRV-14 | 629 | ND | ND |
| 46 |  |  |  |  |

While the invention has been described in terms of preferred embodiments and specific examples, those skilled in the art will recognize through routine experimentation that various changes and modifications can be made without departing from the spirit and scope of the invention. Thus, the invention should be understood as not being limited by the foregoing detailed description, but as being defined by the appended claims and their equivalents.

We claim:

1. A compound having the formula:

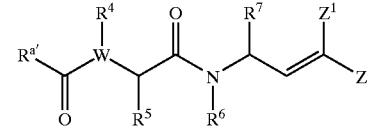

wherein:

W is CH;

$R^{a'}$ is an alkyl, cycloalkyl, or aryl group, where said alkyl, cycloalkyl, and aryl group is unsubstituted or substituted with one or more suitable substituents, provided that $R^{a'}$ is not an amino-substituted alkyl group;

$R^4$ and $R^6$ are each independently H or a lower alkyl group;

$R^5$ is H or an alkyl group;

$R^7$ is a moiety having the formula:

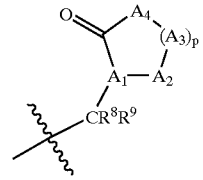

wherein:

$R^8$ and $R^9$ are each independently H or lower alkyl;

p is an integer of from 1 to 5;

$A_1$ is CH;

when p is 1, 2, 3, 4, or 5, $A_2$ is $C(R^{10})(R^{11})$ where each $R^{10}$ and $R^{11}$ is independently H or a lower alkyl group;

each $A_3$ present is independently $C(R^{10})(R^{11})$, where each $R^{10}$ and $R^{11}$ is independently H or a lower alkyl group;

when p is 1, 2, 3, 4, or 5, $A_4$ is $N(R^{13})$, $C(R^{10})(R^{11})$, or O, where each $R^{10}$, $R^{11}$ and $R^{12}$ is independently H or a lower alkyl group, each $R^{13}$ is H or an alkyl, aryl, or acyl group, and each $R^{14}$ is H or an alkyl or aryl group; and Z and $Z^1$ are each independently H, F, an alkyl, cycloalkyl, or aryl group, where the alkyl, cycloalkyl, or aryl group is unsubstituted or substituted with one or more suitable substituents —C(O)$R^{15}$, —CO$_2R^{15}$, —CN, —C(O)NR$^{15}R^{16}$, —C(O)NR$^{15}$OR$^{16}$, —C(S)$R^{15}$, —C(S)OR$^{15}$, —C(S)NR$^{15}R^{16}$, —C(=NR$^{15}$)R$^{16}$, —C(=NR$^{15}$)OR$^{16}$, —NO$_2$, —SOR$^{16}$, —SO$_2R^{15}$, —SO$_2$NR$^{15}R^{16}$, —SO$_2$(NR$^{15}$)(OR$^{16}$) —SONR$^{15}$, —SO$_3R^{15}$, —PO(OR$^{15}$)$_2$, —PO(OR$^{15}$)(OR$^{16}$), —PO(NR$^{15}R^{16}$)(OR$^{17}$), —PO(NR$^{15}R^{16}$)(NR$^{17}R^{18}$), —C(O)NR$^{15}$NR$^{16}R^{17}$, —C(S)NR$^{15}$NR$^{16}R^{17}$, where $R^{15}$, $R^{16}$, $R^{17}$ and $R^{18}$ are each independently H or an alkyl, cycloalkyl, aryl, acyl or thioacyl group, where the alkyl, cycloalkyl, aryl, acyl or thioacyl group is unsubstituted or substituted with one or more suitable substituents, or Z and $Z^1$, together with the atoms to which they are bonded, form a cycloalkyl group, where Z and $Z^1$ are as defined above;

or a prodrug, pharmaceutically acceptable salt, or pharmaceutically acceptable solvate of said compound.

2. The compound according to claim 1, wherein:

$A_1$ is CH;

$A_2$ is C($R^{10}$)($R^{11}$), where each $R^{10}$ and $R^{11}$ is independently H or a lower alkyl group;

each $A_3$ present is independently C($R^{10}$)($R^{11}$), where each $R^{10}$ and $R^{11}$ is independently H or a lower alkyl group;

when p is 1, 2, 3, 4, or 5, $A_4$ is N($R^{13}$), C($R^{10}$)($R^{11}$), or O, where each $R^{10}$, $R^{11}$ and $R^{12}$ is independently H or a lower alkyl group, each $R^{13}$ is H or an alkyl, aryl, or acyl group, and each $R^{14}$ is H or an alkyl or aryl group; and Z and $Z^1$ are each independently H, F, an alkyl, cycloalkyl, or aryl group, where the alkyl, cycloalkyl, or aryl group is unsubstituted or substituted with one or more suitable substituents, —C(O)$R^{15}$, —CO$_2R^{15}$, —CN, —C(O)NR$^{15}R^{16}$, —C(O)NR$^{15}$OR$^{16}$, —C(S)$R^{15}$, —C(S)NR$^{15}R^{16}$, —NO$_2$, —SOR$^{16}$, —SO$_2R^{15}$, —SO$_2$NR$^{15}R^{16}$, —SO$_2$(NR$^{15}$)(OR$^{16}$), —SONR$^{15}$, —SO$_3R^{15}$, —PO(OR$^{15}$)$_2$, —PO(OR$^{15}$)(OR$^{16}$), —PO(NR$^{15}R^{16}$)(OR$^{17}$), —PO(NR$^{15}R^{16}$)(NR$^{17}R^{18}$), —C(O)NR$^{15}$NR$^{16}R^{17}$, —C(S)NR$^{15}$NR$^{16}R^{17}$, where $R^{15}$, $R^{16}$, $R^{17}$ and $R^{18}$ are each independently H or an alkyl, cycloalkyl, aryl, acyl or thioacyl group, where the alkyl, cycloalkyl, aryl, acyl or thioacyl group is unsubstituted or substituted with one or more suitable substituents, or Z and $Z^1$, together with the atoms to which they are bonded, form a cycloalkyl group, where Z and $Z^1$ are as defined above.

3. The compound according to claim 1 or 9, having the formula:

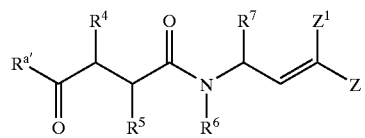

wherein $R^{a'}$ is an alkyl, cycloalkyl, or aryl group, where said alkyl, cycloalkyl, and aryl group is unsubstituted or substituted with one or more suitable substituents, and $R^4$, $R^5$, $R^6$, $R^7$, Z and $Z^1$ are defined as in claim 8 or 9, respectively, provided that $R^{a'}$ is not amino-substituted alkyl.

4. The compound according to claim 1 or 2, having the formula:

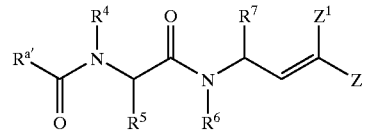

wherein $R^{a'}$ is an alkyl, cycloalkyl, or aryl group, where said alkyl, cycloalkyl, or aryl group is unsubstituted or substituted with one or more suitable substituents, and $R^4$, $R^5$, $R^6$, $R^7$, Z and $Z^1$ are defined as in claim 8 or 9, respectively, provided that $R^{a'}$ is not amino-substituted alkyl.

5. The compound, prodrug, pharmaceutically acceptable salt, or pharmaceutically acceptable solvate according to claim 2, wherein Z and $Z^1$ are each independently selected from H, lower alkyl which is unsubstituted or substituted with one or more suitable substituents, —CO$_2$H, —CO$_2$-alkyl and —CO$_2$-cycloalkyl.

6. The compound according to claim 2, wherein $Z^1$ is H and Z is —CO$_2$CH$_2$CH$_3$, —CO$_2$(CH(CH$_3$)$_2$), —CO$_2$(C(CH$_3$)$_3$), —CO$_2$CH$_2$(C(CH$_3$)$_3$), —CO$_2$(cyclo-C$_3$H$_9$).

7. The compound according to claim 3, having the formula:

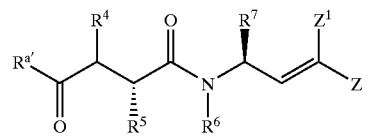

wherein $R^{a'}$ is an alkyl, cycloalkyl, or aryl group, where said alkyl, cycloalkyl, and aryl group is unsubstituted or substituted with one or more suitable substituents, and each $R^4$, $R^5$, $R^6$, $R^7$, Z and $Z^1$ are defined as in claim 3.

8. The compound according to claim 4, having the formula:

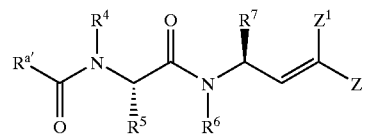

wherein $R^{a'}$ is an alkyl, cycloalkyl, or aryl group, where said alkyl, cycloalkyl, and aryl group is unsubstituted or substituted with one or more suitable substituents, and each $R^4$, $R^5$, $R^6$, $R^7$, Z and $Z^1$ are defined as in claim 4.

9. A pharmaceutical composition comprising:

a therapeutically effective amount of at least one agent selected from compounds, prodrugs, pharmaceutically acceptable salts, and pharmaceutically acceptable solvates defined in any one of claim 1 or 2; and a pharmaceutically acceptable carrier, diluent, vehicle, or excipient.

* * * * *

UNITED STATES PATENT AND TRADEMARK OFFICE
CERTIFICATE OF CORRECTION

PATENT NO.   : 6,872,745 B2
DATED        : March 29, 2005
INVENTOR(S)  : Thoedore O. Johnson, Jr. et al.

It is certified that error appears in the above-identified patent and that said Letters Patent is hereby corrected as shown below:

Title page,
Item [56], References Cited, OTHER PUBLICATIONS,
"Murray et al." reference, "incorpting" should read -- incorporating --;
"Webber et al." reference (second occurrence), "J. Med." should be italicized;
"McWilliams et al." reference, "1,2-Mmigration" should read -- 1,2-Migration --;
"Bowden et al." reference, "Orgnic" should read -- Organic --;
"Dragovich et al." reference (fifth occurrence), "vol. A1," should read -- vol. 41, --;
"DeJohn et al." reference, "6-Vinyl-1,2-dihyrdo-2-oxo-" should read -- 6-Vinyl-1,2-dihyrdo-2-oxo- --, and "1,4-Dihyrdo-4-oxo-" should read -- 1,4-Dihydro-4-oxo- --;
"Fasseur et al." reference, "Studies" should read -- Studies --, and "Acid:," should read -- Acid", --;
"Straub et al." reference, "enzyme" should read -- Enzyme --, and "cycloaddition" should read -- Cycloaddition --;
"Crossley et al." reference, "(1998" should read -- (1998) --;
"Diana et al." reference, "Provides" should read -- Provide --;
"Jackson" reference, "et. al.," should read -- et al., --, and "4-Oxo-∝-amnio" should read -- 4-Oxo-∝-amino --; and
"Askin et al." reference, "Isotere" should read -- Isostere --.

Column 4,
Line 4, "aaryl," should read -- aryl, --.

Column 7,
Line 6, "are" should read -- art --; and
Line 9, "Wwhen" should read -- When --.

Column 10,
Line 56, "hydroxamino" should read -- hydroxylamino --.

Column 11,
Line 19, "hydroxamino" should read -- hydroxylamino --; and
Line 51, "radical" should read -- radical. --.

Column 12,
Line 35, "$R^d$" should read -- $R_d$ --.

Column 13,
Line 61, "—C(S)OR$^5$," should read -- —C(S)OR$^{15}$, --.

UNITED STATES PATENT AND TRADEMARK OFFICE
CERTIFICATE OF CORRECTION

PATENT NO. : 6,872,745 B2
DATED : March 29, 2005
INVENTOR(S) : Thoedore O. Johnson, Jr. et al.

It is certified that error appears in the above-identified patent and that said Letters Patent is hereby corrected as shown below:

Column 15,
Line 50, "($NR^{17}R^{18}$," should read -- ($NR^{17}R^{18}$), --.

Column 18,
Line 67, "are" should read -- is --.

Column 19,
Line 7, "comprise" should read -- comprises --.

Column 20,
Line 51, "loweralkoxyalkyl" should read -- lower alkoxyalkyl --.

Column 21,
Line 21, "describe" should read -- to describe --; and
Line 24, "enatiomerically" should read -- enantiomerically --.

Column 25,
Line 35, "are" should read -- art --; and
Line 39, "is  O);" should read -- is  O);--.

Column 26,
Line 20, "($C_1$-$C_4$" should read -- ($C_1$-$C_4$) --;
Line 27, "$R^3$" should read -- $R^a$ --; and
Line 30, "$C_3$-$C_8$" should read -- ($C_3$-$C_8$) --.

Column 28,
Line 20, "is" (second occurrence) should be deleted.

Column 29,
Line 21, "$C_3$-$C_8$" should read -- ($C_3$-$C_8$) --;
Line 25, "($C_1$-$C_4$alkylaminocarbonyl-($C_1$-$C_4$)alkyl," should read -- ($C_1$-$C_4$) alkylaminocarbonyl-($C_1$-$C_4$)alkyl, --; and
Line 31, "thereof unsubstituted" should read -- thereof is unsubstituted --.

Column 66,
Line 67, "substituents," should read -- substituents. --.

Column 77,
Line 27, "ether)" should read -- ether), --; and
Line 62, "Gln-resin)" should read -- Gln-resin). --.

UNITED STATES PATENT AND TRADEMARK OFFICE
CERTIFICATE OF CORRECTION

PATENT NO. : 6,872,745 B2
DATED : March 29, 2005
INVENTOR(S) : Thoedore O. Johnson, Jr. et al.

It is certified that error appears in the above-identified patent and that said Letters Patent is hereby corrected as shown below:

Column 79,
Line 17, "Example 1," should read -- Example 1 --.

Column 82,
Line 2, "(3H, s,)," should read -- (3H, s), --.

Column 84,
Line 60, "(I1H," should read -- (1H, --.

Column 88,
Line 8, "J7.7)," should read -- J=7.7), --; and
Line 35, "Phe-Gin" should read -- Phe-Gln --.

Column 96,
Line 50, "phenyl)-1H-pyrrole-2-carbonyl]-amino-3-3-" should read -- phenyl)-1H-pyrrole-2-carbonyl]-amino-3- --.

Column 115,
Line 11, "$-SO_2(NR^{15})(OR^{16})$" should read -- $SO_2(NR^{15})(OR^{16})$, --; and
Line 52, "or 9," should read -- or 2, --.

Column 116,
Line 1, "claim 8 or 9," should read -- claim 1 or 2, --;
Line 17, "not amino-substituted" should read -- not an amino-substituted --.
Line 26, "$CO_2(cyclo-C_3H_9)$." should read -- $CO_2(cyclo-C_5H_9)$. --.

Signed and Sealed this

Fourteenth Day of March, 2006

JON W. DUDAS
*Director of the United States Patent and Trademark Office*